US007494459B2

(12) United States Patent
Anstadt et al.

(10) Patent No.: US 7,494,459 B2
(45) Date of Patent: Feb. 24, 2009

(54) SENSOR-EQUIPPED AND ALGORITHM-CONTROLLED DIRECT MECHANICAL VENTRICULAR ASSIST DEVICE

(75) Inventors: Mark P. Anstadt, Augusta, GA (US); George L. Anstadt, Tipp City, OH (US); Stuart G. MacDonald, Pultneyville, NY (US); Jeffrey L. Helfer, Webster, NY (US); George W. Anstadt, Pittsford, NY (US)

(73) Assignee: Biophan Technologies, Inc., Pittsford, NY (US)

( * ) Notice: Subject to any disclaimer, the term of this patent is extended or adjusted under 35 U.S.C. 154(b) by 0 days.

(21) Appl. No.: 10/607,434

(22) Filed: Jun. 26, 2003

(65) Prior Publication Data

US 2004/0267086 A1 Dec. 30, 2004

(51) Int. Cl.
*A61M 1/10* (2006.01)
(52) U.S. Cl. ........................................................ 600/17
(58) Field of Classification Search .................. 600/16, 600/17; 623/3.16, 3.2, 3.21; 601/148–150, 601/152, 153
See application file for complete search history.

(56) References Cited

U.S. PATENT DOCUMENTS

| 2,826,193 | A | 3/1958 | Vineberg |
| 3,034,501 | A | 5/1962 | Hewson |
| 3,053,249 | A | 9/1962 | Smith |
| 3,233,607 | A | 2/1966 | Bolie |

(Continued)

FOREIGN PATENT DOCUMENTS

DE  199 51 220 A1  4/2001

OTHER PUBLICATIONS

Author: Victor L. Poirier, Title: The LVAD: A Case Study, Source: Bridge Archives, Published in: The Bridge, vol. 27, No. 4—Winter 1997, Publication of: National Academy of Engineering of the National Academies, Taken from website: http://www.nae.edu/nae/naehome.nsf/weblinks/NAEW-4NHM83?opendocument.

(Continued)

*Primary Examiner*—Carl H. Layno
*Assistant Examiner*—Frances P Oropeza
(74) *Attorney, Agent, or Firm*—Buchanan Ingersoll & Rooney PC

(57) ABSTRACT

A process for assisting the function of a heart disposed within a body, and comprising an outer wall, comprising the steps of measuring at least one parameter that is indicative of the function of the heart, applying a compressive force to a portion of the outer wall of the heart, and applying an expansive force to the portion of the outer wall of the heart. The process is preferably performed with an apparatus comprising a cup-shaped shell having an exterior wall, an interior wall, an apex, and an upper edge; a liner having an outer surface and an inner surface, an upper edge joined to said interior wall of the cup-shaped shell, and a lower edge joined of the interior wall of the cup-shaped shell, thereby forming a cavity between the outer surface thereof and the interior wall of the shell; and a drive fluid cyclically interposed within the cavity, the drive fluid applying a uniform force on a portion of the outer wall of the heart.

52 Claims, 55 Drawing Sheets

U.S. PATENT DOCUMENTS

| | | |
|---|---|---|
| 3,279,464 A | 10/1966 | Kline |
| 3,371,662 A | 3/1968 | Heid et al. |
| 3,376,863 A | 4/1968 | Kolobow et al. |
| 3,449,767 A | 6/1969 | Bolie |
| 3,455,298 A | 7/1969 | Anstadt |
| 3,478,737 A | 11/1969 | Rassman |
| 3,513,836 A | 5/1970 | Sausse |
| 3,587,567 A | 6/1971 | Schiff |
| 3,590,815 A | 7/1971 | Schiff |
| 3,613,672 A | 10/1971 | Schiff |
| 3,674,381 A | 7/1972 | Schiff |
| 4,048,990 A | 9/1977 | Goetz |
| 4,192,293 A | 3/1980 | Asrican |
| 4,281,669 A | 8/1981 | MacGregor |
| 4,448,190 A | 5/1984 | Freeman |
| 4,485,387 A | 11/1984 | Drumheller |
| 4,536,893 A | 8/1985 | Parravicini |
| 4,621,617 A | 11/1986 | Sharma |
| 4,662,358 A | 5/1987 | Farrar et al. |
| 4,684,143 A | 8/1987 | Sato |
| 4,690,134 A * | 9/1987 | Snyders ................. 601/153 |
| 4,957,477 A | 9/1990 | Lundback |
| 4,979,936 A | 12/1990 | Stephenson et al. |
| 5,006,111 A | 4/1991 | Inokuchi et al. |
| 5,089,017 A | 2/1992 | Young et al. |
| 5,098,369 A | 3/1992 | Heilman et al. |
| 5,098,442 A | 3/1992 | Grandjean |
| 5,119,804 A | 6/1992 | Anstadt |
| 5,131,905 A * | 7/1992 | Grooters ................. 600/16 |
| 5,156,154 A | 10/1992 | Valenta, Jr. et al. |
| 5,158,978 A | 10/1992 | Rubin |
| 5,169,381 A | 12/1992 | Snyders |
| 5,205,722 A | 4/1993 | Hammond |
| 5,256,132 A | 10/1993 | Snyders |
| 5,273,518 A | 12/1993 | Lee et al. |
| 5,330,505 A | 7/1994 | Cohen |
| 5,364,337 A | 11/1994 | Guiraudon et al. |
| 5,368,451 A | 11/1994 | Hammond |
| 5,374,287 A | 12/1994 | Rubin |
| 5,383,840 A | 1/1995 | Heilman et al. |
| 5,385,528 A | 1/1995 | Wilk |
| 5,429,584 A | 7/1995 | Chiu |
| 5,476,502 A | 12/1995 | Rubin |
| 5,496,353 A | 3/1996 | Grandjean et al. |
| 5,533,958 A | 7/1996 | Wilk |
| 5,558,617 A | 9/1996 | Heilman et al. |
| 5,562,595 A | 10/1996 | Neisz |
| 5,658,237 A | 8/1997 | Francischelli |
| 5,674,259 A | 10/1997 | Gray |
| 5,697,884 A | 12/1997 | Francischelli et al. |
| 5,697,952 A | 12/1997 | Francischelli et al. |
| 5,707,336 A | 1/1998 | Rubin |
| 5,713,954 A * | 2/1998 | Rosenberg et al. ............ 600/17 |
| 5,716,379 A | 2/1998 | Bourgeois et al. |
| 5,738,627 A | 4/1998 | Kovacs et al. |
| 5,749,839 A | 5/1998 | Kovacs |
| 5,800,334 A | 9/1998 | Wilk |
| 5,861,558 A | 1/1999 | Buhl |
| 5,876,345 A | 3/1999 | Eaton et al. |
| 5,902,229 A | 5/1999 | Tsitlik et al. |
| 5,908,378 A | 6/1999 | Kovacs et al. |
| 5,910,124 A | 6/1999 | Rubin |
| 5,919,209 A | 7/1999 | Schouten |
| 5,971,910 A * | 10/1999 | Tsitlik et al. .................. 600/16 |
| 5,971,911 A | 10/1999 | Wilk |
| 5,980,571 A | 11/1999 | Nomura et al. |
| 6,042,532 A | 3/2000 | Freed et al. |
| 6,044,298 A | 3/2000 | Salo et al. |
| 6,059,750 A | 5/2000 | Fogarty et al. |
| 6,076,013 A | 6/2000 | Brennan et al. |
| 6,095,968 A | 8/2000 | Snyders |
| 6,110,098 A | 8/2000 | Renirie et al. |
| 6,123,726 A | 9/2000 | Mori et al. |
| 6,132,363 A | 10/2000 | Freed et al. |
| 6,183,412 B1 | 2/2001 | Benkowski et al. |
| 6,206,820 B1 | 3/2001 | Kazi et al. |
| 6,238,334 B1 * | 5/2001 | Easterbrook et al. .......... 600/16 |
| 6,251,061 B1 | 6/2001 | Hastings et al. |
| 6,254,525 B1 | 7/2001 | Reinhardt et al. |
| 6,282,445 B1 | 8/2001 | Reinhardt et al. |
| 6,298,266 B1 | 10/2001 | Rubin et al. |
| 6,309,380 B1 | 10/2001 | Larson et al. |
| 6,328,689 B1 | 12/2001 | Gonzalez |
| 6,408,205 B1 | 6/2002 | Renirie et al. |
| 6,432,039 B1 | 8/2002 | Wardle |
| 6,438,411 B1 | 8/2002 | Guttman et al. |
| 6,464,655 B1 | 10/2002 | Shahinpoor |
| 6,485,407 B2 | 11/2002 | Alferness |
| 6,508,756 B1 | 1/2003 | Kung et al. |
| 6,540,659 B1 | 4/2003 | Milbocker et al. |
| 6,547,716 B1 | 4/2003 | Milbocker |
| 6,572,534 B1 | 6/2003 | Milbocker et al. |
| 6,602,182 B1 | 8/2003 | Milbocker et al. |
| 6,612,978 B2 | 9/2003 | Lau et al. |
| 6,616,596 B1 | 9/2003 | Milbocker et al. |
| 6,622,045 B2 | 9/2003 | Snell et al. |
| 6,626,821 B1 * | 9/2003 | Kung et al. ................... 600/16 |
| 6,641,604 B1 | 11/2003 | Adelman et al. |
| 6,682,474 B2 | 1/2004 | Lau et al. |
| 6,730,016 B1 | 5/2004 | Cox et al. |
| 6,757,561 B2 | 6/2004 | Rubin et al. |
| 6,765,144 B1 | 7/2004 | Wang et al. |
| 6,808,483 B1 | 10/2004 | Ortiz et al. |
| 6,846,296 B1 | 1/2005 | Milbocker et al. |
| 2004/0010180 A1 | 1/2004 | Scorvo |
| 2004/0059183 A1 | 3/2004 | Jansen et al. |
| 2004/0078067 A1 | 4/2004 | Thompson et al. |
| 2004/0102674 A1 | 5/2004 | Zadini et al. |
| 2004/0116769 A1 | 6/2004 | Jassawalla et al. |
| 2004/0167375 A1 | 8/2004 | Couvillon, Jr. |
| 2004/0225177 A1 | 11/2004 | Coleman et al. |
| 2005/0113632 A1 | 5/2005 | Ortiz et al. |
| 2005/0148814 A1 | 7/2005 | Fischi et al. |

OTHER PUBLICATIONS

Anstadt, Mark P., et al., "Direct Mechanical Ventricular Actuation: A Review," Resuscitation, 21 (1991) 7-23. Elseview Scientific Publishers Ireland Ltd.

Anstadt, Mark P., et al., "Pulsatile Reperfusion After Cardiac Arrest Improves Neurologic Outcome," Annals of Surgery, 1991, 214(4): 478-490. Am. Surgical Assn.

Anstadt, G, et al., "A New Instrument for Prolonged Mechanical Cardiac Massage," Circulation, 1965, vol. 31 and 32, Supplement II, 43-44. Lippencott Williams & Wilkins.

"Hemodynamic Analysis of Direct Mechanical Ventricular Actuation: Its Application to Control of the Anstadt Cup," R.A. Perez-Tamayo, UMI Company, UMI No. 9600598, 1995. (Doctoral Disseertation.)

Rosendorf, Clive, M.D.; "Essential Cardiology"; 2001; pp. 23-699; W.B. Saunders Co.

McGee, David C., M.D., et al.; "Preventing Complications of Intravenous Catheterization"; New England Journal of Medicine; Mar. 20, 2003; pp. 1123; Massachusetts Medical Society, Waltham.

Gabriel, Manal M., et al.; "In Vitro Evaluation of the Efficacy of a Silver Coated Catheter"; Current Microbiology; 1996; pp. 1-5; vol. 33; Springer-Verlag, New York.

Winfree, Arthur T.; "When Time Breaks Down—The Three-Dimensional Dynamics of Electrochemical Waves and Cardiac Arrhythmias"; 1987; 340 pages; Princeton University Press, Princeton.

Wax, Steven G.; "Electro-Active Polymer Actuators and Devices"; Proceedings of SPIE; Mar. 1999; vol. 3669.

* cited by examiner

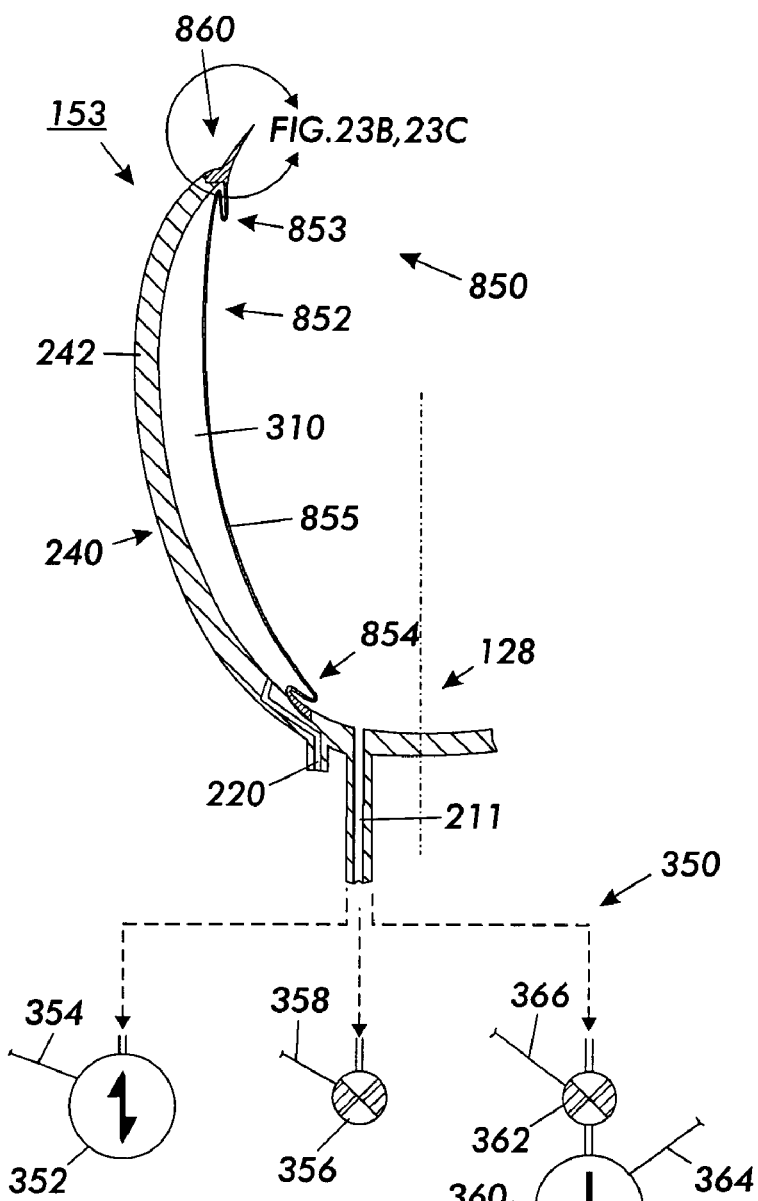
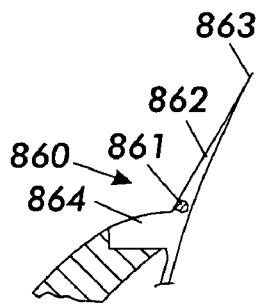
FIG. 23B
FIG. 23A
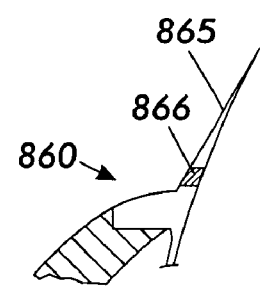
FIG. 23C

SENSOR-EQUIPPED AND ALGORITHM-CONTROLLED DIRECT MECHANICAL VENTRICULAR ASSIST DEVICE

This invention relates in one embodiment to devices that assist a weak heart in providing the required pumping of blood, and more particularly to a mechanical cardiac assistance device which envelops the heart and applies periodic and focused hydraulic pressure waves to the heart in order to drive ventricular action (compression and expansion) in the proper sequence and intensity.

FIELD OF THE INVENTION

Mechanical devices that assist the human heart by providing proper systolic and diastolic actuation and circulatory function.

BACKGROUND OF THE INVENTION

Traditional medical and surgical treatment of patients with failing pump function of the heart is limited to blood-contacting devices which are technically difficult to install and result in complications related to such blood contact as well as technical aspects of device installation. Inadequate cardiac output remains a cause of millions of deaths annually in the United States. Mechanical devices are proving to be a practical therapy for some forms of sub-acute and chronic low cardiac output. However, all currently available devices require too much time to implant to be of value in acute resuscitation situations, resulting in loss of life before adequate circulatory support can be provided. Furthermore, other non-blood contacting devices similar to the current invention provide inadequate augmentation of cardiac function. Mechanical cardiac assistance devices generally operate by providing blood pumping support to the circulation to assist the failing heart.

A number of mechanical techniques for assisting heart function by compressing its outer epicardial surface have been described and studied. These methods have focused on improving cardiac performance by assisting the systolic (positive pumping) function of the heart. Such techniques have been described as "direct cardiac compression" (DCC). DCC methods have been investigated only in the laboratory setting, and there are no uses of such devices in human subjects known to the applicants. Investigations regarding DCC have focused primarily on left ventricular (LV) systolic and diastolic performance. Examples of DCC techniques include, but are not limited to, cardiomyoplasty (the technique of wrapping skeletal muscle around the heart and artificially stimulating it), the Cardio support system (Cardio Technologies, Inc., Pinebrook, N.J.) and the "Heart Booster" (Abiomed, Inc., Danvers, Mass.). Cumulative results from laboratory investigations using these devices have all resulted in similar findings. Specifically, DCC has been shown to enhance left ventricular (LV) pump function without any apparent change in native LV oxygen consumption requirements; thereby, DCC has been shown to improve LV pump function without increasing myocardial oxygen consumption and/or requiring extra work from the heart.

DCC devices have been shown to only benefit hearts with substantial degrees of LV failure. Specifically, DCC techniques only substantially improve the systolic function of hearts in moderate to severe heart failure. In addition, the benefits of DCC techniques are greater when applied to the relatively dilated or enlarged LV. Therefore the relative degree of assistance provided by DCC improves as heart failure worsens and the heart enlarges or dilates from such failure. DCC techniques clearly have a negative effect on diastolic function (both RV and LV diastolic function). This is exhibited by reductions in diastolic volume that, in part, explains DCC's inability to effectively augment the heart without at least moderate degrees of failure. This also explains DCC's efficacy being limited to sufficient degrees of LV size and/or dilatation, with significant dependence on preload, and/or ventricular filling pressures. Thus, DCC requires an "adequate" degree of heart disease and/or heart failure to benefit the heart's function. In addition, DCC devices have negative effects on the dynamics of diastolic relaxation and, in effect, reduce the rate of diastolic pressure decay (negative dP/dt max), increasing the time required for ventricular relaxation. This better explains why DCC techniques require substantial degrees of LV and RV loading (i.e. increased left and right atrial pressure or "preload") to be effective, as such increases serve to augment ventricular filling. This latter point is particularly true with smaller heart size and/or less ventricular distension.

The critical drawbacks to DCC methods are multi-factorial and are, in part, summarized in the following discussion. First, and foremost, these techniques do not provide any means to augment diastolic function of the heart necessary to overcome their inherent drawback of "effectively" increasing ventricular stiffness. This is illustrated by the leftward shifts in the end-diastolic pressure-volume relationship (EDPVR) during DCC application. This effect on the EDPVR is seen with DCC devices in either the assist or non-assist mode. Clearly, RV diastolic function is impaired to a far greater degree by DCC due to the nature both the RV wall and intra-cavity pressures. Furthermore, studies of DCC devices have all overlooked the relevant and dependent impact these techniques have on right ventricular dynamics, septal motion and overall cardiac_function. Because the right ventricle is responsible for providing the "priming" blood flow to the left ventricle, compromising right ventricular function has a necessary secondary and negative impact on left ventricular pumping function when these load-dependent devices are utilized. Furthermore, the ventricular septum lies between the right and left ventricle and is directly affected by the relevant forces placed on both the RV and LV. Another related and fundamental drawback to DCC devices is their inability to continuously monitor ventricular wall motion and chamber dynamics that are intuitively critical to optimizing the assist provided by such mechanical actions on the right and left ventricular chambers which behave in an complex, inter-related fashion. Finally, studies regarding DCC methods have failed to adequately examine the effects of these devices on myocardial integrity.

The Direct Mechanical Ventricular Assist device (hereinafter abbreviated as DMVA) is an example of one type of mechanical cardiac assistance device. In general, a DMVA system comprises two primary elements: (a) a Cup having dynamic characteristics and material construction that keep the device's actuating liner membrane or diaphragm closely conformed to the exterior surface (or epicardium) of the heart throughout systolic and diastolic actuation, and (b) a Drive system and control system combination that cyclically applies hydraulic pressure to a compression and expansion liner membrane or membranes located on the interior surfaces of the Cup in a manner that augments the normal pressure and volume variations of the heart during systolic and diastolic actuation. The cyclic action of the device cyclically pushes and pulls on the left and right ventricles of the heart.

By providing this cyclic motion at the appropriate frequency and amplitude, the weakened, failing, fibrillating, or asystolic heart is driven to pump blood in a manner which approximates blood flow generated by a normally functioning heart. Pushing inwardly on the exterior walls of the heart compresses the left and right ventricles into systolic configuration(s), thereby improving pump function. As a result, blood is expelled from the ventricles into the circulation. Immediately following each systolic actuation, the second phase of the cycle applies negative pressure to the liner membrane to return the ventricular chambers to a diastolic configuration by pulling on the outer walls of the heart. This is termed diastolic actuation and allows the ventricular chambers to refill with blood for the next compression.

In the preferred embodiment of the present invention, the Cup is installed on the heart typically by using apical vacuum assistance, i.e. vacuum applied to the apex of the Cup. Such a preferred embodiment enables a non-traumatic and technically simple means of cardiac attachment of the Cup device in the patient and facilitates diastolic actuation. To install the Cup, the heart is exposed by a chest incision., The Cup is positioned over the apex of the heart in a position such that the apex of the heart is partially inserted therein. A vacuum is applied to the apex of the Cup, thereby pulling the heart and the Cup together, such that the apices of the Cup and the heart, and the inner wall of the Cup and the epicardial surface of the heart become substantially attached. Connections are then completed for any additional sensing or operational devices (typically integrated into a single interface cable) if the particular Cup embodiment comprises such devices. This procedure can be accomplished in minutes, and it is easy to teach to individuals with minimal surgical expertise.

Effective DMVA requires that the Cup and Drive system satisfy multiple and complex performance requirements. Preferred embodiments of the Cup of the present invention satisfy these critical performance requirements in a manner that is superior to prior art DMVA devices.

Heretofore, a number of patents and publications have disclosed Direct Mechanical Ventricular Assist devices and other cardiac assistance devices, the relevant portions of which may be briefly summarized as follows:

U.S. Pat. No. 2,826,193 to Vineberg discloses a Ventricular Assist device that is held to the heart by a flexible draw-string. Vineberg uses a mechanical pump to supply systolic pressure to the heart to assist the heart's pumping action.

U.S. Pat. No. 3,034,501 to Hewson discloses a similar Ventricular Assist device, comprised of silastic, which permits varying pressures to be exerted on various portions of the heart.

U.S. Pat. No. 3,053,249 to Smith discloses a Ventricular Assist device capable of delivering systolic pressure to a heart. The Smith device utilizes adhesive straps to attach the device to the heart.

U.S. Pat. No. 3,233,607 to Bolie illustrates a Direct Assist device that varies the level of systolic pressure depending on the changes of blood flow occasioned by exercise. The Bolie device claims to be fully implantable. U.S. Pat. No. 3,449,767 to Bolie discloses a system for controlling the pressure delivered to the balloons that control the DMVA unit.

U.S. Pat. No. 3,279,464 to Kline teaches a method of manufacture of a Ventricular Assist device. Kline's device provides only systolic pressure to the heart.

U.S. Pat. No. 3,371,662 to Heid discloses a Ventricular Assist device in the form of a cuff. The cuff may be implanted with defibrillating electrodes.

U.S. Pat. No. 3,376,863 to Kolobow illustrates a Ventricular Assist device that delivers systolic pressure to the heart. The Kolobow device possesses an expandable collar about the periphery of the device's opening. The heart may be sealed within the device by expanding the collar.

U.S. Pat. No. 3,455,298 of Anstadt discloses a Direct Mechanical Ventricular Assist device capable of delivering both systolic and diastolic pressures. The diastolic action is achieved by use of a vacuum. A second vacuum source functions to hold the device to the heart. Anstadt further defines the geometry of the device in U.S. Pat. No. 5,199,804. The geometry of the invention is described so as to accommodate hearts of various sizes as well as prevent the heart from being expelled from the device during the systolic expansion of the bladders.

U.S. Pat. No. 3,478,737 of Rassman discloses a Ventricular Assist device in the form of a cuff.

U.S. Pat. No. 3,513,836 to Sausee discloses a Ventricular Assist device that delivers systolic pressure to the heart by a multiplicity of bladders. Increasing the pressure in selected bladders may preferentially pressure selected portions of the heart.

U.S. Pat. No. 3,587,567 to Schiff discloses a Direct Mechanical Ventricular Assist device that is capable of delivering both systolic and diastolic pressures to a heart. The device may further comprise electrodes that permit defibrillation of the heart. The device is held to the heart by a mild vacuum pressure, which also supplies the diastolic action.

U.S. Pat. No. 3,613,672 to Schiff discloses a cup with a flexible outer shell that allows for the insertion of the device through a relatively small surgical incision. The patent also discloses the use of sensors, such as electrocardiogram equipment, in conjunction with the cup. Additional reference may be had to U.S. Pat. Nos. 3,590,815 and 3,674,381 also to Schiff.

U.S. Pat. No. 4,048,990 to Goetz discloses a Ventricular Assist device that delivers both systolic and diastolic pressures to a heart. The outer shell of the Goetz device is inflatable, so as to allow installation with minimal trauma to the patient.

U.S. Pat. No. 4,448,190 to Freeman discloses a Ventricular Assist device that delivers systolic pressure to a heart by means of a strap physically attached to the heart. A similar device is disclosed in U.S. Pat. Nos. 5,383,840 and 5,558,617 to Heilman. The Heilman patent discloses the use of defibrillation devices and materials that promote tissue in-growth to assist in adhering the device to the heart.

U.S. Pat. No. 4,536,893 to Parravicini discloses a Ventricular Assist device in the form of a cuff that applies pressure to selected portions of the heart. The patent also discloses the use of sensors, such as an electrocardiograph, in conjunction with the cuff.

U.S. Pat. No. 4,621,617 to Sharma discloses a Ventricular Assist device wherein the heart is disposed within two sheets of metal. An electromagnetic field draws the sheets together, thus compressing the heart.

U.S. Pat. No. 4,690,134 to Snyders discloses a Ventricular Assist device with a collapsible outer shell. Such a device may be installed with minimal trauma to the patient. Additional reference may be had to U.S. Pat. Nos. 5,169,381 and 5,256,132 also to Snyders.

U.S. Pat. No. 4,979,936 to Stephenson discloses a fully implantable Ventricular Assist device. Stephenson's device comprises a first bladder fluidly connected to a second bladder. The first bladder is disposed within a muscle, while the second bladder is disclosed next to or around the heart. The muscle may then be electrically contracted, thus, forcing fluid out of the first bladder and into the second bladder. The expansion of the second bladder thus compresses the heart.

U.S. Pat. No. 5,273,518 to Lee discloses a fully implantable Ventricular Assist device similar to the muscle powered devices mentioned above. U.S. Pat. Nos. 5,098,442 and 5,496,353 to Grandjean, 5,562,595 to Neisz, 5,658,237, 5,697,884, and 5,697,952 to Francischelli, 5,716,379 to Bourgeois and 5,429,584 to Chiu disclose a similar device. U.S. Pat. No. 5,364,337 to Guiraudon discloses a means for controlling the contraction of the muscle, which in turn, controls the compression of the heart.

U.S. Pat. No. 5,098,369 to Heilman discloses a Ventricular Assist device that is comprised of materials that allow for tissue in-growth, thus adhering the device to the heart. The use of defibrillating electrodes and electrocardiographs are also disclosed.

U.S. Pat. No. 5,131,905 to Grooters discloses a Ventricular Assist device that applies systolic pressure to the heart. The Grooters device is held in position around the heart by a plurality of straps.

U.S. Pat. Nos. 5,385,528, 5,533,958, 5,800,334, and 5,971,911 to Wilk disclose a Direct Mechanical Ventricular Assist device suitable for emergency use. The inflatable device may be quickly installed in an emergency situation through a small incision. U.S. Pat. No. 6,059,750 to Fogarty discloses a similar device.

U.S. Pat. No. 5,713,954 to Rosenberg discloses a Ventricular Assist device in the form of a cuff that provides systolic pressure to a heart. The disclosed cuff is suitable for applying pressure to specified portions of the heart, may be equipped with EKG sensors, and is fully implantable.

U.S. Pat. Nos. 5,738,627 and 5,749,839 to Kovacs disclose a Direct Mechanical Ventricular Assist device that provides both systolic and diastolic pressure to a heart. The disclosed cup adheres to the heart by way of a vacuum, which also provides' diastolic pressure to the heart. The opening of the device is equipped with an inflatable collar. When inflated, the collar provides a seal to assist in establishing the vacuum.

U.S. Pat. No. 6,076,013 to Brennan discloses a cup that senses electrical activity within the heart and provides electrical stimulation to assist the heart in its contractions.

U.S. Pat. No. 6,110,098 to Renirie discloses a method for treatment of fibrillation or arrhythmias through the use of subsonic waves.

U.S. Pat. No. 6,206,820 to Kazi discloses a Ventricular Assist device that compresses only the left ventricle and allows the other cardiac regions to expand in response to the contraction.

U.S. Pat. No. 6,238,334 to Easterbrook discloses a Ventricular Assist device that provides both systolic and diastolic pressure to a heart. Easterbrook discloses the use of a cup to apply a substantially uniform pressure to the heart's surface, which is necessary to avoid bruising of the muscle issue. Through the reduction of transmural pressure, a substantially lower driving pressure may be utilized. This assists to avoid traumatizing heart tissue.

U.S. Pat. No. 6,251,061 to Hastings discloses a Ventricular Assist device that provides systolic pressure to a heart through the use of ferrofluids and magnetic fields.

U.S. Pat. No. 6,432,039 to Wardle discloses a Ventricular Assist device that comprises a multiplicity of independently inflatable chambers that delivery systolic pressure to selected portions of a heart. Wardle also discloses the use of redundant "recoil" inflatable balloons.

U.S. Pat. No. 6,464,655 to Shashinpoor discloses a fully implantable robotic hand for selectively compressing the ventricles of a heart. The robotic hand is programmable via a microprocessor.

U.S. Pat. Nos. 6,328,689 to Gonzalez and 6,485,407 to Alfemess disclose a flexible jacket adapted to be disposed about a lung. By applying expansive and compressive forces, the lung may be assisted.

Optimal DMVA performance requires that the Cup be properly fit on the heart, be adequately sealed against the ventricular epicardium, and that the volume vs. time displacement profile of the Cup liner(s) produces the desired ventricular dynamics to achieve optimal, dynamic systolic and diastolic conformational changes of the ventricular myocardium. The optimum pressure-flow drive mechanics will vary from patient to patient, depending upon such factors as the actual fit of the Cup to the heart, the specific nature of the patient's disease, and the patient's normal cardiac rhythm. These factors make it difficult to pre-operatively define the optimum liner time-displacement profiles or hydraulic drive unit control parameters capable of satisfying every patient's unique DMVA requirements.

It is well known that diseased heart tissue can be very fragile, i.e. such tissue is of lower resistance to shear forces and/or less tensile strength than healthy heart tissue. Thus physicians lacking due caution can easily perforate or injure diseased hearts with their fingers while applying gentle pressure during open heart massage by the high pressure at a finger tip adjacent to a low pressure or pressure void between fingers. This previous example describes an acute or rapidly induced emergency situation. However, the persistent application of forces to the heart can also cause potentially catastrophic damage to the heart by fatiguing and severely bruising the heart muscle and/or abrading the heart surface, which can ultimately prevent the heart from functioning.

Direct mechanical ventricular actuation (DMVA) is a means of providing ventricular actuation to achieve biventricular compression (termed "systolic actuation") and active biventricular dilatation (termed "diastolic actuation"). In one embodiment, DMVA utilizes continuous suction to maintain a seal between the actuating diaphragm and the surface of the heart, which enables the device not only to compress the heart, but also effectively provide diastolic actuation by virtue of the diaphragm maintaining attachment to the epicardial surface during the phase of ventricular actuation. Therefore, DMVA overcomes major drawbacks of DCC devices by augmenting diastolic function. This is essential, given that any such DCC device that encompass the ventricles and applies external forces will have inherently negative impacts on diastolic function. The present invention overcomes this, by enhancing diastolic function as demonstrated by an increased rate of diastolic pressure decay and an associated reduced time constant for active ventricular chamber dilatation ("diastolic actuation").

The general principles of effective ventricular compression and ventricular dilatation can only be delivered in an optimal fashion if the effects on both right and left ventricular function are taken into account and such forces are applied in the appropriate temporal and spatial distribution, which is dictated by the material characteristics and delivery of the appropriate drive mechanics using appropriately fashioned pressure and/or flow dynamic profiles. These drive dynamics and material characteristics of the diaphragm and housing of the device are also critical in achieving the best functional result, with the least cardiac trauma.

The appropriate dynamic fit of the DMVA device and its interaction with the heart throughout the actuating cycle is critical, and mandates that RV/LV dynamics are monitored. In particular, fit of the device in the diastolic mode must allow for adequate expansion of both the LV and RV chambers, with particular attention to the RV due to its lower-pressure, compliant properties. Inadequate size and/or diastolic assist will predominantly compromise RV filling, resulting in diminished RV output, and in turn, reductions in overall cardiac output. In contrast, systolic actuation places emphasis on adequate degrees of LV compression. Adequate LV chamber compression requires attention to regulation of variables including maximum systolic drive volume delivery, maximum systolic pressure, and systolic duration.

More simply stated, adequate LV compression is that degree of compression that results in LV stroke volumes approximately equal to optimal RV stroke volumes. The inter-relationship of these chambers dictates that both RV and LV chambers need to be monitored. Appropriate RV and LV actuation by the DMVA system requires active, real-time measurement of both operational parameters and hemodynamic responses, which are utilized in the DMVA adaptive control algorithms to achieve optimal pump function and other more sophisticated operations such as device weaning and analysis of myocardial recovery.

Functional interactions between the right ventricle and left ventricle under mechanical systolic and diastolic actuation are relatively complex and difficult to describe and/or characterize. These are dynamic interactions that are not necessarily predictable based on pre-measured variables, but rather depend on a broad number of physiologic variables. These interactions are not independent; thus the behavior of one chamber has an impact on the other. Continuous monitoring of these two chambers allows the drive control to utilize an adaptive algorithm to constantly alter DMVA control parameters to achieve optimal cardiac actuation and hemodynamic output. Examples of this include, but are not limited to adjustment of pressure/volume relationships to maintain balanced RV/LV output, control of pressure rise times to avoid herniation of the right ventricle, and reduction of negative drive pressure during diastole based on loss of contact between the DMVA liner and the heart wall.

The variability of a broad range of physiologic states across the patient population will dictate that these and other parameters will require responses that may be somewhat unique to each patient. Thus parametric control that benefits from broad demographic information, from physician input, and from real-time patient response data will result in the best outcome for the individual patient.

Therefore a heart-assist device is needed that does not cause damage to the heart as a result of its mechanical action on the heart. There also exists a need for a sensing and control means to ensure that such a device (1) is properly positioned and/or installed on the heart, (2) adequately seals against the heart, (3) achieves the desired systolic and diastolic action at installation and over the implanted life of such device, (4) operates within desired parameters to achieve optimal cardiovascular support, and (5) detects changes, such as impending device failure, in time to take corrective action.

There is also a need for a process to accomplish the above tasks very quickly, in order to avoid brain death and other organ damage. The inherent ability of the DMVA Cup of the present invention to be installed in a very short period of time with no surgical connection to the cardiovascular system of the patient needed enables the Cup of the present invention to save patients who require acute resuscitation, as well as to minimize the number of failed resuscitations due to improper installation or drive mechanics.

There is also a need for a device that does not contact the blood so that anticoagulation countermeasures are not needed, and so that the potential for infection within the blood is reduced.

It is therefore an object of this invention to provide a Direct Mechanical Ventricular Assist device that does not do damage to the heart as a result of its mechanical action on the heart.

It is a further object of this invention to provide a Direct Mechanical Ventricular Assist device that is technically straightforward to properly install on the heart.

It is an additional object of this invention to provide a Direct Mechanical Ventricular Assist device that may be installed on the heart and rendered functional by a procedure that is accomplished in a few minutes.

It is another object of this invention to provide a Direct Mechanical Ventricular Assist device that adequately seals against the heart, thereby enabling more precise operation of the device.

It is an additional object of this invention to provide a Direct Mechanical Ventricular Assist device that drives the systolic and diastolic action of the heart within precisely defined and controlled parameters.

It is a further object of this invention to provide a Direct Mechanical Ventricular Assist device that provides a healing environment within the body of the patient, including the heart itself.

It is another object of this invention to provide a Direct Mechanical Ventricular Assist device that provides measurements of the systolic and diastolic action of the heart to which it is fitted.

It is a further object of this invention to provide a Direct Mechanical Ventricular Assist device that provides an image of the functioning heart to which it is fitted.

It is a further object of this invention to provide a Direct Mechanical Ventricular Assist device that contains sensors and provides sensory feedback relative to the functioning heart to which it is fitted.

It is another object of this invention to provide a Direct Mechanical Ventricular Assist device that can provide electrical signals to the heart to pace the systolic and diastolic functions thereof.

It is an object of this invention to provide a Direct Mechanical Ventricular Assist device that has no direct contact with circulating blood, thereby reducing the risk for thrombogenic and bleeding complications, decreasing the potential for infection of the blood, and eliminating the need for anticoagulation that has many serious complications, especially in patients with serious cardiovascular disease and recent surgery.

It is another object of this invention to provide electrophysiological support, such as pacing and synchronized defibrillation, that can be integrated with mechanical systolic and diastolic actuation.

It is another object of the present invention to provide a DMVA device that can augment cardiac function without any surgical insult to the heart and/or great vessels.

It is another object of the present invention to provide a DMVA device that can put the heart to rest so that it can heal itself from an acute insult while having an improved flow of oxygenated blood.

It is a further object of the present invention to provide a DMVA device having a detachable liner, which can thus enable the DMVA device to be removed from the patient with no trauma to the heart of the patient.

It is a further object of the present invention to provide a DMVA device having a therapeutic liner or seal, thereby enabling the direct administration of therapeutic agents to the heart of the patient.

It is a further object of the present invention to provide a DMVA device that allows dynamic monitoring of the operation thereof, and the resultant right ventricle and left ventricle actuation, to permit optimization of pump function of the heart.

It is a further object of the present invention to provide a DMVA device comprising a volumetrically regulated fluid drive utilizing drive flow/volume sensors integrated with sensing and analysis of DMVA device/biventricular interactions, thereby enabling optimization of resulting biventricular actuation.

It is a further object of the present invention to provide a DMVA device comprising a pressure regulated drive that regulates DMVA drive mechanics independent of volume, utilizing analysis of drive pressure dynamics integrated with analysis of volume changes with the cup and within the right and left ventricles.

SUMMARY OF THE INVENTION

In accordance with the present invention, there is provided a process for assisting the function of a heart disposed within a body and comprising an outer wall, said process comprising the steps of measuring at least one parameter that is indicative of said function of said heart, applying a compressive force to a portion of said outer wall of said heart, and applying an expansive force to said portion of said outer wall of said heart.

In accordance with the present invention, there is further provided an apparatus for assisting the function of a heart disposed within a body and comprising an outer wall, said apparatus comprising a cup-shaped shell having an exterior wall, an interior wall, an apex, and an upper edge; a liner having an outer surface and an inner surface, an upper edge joined to said interior wall of said cup-shaped shell, and a lower edge joined of said interior wall of said cup-shaped shell, thereby forming a cavity between said outer surface thereof and said interior wall of said shell; and a drive fluid cyclically interposed within said cavity, said drive fluid applying a uniform force on a portion of said outer wall of said heart.

In accordance with the present invention, there is further provided an apparatus for assisting the function of a heart disposed within a body, and comprising an outer wall, said apparatus comprising a cup-shaped shell having an exterior surface and an interior surface; a liner having an outer surface, an upper edge joined to said interior surface of said cup-shaped shell, and a lower edge joined of said interior surface of said cup-shaped shell, thereby forming a cavity between said outer surface thereof and said interior surface of said shell; a drive fluid cyclically interposed within said cavity; and at least one sensor measuring at least one parameter.

In accordance with the present invention, there is further provided a process for assisting the function of a heart disposed within a living body of a patient, and comprising an outer wall, said process utilizing a controller and comprising the steps of importing at least one value of at least one parameter relating to said function of said heart into said controller; using an algorithm to formulate at least one command instruction, based upon said at least one value of said one parameter; and exporting said at least one command instruction from said controller.

In accordance with the present invention, there is further provided a therapeutic apparatus for delivering at least one therapeutic agent directly and preferentially to a desired tissue to be treated, comprising at least one membrane comprised of means to deliver said agent to said desired tissue, said membrane being in contact with at least a part of said desired tissue to be treated; and at least one shell surrounding said membrane, said shell isolating said membrane from tissues other than said desired tissue to be treated.

In accordance with the present invention, there is further provided an apparatus for assisting the pumping of circulating blood by a heart disposed within a body, and comprising an outer wall, said apparatus comprising means for applying a uniform force to a portion of said outer wall of said heart by a membrane; means to drive said membrane by cyclic application of a drive fluid thereto; and means for cyclic pumping of said drive fluid implanted within said body, wherein said circulating blood is isolated from contact with said apparatus.

In accordance with the present invention, there is further provided an apparatus for assisting the function of a heart disposed within a body, and comprising an outer wall, said apparatus comprising a cup-shaped shell having an exterior wall, an interior wall, and an upper edge; a liner having an outer surface, an upper edge joined to said interior wall of said cup-shaped shell, and a lower edge joined of said interior wall of said cup-shaped shell, thereby forming a cavity between said outer surface thereof and said interior wall of said shell; a drive fluid cyclically interposed within said cavity; and a seal comprising a base joined to said upper edge of said cup-shaped shell, a tip, and means for deploying said tip of said seal contiguously with said outer wall of said heart.

In accordance with the present invention, there is further provided an apparatus for assisting the function of a heart disposed within a body, and comprising an outer wall, said apparatus comprising a cup-shaped shell having an exterior wall, an interior wall, and an upper edge; and a liner having an outer surface and an inner surface, an upper edge joined to said interior wall of said cup-shaped shell, and a lower edge joined of said interior wall of said cup-shaped shell, thereby forming a cavity between said outer surface thereof and said interior wall of said shell, wherein said liner is detachable from said cup-shaped shell.

In accordance with the present invention, there is further provided an apparatus for assisting the function of a heart disposed within a body, and comprising an outer wall, said apparatus comprising a cup-shaped shell having an exterior wall, an interior wall, and an upper edge; and a liner having an outer surface and an inner surface, an upper edge joined to said interior wall of said cup-shaped shell, and a lower edge joined of said interior wall of said cup-shaped shell, thereby forming a cavity between said outer surface thereof and said interior wall of said shell, wherein said liner comprises a first therapeutic agent.

The DMVA device of the present invention described above is advantageous because compared to other prior art devices, it precisely drives the mechanical actuation of the ventricular chambers of the heart without damaging the tissue thereof, or the circulating blood; it may be installed by a simple procedure that can be quickly performed; it provides functional performance and image data of the heart; and it can provide electrophysiological monitoring and control of the heart, including pacing and cardioversion-defibrillation electrical signals to help regulate and/or synchronize device operation with the native electrical rhythm and/or contractions thereof. As a result of the invention, a greater variety of patients with cardiac disease can be provided with critical life-supporting care, under a greater variety of circumstances, including but not limited to, resuscitation, bridging to other therapies, and extended or even permanent support. Finally the device can support the heart through a period of acute injury and allow healing that results, in some conditions, to full recovery of unsupported heart function, which has not been achieved by any other device.

BRIEF DESCRIPTION OF THE DRAWINGS

The invention will be described by reference to the following drawings, in which like numerals refer to like elements, and in which:

FIG. 23A is a cross-sectional view of another embodiment of the DMVA apparatus, further comprising means for disengagement of the seal thereof that is attached to the heart;

FIGS. 23B and 23C are detailed cross-sectional views of embodiments of detachable seals of the DMVA apparatus of FIG. 23A;

Figure 1A:
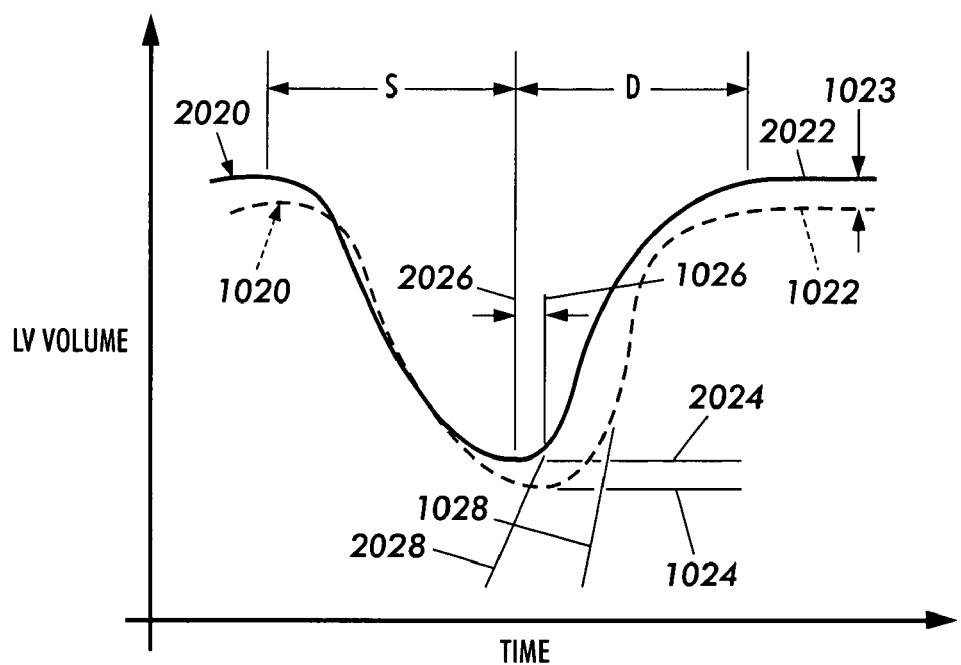
FIGS. 1A-1H are graphical representations of time dependent pressure and volume relationships of blood displaced by the left and right ventricles of a healthy human heart, of an unhealthy human heart, and of a DMVA-assisted heart during systole and diastole.

The present invention will be described in connection with a preferred embodiment, however, it will be understood that there is no intent to limit the invention to the embodiment described. On the contrary, the intent is to cover all alternatives, modifications, and equivalents as may be included within the spirit and scope of the invention as defined by the appended claims.

DESCRIPTION OF THE PREFERRED EMBODIMENTS

For a general understanding of the present invention, reference is made to the drawings. In the drawings, like reference numerals have been used throughout to designate identical elements.

In describing the present invention, a variety of terms are used in the description. Standard terminology is widely used in cardiac art. For example, one may refer to Bronzino, J. D., *The Biomedical Engineering Handbook*, Second Edition, Volume I, CRC Press, 2000, pp. 3-14 and 418-458; or *Essential Cardiology*, Clive Rosendorf M. D., ed., W.B. Saunders Co., 2001, pp. 23-699, the disclosures of which are incorporated herein by reference.

As used herein, the term Cup is meant to indicate the Direct Mechanical Ventricular Assist device of the present invention, such device comprising a cup-shaped outer shell. The terms Cup, DMVA Cup, DMVA device, and DMVA apparatus are used interchangeably in this specification and are intended to denote the overall Direct Mechanical Ventricular Assist device of the present invention in its various embodiments, unless specifically noted otherwise.

As used herein, the abbreviation LV is meant to denote the term "left ventricle", or "left ventricular" and the term RV is meant to denote the term "right ventricle, or "right ventricular", as appropriate for the particular context. "Right" and "left" as used with respect to the ventricles of the heart are taken with respect to the right and left of the patient's body, and according to standard medical practice, wherein the left ventricle discharges blood through the aortic valve into the aorta, and the right ventricle discharges blood through the pulmonic valve into the pulmonary artery. However, the Figures of the instant application, which depict the present invention and the heart contained therein are taken as viewed facing the patient's body. Accordingly, in such Figures, the left ventricle depicted in any such Figure is to the right, and vice-versa just as is done in convention when viewing radiographs and figures of related organs in the medical field. For the sake of clarity in such Figures, the left and right ventricles are labeled "LV" and "RV", respectively.

As used herein, the terms "normal heart", and "healthy heart" are used interchangeably, and are meant to depict a nominal, unafflicted human heart, not in need of DMVA assistance or other medical care.

As used herein, the term cardiac function is meant to indicate a function of the heart, such as the pumping of blood in systemic and pulmonary circulation; as well as other functions such as healing and regeneration of the heart following a traumatic event such as e.g., myocardial infarction. Parameters indicative of such functions are physical parameters, including but not limited to blood pressure, blood flow rate, blood volume, and the like; and chemical and biological parameters such as concentrations of oxygen, carbon dioxide, lactate, etc.

As used herein, the term cardiac state is meant to include parameters relating to the functioning of the heart, as well as any other parameters including but not limited to dimensions, shape, appearance, position, etc.

Critically important to the effective operation of DMVA is the continuous monitoring of changes in both right and left ventricular geometry (e.g. RV and LV end systolic and end diastolic volumes and dimensional characteristics); 2) Ventricular dynamics (e.g. dynamic changes in chamber size, flow velocities, calculated pressure gradients and wall motion alterations throughout the DMVA cycle); 3) ventricular interactions (the dependent effects that items 1 and 2 have on one another; 4) device/cardiac interactions (e.g. the relationship between the device's actuating diaphragm and the epicardial surface throughout the actuating cycle, and e.g. the effects on conformational changes in ventricular wall contour, RV herniation).

Therefore, in one embodiment of the present invention depicted in FIGS. 6A-7 and described subsequently in this specification, at least one ultrasonic probe is integrated within the DMVA heart cup and utilized to continuously monitor the right and left ventricular chambers and the related device-epicardial interactions that dictate these conformational changes, dynamics, volumetric changes, flow velocities of the RV and LV throughout DMVA actuating cycle. Such visual and sensory analysis of right and left ventricular compression allows control parameters to be adjusted using control algorithms in a continuous manner to achieve optimal profile to achieve maximal right and left ventricular support. This monitoring is critical for a number of reasons relating to the unique challenges of supporting the heart using DMVA.

There are a number of control algorithms that the DMVA drive control will implement in achieving optimal cardiac actuation. For example, the ongoing changes in pulmonary and systemic vascular resistance and flow velocities occur during DMVA support are, in part, dictated by the right and left ventricles' response to external actuating forces. The force delivery from the drive can be adjusted in response to these measured variables to both achieve more favorable hemodynamics, and ensure force delivery is adequate to overcome the inherent resistance characteristics of the pulmonary and systemic vascular beds and valvular structures. The systolic and diastolic actuating forces need to be adjusted in order to achieve an optimal biventricular effect. These forces are adjusted (change in pressure/time and/or change in volume/time) to effect incremental parts of both the systolic and diastolic actuating phases. Some generic examples of such drive dynamic optimization are explained in the following paragraphs.

The early part of systolic actuation primarily focuses on right ventricular dynamics. Visualization of the right ventricular chamber implies that early systolic compressive forces are relatively gentle and allow maximal compression of the right ventricle. Compression of the right ventricle must focus on avoiding and/or reducing the degree of right ventricular herniation that is the result of abrupt early systolic compression. Such RV herniation seen at the base (upper edge) of the device essentially allows blood to accumulate in that portion of the right ventricular free wall that is bulging outside of the device. Such herniation of blood is associated with equal reductions in pulmonary blood flow and overall reduced cardiac output as these reductions in flow are mirrored by reduced left ventricular filling.

The later half of the systolic actuation cycle focuses on maximal left ventricular compression, while avoiding excessive left ventricular compression. Some key characteristics of left ventricular compression include achieving that degree of left ventricular compression, which results in the greatest ventricular ejection without allowing endocardial (inner) surfaces of the heart to touch one another. If the LV is not adequately compressed, blood will accumulate within the lungs and lead to pulmonary edema.

Both the absolute degree of systolic compressive force and the timing of systolic compression are altered in an effort to maximize left ventricular emptying characteristics. By following these principles, left ventricular forward flow is maximized (as evidenced by the greatest reduction in left ventricular volume during compression) while trauma associated with contact of the inner ventricular chambers is avoided. In other words, with optimal LV compression (systolic actuation) there is always a fluid medium between the inner surfaces of the heart. Excessive forces can lead to excessive displacement of left ventricular blood allowing the inner surfaces to touch one another and traumatize one another. Likewise, excessive forces during early compression result in herniation and friction between the right ventricular free wall and septum within the right ventricular chamber.

Similarly, right and left ventricular dynamics are monitored to insure optimal diastolic actuation. A fundamental principle of optimal DMVA assistance is accomplishing right and left ventricular diastolic actuation, while achieving maximal diastolic volumes. This is achieved by increasing the negative dP/dt (change in pressure/change in time) and/or dV/dt (change in volume/change in time) to achieve an optimal diastolic actuation that augments the rate of diastolic filling and overcomes the inherent otherwise negative (constrictive) effects of DCC, or any compression methods. Such diastolic actuation is adjusted to that point where maximal dP/dt is achieved without allowing separation between the actuating diaphragm and epicardial surface of the heart.

Any separation of the actuating diaphragm from the epicardial surface of the heart indicates that the negative applied forces during that phase of the actuating cycle are too abrupt and need to be delivered in a more gradual fashion. Separation of the liner from the heart during diastolic actuation essentially removes the actuating force from the epicardium resulting in the heart growing passively and/or going in a non-assisted manner. The details of embodiments of the DMVA apparatus of the present invention comprising means for sensing of left and right ventricular chambers and the related changes/drive control algorithms in drive mechanics will be detailed to a greater extent subsequently in this specification.

The preferred material characteristics will also be further defined subsequently in this specification. However, general characteristics are provided in the following paragraphs. The optimal characteristics for the liner may best be generally described as that which has near "isotropic" behavior. In other words, the liner material acts on the ventricular muscle in a manner that allows the ventricular muscle to change its conformational shape in a manner that best follows the heart's natural tendencies. In this manner, the material does not "deform" the heart outside of a range dictated by the muscle's natural tendency to change conformation when such external forces are applied.

However, this is not to say that the heart is compressed in a manner that replicates the normal beating state. On the contrary, the systolic and diastolic conformational changes that result from DMVA actuation clearly differ to some degree from what one expects during contraction and dilatation of an otherwise normal functioning heart. However, it is important that the liner and Cup shell materials allow the myocardium to undergo such mechanically induced conformational changes in a manner that permits the muscle to deform based on its physical characteristics and tendencies. Less ideal materials lead to more potential trauma and have their own tendency to fold and deform in a manner that alters the heart's "natural" tendency and these types of material characteristics lead to myocardial injury.

The compliant nature of the device housing permits it to constantly change shape in response both to the actuating forces applied to the heart and changes in the heart's size and/or shape. This characteristic contributes to decreased ventricular trauma, ease of application as the housing can be deformed to fit through small incisions, and important dynamic conformational changes that constantly respond to the heart's changing shape. The housing of the device is constructed of a flexible material that has appropriate compliance and elastic properties that allow it to absorb the systolic and diastolic actuating forces in a manner that somewhat buffers the effect of the liner on the heart. (For example, abrupt reductions in drive fluid pressure are dampened such that cavitation and disengagement with the heart are avoided, and during systole, abrupt increases in drive fluid pressure are dampened such that bruising of the heart are avoided.) The unique qualities of this housing lessen the risk for inadvertent excessive forces to be applied to the heart at any time of the cycle. The shell conforms to the dynamic changes in the right and left ventricles throughout compression and relaxation cycles as well as overall, ongoing changes related to variances in heart size over time which occur as a consequence of continued mechanical actuation and related "remodeling" effects on the heart.

Sensor and Control Related Aspects of the Invention

The present invention also comprises a method for utilizing sensors and sensor data to (1) help install DMVA devices and to (2) assess cardiac performance under the influence of DMVA. The sensor data so obtained helps real-time verification that the device has been properly installed, and is operating properly and achieving desired cardiac performance. The sensory data also allows the operating parameters of the Cup to be adjusted in real time to respond to changing physiology of the patient's cardiovascular system. There are at least ten sensor and control related aspects to the present invention, all of which are described herein:

1. A method for using sensor data in conjunction with cardiac assist devices (not limited only to DMVA or DMVA Cups) to perform such functions as guiding device installation, and optimization of device performance and guiding the placement and operation of other cardiac devices and systems.
2. Specific cardiac performance measures appropriate for sensing (sensor data).
3. Specific device feedback control parameters.
4. Specific feedback control methods and algorithms.
5. Specific sensor types and sensor locations.
6. The use of contrast agents to enhance sensor sensitivity and specificity.

7. Sensor interfaces.
8. User interfaces.
9. Sensor data recording and analysis capabilities.
10. Specific device performance measures appropriate for sensing (sensor data).

These aspects of the present invention will be described briefly here in the specification, and in more detail subsequently, with reference to the drawings.

Invention aspect 1: A method for using sensor data in conjunction with cardiac assist devices is briefly described as follows, and subsequently described in detail with reference to FIG. 5A. This aspect is directed to a general method for using sensor data to guide installation of DMVA devices, and to assess cardiac performance under the influence of DMVA. The method includes the following steps, which are offered here as illustrative and not limiting:

Step 1: Establish patient baseline performance.
Step 2: Establish required performance improvement objectives.
Step 3: Pre-check DMVA device to verify critical aspects of performance (Optional)
Step 4: Surgically install DMVA device in the patient.
Step 5: Actuate DMVA device using predetermined settings from steps 1 and 2.
Step 6: Operate the DMVA device and collect sensor data. See also Invention Aspects #5 (Specific sensor types and sensor locations)
Step 7: Analyze sensor data. See also Invention Aspects #2 (Sensor Data), #9 (Sensor data recording and analysis capabilities), and #10 (Specific device performance measures appropriate for sensing) for specific data and data analysis methods.
Step 8: Adjust DMVA control parameters.
Step 9: Repeat steps 6-7 until desired cardiac performance is achieved.
Step 10: Program data recorder-transmitter (Optional)
Step 11: Prepare patient for recovery.
Step 12: Monitor patient's cardiac performance Invention Aspect 2: Sensor data. The sensor data collected in Step 6 of the preceding method of Invention Aspect 1 preferably includes without limitation the types of data listed below. The specific sensor types and sensor locations (also see Invention Aspect 5) will subsequently be described in more detail in conjunction with FIGS. 6A-14.

1. Anatomical data, such as—e.g., motion of the heart wall sensed by implanted accelerometers; fit of the Cup to the heart sensed by an implanted ultrasound transducer/sensor device; and/or cardiac ventricular blood volume displacement inferred by a sensor that measures the DMVA device working fluid volume. Additionally, the DMVA device includes sensor data such as e.g., data from an ultrasonic transducer/sensor that can be analyzed and compiled to produce images of the heart and Cup. Such image data is particularly useful, as it provides the physician with the information required to verify proper fit of the Cup to the heart, and to verify that proper systolic and diastolic actuation are being achieved, including but not limited to dynamic changes in ventricular wall and septal geometry, RV/LV relationships, and epicardial-liner relationships.
2. Hemodynamic data, such as the following: a) blood flow rate, inferred by calculation from the DMVA device working fluid flow rates; b) right ventricle—left ventricle interactions; c) aortic blood pressure, such as by normalization of e.g., traditionally obtained blood pressure data and/or calculations based on data from pressure sensors located in the DMVA device working fluid at a point near the contact with the myocardium, and/or pressure/volume data from the working fluid, and/or acoustic data from the flow at the aortic valve over time; d) pulmonic blood pressure, such as by normalization of e.g., traditionally obtained blood pressure data and/or calculations based on data from pressure sensors located in the DMVA device working fluid at a point near the contact with the myocardium, and/or pressure/volume data from the working fluid, and/or acoustic data from the flow at the pulmonic valve over time; e) RV and LV stroke volumes; f) flow velocities across all four cardiac valves, based upon measured or calculated pressure gradients.
3. Functional data, such as cardiac ejection fraction, obtained from calculations based upon the above anatomical and/or hemodynamic data and/or calculations based on direct ultrasound images from the Cup's entrained ultrasound transducer/sensor device; and RV-LV fit and relationships.
4. Electrophysiological data, such as electrical voltages and changes in voltages over time obtained by electrical sensors located on the interior surfaces of the Cup and in contact with the myocardium; voltage differences, obtained by comparisons between such sensors located at different points on the myocardium; voltage differences over time, obtained from such multiple sensors; electrical currents and current changes over time obtained from such electrical sensors. It is to be understood that in some embodiments, the DMVA Cup will electrically isolate the heart to some extent, making standard electrocardiographic monitoring more difficult. However, this isolation also enables electrophysiological monitoring and stimulation devices located within the Cup to operate more effectively; since they are less susceptible to electrical noise, particularly from external sources. Thus, the DMVA Cup is able to focus the delivery of electrical stimulation energies to tissues enclosed therein. To use such a property advantageously, the DMVA Cup further comprises integrated electrical measurement capabilities (such as e.g., electrocardiograms) and integrated electrical stimulation capabilities (such as e.g., pacing and cardioversion-defibrillation), wherein such measurement capabilities and such stimulation capabilities are further integrated into a feedback control loop by which the natural contractions of the heart within the Cup are fully controlled, as well as being assisted. In one further embodiment, the practice of apical pacing is used, wherein electrical stimulation signals are applied to the heart at the apex of the DMVA Cup. In such an embodiment, the apical pacemaker is grounded to the patient so that a current applied thereto does not produce a potential difference, thereby enhancing safety for the patient.
5. Biochemical/biologic data; such as the following examples: a) blood oxygenation from an optical oxygen sensor in contact with the myocardium; b) blood glucose from optical glucose sensors in contact with the myocardium; c) osmolality from an optical osmolality sensor; d) lactate or lactic acid or other fatigue marker from a fluorescence probe sensor or near infrared sensor; e) drug uptake, from optical drug sensors in contact with tissue; and f) molecular markers of cell signaling, cellular stress and ventricular remodeling, including but not limited to cytokines, parahormones, nitric oxide, free-oxygen radicals, heat-shock proteins, metalloproteinases and related cellular substrates.

6. Acoustical data, such as the naturally occurring sounds of the heart and lungs. More specifically such data may include the following: a) data from microphones in contact with the heart that detect naturally occurring sounds, such as those sounds generated by muscle contraction, operation of the valves of the heart, heart murmur/arrhythmia, laminar or turbulent blood flow within the ventricles or through the heart valves; and the $S_1, S_2, S_3,$ and $S_4$ sounds; b) data from microphones in contact with the lung(s) that detect breath sounds collected for purposes such as monitoring of respiratory rate; c) data from microphones in contact with the working fluid powering the Cup that detect sound generated by leaks and partial blockages or kinking; d) data from microphones that detect the response of tissue to sonic energy introduced into such tissue, such as ultrasonic energy or Doppler frequency sonic energy detected at microphones in all of such locations; e) data from microphones that detect sound indicators of device—cardiac interactions including frictional/abrasive actions, liner separation from the surface of the heart, and liner-housing contact/separation.

7. Tissue characteristics data, such as the following: a) stiffness, derived from data from strain gauges in contact with various points on the myocardial surface; b) the extent of vascularization, derived from data from optical sensors of capillary blood flow in contact with the myocardium; and c) drug or other therapeutic agent uptake, derived from data from sensors in the device.

8. Temperature data, such as such as the following: a) temperature of the myocardium, derived from data from temperature sensors located in contact with the myocardium; b) temperature of the drive fluid, derived from data from temperature sensors located in contact with the drive fluid; c) temperature from the lungs derived from data from temperature sensors located in the portion of the Cup that is in contact with the lung; and e) core body temperature measurement derived from data from temperature sensors located on the exterior of the shell wall of the DMVA Cup, or on the fluid drive or vacuum tubing thereof. Such core body temperature data are particularly useful in the early detection of infection, and in instances where the DMVA drive fluid is cooled in order to provide cooling of the myocardium, the brain, and/or the core body temperature.

9. Optical data, such as from optical sensors that detect a) motion, spectral absorption variation, and/or refractive index variation produced by the simultaneous introduction of other forms of energy, such as mechanical energy, e.g., vibration and/or ultrasound; b) the response of tissue to optical interrogation with different wavelengths and/or combinations of wavelengths of light.

10. Mechanical data, such as the mechanical strain of critical Cup features, e.g., liner and/or Cup shell flexures.

Invention Aspect 3: DMVA feedback control parameters. The above sensor data can be used to control DMVA operation and cardiac performance. In the present invention these parameters preferably include without limitation the following device control parameters, which will subsequently be described in more detail with reference to FIGS. 15, 26, and 27:

1. The total volume of fluid delivered to or removed from the Cup liners.
2. Differential volumes of fluid delivered to or removed from the Cup liners (e.g. RV versus LV).
3. The rate of fluid flow to or from the Cup liners.
4. The pressure with which the fluid is delivered to or removed from the Cup liners.
5. The timing of fluid delivery to or removal from the Cup, relative to such factors as cardiac electrophysiological rhythm, respiratory cycle, and synchronization between RV and LV function; and the relationship between such timing and rates of change of fluid pressure and fluid volume to/from the Cup.
6. The frequency of fluid delivery to or removal from the Cup, relative to such factors as metabolic demand, respiratory rate, blood oxygenation, and heart rate.
7. The temperature of the fluid delivery to or removal from the Cup, relative to such factors as myocardial temperature, body temperature, lung temperature, and/or clinical data from the patient.
8. The electrical pacing of the heart, such as by the physical action of the device on the heart and/or a pacemaker incorporated into the Cup located at the apex of the heart, or elsewhere; all of which can be alternated to best suit the condition of the heart.
9. The actuation of other cardiac assist devices, such an intra-aortic balloon assist device.
10. The actuation of respiratory assist devices, such as a respirator.
11. The actuation of alarm circuits, such as to alert the clinical and/or technical staffs of device malfunction or unacceptable patient responses.
12. The conformational changes of the RV free wall, LV free wall and septum during systolic and diastolic actuation.
13. The liner-cardiac interactions including linear slippage and separation.
14. The geometric-volumetric and relevant spatial changes in the RV and LV and their dependent actions on one-another.
15. Volume/geometric changes between the liner and shell.

Invention Aspect 4: DMVA feedback control methods and algorithms. The above sensor data of invention aspect #2 can be analyzed to control DMVA operation and cardiac performance in multiple ways including without limitation the following device control methods and algorithms, some of which will subsequently be described in more detail with reference to FIGS. 15, 26, and 27.

1. Procedures to verify proper DMVA device installation. This method and algorithm includes without limitation the ability to a) verify that the Cup is properly seated on and oriented against the heart; b) verify adequate sealing of the Cup against the heart; c) verify the absence of excessive volumes of fluid between the Cup liner and myocardium; d) verify proper systolic and diastolic motion of the heart, including right and left ventricles and RV-LV interactions; e) verify absence of leaks in the device; f) verify absence of leaks in the lungs; g) verify normal outflow characteristics of the heart; and/or h) maintain constant thorax volume to help reduce psychological issues.
2. Method and algorithm to achieve effective RV and LV actuation, including RV and LV geometric/volume changes. This method and algorithm includes without limitation the ability to finely control ventricular pressure-volume relationships and conformational changes of the LV and RV free wall, septum and ventricular cavities over the full range of cardiac output. Detailed descriptions of embodiments of this method and algorithm are provided subsequently in this specification, with reference in particular to FIGS. 1A-1M, 2A-2I, and 5B.

3. Method and algorithm to minimize trauma to myocardial tissues. This method and algorithm includes without limitation the abilities to a) achieve uniform or near uniform contact force and/or pressure across the liner-myocardium interface to minimize or eliminate deep bruising, such as that resulting from shear between tissue planes that is generated by variations in surface pressures on said tissue planes; b) minimize shear stress at the liner-myocardium interface and at the seal-myocardium interface to avoid abrasion of myocardial tissues; and c) minimize the LV endocardial-endocardial contact/trauma as well as reduce the RV-septal herniations and associated abrasions of these two endocardial surfaces.

4. Method and algorithm to achieve effective compression of the heart during systole, and effective expansion of the heart during diastole. This method and algorithm includes without limitation the ability to a) achieve optimal RV-LV filling, emptying, conformational/geometric changes and related interactions; and b) control the optimum range of Cup liner position-time profiles during systole and diastole, including the use of Cup walls with controlled flexibility to provide "elastic recoil" helpful to achieve effective diastolic action. Detailed descriptions of embodiments of this method and algorithm are provided subsequently in this specification, with reference in particular to FIGS. 1A-1M, and 2A-2I.

5. Methods and algorithms to help promote natural healing of the heart, including the following, for which detailed descriptions are provided subsequently in this specification, with reference in particular to FIGS. 1A-1M, 2A-2F, 26, and 27:

a) Method of complimentary support. This method controls the amount of work performed on the heart by the DMVA device based upon the amount of work that the heart is capable of performing on its own. Adjusting compression to allow cardiac conditioning using compressions for alternate cardiac cycles and using the un-compressed cycle to analyze the heart's native function and then adjusting the systolic and diastolic actions in accordance with this learned information. Such conditioning may occur for time intervals that are dictated by the heart's subsequent behavior. Evidence of reduced function may indicate the need for more support while evidence of increased native heart function may indicate recovery that would permit further reductions in support, and/or longer conditioning intervals.

The work performed by the DMVA device to achieve required cardiac output will be related to the pumping ability of the native heart without DMVA assistance. A severely damaged or totally arrested heart requires more work from the DMVA device than a heart that was capable of pumping at normal capacity. The native heart's function will be measured during non-compression/non-actuating cycles of DMVA support during either intervals of non-actuation or during 1:2 actuation. DMVA assist can then be provided in a graduated manner depending on the underlying heart's function. Drive variables such as timing of actuation and the relative forces applied throughout the DMVA cycle can be appropriately adjusted to address both overall changes in function as well as differences in RV vs. LV dysfunction and more specific aspects of diastolic vs. systolic dysfunction within the cardiac cycle.

In this manner, DMVA forces can be directed to specifically address the components of RV vs. LV and systolic vs. diastolic dysfunction. Furthermore, the device can be adjusted over time in accordance to the recovery of myocardial function, which may differ between the RV and LV and/or between systole vs. diastole. Appropriate adjustments within the DMVA actuation drive parameters will respond and optimize the pertinent needs of the heart to improve conditioning and reduce excessive actuation whenever possible. Trial conditioning algorithms will be designed in this manner.

In one embodiment of the present invention, fluid flow volume sensors, and/or fluid flow rate sensors, and/or fluid pressure sensors within the liner and/or drive assembly supply this information to the control unit, which delivers only enough fluid to the liners to make up the hemodynamic performance that the heart is incapable of supplying by itself. In this way, the DMVA device provides variable heart assistance capable of augmenting heart function as much or as little as is required to achieve normal cardiac output, thereby enabling the heart to continue to perform in an effective manner, making it possible for natural healing mechanisms to continue to operate effectively, and to prevent deconditioning of the myocardium. Brief periods of inactivation of the Cup, or even counter-pulsatile flow to recondition and/or challenge the heart, are possible. Again, use of unassisted intervals or 1-to-2 (alternate cycles), 1-to-3,1-to-4 etc., augmented assist cycles will allow periodic assessment of cardiac function which will dictate tailoring of drive parameters to allow conditioning, and determination of when DMVA assist can be reduced or possibly removed.

It is to be understood that working fluid pressure and volumetric flow rate can be measured in many ways. In yet another embodiment of the present invention, this can include without limitation the measurement of the actual physical displacement of the liners, physical displacement or movement of drive system pumps, the energy required to move drive system pumps, etc.

b) Method of synchronous support. This method synchronizes the actuation of the DMVA device to the heart's natural rhythm, thereby providing a hemodynamic output in phase with the heart's natural rhythm. Adjustments in compression can be altered in relation to the electophysiology of the heart to accomplish varied degrees of cardiac assist. Earlier application of forces will be used when the goal is to maximally reduce cardiac work and compress the heart prior to its native contraction. Alternatively, delaying actuating forces in an incremental fashion will allow the heart to take on a greater degrees of work. These principles will be applied to both optimization of general DMVA actuation and to the previously stated aims of conditioning the heart.

c) Method of asynchronous support. This method actuates the DMVA device at a frequency that is out of phase with heart rhythm. This method is preferable if the patient's own natural cardiac rhythm is defective, and is used to help the heart return to a desired cardiac rhythm. In this embodiment, the device can function as a mechanical pacemaker and "overdrive" the pacing mechanisms of the heart to achieve a more favorable electrophysiological result, which will serve to improve overall pump function and aid in recovery aspects of DMVA therapy. Accordingly, either the use of an integrated electrical pacemaker, or the principles of the mechanical stimulus of DMVA compression creating an electrical stimulus, or both, can both play a role depending on which proves to be more ideal and/or advantageous for the particular set of goals to be achieved by the DMVA Cup (e.g., improving general pump function, conditioning etc.)

d) Method of training. In a further embodiment of the present invention, Cup liner inflation/deflation is controlled to provide periodic training episodes. During this method, lactate, lactic acid, or molecular markers such as cytokines, parahormones, heat shock proteins, ANP, metalloproteinases, and other fatigue markers, or markers of muscle strain demonstrated electrophysiologically, are monitored to allow the heart to be safely challenged without inducing excessive fatigue in the heart. Alternatively or additionally, the electrogardiographic output of the patient is monitored, wherein certain EKG characteristics may be detected, such characteristics being indicative of anoxia of tissue.

e) Method of support coupled with artificial pacing of the heart. This method synchronizes the actuation of the DMVA device to the cardiac rhythm by synchronization with artificial pacing, such as with electrical pacing electrodes incorporated into the Cup, thereby providing a hemodynamic output that is in phase with the paced heart rhythm.

f) Method of optimal DMVA. This method utilizes electrical stimulation to cause the heart to contract by an optimal DMVA flow rate.

6. The use of diagnostic methods to help guide DMVA support. Reference may be had within this specification to Invention Aspects 9 (Recording and Analysis of Sensor Data), specifically Section 7 (Biochemical data), Section 8 (Temperature data), and Section 9 (Optical data) for a more detailed description of these methods and algorithms.

7. Methods to verify proper device operation and reliability. Reference may be had within this specification to Invention Aspect 10, Specific device performance measures appropriate for sensing, for a more detailed description of methods and algorithms.

8. Methods to use the DMVA device to measure function of the heart. In one embodiment, this method uses the device to measure change in pressure within the DMVA fluid drive tubing and/or liner cavity created by heart contraction to determine need for ongoing DMVA mechanical support or other therapy(s).

Invention Aspect 5: Specific sensor types and sensor locations. Specific sensor types to obtain DMVA operational data and patient data include the following, which are subsequently described in more detail in this specification with reference to FIGS. 6A-13:
1. Ultrasound sensors
2. Magnetic resonance imaging (MRI) coils
3. Strain gauges
4. Thermometers
5. Accelerometers
6. Pressure transducers
7. Microphone/Sound generator arrays
8. Optical sensor/illuminator arrays: Camera/IR Detectors/ Chemical sensors
9. Electrical signal detection
10. Electrical energy delivery electrodes Specific sensor locations to obtain DMVA operational data and patient data include the following:
1. In contact with the lung
2. In contact with the heart
3. In contact with the drive line chest entry site
4. In the Cup drive fluid
5. In the wall of the Cup
6. In the membrane of the liner
7. Attached to an externally controlled 3-D motion device free to move within the mediastinum.

Invention Aspect 6: Contrast agents to enhance sensor sensitivity and specificity. The minimal dimensions of components of the DMVA device, such as the Cup liner, make such components difficult to image with ultrasound, MRI, and X-ray imaging procedures. In further embodiments of the present invention, imaging contrast agents are incorporated into critical components of the Cup to enhance the images obtained thereof. Such imaging contrast agents may include ultrasonic contrast agents, magnetic resonance imaging contrast agents, and radiopaque contrast agents, and are subsequently described in more detail in this specification with reference to FIG. 14.

Invention Aspect 7: Sensor interfaces. The sensors integrated into the DMVA device can be linked to external data recording, data analysis, and data reporting systems in several ways, including without limitation the following means:
1. Intra-operatively (i.e. directly through surgical incisions).
2. Percutaneously (i.e. directly through minimally invasive surgical incisions such as a puncture, or directly through the skin).
3. Telemetrically (i.e. transmission to remotely located receivers located away from the patient). In this embodiment, the DMVA system contains telemetry means for transmitting physiological data to internal or external event recorders, or external receiving means. The telemetry means can include transmission of measurements directly from the sensors, or transmission to the control unit, which in turn transmits the desired information. In such an embodiment, the internal event recorder and/or transmission means may receive their power from the external device collecting the data, via such means as radio frequency, or optical transmission through tissue.

Invention Aspect #8: User interfaces. The user interfaces used with the present invention include without limitation the following means to provide information to the health care professional:
1. Visual displays for anatomical data, as well as the display of hemodynamic data, functional data, electrophysiological data, biochemical data, acoustical data, and tissue characteristics, using known methods for visually encoding these parameters.
2. Graphical displays of multivariate data such as ECG traces, electrophysiological maps, and acoustical signatures, blood pressure-time profiles, etc.
3. Quantitative feedback of scalar measures of parameters such as hemodynamic data, functional data, electrophysiological data, biochemical data, acoustical data, and tissue characteristics.
4. As above, but for tracking and rewarding training progress.

Invention Aspect #9: Sensor data recording and analysis capabilities. Specific data recording and analysis capabilities of the present invention are dependent upon the type of data being recorded and analyzed and include the following, to be described subsequently in detail in this specification with reference in particular to FIGS. 6A-15:

1. Image data pertaining to the operation of the DMVA device, and to the assisted heart contained therein. Image data includes data collected from ultrasound probes, MRI receive or transmit coils, X-ray images, computed tomography images, or images from other imaging methods. Image data can be recorded and analyzed to make anatomical assessments of the heart and DMVA device. More specifically; image data can be examined to assess the following: a) The fit of the DMVA device (e.g. Cup) to the heart; b) The motion of the heart walls and chambers under DMVA support; c) Cardiac right and left ventricular and atrial inputs (e.g. filling effectiveness); d) Cardiac ventricular and atrial outputs (e.g. cardiac ejection fraction); e) Blood flow rate and blood flow velocity (e.g. analysis of Doppler ultrasound images), all of which can be used to predict and optimize the effectiveness of DMVA device operation; f) specific RV/LV interactions, geometric changes, and/or rate of volume changes; g) functional assessment of the native heart's performance and the relative effect of the device on such pump performance; and proper operation and overall reliability of the DMVA device.
2. Accelerometer data to assess the mechanical motion of critical heart and DMVA device parameters. Analysis of accelerometers implanted into the DMVA device (e.g. liner walls) can be analyzed to assess the mechanical motion of critical heart and DMVA device parameters, including the motion of the heart walls and chambers under DMVA support, and the motion of the DMVA liners under the control of the Drive Unit, which can be used to predict and optimize the effectiveness of DMVA device operation, and to verify proper operation of the DMVA device and therefore the reliability of the device.
3. Data relating to the pressure and flow of DMVA drive fluid, which is correlated with the performance of the assisted heart contained within the DMVA device. The motion of the DMVA device working fluid translates directly to the displacement of the heart walls and chambers. Therefore DMVA device working fluid data can be analyzed to assess the mechanical motion of the heart walls under DMVA support, which in turn can be analyzed to estimate cardiac right and left ventricular and atrial inputs (e.g. filling effectiveness), estimate cardiac right and left ventricular and atrial outputs (e.g. cardiac ejection fraction), and estimate blood flow rates and velocities. The motion of DMVA working fluid data can also be used to estimate right and left ventricle blood pressure through calibration of working fluid flow rate to traditionally obtained blood pressure. The pressure of the DMVA device working fluid translates directly to the pressure placed on the heart walls and chambers. DMVA device working fluid pressure can be recorded from pressure sensors located in the DMVA device working fluid at a point near the contact with the myocardium, or from pressure-volume data recorded from within the working fluid pumping system. These data can be analyzed to estimate pulmonary and systemic blood pressure blood pressure directly, or indirectly through calibration of fluid pressure to traditionally obtained blood pressure.
4. Blood pressure data that is sensed and recorded directly through the use of traditional blood pressure measurement sensors incorporated into the DMVA device, such as in-vivo pressure sensors or external "cuff-based" sensors. These data can be recorded and analyzed to provide pulmonary and systemic blood pressure feedback to the DMVA device.
5. Acoustical data that is collected and analyzed by microphones located externally or on or within the DMVA device including sounds produced by the DMVA device and sounds produced by patient respiration, circulation, and tissue responses, such as the following: a) sounds such as that generated by blood flow through the aortic valve or pulmonic valve, which have been shown to correlate with the rate of blood flow through such valves, and which, can be analyzed to estimate the rate of blood flow through such valves achieved by the DMVA device; b) sounds and/or vibrations such as that generated by muscle contraction (such as e.g., contraction of the heart or diaphragm muscle), which can be analyzed with signal processing methods such as fast Fourier transforms or other suitable techniques to estimate the condition of the muscle and/or the presence of disease or fatigue; c) sounds such as breath sounds, which can be analyzed to determine and monitor respiratory rate; d) sounds generated by the DMVA system, including sounds generated by working fluid leaks, partial blockages or kinking, which can be analyzed to verify proper operation of the device and to predict and prevent future device failures; and e) sounds generated by tissues in response to sound energy introduced into the tissues, such as ultrasound energy or Doppler frequency sound energy, which can be analyzed to determine distance, shape, velocity, flow, particle size distribution, and the like. In particular, the well-known first, second, third, and fourth heart sounds S1, S2, S3, and S4 may be collected by such microphones or other acoustic detection means and analyzed with appropriate signal processing methods and algorithms. The use of such heart sounds in diagnosis of cardiovascular conditions is described in Chapter 7 of the text *Essential Cardiology Principles and Practice*, C. Rosendorf, 2001, the disclosure of which is incorporated herein by reference. In one embodiment, the geometry of the DMVA Cup of the present invention provides enhanced ability to measure cardiac sounds by virtue of the isolating effect of the shell and liner; the density differences between the heart and Cup shell, and Cup shell and drive fluid; and the approximately parabolic shape of the Cup shell which focuses such sounds within the shell.
6. Electrophysiological data that can be recorded by sensors located on or within the DMVA device and in contact with the heart, including the following: a) cardiac rhythm, rhythm disturbances/dysrhythmias; b) cardiac voltages; c) changes in voltages over time; d) spatial voltage differences, such as differences obtained by comparisons between said sensors located at different points on the myocardium; e) temporal voltage differences, such as differences obtained from single or multiple sensors over time; f) current within tissues; g) changes in current over time, such as obtained from single or multiple sensors over time; h) spatial current differences, such as differences obtained by comparisons between said sensors located at different points on the myocardium; i) temporal current differences, such as differences obtained from single or multiple sensors over time; and j) RV/LV electromechanical relations. Alternatively, sensors may be located external to the DMVA device, such as surface-mounted EKG sensors that are in communication with the DMVA system. The data from these sensors can be analyzed to assess the electrophysiological performance of the heart and synchronize (or de-synchronize) the operation of the DMVA device with the electrical rhythm of the heart.

7. Biochemical/metabolic data acquired, recorded and analyzed from sensors located on or within the DMVA device and in contact with the myocardium, blood, or other tissues, include the following: a) measurement of blood oxygenation, such as from an optical oxygen sensor in contact with the myocardium or blood, which is analyzed to determine the effectiveness of DMVA pulmonary support; b) measurement of blood glucose, such as from optical glucose sensors in contact with the myocardium or blood, which is analyzed to determine the effectiveness with which glucose is delivered to the myocardium; c) measurement of tissue osmolality, such as from optical osmolality sensor, which is analyzed to determine the pH of the myocardium; d) measurement of tissue lactate or lactic acid, molecular markers of the myocardium including but not limited to nitric oxide, oxygen free radicals, heat shock proteins, ANP, parahormones, metalloproteinases or other fatigue markers, which are analyzed to determine the fatigue characteristics of the myocardium; and e) measurement of drug or other therapeutic agent uptake, such as from optical drug sensors in contact with tissue, which is analyzed to determine the concentrations of drugs or other therapeutic agents in the myocardium.

8. Temperature data that can be recorded and analyzed from sensors located on or within the DMVA device pertaining to the DMVA device, the myocardium, the blood, and/or the lungs, including the following a) temperature of the myocardium obtained from temperature sensors located in contact with the myocardium, which for example can be analyzed to determine the presence of infection in myocardial tissues; b) temperature of the drive fluid obtained from temperature sensors located in contact with the drive fluid, which for example can be used to regulate and monitor the temperature of the myocardium; and c) temperature of the lungs, such as from temperature sensors located in the portion of the Cup that is in contact with a lung, which can be used for example to monitor the temperature at which respiration takes place.

9. Optical data that can be recorded and analyzed from sensors located on or within the DMVA device pertaining to the DMVA device, the myocardial tissue, and/or the blood, including the following: a) spectral absorption variation, motion, and/or refractive index variation, which can be analyzed for example to determine the extent of vascularization of myocardial tissues, drug uptake, etc; b) response of tissue to optical interrogation with different wavelengths and/or combinations of wavelengths of light, which can be analyzed for example to determine drug uptake; and c) opto-mechanical data, such as variations in motion, spectral absorption, and/or refractive index produced by the simultaneous introduction of other forms of energy, such as mechanical energy, such as vibration and/or ultrasound, which can be analyzed for example to determine tissue conditions such as e.g., muscular degeneration, including compositional changes indicated by the presence of fat and/or fibrous tissue, and by the loss of contractility, elasticity, density, range of motion, and bulk thickness.

10. Strain data obtained from strain gauges in contact with various points on the myocardial surface that can be analyzed to determine tissue physical characteristics, such as e.g., tissue "stiffness".

Invention Aspect 10: Specific device performance measures appropriate for sensing. Critical DMVA system performance parameters which are indicative of the quality of system performance and suitable for measurement include the following, to be described subsequently in detail in this specification with reference in particular to FIGS. 6A-15:

1. Differences and/or similarities in RV and LV volumes.
2. Systolic and diastolic volumes.
3. The dynamics of RV and LV compression and decompression.
4. The total volume of fluid delivered to or removed from the Cup liners.
5. Rate and dynamics of ventricular emptying and filling during systolic and diastolic actuation, respectively, for both the RV and LV; the rate and flow characteristics across the native cardiac valves; and the conformational changes in the septum and LV and RV free walls during both systolic and diastolic actuation and the relationship of LV changes on RV changes as vice-versa. Measurement of the volume of working fluid delivered to or removed from the Cup equates directly to displacement of the Cup liners, and therefore can be used to verify proper systolic and diastolic actuation of the heart. Differences between the volume of working fluid delivered to or removed from the Cup liners can also be measured. Differences in fluid delivered to and from the Cup liner would suggest a leak in the fluid delivery system and reason for immediate corrective action.
6. The rate of fluid flow to or from the Cup liners. When an incompressible drive fluid is used in the DMVA device, the rate of fluid flow into or out of the Cup liner equates directly to the rate of displacement of the Cup liners, which in turn equates directly to the rate of cardiac output and the volume of such output. Therefore, in such an embodiment, measurement of working fluid flow rate can be used to verify desired cardiac volumetric output and pressure thereof.
7. The pressure with which the fluid is delivered to or removed from the Cup liners. The pressure at which working fluid is delivered to or removed from the Cup liner correlates with the rate of displacement of the Cup liners which in turn correlates directly with systolic or diastolic blood pressure. Therefore, measurement of working fluid pressure can be used to verify and/or infer cardiac blood pressure. Also; a reduction in working fluid pressure at a given working fluid flow rate could suggest a leak in the fluid delivery system and reason for immediate corrective action. Also; an increase in working fluid pressure at a given working fluid flow rate could suggest a potential obstruction in the fluid delivery system and reason for immediate corrective action, or could alternatively indicate an increased resistance to pulmonary or aortic blood flow in the patient, which would also indicate immediate medical action.
8. The energy consumption of the DMVA drive system. Increases in drive system energy consumption to maintain a constant volume and/or rate of working fluid output could suggest impending failure of drive unit and/or Cup components and reason for immediate corrective action. A preferred way of analyzing energy consumption is to compare the ratio of the product of the drive unit output pressure and volume rate of working fluid flow to the drive unit input energy, which in one embodiment can be in the form of the product of drive unit input voltage and current. A decrease in this value suggests a decrease in system operating efficiency and reason for immediate corrective action. Alternately an increase in the above ratio indicates an improvement in cardiac performance, since less energy is required to establish a given level of cardiac output.

9. Working DMVA fluid pressure-volume relationship as a function of time. Since liner displacement equates directly to cardiac performance, and changes in the actuating volumes directly relate to displacement of the RV and LV and therefore cardiac output, measurement of working fluid pressure-volume-time relationships enables prediction of pump function, and working fluid—RV/LV interactions.

10. Acoustic data generated by the DMVA system. Acoustical data collected from microphones located on or within the DMVA device can be used to identify early-on impending failures of Cup and/or drive unit subsystems and components.

11. The timing of working fluid flow. Measuring the timing of fluid delivery to or removal from the Cup, relative to cardiac electrophysiological rhythm, enables verification that the DMVA support is in proper synchronization with heart electrical or mechanical activity or other patient support devices such as a respirator.

12. The frequency of working fluid flow relative to cardiac rhythm. Measuring the frequency of fluid delivery to or removal from the Cup, relative to such factors as respiratory rate, or blood oxygenation, enables verification that the DMVA support is keeping up with metabolic demand.

13. The temperature of the fluid delivered to and removed from the Cup. Measuring working fluid temperature ensures that the Cup is maintaining proper myocardial temperature. It is to be understood that such temperature may be more than or less than normal temperatures, and that the temperature of the drive fluid may be controlled in such a manner as to control the temperature of the patient.

14. The mechanical strain of critical Cup features. Measurement of the strain of critical features of the Cup, such as liner flexure points, can be used to predict future device failures well in advance of their occurrence, and therefore enable action to be taken to avoid the effects of such failures. Alternatively, redundant liners may be used to prevent the effect of a single membrane liner failure.

15. Leakage of body fluids into the Cup. Measurement of the flow of body fluid into the Cup, such as between the Cup liner and myocardial tissues, provides an indication of the failure of the Cup seal, which can adversely affect the systolic and diastolic actuation provided by the Cup. A preferred means to measure this flow is to measure the flow of fluid through the drain (vacuum port) in the Cup. Analysis of any fluid collected enables determination of the source thereof, and whether related medical action is needed.

In summary, therefore, the DMVA device of the present invention in its numerous embodiments is a device that provides mechanical assistance to the ventricles of the heart, comprising electronic digital and/or analog and/or image sensing means to sense operational parameters thereof or of the myocardium; data acquisition means to acquire data on such parameters; computing means to analyze such parametric data, and to derive and/or select algorithms to control to drive fluid volume and/or pressure of the drive fluid thereof, thereby controlling the driving of the ventricles of the heart. With regard to physical structure, the DMVA device of the present invention in its numerous embodiments comprises an integrated drive system that controls the pressure and/or flow rate of drive fluid delivered thereto and withdrawn therefrom, and a shell and liner which contact and displace the ventricles of the heart in an a traumatic manner, i.e. a manner that does not cause trauma to the tissue of the heart.

The DMVA device of the present invention will now be described in detail, with reference to FIGS. 1A-29. This description will begin with a description of the systolic and diastolic cycles of a healthy human heart, the systolic and diastolic cycles of an unhealthy human heart (of which there are many variants), and in general, how the DMVA device of the present invention provides assistance to an unhealthy human heart, such that on a short time scale, such heart is assisted in providing life sustaining circulatory function. In a subsequent description in this specification, the manner in which the DMVA device of the present invention provides assistance to an unhealthy human heart on a long time scale according to various algorithms is provided. In some embodiments, such assistance entails the delivery of therapeutic drugs or other therapeutic agents, and/or cardiac regeneration agents, such that the heart is assisted in an overall healing process and is restored to a state in which DMVA is no longer required. Such therapeutic agents include but are not limited to anti-inflammatory agents, gene therapy agents, gene transfer agents, stem cells, chemo-attractants, cell regeneration agents, ventricular remodeling agents, anti-infection agents, tumor suppressants, tissue and/or cell engineering agents, imaging contrast agents, tissue staining agents, nutrients, and mixtures thereof.

It is to be understood that the FIGS. 1A-1M, which depict time-dependent volumes, pressures, and flow rates of blood displaced by the ventricles of DMVA-assisted and non-assisted hearts are illustrative in nature, and are not meant to indicate precise quantitative values thereof, nor the sole beneficial functions thereof. It is to be further understood that representations of such parameters with respect to an "unhealthy heart" are also illustrative in nature, and may vary widely, depending upon the particular cardiac disorder that is affecting such unhealthy heart, which can vary from incremental degrees of worsening dysfunction to cardiac standstill ("cardiac arrest"). Accordingly, the particular representations of DMVA assistance to such examplary unhealthy hearts are to be taken as one embodiment of assistance thereto, and that many other time dependent pressure, volume, and/or flow rate curves and resulting mechanical assistance can be provided by the DMVA device to such unhealthy or even non-beating hearts, which may be equally or more beneficial. A key attribute of the DMVA device of the present invention is the capability thereof to sense the performance of the heart and the performance of the device itself, and with embedded algorithms in the control system thereof, to select and execute a beneficial sequence of assistive actions to the heart to which it is fitted.

In the following description of FIGS. 1A-1M, references to ventricular volume are taken with respect to the blood volume contained within the ventricles, rather than blood volume displaced from the ventricles. Thus it will be apparent that blood volume in the ventricles is shown to decrease to a minimum at the completion of systole, and to increase to a maximum at the completion of diastole. Blood pressure is to be considered from a frame of reference within the ventricles unless noted otherwise. Also with regard to FIGS. 1A-1M and in various subsequent Figures, the use of the upper case letter "S" is meant to indicate systole, and the use of the upper case "D" is meant to indicate diastole.

FIGS. 1A-1H are graphical representations of time dependent pressure and volume relationships of blood displaced by the left and right ventricles of a healthy human heart, of an unhealthy human heart, and of a DMVA-assisted heart during systole and diastole. FIG. 1A in particular is a representation of the time dependence of the volume of the left ventricle during one complete cardiac cycle including systole (S) and diastole (D), for a normal healthy heart and for one embodiment of a DMVA-assisted heart. Referring to FIG. 1A, there is depicted the time dependent left ventricular volume curve 2020(solid line) for a healthy heart, and the time dependent left ventricular volume curve 1020 (dashed line) for one embodiment of a DMVA-assisted heart, illustrated in general in FIGS. 2A-2I and subsequently described in this specification.

Several preferred features of the DMVA apparatus and method of the present invention are illustrated in curve 1020 of FIG. 1A. In the preferred embodiment, the DMVA Cup is fitted to the heart such that the end diastolic volume 1022 of the DMVA assisted heart is slightly less (by volume difference 1023) than the end diastolic volume 2022 of a normal heart. In this manner, an enlarged heart to which the DMVA device is fitted is favorably constrained or "girdled" from its otherwise dilated geometry and appropriately supported. Although, the normal heart is somewhat constrained by such fitting of the device, additional systolic and diastolic actuation compensate for such decreases in end-diastolic volume during the course of DMVA assistance resulting in stroke volume similar to the normal state. The overall coupling and response of the heart to DMVA assistance is enhanced.

Another preferred feature of the DMVA apparatus and method is the ability thereof to compress the left ventricle to a lesser end systolic volume 1024 than the normal heart LV end-systolic volume 2024. Thus, although in one embodiment, the cardiac cycle in DMVA assistance begins at a lower LV end diastolic volume 1022, it achieves a correspondingly lower LV end systolic volume 1024, so that the total blood volume displaced from the left and right ventricles (stroke volume) is comparable to that of a normal heart. In spite of this further compression of the heart by one embodiment of the DMVA device, such device achieves the compression in a manner that does not significantly bruise of abrade the heart, as will be described subsequently in this specification.

In the embodiment depicted in FIG. 1A, the DMVA device achieves end-systolic volume 1024 at a time 1026 of the actuating cycle slightly later than the time 2026 of a normal heart's cardiac cycle. And, the DMVA device ensures adequate LV compression by such relative increases in this portion of the actuating cycle. Thus, in order to achieve adequate diastolic filling, and achieve such filling within the remaining time of the actuating cycle, the DMVA device is operated such that it provides active assistance to the heart in diastole. Such active assistance is indicated by the steeper slope 1028 (change in volume/change in time or dV/dt) of the DMVA-assisted LV volume curve 1020, compared to the slope 2028 of the normal heart LV volume curve 2020. Such assistance is notably important to overcome such forces that otherwise impair diastolic filling and constrain end-diastolic geometry as seen with related devices. The sensors, control algorithms, and numerous structural features such as the Cup shell, liner, and seal of the DMVA device that are described subsequently in this specification enable this active assistance capability.

Figure 1B:
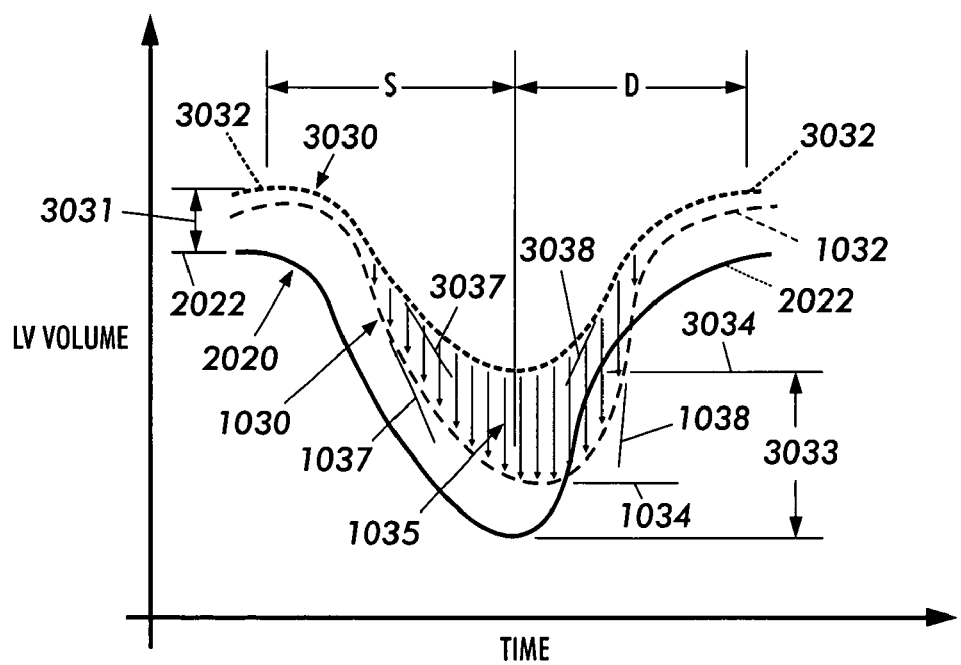

Such sensors, algorithms, and features enable the DMVA device and method to be adapted as required to provide assistance to an unhealthy heart in a manner that is optimal for the particular disorder afflicting such heart. FIG. 1B is a representation of the time dependence of the volume of the left ventricle during one complete cardiac cycle including systole (S) and diastole (D), for a normal healthy heart, for another embodiment of a DMVA-assisted heart, wherein such heart is unhealthy and in a distended condition such as the heart depicted in FIGS. 2P-2R and described subsequently in this specification. Referring to FIG. 1B, curve 3030 (dotted line) represents the left ventricular volume of the unhealthy heart during a cardiac cycle, as compared to the LV curve 2020 (solid line) for a normal heart. It will be apparent that there is a substantial difference 3031 between the end diastolic volume 2022 of a healthy heart, and the end diastolic volume 3032 of the unhealthy, dilated heart in FIG. 1B. It will be further apparent that the volumetric output of such an unhealthy heart is much less than a normal heart, as indicated by the difference 3033 between the end systolic volumes thereof.

Curve 1030 (dashed line) depicts the LV volume of the assisted unhealthy heart, which is provided assistance by the DMVA device. The DMVA device is fitted and programmed to operate at a lesser end diastolic volume 1032 than the end diastolic volume 3032 of the unhealthy heart, which benefits the unhealthy heart by reducing myocardial stretch and/or wall tension. The embodiment depicted in FIG. 1B, illustrates that DMVA support of the unhealthy, dilated heart operates at a higher end diastolic volume than the end diastolic volume 2022 of an otherwise normal beating heart without DMVA assist. Ventricular remodeling during assistance may allow the DMVA assisted heart to achieve lower end-diastolic volumes that may benefit the heart by improving its chance for recovery. However, in any event, the DMVA assisted heart can achieve end systolic volume(s) 1034 that are significantly less than the end systolic volume(s) 3034 of the unhealthy unassisted heart in order to effectively improve stroke volume and improve total cardiac output. Thus a substantial difference in output between the unhealthy heart and the assisted heart is achieved, as indicated by the relative area 1035 between curves 1030 and 3030. It will be apparent that the net stroke volume output of the assisted heart is approximately the same as that of a healthy heart and can be varied by adjustments in drive dynamics as deemed appropriate to both minimize myocardial stress and achieve optimal ventricular dynamics. Adjustments in cycle rate can be further adjusted to effect overall cardiac output as dictated by physiologic needs of the body. This output is achieved while "tailoring" the fit and operation of the DMVA device to the particular unhealthy heart in a manner that does not damage such heart while providing assistance thereto. In the embodiment depicted in FIG. 1B, the unhealthy heart is provided with active assistance during systole and diastole, as indicated by the relatively steep slopes 1037 and 1038, respectively, of curve 1030 as compared to the relatively gradual slopes 3037 and 3038, respectively of curve 3030 for the unassisted unhealthy heart.

Figure 1C:
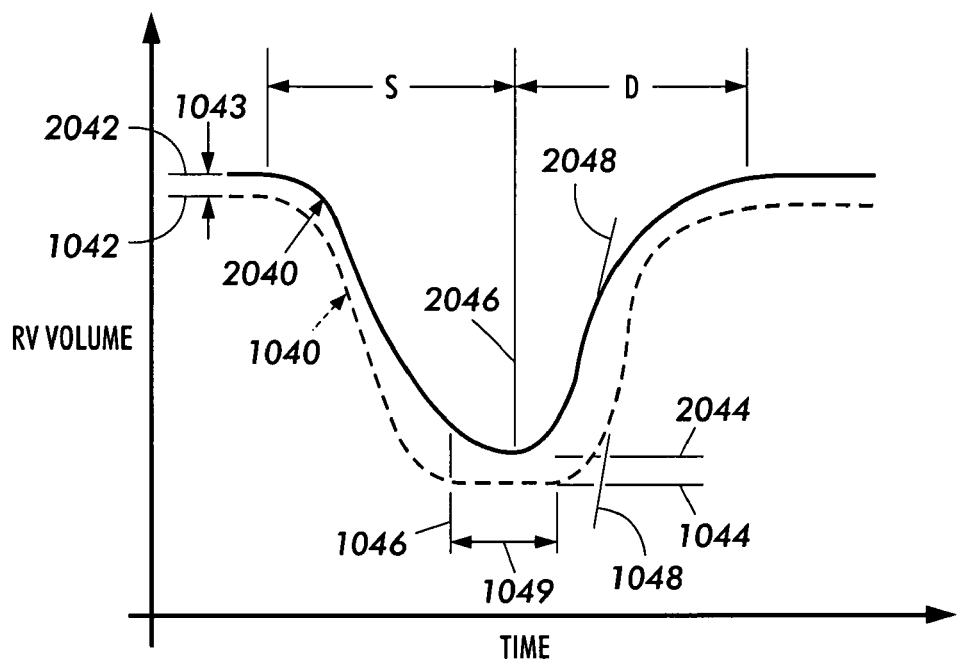

FIG. 1C is a representation of the time dependence of the volumetric changes of the right ventricle during one complete cardiac cycle for a normal healthy heart and for one embodiment of a DMVA-assisted heart. Referring to FIG. 1C, there is depicted the time dependent right ventricular volume curve 2040 (solid line) for a healthy heart, and the time dependent right ventricular volume curve 1040 (dashed line) for one embodiment of a DMVA-assisted heart, illustrated in general in FIGS. 2A-2I and subsequently described in this specification.

In the DMVA embodiment depicted in FIG. 1C, some similar preferred features are illustrated in curve 1040, as were depicted in curve 1020 of FIG. 1A. In the preferred embodiment, the volume of the DMVA Cup and the displacement of the liner therein are fit such that the RV end diastolic volume 1042 of the DMVA assisted heart is slightly less (by volume difference 1043) than the RV end diastolic volume 2042 of a normal heart, as for the LV end diastolic volumes 1022 and 2022 of FIG. 1A. Additionally, the DMVA apparatus has the ability thereof to compress the right ventricle to a lesser end systolic volume 1044 than the normal heart RV end systolic volume 2044. Thus as in FIG. 1A, although the cardiac cycle in DMVA assistance begins at a lower RV end diastolic volume 1042, it achieves a correspondingly lower RV end systolic volume 1044, so that the total blood volume displaced from the right ventricle is comparable to that of a normal heart.

In the embodiment depicted in FIGS. 1A and 1C, the timing of DMVA assisted systolic action of the right ventricle differs from that of the left ventricle. Such a DMVA embodiment is driven by a single fluid source and comprises a single cavity within the Cup. Hence the liner therein is subjected to a single fluid pressure source uniformly distributed over the surface thereof, and hence simultaneously over the surface of the RV and LV walls. In general (although exact circumstances will vary depending upon the particular disorder of the unhealthy heart), because of the relative timing of the tricuspid and mitral valve closings and pulmonary and aortic valve openings, and because the nominal pulmonary blood pressure is substantially lower compared to the nominal aortic blood pressure, and the RV free-wall is generally less resistant than the LV free wall to such forces, the right ventricle will yield and compress before the left ventricle and to a greater extent, as depicted in FIG. 2C.

Thus, as indicated by the sequence of FIGS. 2A-2G, the systolic actuation and corresponding displacement of blood from the right ventricle begins substantially in advance of and is completed before the corresponding displacement of blood from the left ventricle. In the embodiment depicted in FIGS. 1C and 1A, systolic actuation of the right ventricle is relatively complete at a time 1046 that is substantially earlier and/or more rapid than the normal RV ejection time that comparatively ends at time 2046. The overall time for RV ejection is thereby relatively abbreviated. During the time interval 1049 required to complete DMVA assisted systole for the left ventricle and to begin diastole, the right ventricular free wall is squeezed, fixed and maintained in a position with the septum at a relatively constant end systolic volume 1044.

Subsequently, active diastolic assistance is provided to the right ventricle, as for the left ventricle assistance described and shown in FIG. 1A. It will be apparent that the slope 1048 (change in volume/change in time or dV/dt) of curve 1040 for the DMVA assisted heart is generally steeper than the corresponding slope 2048 of curve 2040 for the normal heart for right ventricular diastolic actuation, as was previously noted for the left ventricular diastolic actuation.

Figure 1D:
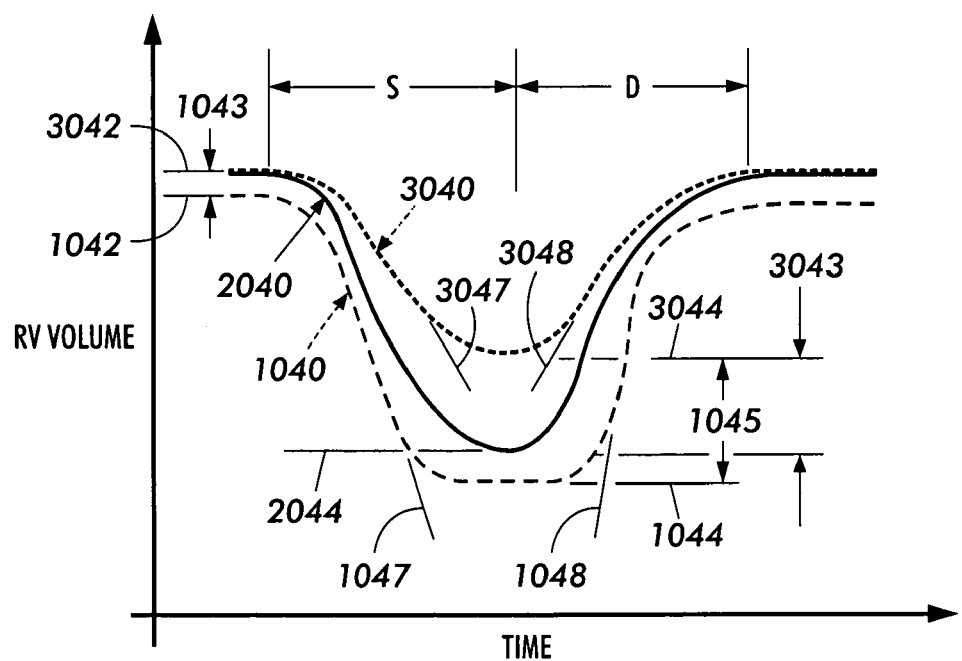

FIG. 1D is a representation of the time dependence of the volume of the right ventricle during one complete cardiac cycle for a normal healthy heart (curve 2040, solid line), and for an embodiment of a DMVA-assisted heart, wherein such heart is unhealthy (curve 1040, dashed line). Referring to FIG. 1D, curve 3040 (dotted line) represents the right ventricular volume of the unhealthy heart during a cardiac cycle, as compared to the RV curve 2040 for a normal heart. It will be apparent that the volumetric output of such an unhealthy heart is much less than a normal heart, as indicated by the difference 3043 between the end systolic volumes thereof.

Curve 1040 depicts the RV volume of the assisted unhealthy heart, which is provided assistance by the DMVA device. In the embodiment depicted in FIG. 1D, the DMVA device is fitted and programmed to operate at a slightly lesser end diastolic volume 1042 than the end diastolic volume 3042 of the unhealthy heart. As with the LV, such reductions in end-diastolic volumes benefit the heart by reducing diastolic stretch of the heart muscle and improve the opportunity for healing. However, the DMVA assisted heart can achieve end systolic volumes 1044 that are significantly less than the end systolic volume 3044 of the unhealthy unassisted heart in order to obtain an adequate stroke volume. Thus a substantial difference in output between the unhealthy heart and the assisted heart is achieved, as indicated by the difference 1045 between end systolic volumes 1044 and 3044. In the embodiment depicted in FIG. 1D, the end systolic volume 1044 of the DMVA assisted heart is less than the end systolic volume 2044 of a normal heart; however in other embodiments, the DMVA device is programmed to substantially match the end diastolic volume 2042 (see FIG. 1C) and the end systolic volume 2044 of a healthy heart, such that the net RV blood volume output of the assisted heart is approximately the same as that of a healthy heart. This output is achieved while "tailoring" the fit and operation of the DMVA device to the particular unhealthy heart in a manner that does not damage such heart while providing assistance thereto. In the embodiment depicted in FIG. 1D, the unhealthy heart is provided with active assistance during systole and diastole, as indicated by the relatively steep slopes 1047 and 1048 as compared to the relatively weak slopes 3047 and 3048 of curve 3040 for the unassisted unhealthy heart.

Figure 1E:
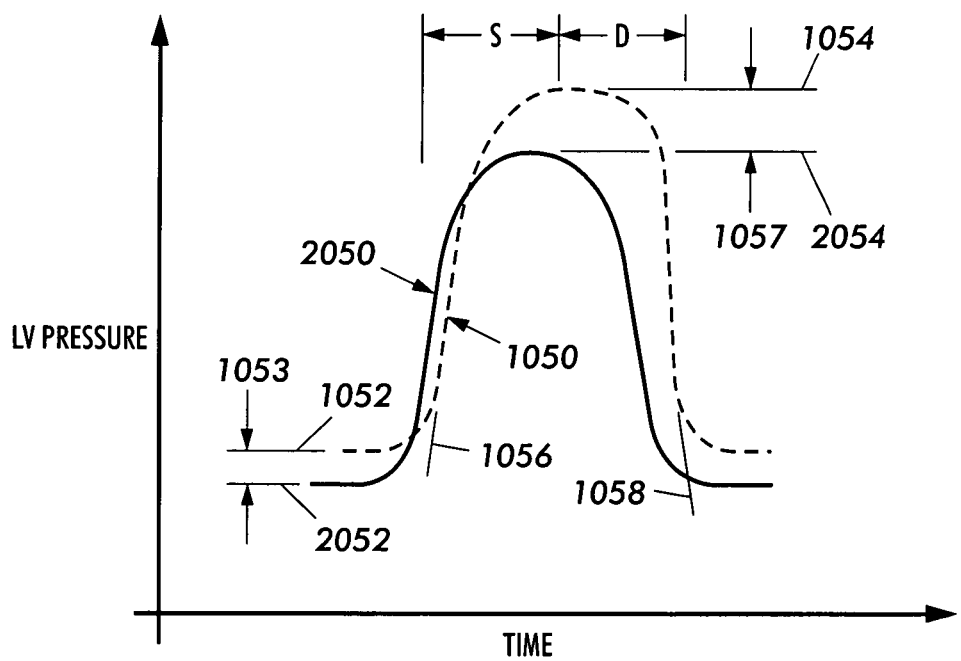

FIG. 1E is a representation of the time dependence of the blood pressure within the left ventricle during one complete cardiac cycle for a normal healthy heart and for one embodiment of a DMVA-assisted heart. The curve representing the DMVA assisted heart is "shifted" slightly to the right for the purpose of illustrating general differences in these two cycles. However, DMVA assistance of the heart would optimally begin before natural contraction of the heart to reduce the work of the heart. With this understanding, FIG. 1E depicts the time dependent left ventricular pressure curve 2050 for a healthy heart (solid line), and the time dependent left ventricular pressure curve 1050 (dashed line) for one embodiment of a DMVA-assisted heart, illustrated in general in FIGS. 2A-2I and subsequently described in this specification. In the preferred embodiment, the DMVA Cup is fitted to the heart, with the displacement of the liner therein such that the very early diastolic pressure 1052 of the DMVA assisted heart may be slightly less than the very early diastolic pressure 2052 of a normal heart. (However this is not shown in pressure difference 1053.) The end-diastolic pressures are however increased (as illustrated in pressure difference 1053) which reflects the fit of the DMVA device and its physical effect on ventricular pressures in the normal heart. In this manner however, an enlarged heart to which the DMVA device is fitted is constrained and supported; and an unenlarged heart is prevented from undesired enlargement as was described for FIG. 1A.

Another preferred feature of the DMVA apparatus and method is the ability thereof to pressurize the left ventricle to a greater peak systolic pressure 1054 than the normal heart LV maximum systolic pressure 2054. Yet another preferred feature is the ability to attain greater relative increases and decreases in pressure (dP/dt) as indicated by slopes 1056 and 1058 respectively, when compared to those of a healthy heart. Such capabilities enable the DMVA device to be more effectively matched to the requirements of the particular unhealthy heart needing assistance but are also adjusted to the lowest incremental rise required in order to reduce the likelihood of cardiac injury. The DMVA apparatus of the present invention is thus atraumatic with respect to the heart.

Figure 1F:
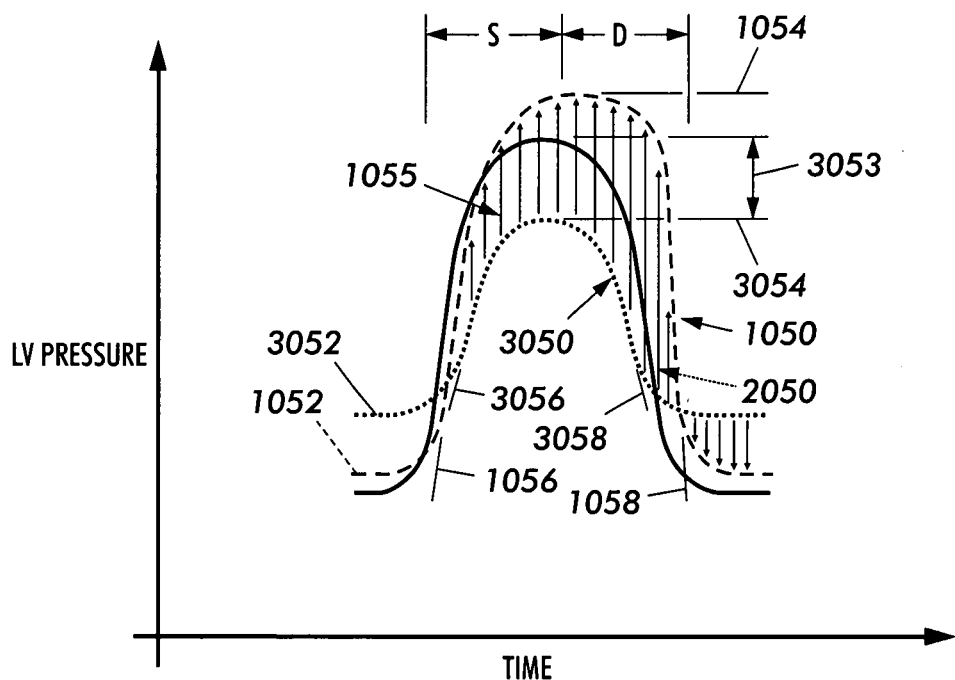

FIG. 1F is a representation of the time dependence of the pressure of the left ventricle during one complete cardiac cycle for a normal healthy heart, and for an embodiment of a DMVA-assisted heart, wherein such heart is unhealthy.

Referring to FIG. 1F, curve 3050 (dotted line) represents the left ventricular pressure of the unhealthy heart during a cardiac cycle, as compared to the LV curve 2050 (solid line) for a normal heart. It will be apparent that the LV pressure of such an unhealthy heart is much less than a normal heart, as indicated by the difference 3053 between the peak systolic pressures thereof. Curve 1050 (dashed line) depicts the LV pressure of the assisted unhealthy heart, which is provided assistance by the DMVA device.

In the embodiment depicted in FIG. 1F, the DMVA device is fitted and programmed to operate at a lower diastolic pressures 1052 than the diastolic pressure 3052 of the unhealthy heart. Although not shown in FIG. 1F, the DMVA device has the further ability to reduce early diastolic pressures even below that of the normal healthy heart by virtue of diastolic actuation. Additionally, the DMVA assisted heart achieves a peak systolic pressure 1054 that is significantly greater than the peak systolic pressure 3054 of the unhealthy unassisted heart. Furthermore, a substantial difference in pressure between the unhealthy heart and the assisted heart is maintained for a greater portion of the cardiac cycle, as indicated by the region 1055 between pressure curves 1050 and 3050. This is followed by a more rapid decrease in pressure (dP/dt) as indicated by slope 1058 of curve 1050. Thus, in the embodiment depicted in FIG. 1F, the unhealthy heart is provided with active assistance during systole and diastole, as indicated by the relatively steep slopes 1056 and 1058 as compared to the relatively weak slopes 3056 and 3058 of curve 3050 for the unassisted unhealthy heart. As indicated previously, such values of dP/dt for the DMVA assisted heart, while significantly greater (i.e. steeper in slope) than those of an unassisted unhealthy heart they are adjusted to be somewhat more approximate to the overall characteristics of those for a healthy heart.

Figure 1G:
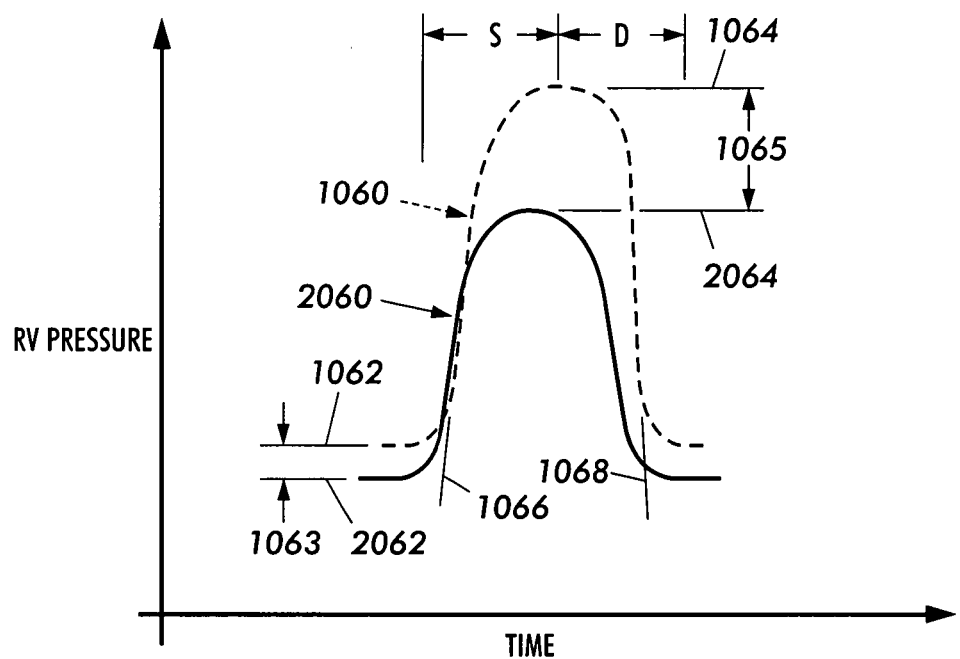

FIG. 1G is a representation of the time dependence of the blood pressure within the right ventricle during one complete cardiac cycle for a normal healthy heart and for one embodiment of a DMVA-assisted heart. Referring to FIG. 1G, there is depicted the time dependent right ventricular pressure curve 2060 (solid line) for a healthy heart, and the time dependent right ventricular pressure curve 1060 (dashed line) for one embodiment of a DMVA-assisted heart, illustrated in general in FIGS. 2A-2I and subsequently described in this specification. In the preferred embodiment, the DMVA Cup is fitted to the heart, and the displacement of the liner therein is controlled such that the RV diastolic pressure 1062 of the DMVA assisted heart is slightly greater (by pressure difference 1063) than the RV diastolic pressure 2062 of a normal heart. Again, as with the LV and not shown in this figure is the ability of DMVA to achieve early diastolic pressures that are actually lower that the normal beating heart which reflects the devices pronounced capability to augment diastolic filling.

Another feature of the DMVA apparatus and method is the production of pressure in the right ventricle to a greater peak systolic pressure 1064 than the normal heart RV maximum systolic pressure 2064. It can be seen that the pressure difference 1065 between these peak systolic pressures is greater than the corresponding difference 1057 between the peak systolic pressure 1054 of the assisted heart and the peak systolic pressure 2054 of the normal heart (see FIG. 1E). This greater difference is due to the additional pressure needed to displace blood from the left ventricle. Such an increased pressure, which is provided by the DMVA fluid drive system, occurs during the time that the RV is nearly fully compressed by the action of the DMVA device. Thus the higher peak systolic pressures 1064 of the DMVA assisted heart are reflected into the pulmonary circulation and do not produce an increase in pulmonary blood pressure within the patient.

Figure 1H:
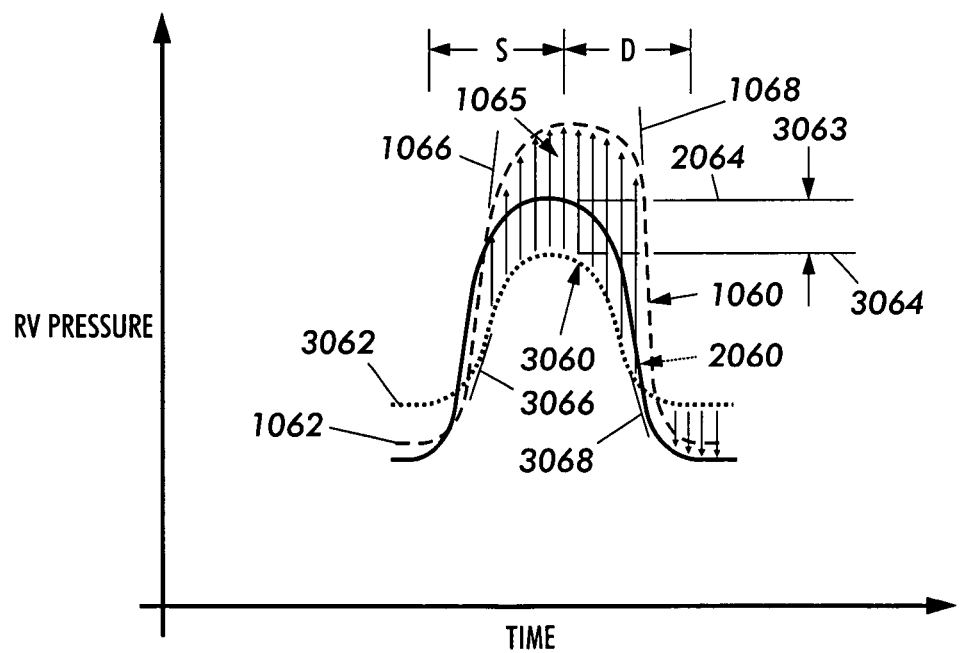

FIG. 1H is a representation of the time dependence of the pressure of the right ventricle during one complete cardiac cycle for a normal healthy heart, and for an embodiment of a DMVA-assisted heart, wherein such heart is unhealthy. Referring to FIG. 1H, curve 3060 (dotted line) represents the right ventricular pressure of the unhealthy heart during a cardiac cycle, as compared to the RV curve 2060 (solid line) for a normal heart. It will be apparent that the RV systolic pressure of such an unhealthy heart is much less than a normal heart, as indicated by the difference 3063 between the peak systolic pressures thereof. Curve 1060 (dashed line) depicts the RV pressure of the assisted unhealthy heart, which is provided assistance by the DMVA device and it should be noted again that the early diastolic pressures can be less than that of the normal beating heart (not shown) by virtue of the ability of DMVA to actuate the heart into a diastolic configuration and thereby assist in early diastolic filling.

In the embodiment depicted in FIG. 1H, the DMVA device is fitted and programmed to operate at a lower early diastolic pressure 1062 than the early diastolic pressure 3062 of the unhealthy heart. However, the DMVA assisted heart achieves a peak RV systolic pressure 1064 that is significantly greater than the peak RV systolic pressure 3064 of the unhealthy unassisted heart. Additionally, a substantial difference in pressure between the unhealthy heart and the assisted heart is maintained for a greater portion of the cardiac cycle, as indicated by the region 1065 between systolic pressure curves 1060 and 3060. This is followed by a more rapid decrease in pressure (dP/dt) as indicated by slope 1068 of curve 1060. Thus, in the embodiment depicted in FIG. 1H, the unhealthy heart is provided with active assistance during systole and diastole, as indicated by the relatively steep slopes 1066 and 1068 as compared to the relatively weak slopes 3066 and 3068 of curve 3060 for the unassisted unhealthy heart. As indicated previously, such values of dP/dt for the DMVA assisted heart, while significantly greater (i.e. steeper in slope) than those of an unassisted unhealthy heart, are more closely representative of those for a healthy heart.

Figure 1I:
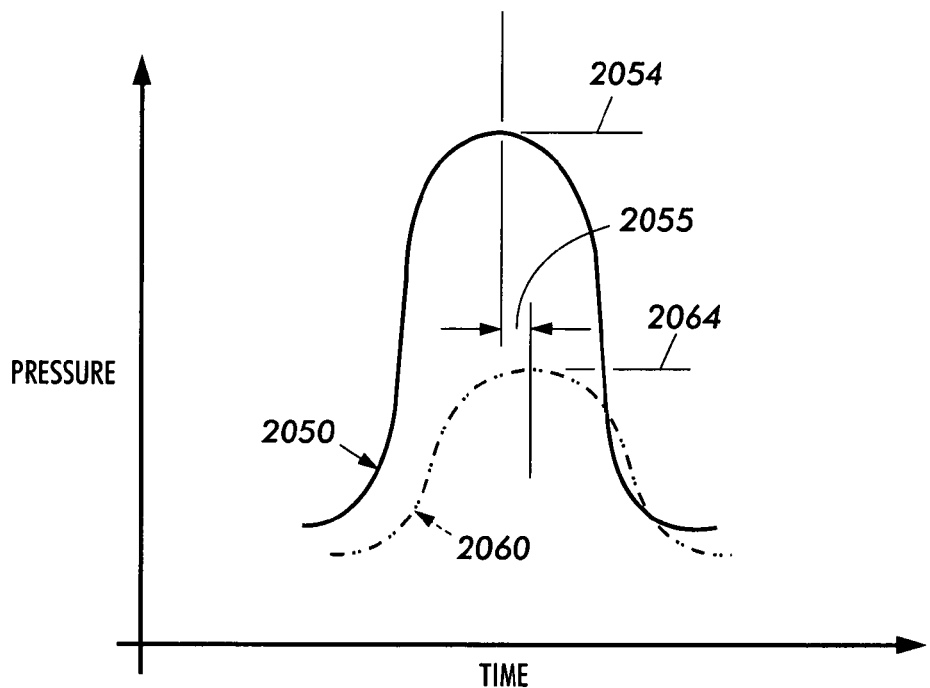
FIGS. 1I-1J are graphical representations of time dependent blood pressure within the left and right ventricles of a healthy human heart, and of a DMVA-assisted heart, respectively, during systole and diastole.
Figure 1J:
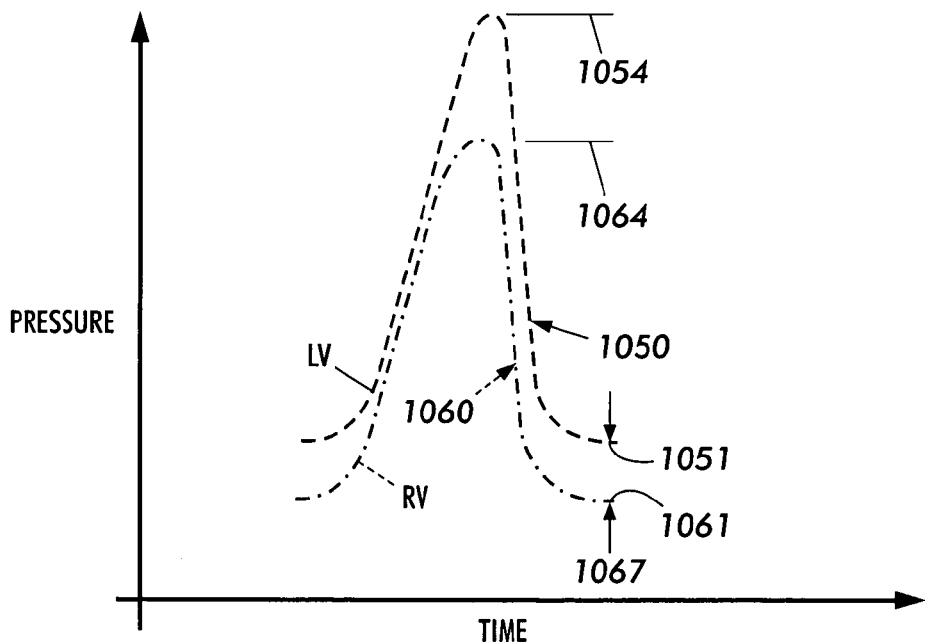

FIGS. 1I-1J are graphical representations of time dependent blood pressure within the left and right ventricles of a healthy human heart, and of a DMVA-assisted heart during systolic and diastolic actuation. Referring to FIG. 1I, which depicts the left ventricle pressure 2050 (solid line) and the right ventricle pressure 2060 (dash/double-dot line) for a healthy heart on the same time axis, it can be seen that the peak systolic pressure 2054 of the left ventricle is considerably higher than the peak systolic pressure 2064 of the right ventricle. It can also be seen that there is typically a small time difference 2055 between the occurrence of the peak systolic pressure 2054 of the left ventricle and the peak systolic pressure 2064 of the right ventricle.

FIG. 1J depicts the left ventricle pressure 1050 (dashed line) and the right ventricle pressure 1060 (dash/dot line) of a heart assisted by one embodiment of the DMVA apparatus. Referring to FIG. 1J, it can be seen that pressure increases occur approximately simultaneously, since the DMVA drive fluid is applying the same uniform pressure through the action of the liner therein to both ventricles. Accordingly, the peak systolic pressures 1054 of the left ventricle and 1064 of the right ventricle occur at approximately the same time. Therefore, the overall pressure rise of the RV is shifted to the left compared to the normal beating heart. It will also be apparent the peak systolic pressure 1054 of the left ventricle is considerably higher than the peak systolic pressure 1064 of the right ventricle, as a consequence of the higher pressure needed for systemic circulation as compared to pulmonary circulation. It can also be seen that the minimum right ventricle diastolic pressure 1061 is substantially lower than the corresponding minimum left ventricle diastolic pressure 1051. In some circumstances wherein particularly vigorous diastolic assistance is required, minimum right ventricle diastolic pressure 1061 may even become slightly sub-atmospheric.

With regard to FIGS. 1I and 1J, it is to be understood that there is no intent that such Figures are depicted on the same time scale, and that the cardiac cycle of a DMVA assisted heart occurs on approximately the same time scale as for the cardiac cycle of a normal heart.

Figure 1K:
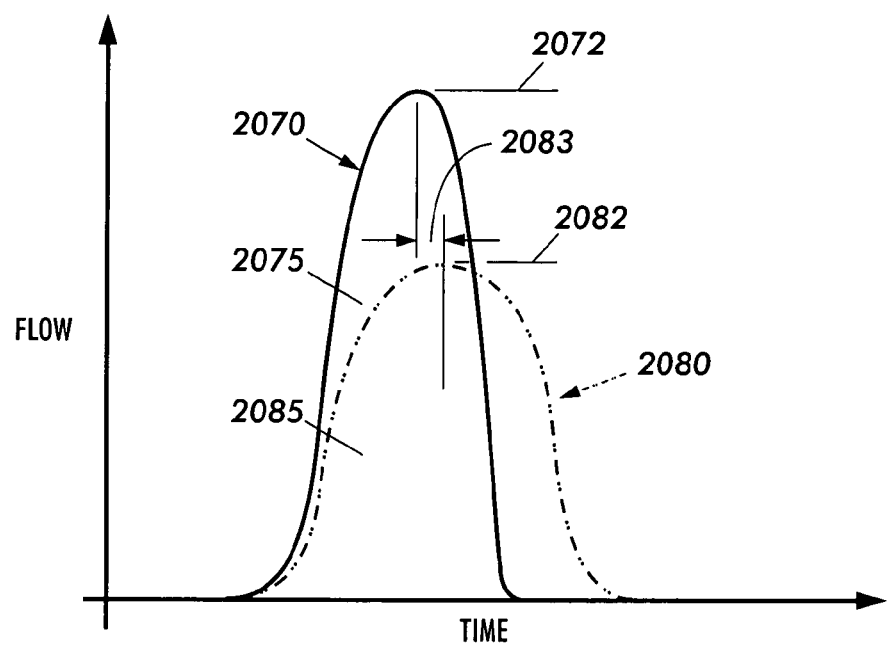
FIGS. 1K-1L are graphical representations of time dependent blood flow rates ejected from the left and right ventricles of a healthy human heart, and of a DMVA-assisted heart during systole.
Figure 1L:
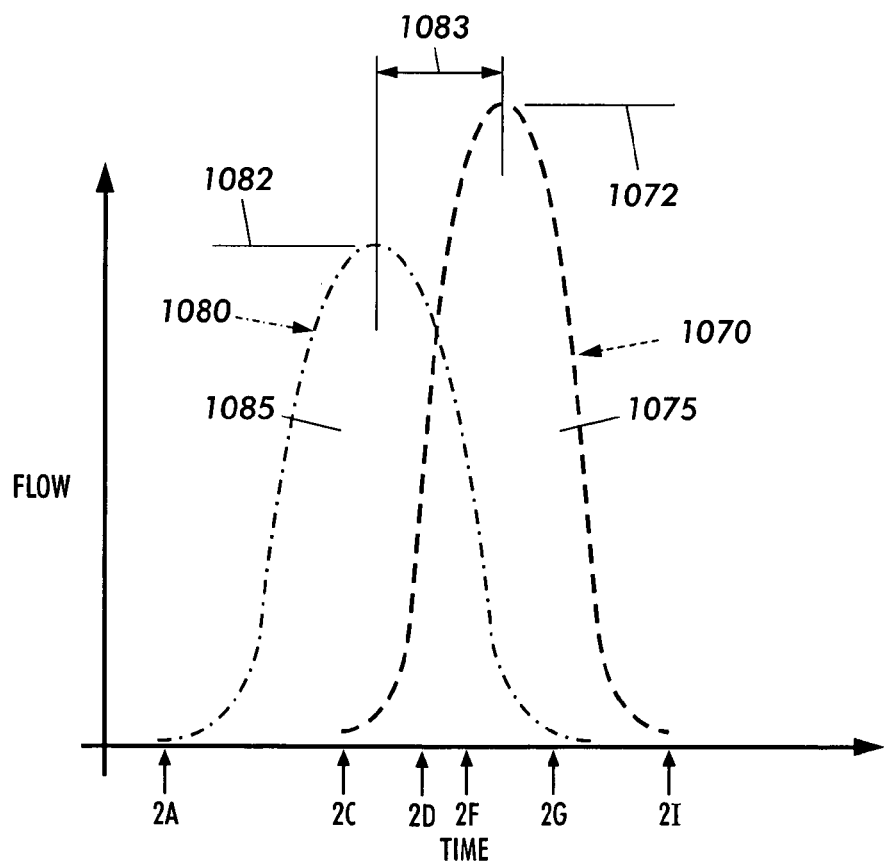

FIGS. 1K-1L are graphical representations of time dependent blood flow rates ejected from the left and right ventricles of a healthy human heart, and of a DMVA-assisted heart during systole. Referring to FIG. 1K, which depicts the blood flow rate 2070 (solid line) ejected from the left ventricle and the blood flow rate 2080 (dash/double-dot line) ejected from the right ventricle for a healthy heart on the same time axis, it can be seen that the ejections are nearly concurrent, with the peak flow 2072 from the left ventricle preceding the peak flow 2082 from the right ventricle by a small interval 2083. It can also be seen that the flow for the right ventricle occurs over a somewhat longer time interval, and that the area 2075 representing the total volume displaced from the left ventricle is approximately equal to the area 2085 representing the total volume displaced from the right ventricle, since the volume of systemic circulation is approximately equal to the volume of pulmonary circulation, with some variation due to the physiologic shunting of blood. It is also noted that these relationships will vary in accordance with different cardiovascular disease states.

FIG. 1L depicts the blood flow rate 1070 ejected from the left ventricle and the blood flow rate 1080 ejected from the right ventricle of a heart assisted by one embodiment of the DMVA apparatus. Referring to FIG. 1L, it can be seen that the ejections are not concurrent, but that the ejections overlap to some degree. The peak flow 1082 from the right ventricle precedes the peak flow 1072 from the left ventricle by interval 1083. It can also be seen that, unlike the function of a normal heart, the majority of flow from the left ventricle occurs over a somewhat shorter time interval, but like that of the normal heart, the area 1085 representing the total volume displaced from the right ventricle is approximately equal to the area 1075 representing the total volume displaced from the left ventricle. Thus the volume of systemic circulation is approximately equal to the volume of pulmonary circulation in a DMVA assisted heart with appropriate small variations according to physiologic shunts. Again, it should also be understood that these relationships will vary in accordance with different cardiovascular disease states With regard to the timing of blood flows of the DMVA assisted heart, it can be seen by reference to FIGS. 2A-2I (to be subsequently explained in detail in this specification) that the DMVA apparatus compresses and empties the right ventricle prior to the time at which such apparatus compresses and empties the left ventricle and in a relatively abbreviated time span within any given comparative cycle rate when contrasted to the normal beating heart. As previously explained, the precedence of the right ventricle is due to the timing of the pulmonary and aortic valve openings, and because the nominal pulmonary blood pressure is lower compared to the nominal aortic blood pressure and also due to the generally less resistant, thin RV wall when compared to the thicker LV free wall and septum.

Figure 1M:
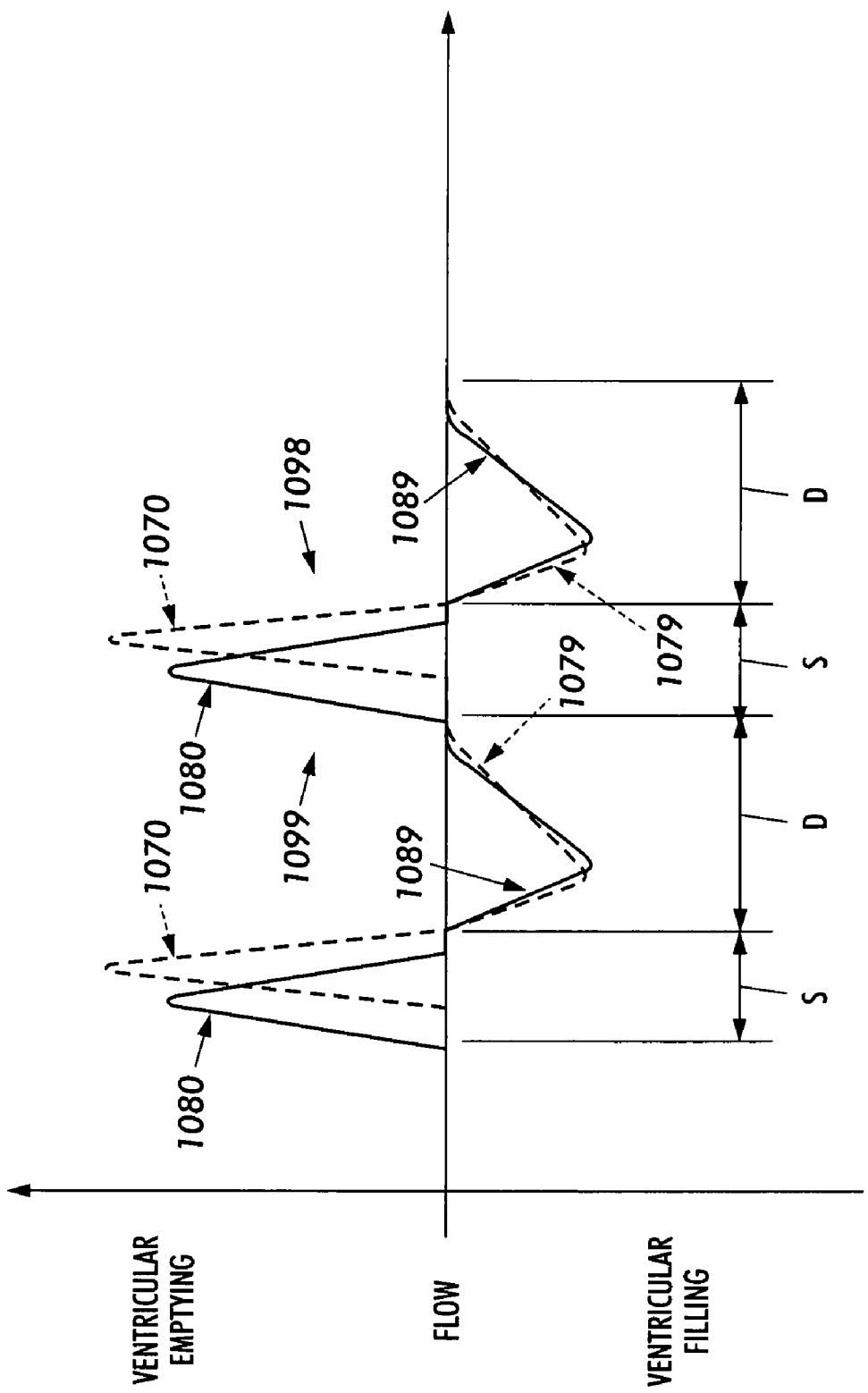
FIG. 1M is a graphical representation of time dependent blood flow rates into and out of the ventricles of the heart taken over a sequence of two DMVA assisted complete cardiac cycles.

FIG. 1M is a graphical representation of time dependent blood flow rates into and out of the ventricles of the heart assisted by a DMVA device taken over a sequence of two complete cardiac cycles. Referring to FIG. 1M, there is depicted an overall left ventricle flow plot 1098 (dashed line) and an overall right ventricle flow plot 1099 (solid line) for two cycles. Left ventricle flow plot 1098 comprises curves 1070 (dashed line, one per cycle) during systole, and right ventricle flow plot 1099 comprises curves 1080 (solid line, one per cycle) during systole, each with flow out of the ventricle being taken as a positive value. Left ventricle flow plot 1098 further comprises curves 1079 (dashed line, one per cycle) during diastole, and right ventricle flow plot 1099 comprises curves 1089 (solid line, one per cycle) during diastole, each with flow out of the ventricle being taken as a negative value.

It is to be understood that plots 1098 and 1099 of FIG. 1M are for general illustrative purposes only, and that interpretation of details thereof are not intended to be taken as limiting. For example, the sharp reversals of flow depicted at the apices of curves 1070, 1080, 1079, and 1089 occur in practice as smooth, curved transitions when the time line is expanded or the recordings are made with a greater speed. In addition, there may be a pause of relatively greater duration than indicated between the completion of ventricular filling, and the next cycle of ventricular emptying which are dictated by adjustments in the drive dynamics used to operate the DMVA device. In general, the time scale of a DMVA assisted cardiac cycle is between about 0.5 and 1.0 seconds (120-60 beats per minute). And, such variations in cycle rates will result in relative changes in the pressure and flow characteristics. However, it is to be understood that all of these variables, as well as many others are fully controllable in accordance with the present invention.

Referring again to FIG. 1M, it can be seen that the ejections of blood from the right and left ventricles are not concurrent, but that such ejections do overlap to some degree, as depicted in FIG. 1L. Although, during the embodiment of DMVA-assistance depicted in FIG. 1M, the filling of the left and right ventricles are substantially concurrent, as a consequence of the attachment of the liner of the DMVA device to the ventricular epicardium, and the nearly simultaneous openings of the tricuspid and mitral valves, the DMVA device can be adjusted to create more rapid filling in the early part of diastolic actuation such that the filling of the right and left ventricles would be even more facilitated in the early part of diastolic actuation. In certain circumstances, this may be advantageous, as it enables the controller to utilize more time in systolic compression if these were for example required to more appropriately compress the ventricles in the later half of the cycle. The converse is also true: that is the controller could effectively empty the ventricles more rapidly, and based on the evaluation of the pressure and flow curves, thereby dedicate more time to diastolic actuation to ensure adequate filling. All of these adjustments require the evaluation of the resultant RV and LV volumes to ensure appropriate filling and emptying of the ventricles in each half of the cycle.

In one embodiment to be described subsequently in this specification, the ventricular emptying and ventricular filling blood flows are inferred from a sensor in the DMVA device, which measures the flow of drive fluid delivered to and from such device. In another embodiment, such flows are detected by sensors in the pulmonary artery (RV) and descending aorta (LV). (In the latter case, correction factors must be applied to account for blood flow out of the brachiocephalic, left common carotid, and left subclavian arteries.)

FIGS. 2A-2I are cross-sectional schematic views depicting a sequence of actions of DMVA device of the present invention on a heart, which assists the systolic and diastolic functions thereof depicted graphically in FIGS. 1A-1M. For the sake of simplicity of illustration, only the ventricular portion of the heart that is contained in the DMVA Cup is shown in FIGS. 2A-2I; the atria and valves are not shown, with it being understood that such portions of the heart remain functional as commonly understood. Also for the sake of simplicity of illustration, the liner of the DMVA Cup, which displaces the ventricles to perform systolic and diastolic actuation, is shown as a simple membrane joined to the Cup shell wall. It is to be understood that numerous other liner embodiments of the present invention, as described and shown in this specification, are to be considered within the scope of the description of FIGS. 2A-2I.

Figure 2A:
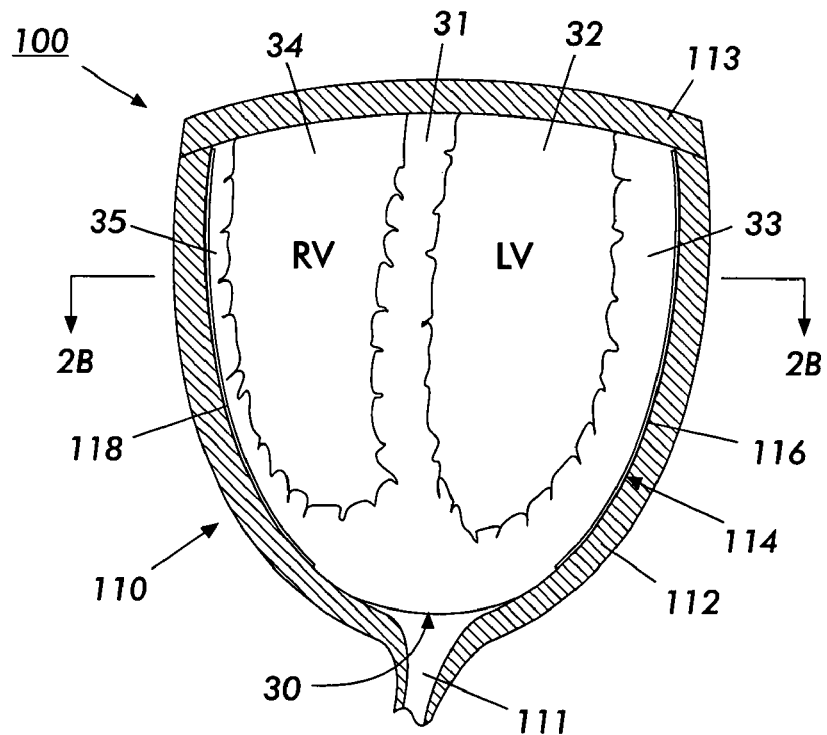
FIGS. 2A-2I are cross-sectional schematic views depicting a sequence of actions of DMVA device of the present invention a heart, which assist the systolic and diastolic functions thereof depicted graphically in FIGS. 1A-1M.
Figure 2B:
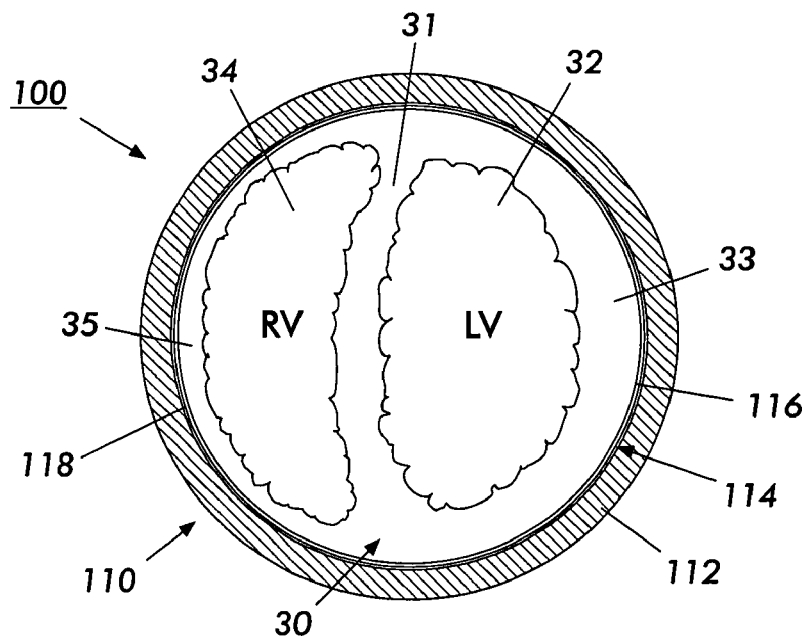
Figure 2C:
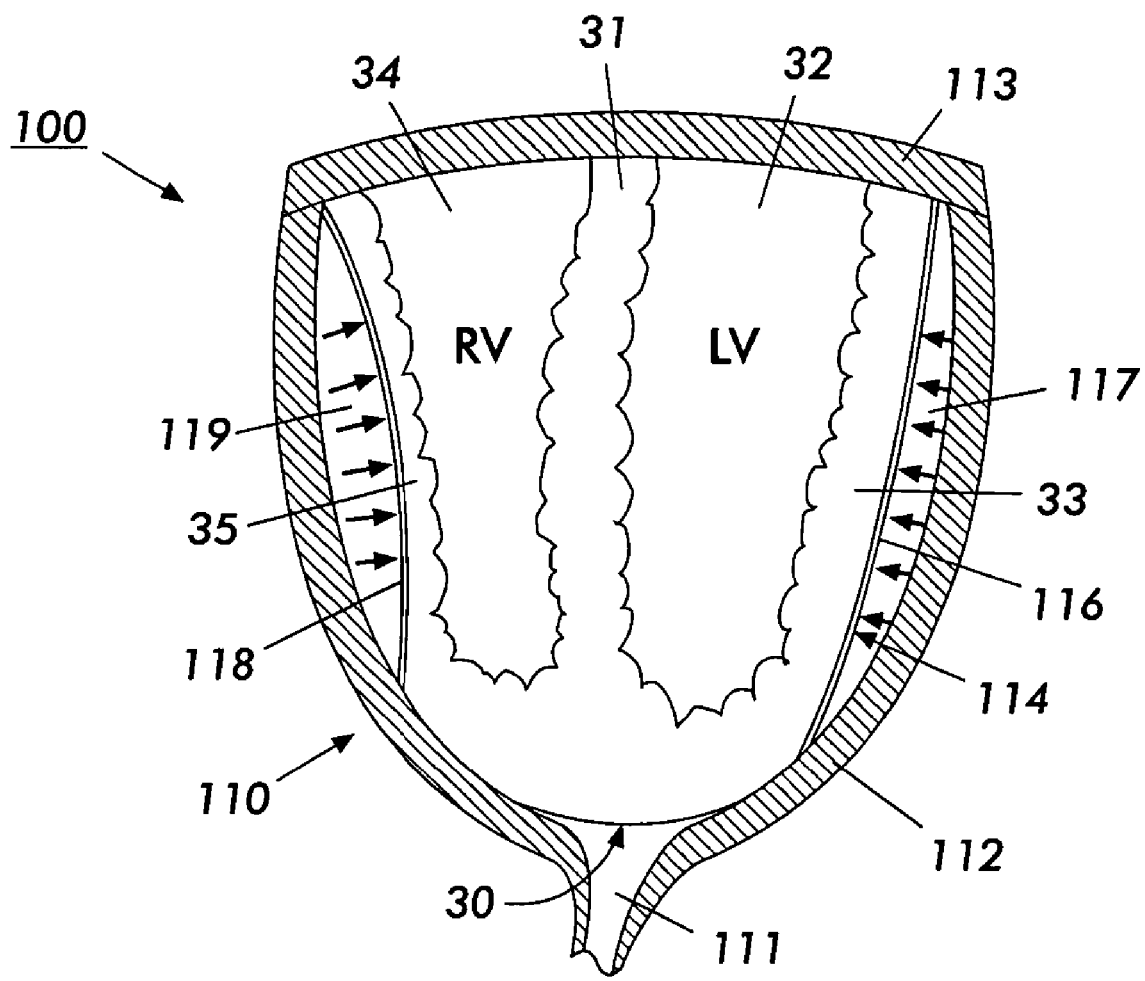

FIG. 2A is a cross-sectional elevation view of a heart in an uncompressed state contained within the DMVA Cup prior to the beginning of systolic compression, and FIG. 2B is a top cross sectional view taken along line 2B-2B of FIG. 2A. The relative timing of the situation of FIG. 2A in the cardiac cycle is shown by arrow 2A of FIG. 1L. Referring to FIGS. 2A and 2B, heart 30 comprising left ventricle 32 and right ventricle 34 is contained and secured within DMVA cup 100 by the action of vacuum drawn from tube 111 and by seal 113. DMVA Cup 100 further comprises a housing 110 with dynamic properties formed by wall 112, and elastic liner 114 attached to wall 112. In operation, a drive fluid is used to displace liner 114, with liner 114 preferably being of unitary construction, comprising a left portion 116 and a right portion 118. Such drive fluid displaces a continuous annular cavity between liner 114 and the inner surface of shell wall 112. Such annular cavity comprises a left cavity portion 117 (see FIG. 2C) and a right cavity portion 119 (see FIG. 2C). Thus the ventricular chambers of the heart are circumferentially compressed with the left ventricular free wall 33 of heart 30 being displaced by the left liner portion 116, and the right ventricular free wall 33 of heart 30 being displaced by right liner portion 118.

FIG. 2C is a cross-sectional elevation view of a heart contained within the DMVA Cup early in the process of systolic compression, approximately at the time indicated by arrow 2C of FIG. 1L. Referring to FIG. 2C, DMVA drive fluid is delivered into a supply port (not shown) in shell wall 112 and displaces liner 114, accumulating in cavity portion 119. The early displacement of liner 114 predominantly compresses right ventricular wall 35 of the heart 30, causing blood to flow from right ventricle 34 as indicated in FIG. 1L and described previously. It can be seen in FIG. 2C that although left ventricle wall 33 has been displaced slightly by liner portion 116, intraventricular septum 31 has also been displaced toward right ventricle 34. Accordingly, left ventricle 32 has not exhibited any volume reduction by DMVA drive fluid, and blood flow from left ventricle 32 has therefore not begun, also indicated at time 2C of FIG. 1L.

Figure 2D:
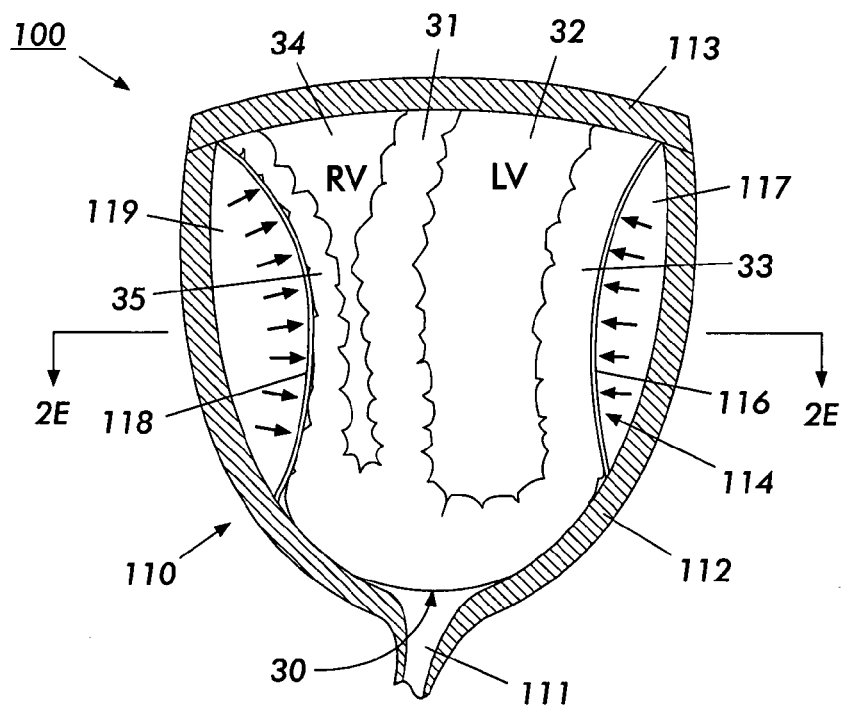
Figure 2E:
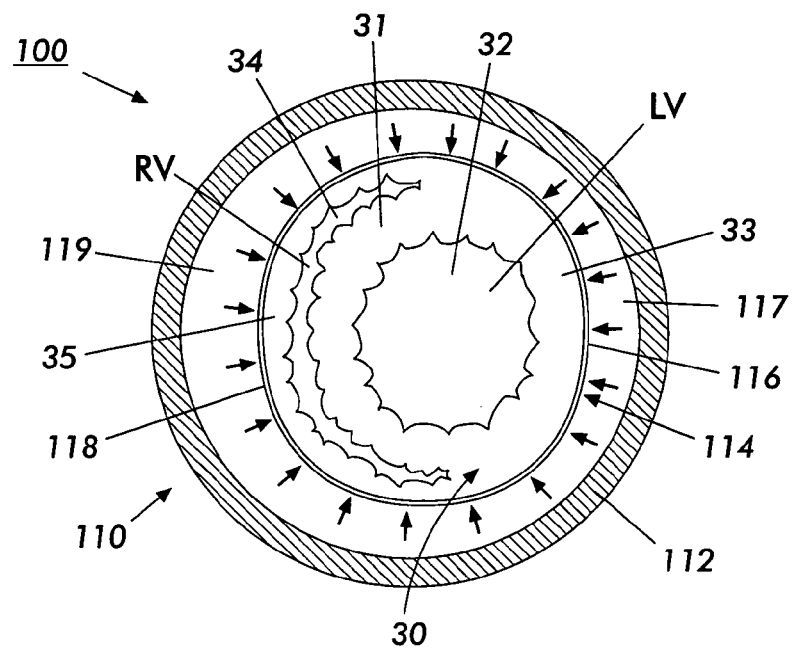

FIG. 2D is a cross-sectional elevation view of a heart contained within the DMVA Cup at roughly the mid-point of systolic compression, and FIG. 2E is a top cross sectional view taken along line 2E-2E of FIG. 2D, approximately at the time indicated by arrow 2D of FIG. 1L. Referring to FIGS. 2D and 2E, DMVA drive fluid continues to flow into a supply port (not shown) in shell wall 112 into cavity portions 117 and 119, further displacing right ventricular wall 33 and left ventricular wall 35 of heart 30. It can be seen that left liner portion 116 provides compression forces on the left ventricular wall 33 of heart that lead to the reduction of the volume of left ventricle 32. Accordingly, blood flows concurrently from right ventricle 34 and left ventricle 32 as indicated in FIG. 1L and described previously.

Figure 2F:
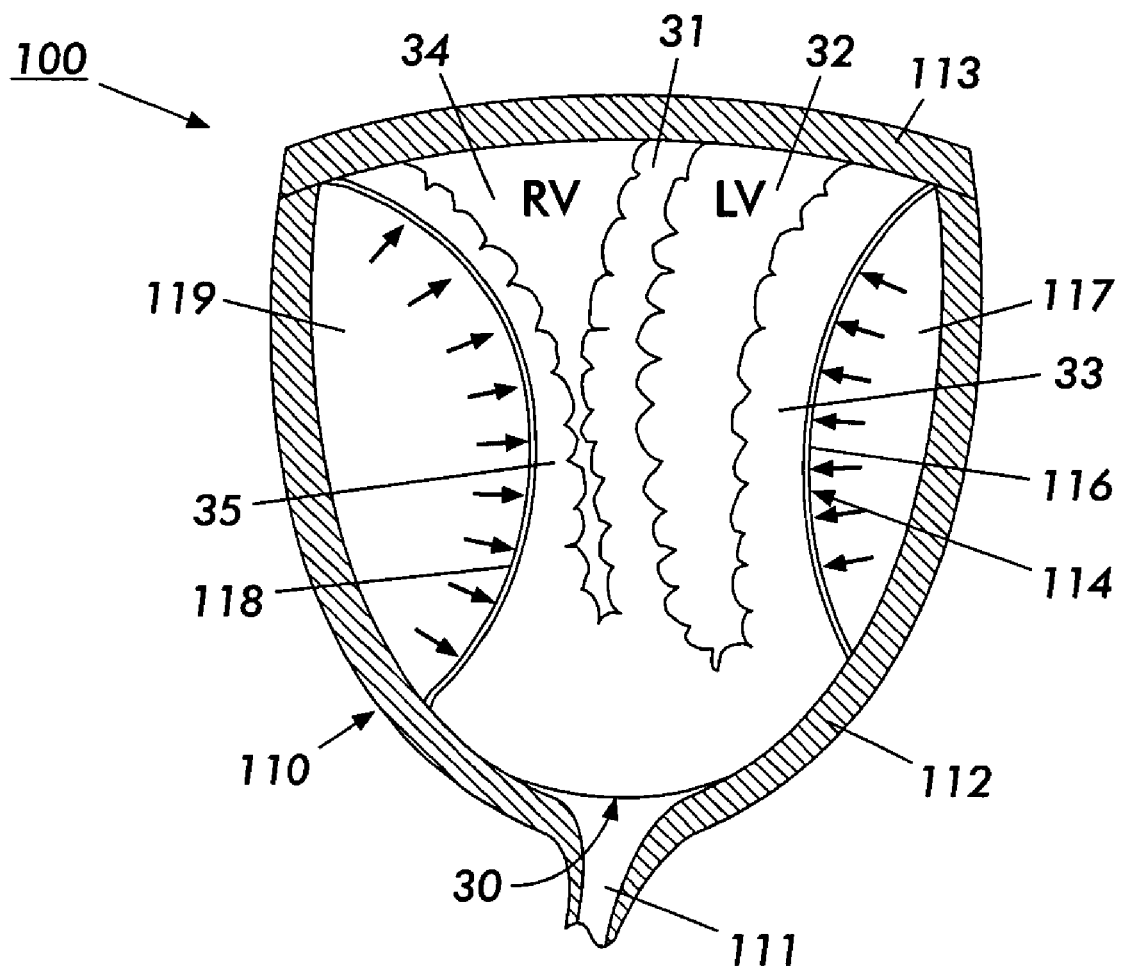
Figure 2G:
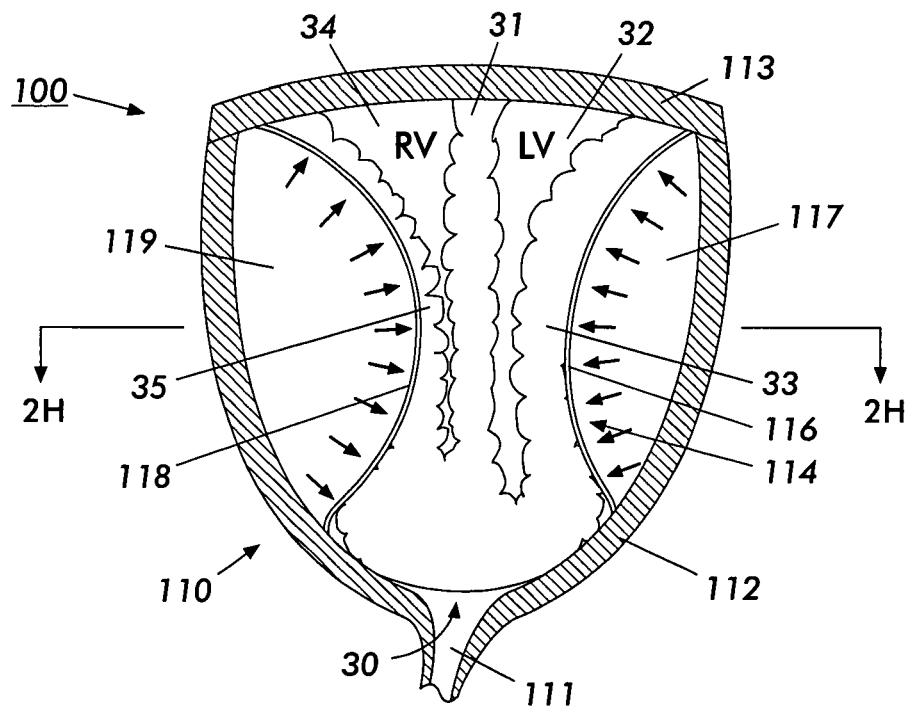

It can also be seen that in the preferred embodiment, the DMVA apparatus of the present invention applies a force uniformly to the heart around the circumference thereof, such that the heart is compressed in a manner that renders the heart with a substantially circular cross section and with a minimum diameter at the plane defined by line 2E-2E of FIG. 2D, and at the plane defined by line 2H-2H in FIG. 2G. As used in this specification, the term cardiac core diameter is meant to indicate this diametrical minimum of the heart that occurs during DMVA assistance by the apparatus of the present invention. The compression of the heart in such a substantially circular cross section is considered an attribute and is made possible by the unique structure of the embodiments of the Cup shells and liners of the present invention.

FIG. 2F is a cross-sectional elevation view of a heart contained within the DMVA Cup at yet a later time during systolic compression, approximately indicated by arrow 2F of FIG. 1L. Referring to FIGS. 2F, DMVA drive fluid continues to flow into a supply port (not shown) in shell wall 112, and has displaced right ventricle 32 to a point where the displacement of the volume of right ventricle 32 is nearly complete. It can be seen that right ventricle wall 35 has been displaced nearly to a point of contact with and is beginning to "mold" to the right side of the septum 31, which has been further displaced toward left ventricle 32, and that the rate of blood flow from right ventricle 34 is decreasing rapidly, as indicated at arrow 2F of FIG. 1L. At this time, blood flow from left ventricle 32 is at a relatively high level, and a substantial volume of left ventricle 32 remains to be displaced.

Figure 2H:
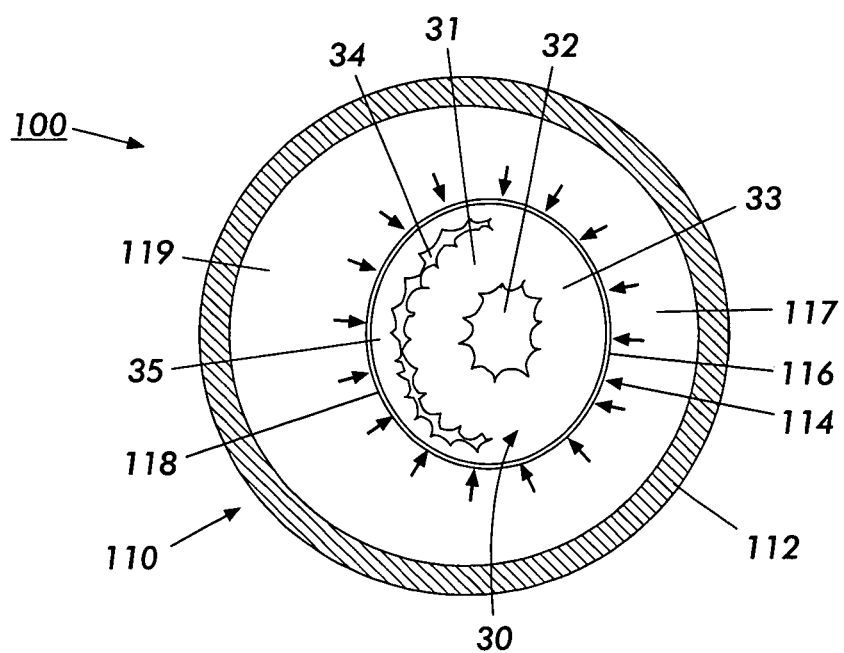

FIG. 2G is a cross-sectional elevation view of a heart contained within the DMVA Cup at a time late in systolic compression, and FIG. 2H is a top cross sectional view taken along line 2H-2H of FIG. 2G, approximately at the time indicated by arrow 2G of FIG. 1L. Referring to FIGS. 2G and 2H, compression of right ventricle 32 is complete, wherein right ventricle wall 35 is in contact and "molded" to the intraventricular septum 31, and wherein blood flow from right ventricle 35 is substantially complete (see FIG. 1L). Blood flow from left ventricle 32 continues at a decreasing flow rate as left ventricle wall 33 and intraventricular septum 31 are compressed in a circumferential fashion.

Figure 2I:
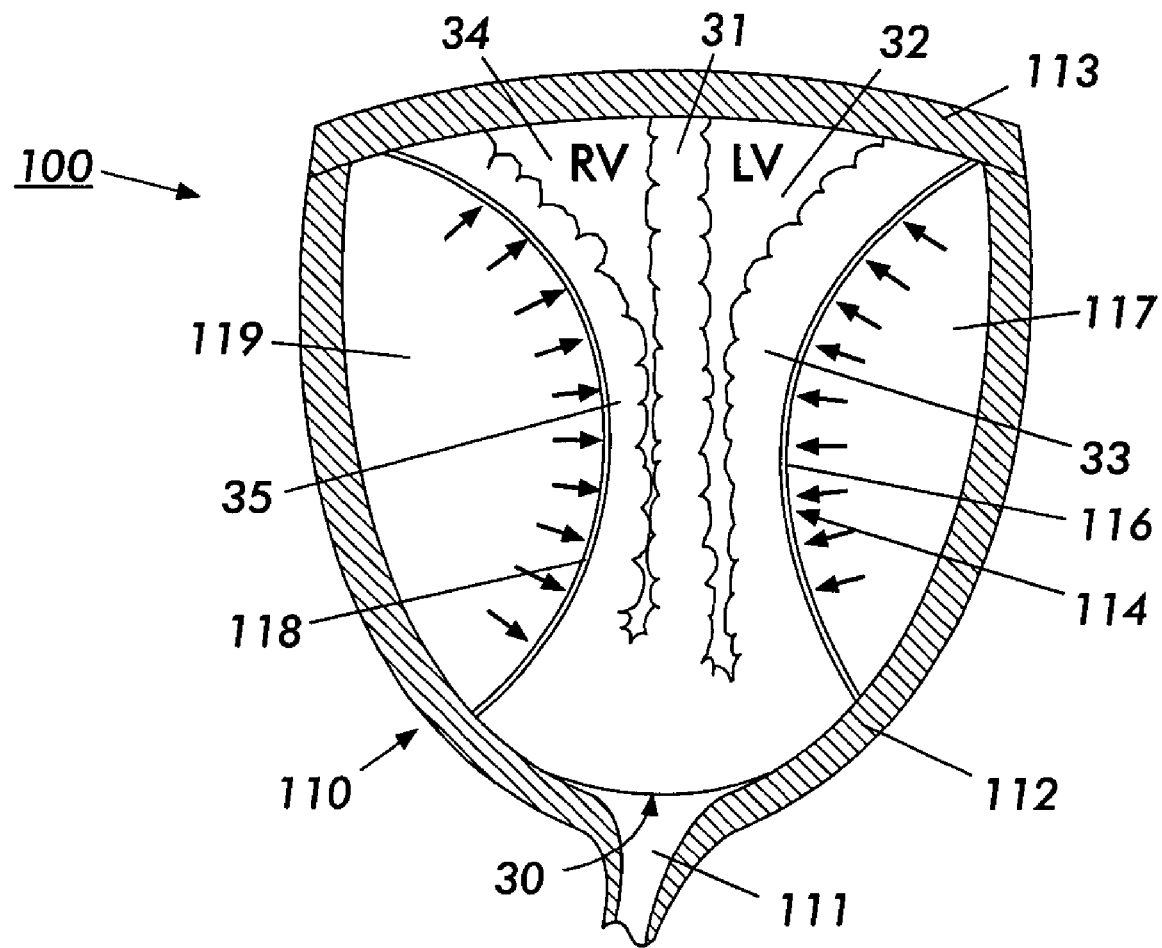

FIG. 2I is a cross-sectional elevation view of a heart contained within the DMVA Cup at the completion of systolic compression, approximately at the time indicated by arrow 2I of FIG. 1L. Referring to FIG. 2I, right ventricle wall 35 has remained squeezed against intraventricular septum 31, left ventricle wall 33 has been nearly displaced to a point of contact with intraventricular septum 31, and blood flow from left ventricle 32 has ceased (see FIG. 1L). In the preferred embodiment, left ventricle 32 is generally not displaced to a point of contact with intraventricular septum 31, as such contact of the heart tissues, if avoidable, is generally undesirable. Because of the high degree of control of the DMVA Cup of the present invention described in this specification, such precise limiting of the displacement of the ventricles 32 and 34 is rendered possible.

FIGS. 2J-2O are cross-sectional schematic views depicting undesired operations and/or effects of a DMVA device, which is lacking proper control and/or structural features in accordance with the present invention. Such conditions are avoided by use of the sensors, controls, and algorithms of the present invention.

Figure 2J:
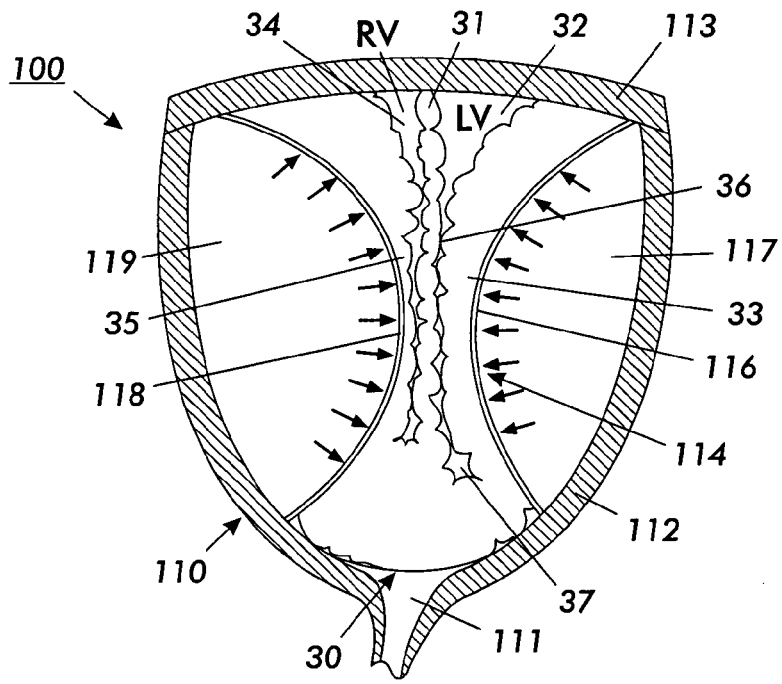
FIGS. 2J-2O are cross-sectional schematic views depicting undesired operations and/or effects of a DMVA device, which is lacking the proper control and/or structural features provided in accordance with the present invention.

Referring to FIG. 2J, there is depicted a heart 30 in a state of excessive compression by DMVA device 100. It can be seen that excessive forces are placed on the entire ventricular mass with the left ventricle 32 excessively compressed to a point where there is a large region 36 of contact between left ventricle wall 33 and intraventricular septum 31. In some instances, entrapment of blood may occur in a pocket 37 formed at the base of left ventricle 32.

Figure 2K:
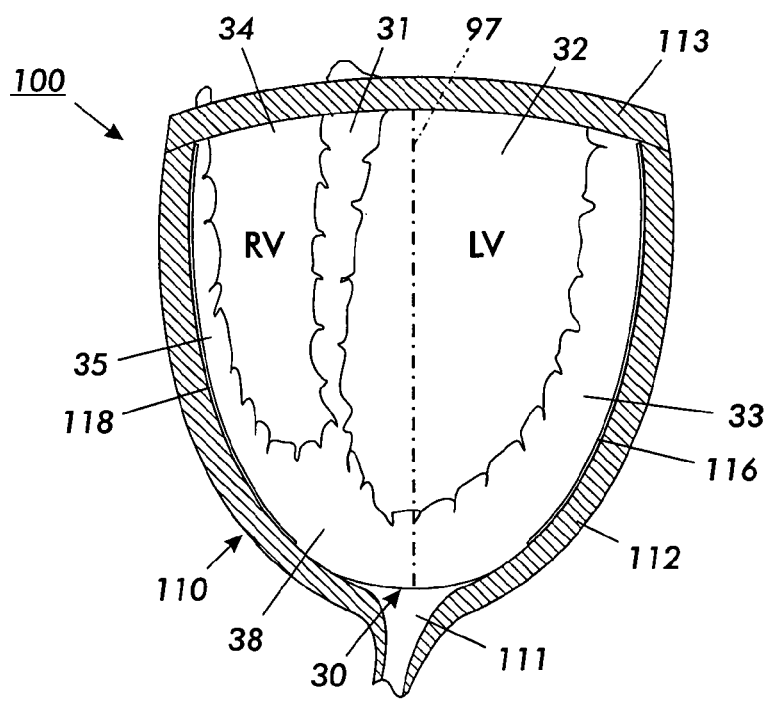

In instances where such excessive compression is sustained over a number of cycles, and particularly if the DMVA Cup 100 is undersized for the particular heart 30, misalignment of the heart within the Cup may occur as depicted in FIG. 2K, wherein the heart is shown at the conclusion of diastolic actuation. Referring to FIG. 2K, it can be seen that the right ventricle 34 has been substantially displaced from with the Cup 100, and that apex 38 of heart 30 has been displaced upwardly away from vacuum tube 111. Such a misalignment distorts predominantly the right ventricle 34, and prevents proper operation of the DMVA Cup 100. RV filling in particular is compromised. Such a circumstance is prevented by the use of a Cup of sufficient size, diastolic actuation suction by the Cup 100, and by the use of sufficient vacuum applied at vacuum port 111.

Figure 2L:
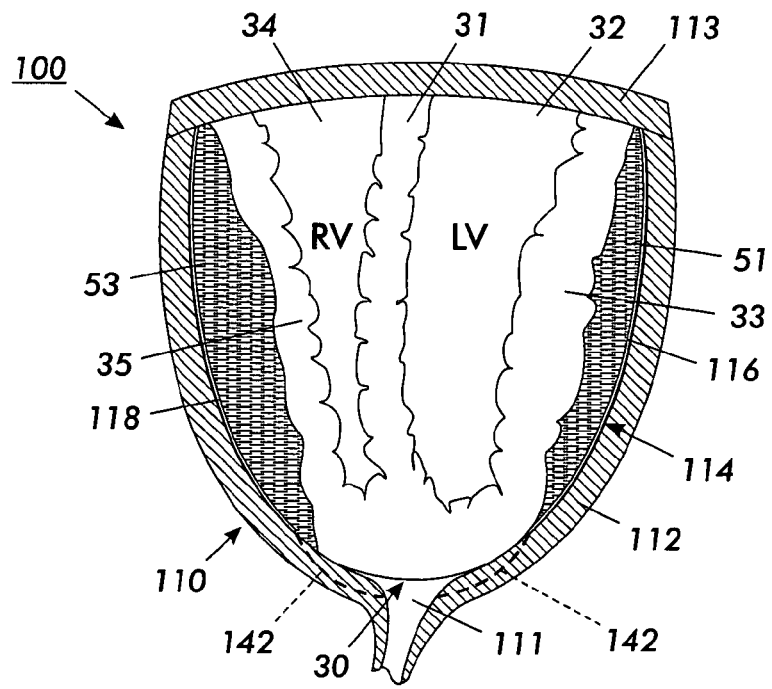
Figure 2M:
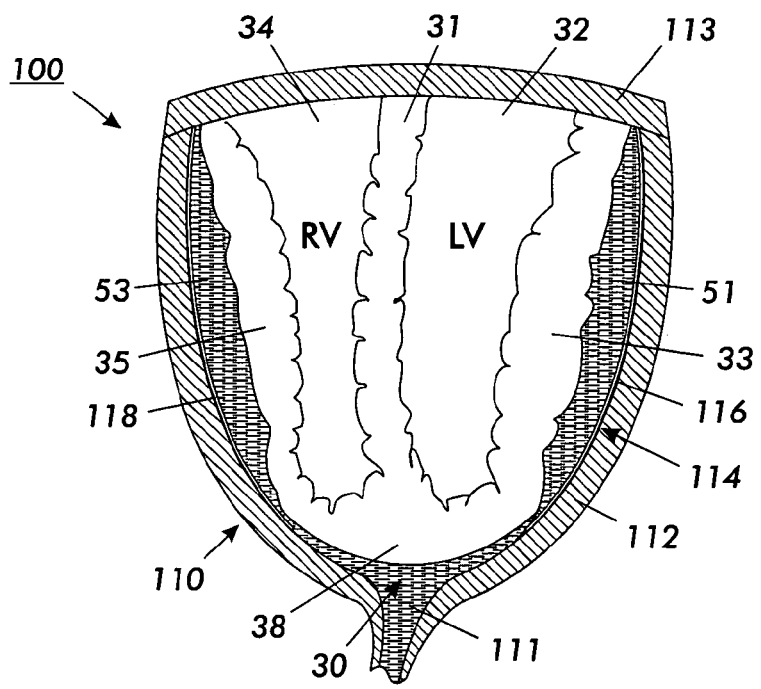

FIG. 2L depicts a situation wherein a type of "cavitation" has occurred during diastolic actuation, such that the left ventricle wall 33 and right ventricle wall 35 have become detached and are no longer contiguous with left liner portion 116 and right liner portion 118, respectively. As used herein the term "cavitation" does not refer to the generation of vacuum or a vapor phase as a result of sudden relative motion in a volatile liquid medium, but refers to the unwanted incursion of a fluid, either liquid or gas, into the interface between the Cup liner and the myocardial surface. Bodily fluid or cavitated air has become entrained in such cavities 51 and 53. Such a condition is caused by one or more of the following: excessive diastolic actuation, i.e. too much vacuum, or too rapid/too early an application of vacuum by the DMVA drive fluid on the heart 30; a poor fit of seal 113 to heart 30; sealing/blocking of port 111 by apex 38 of heart 30; or inadequate vacuum applied to vacuum port 111. In such a situation, RV and LV filling are both compromised, as the DMVA device separates from the heart 30 during diastolic actuation and the heart 30 fills passively and is not afforded diastolic assist. During systole, the heart is expelled from the confines of the housing 110 rather than the blood being expelled from within the ventricles 32 and 34. These are examples of decreased pumping of blood into and out of ventricles 32 and 34 by inappropriate DMVA drive control. In instances where such excessive compression is sustained over a number of cycles, substantially complete detachment of the heart 30 from wall 112 of the Cup shell 110 may occur, as depicted in FIG. 2M. It can be seen that apex 38 of heart 30 has become detached from vacuum port 111 of Cup 100. It is to be understood that the detachment shown in FIGS. 2L and 2M is depicted as an extreme example, but that any accumulation of fluid or gas between the liner 114 and the surface of the heart 30 is to be considered an unacceptable condition.

Figure 2N:
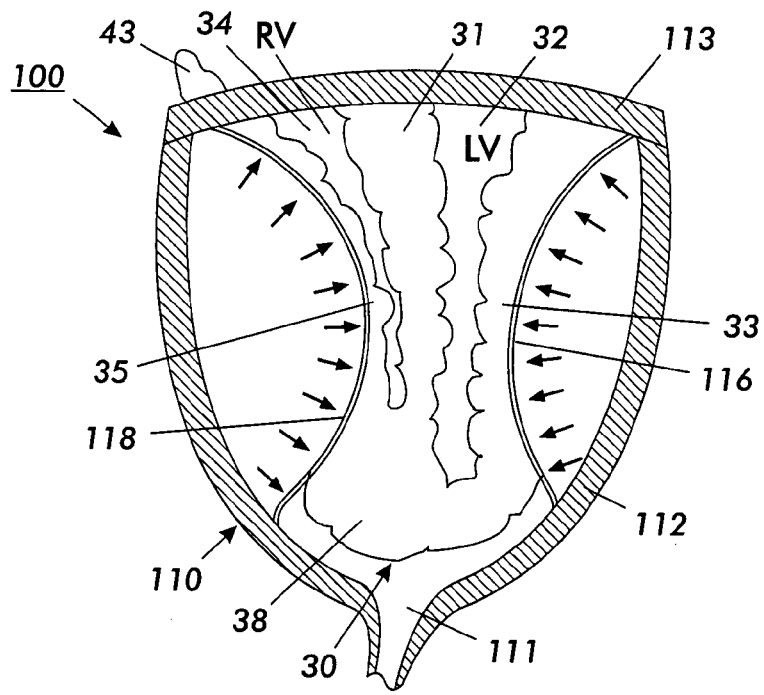
Figure 2O:
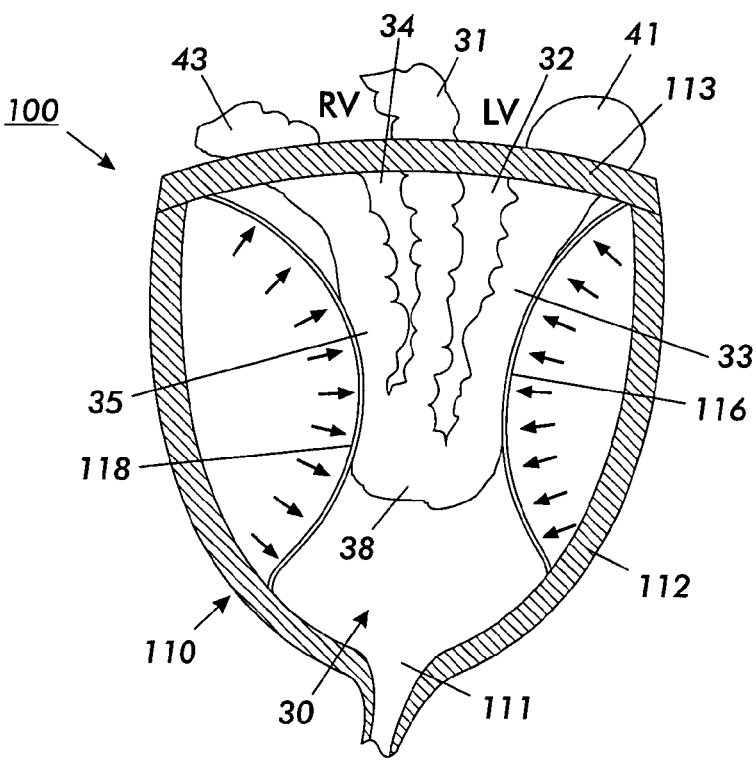

FIG. 2N depicts a situation wherein herniation has occurred during systolic actuation, such that the heart 30 is extruded from the DMVA Cup 100. Such herniation is a consequence of excessive DMVA fluid pressure during early systolic actuation and predominantly affects the RV infundibulum, i.e. the upper portion of the ventricle walls proximate to the atrio-ventricular (AV) groove and/or basal portion of the RV free wall. Referring to FIG. 2N, it can be seen that heart 30 has been forced into misalignment within Cup 100, and that an upper portion 43 of right ventricle wall (infundibulm or basal portion of the RV) 35 has been displaced upwardly beyond seal 113. In instances where such excessive early systolic fluid pressure is sustained over a number of cycles, displacement of both ventricles 32 and 34 of the heart 30 from the Cup 100 may occur, as depicted in FIG. 2O. It can be seen that apex 38 of heart 30 has become detached with cavitation of air or fluid accumulation within the apical portion of the cup as the heart is displaced 111 from the Cup 100, and that upper portion 43 of right ventricle wall 35 and upper portion 41 of left ventricle wall 33 have been displaced beyond seal 113 of Cup 100.

Figure 2P:
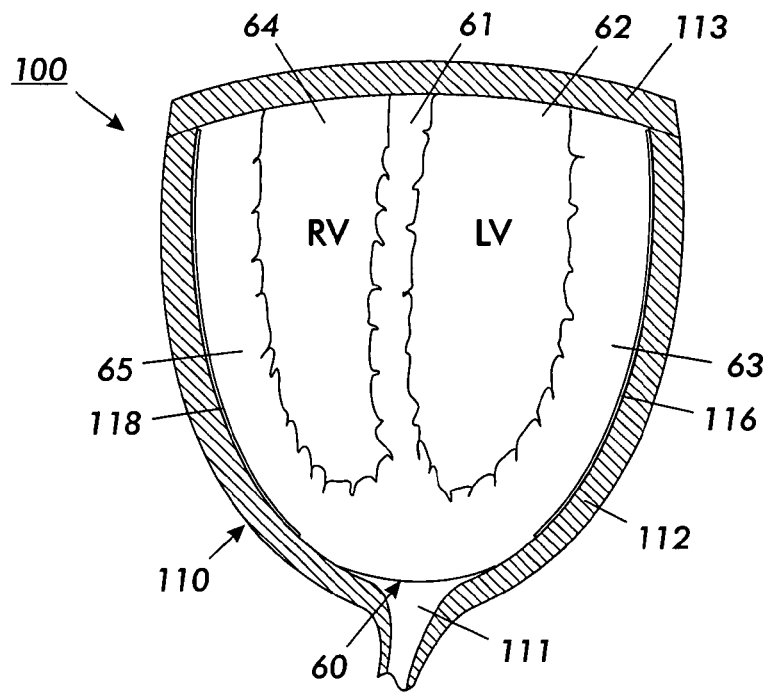
FIGS. 2P-2R are cross-sectional schematic views depicting operations and/or effects of a DMVA device on a heart afflicted with pulmonary hypertension and right ventricular hypertrophy.
Figure 2Q:
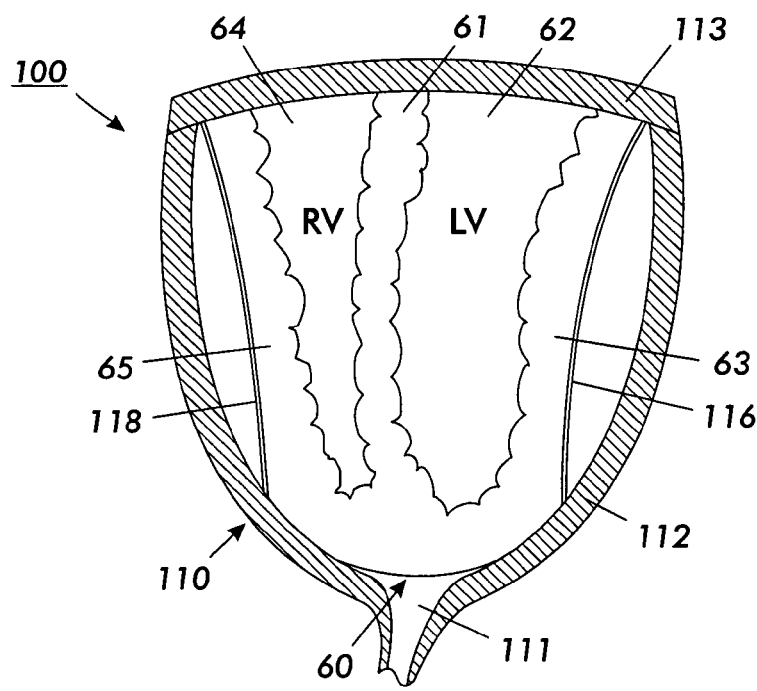
Figure 2R:
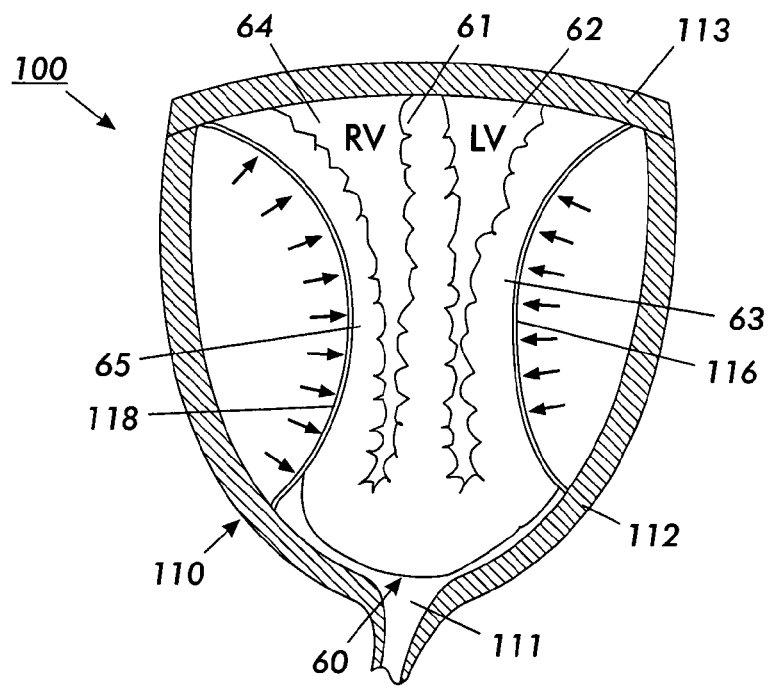

FIGS. 2P-2R are cross-sectional schematic views depicting operations and/or effects of a DMVA device on a heart afflicted with pulmonary hypertension and/or right ventricular hypertrophy. Referring to FIG. 2P, DMVA Cup 100 is depicted therein at the end of diastolic actuation. It can be seen that heart 60 afflicted with pulmonary hypertension (PHT) and/or RV hypertrophy is characterized in particular by a thickening of right ventricle wall 65. The operation of DMVA Cup 100 can be programmed and/or controlled such that the assistance rendered to heart 60 is specifically matched to the needs thereof due to the PHT condition.

FIG. 2Q depicts systolic compression of heart 60, at a point approximately midway through such compression. It can be seen that the compression of right ventricle 64 and left ventricle 62 occur nearly simultaneously, due to the comparable thickness of right ventricle wall 65, and to the higher pulmonary blood pressure of the PHT condition. Referring again to FIG. 1L, which depicts time dependent blood flow rates ejected from the left and right ventricles of a DMVA-assisted non-PHT heart, it can bee seen that there is a substantial time interval 1083 between the peak systolic blood flow 1082 of the right ventricle and the peak systolic blood flow 1072 from the left ventricle. When DMVA assistance is provided to a heart afflicted with PHT, time interval 1083 is much smaller, in some cases even approaching a zero time interval, such that RV and LV blood flows are substantially simultaneous.

FIG. 2R depicts systolic compression of heart 60, at the completion thereof. At end systole, the RV pressure is only slightly less than the LV pressure, in contrast to the difference 1067 shown in FIG. 1J for a DMVA-assisted non-PHT heart. In some instances, a higher DMVA drive fluid pressure and/or systolic duration is required in order to complete systolic actuation for a PHT-afflicted heart. Alteration of such drive dynamics is provided due to the control capabilities of the present invention.

Figure 2S:
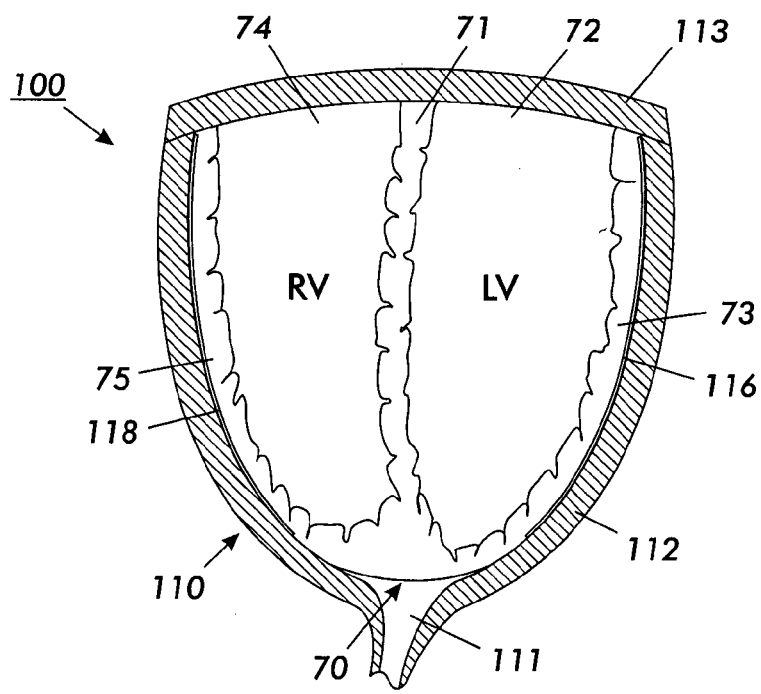
FIGS. 2S-2U are cross-sectional schematic views depicting operations and/or effects of a DMVA device on a heart afflicted with dilated cardiomyopathy.
Figure 2T:
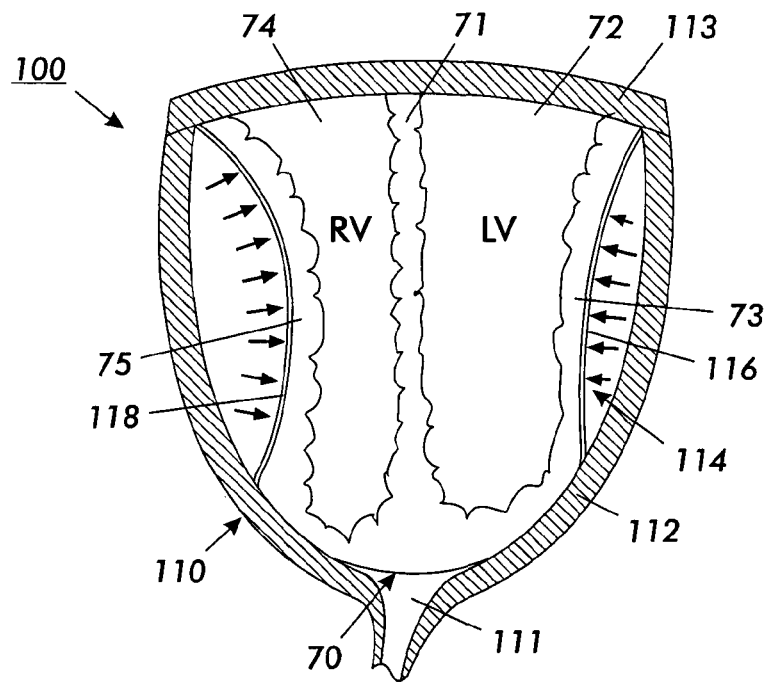
Figure 2U:
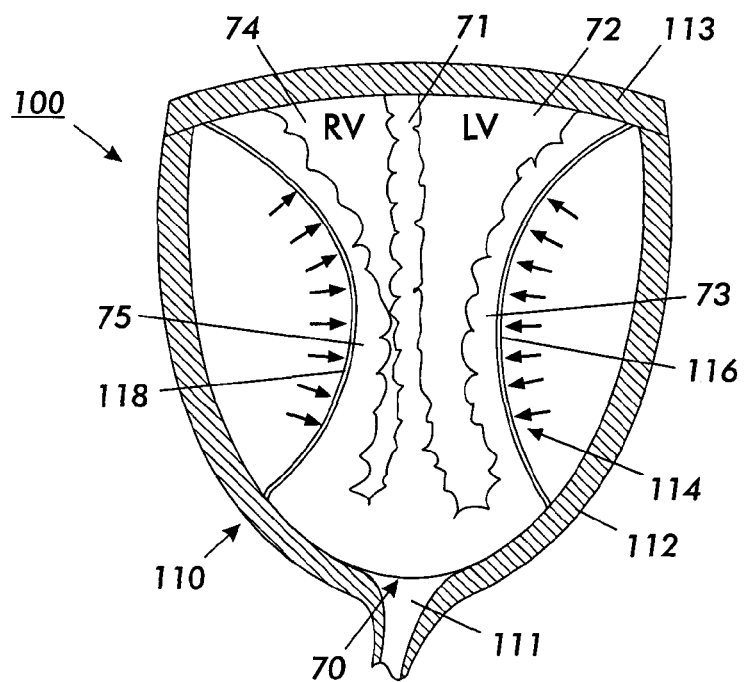

FIGS. 2S-2U are cross-sectional schematic views depicting operations and/or effects of a DMVA device on a heart afflicted with dilated cardiomyopathy. Referring to FIG. 2S, DMVA Cup 100 is depicted therein at the end of diastolic actuation. It can be seen that heart 70 afflicted with dilated cardiomyopathy (DCM) is characterized in particular by an overall dilation or enlargement of heart 70, accompanied by a thinning of left ventricle wall 73, right ventricle wall 75, and intraventricular septum 71, such that the volumes of left ventricle 72 and right ventricle 74 are increased. The operation of DMVA Cup 100 can be programmed and/or controlled such that the assistance rendered to heart 70 is specifically matched to the needs thereof due to the DCM condition.

FIG. 2T depicts systolic compression of heart 70, at a point approximately midway through such compression. It can be seen that the compression of right ventricle 74 and left ventricle 72 occur in a manner similar to that of non-DCM heart 30 of FIG. 2D. FIG. 2U depicts systolic compression of heart 70, at the completion thereof. At end systole, the ventricle volumes (particularly the LV volume) are greater than the corresponding end systole volumes of right ventricle 34 and left ventricle 32 of DMVA-assisted non-DCM heart 30 of FIG. 2I. Such larger end systolic volumes may be acceptable and more appropriate, since DMVA Cup 100 of FIG. 2U has displaced the blood volumes from left ventricle 72 and right ventricle 74 that are comparable to such volumes displaced by a healthy heart, which is a desired result. Delivery of such desired blood volumes is provided due to the control capabilities of the present invention. Alternatively, such large ventricles may require more complete compression to ensure no mismatch between RV and LV outputs. In such circumstances, the cycle rate can be significantly reduced with attendant reductions in systolic dP/dt and reductions overall compression rate which will result in less risk for trauma. Such adjustments are more favorable for long-term support which would more likely be required for potentially bridging such patients to cardiac transplant or other support devices.

In the present invention, the basic design of the Cup completely encompasses the heart from the atrio-ventricular groove (A-V groove) to the apex of the heart. Such a construction affords several advantages. A first advantage, enabled by liners of the present invention working with the Cup shell of the present invention, is the ability of the internal liner to compress or dilate the heart with a motion and force that is perpendicular to the heart tissue as previously described. A second advantage of the Cup's dynamic geometry of the present invention is the ability of the device to act and conform to both right and left ventricles in both systolic and diastolic assist, thereby supporting both pulmonary and systemic circulation. A third advantage is the ability of the device to better maintain both right ventricle and left ventricle function.

The Cup's dynamic geometry, and the fluid drive control means of the DMVA device of the present invention further provide for a full range of compression of the heart during systole, and a full range of expansion of the heart during diastole. This capability enables the DMVA device to provide a full range of Systolic Pressure-Volume Relationships and Diastolic Pressure-Volume Relationships that can be incorporated into drive control algorithms and result in optimal RV and LV pump performance. The present invention also provides total circulatory support without direct blood contact, thereby decreasing the risk of thromboembolic complications including clotting, strokes, and other associated severe morbidity, and in some cases death, as well as significant blood cell lysis, which can adversely affect blood chemistry and patient health. This feature also eliminates the need for anticoagulation drugs which reduces the risk for bleeding.

The present invention is a device that can be placed more rapidly than other existing devices from the start of the procedure, and therefore enables the unique ability to acutely provide life-sustaining resuscitative support, as well as continued short to long term support, as deemed necessary. All other cardiac assist device products (approved or in clinical trials) known to the applicants require surgical implantation with operative times that far exceed the ability of the body to survive without circulation. Physicians will welcome a device that can be placed when routine resuscitation measures are not effective. The number of failed resuscitations in the U.S. annually is estimated to be on the order of hundreds of thousands. The device of the instant invention can support the circulation indefinitely as a means of bridge-to-recovery, bridging to other blood pumps, bridging to transplant, or long-term total circulatory support.

The present invention utilizes a seal design that facilitates the sealability and long-term reliability of the seal. Specific critical seal design features include the seal length, thickness, shape, and durometer; and the location of the seal against the heart at the atrio-ventricular (AV) groove thereof. Additionally, one embodiment of the present invention utilizes a seal material that promotes the controlled infiltration of fibrin, which further improves the sealability and long-term reliability of the seal. Embodiments of the present invention also utilize a liner material that promotes the controlled infiltration of fibrin, which further improves diastolic action and helps to minimize motion of the liner against the heart, which further minimizes abrasion between the liner and heart tissues. In all instances, the degree of infiltration of fibrin is limited, so the DMVA Cup can be easily removed, once the patient has recovered or can safely be bridged to another therapy.

In a further embodiment, the present invention also utilizes a liner that is biodegradable and/or one that becomes permanently attached to the heart's surface (with or without biodegradable properties) such that the device can be removed by detaching the housing from the liner and the liner left in place. Such a liner can then instill favorable mechanical properties to the heart and/or provide drugs or other therapies (e.g., gene therapy etc. as described in greater detail elsewhere in this specification). Such therapeutic agents include but are not limited to anti-inflammatory agents, gene therapy agents, gene transfer agents, stem cells, chemo-attractants, cell regeneration agents, ventricular remodeling agents, anti-infection agents, tumor suppressants, tissue and/or cell engineering agents, imaging contrast agents, tissue staining agents, nutrients, and mixtures thereof. Such agents may be diffused or embedded throughout all or part of the liner, or alternatively, such agents may be contained within a gap formed within a liner comprising a first membrane in contact with the DMVA drive fluid, and a second membrane in contact with the heart, wherein the second membrane is permeable to the agent or agents.

Thereby, the Cup serves a dual purpose of support of the heart for a period of time, and incorporating a therapeutic liner that is responsible for continued treatment of the underlying disorder. The liner can simply provide additional structural integrity through its mechanical properties, serve as a delivery agent, or a combination of both. Furthermore, the liner may simply be inert in its action once the Cup is removed, but provides a simple, safe means of device detachment without otherwise risking bleeding or trauma to the heart that might result if it is removed. In yet another embodiment, and in the case wherein the seal has been caused to be ingrown with myocardial tissue but the remainder of the liner is not ingrown with such tissue, removal of the liner is effected by separation from the seal. Thus only the seal will be left attached to the heart after Cup removal.

Many existing cardiac assist devices, such as Left Ventricular Assist Devices (LVADs) require surgically perforating the cardiac chambers and/or major vessels. The present invention eliminates the need to perforate the heart or major vascular structures, and provides the ability to easily remove the device, leaving no damage to the heart and circulatory system once the heart heals and cardiac function is restored, or when the patient can safely be bridged to another therapy.

Existing cardiac assist devices, such as Left Ventricular Assist Devices (LVADs), which include axial flow pumps, produce blood flow that is non-physiologic and not representative of physiological pulsatile blood flow. The present invention avoids this condition and creates a near-normal physiological pulsatile blood flow with blood passing through the natural chambers and valves of the native heart, which is more beneficial for vital end-organ function and/or resuscitation, particularly as it relates to restoring blood flow following a period of cardiac arrest or low blood flow.

Furthermore, the present invention provides a controllable environment surrounding the heart, which can be used to apply pharmaceutical and tissue regeneration agents, even at localized concentrations that would not be tolerated systemically. This can be accomplished with or without use of a cup liner that is left on the heart following device removal, depending on the needs of the patient.

Furthermore, the present invention is able to augment heart function as is required to create and maintain required hemodynamic stability in a manner that is synchronized with the heart's native rhythm and in a manner that can alter the native rhythm toward a more favorable state. The purely complimentary nature of this support relieves the stress on the heart and promotes its healing.

As previously described, it is known that application of forces to the heart can cause potentially serious, irreversible damage to the heart by fatiguing and severely bruising the heart muscle, which can ultimately prevent it from functioning. The present invention avoids this very serious and potentially life-threatening condition by controlling the direction of forces applied to the heart and by controlling the magnitude of the difference between adjacent forces applied to the heart.

Figure 3A:
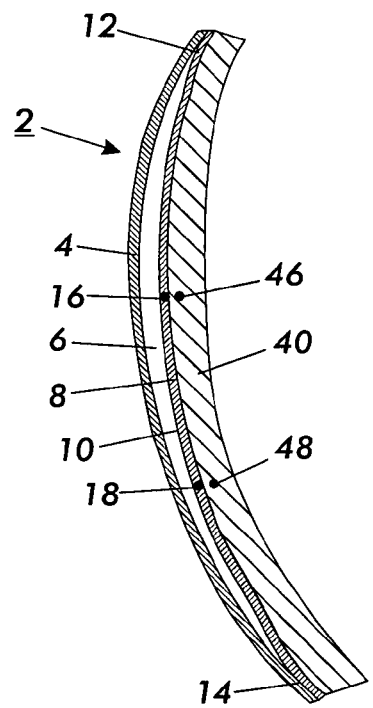
FIGS. 3A and 3B are cross-sectional schematic views depicting the action of a liner of a prior art DMVA device upon the wall of the heart.
Figure 3B:
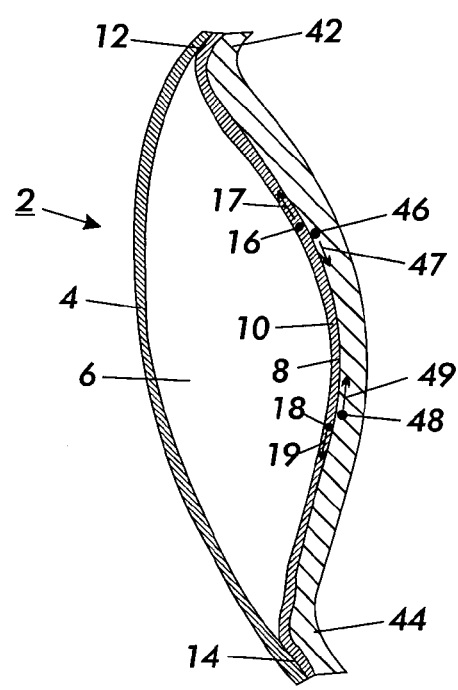

FIGS. 3A and 3B are cross-sectional schematic views depicting the action of a liner of a prior art DMVA device upon the wall of the heart. Referring to FIGS. 3A and 3B, in prior art DMVA devices such as that disclosed in U.S. Pat. No. 5,119,804 of Anstadt, there is provided a DMVA device 2 comprising a rigid or semi-rigid shell wall 4 (in contrast to the present invention's dynamic housing characteristics), and an elastic liner 10 joined to wall 4 at upper region 12 and lower region 14, thereby forming a cavity 6 between such liner and wall 4. The Cup and liner surround the heart, the ventricle wall 40 of which is contiguous with liner 10.

In operation of prior art device 2, a fluid is pumped into cavity 6, thereby displacing liner 10 inwardly from shell wall 4. This displacement forces ventricle wall 40 inwardly a corresponding displacement, thereby resulting in systolic action of the heart. However, it is noted that operation of the prior art device produces several effects that are undesirable. In FIG. 3A depicting the diastole state of the device and heart, at the interstice 8 of liner 10 and ventricle wall 40, point 16 in the liner 10 and point 46 in the ventricle wall 40 are substantially contiguous with each other; and point 18 in the liner 10 and point 48 in the ventricle wall 40 are substantially contiguous with each other. Subsequently it is apparent that in FIG. 3B depicting the systole state of the device and heart, at the interstice 8 of liner and ventricle wall 40, point 16 in the liner 10 and point 46 in the ventricle wall 40 have been displaced from other as indicated by arrows 17 and 47; and point 18 in the liner 10 and point 48 in the ventricle wall 40 have also been displaced from each other as indicated by arrows 19 and 49.

This displacement is a consequence of several factors relating to the manner in which the liner 10 is joined to the shell wall 4 and to the properties of the liner material, which can produce localized non-uniformities in the stretching of the liner. The resulting displacement of point 16 and point 46 away from each other, and point 18 and point 48 away from each other produces localized shear stresses in these regions, which is very undesirable as previously indicated. In addition, such displacement also results in slippage of the liner along the surface of the ventricle wall, which over time can result in the undesirable abrading of the surface of the ventricle wall.

It is also known that there are shear stresses created along the circumferential direction of the ventricle wall, i.e. in the horizontal direction in the ventricle wall. Without wishing to be bound to any particular theory, applicants believe that these stresses are due to the tendency of the liners of prior art devices to self-subdivide during systolic action into nodes, wherein uniform portions of the liner are displaced inwardly, divided by narrow bands of the liner that are displaced outwardly. In one embodiment described in U.S. Pat. No. 5,119, 804 of Anstadt, four such nodes are observed to be present when the device is operated without being fitted to a heart.

It is also apparent that regions 42 and 44 of ventricle wall 40, which are contiguous with upper region 12 and lower region 14 where elastic liner 10 is joined to wall 4, are subjected to intermittent high bending and shear stresses as a result of the repeating transitions between systolic and diastolic action of the device 2. Such intermittent bending and shear stresses can fatigue the heart tissue in these regions 42 and 44, and are thus clearly undesirable.

Figure 4A:
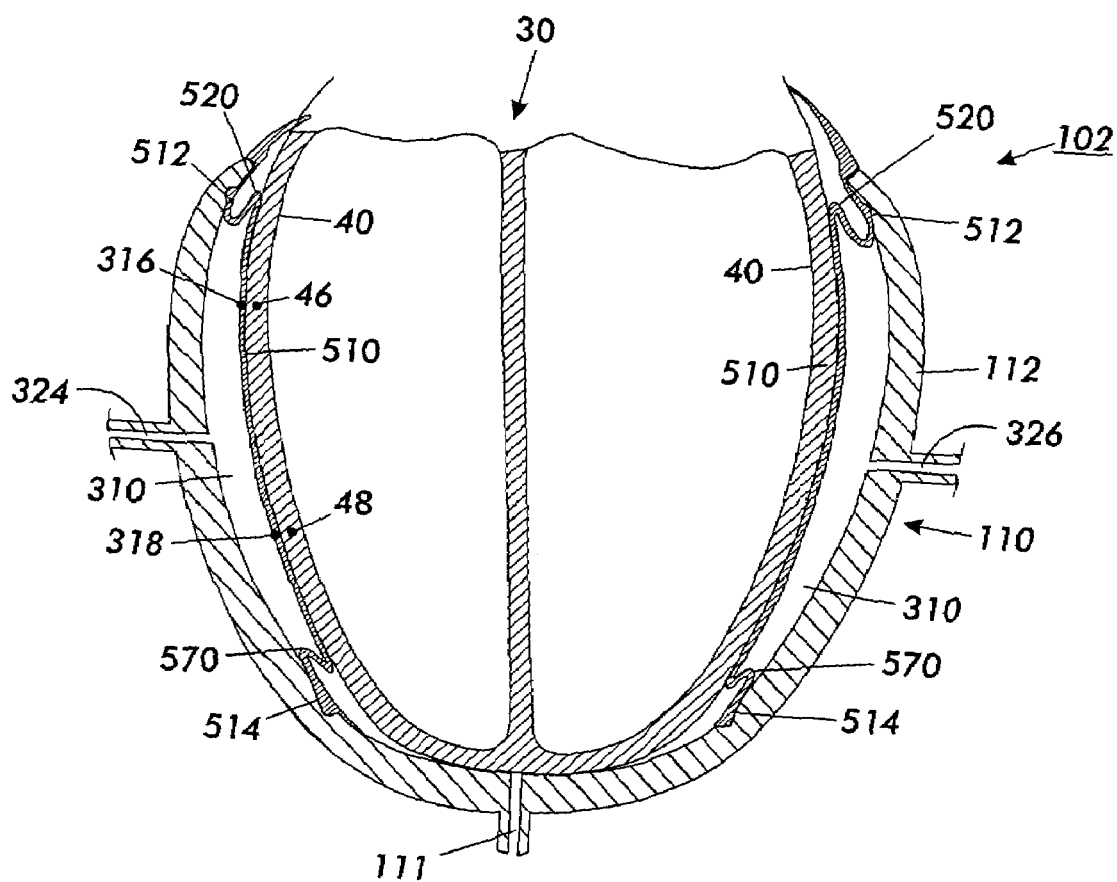
FIGS. 4A, 4B, and 4C are cross-sectional schematic views depicting the action of the liner of one preferred DMVA Cup of the present invention upon the wall of the heart.
Figure 4B:
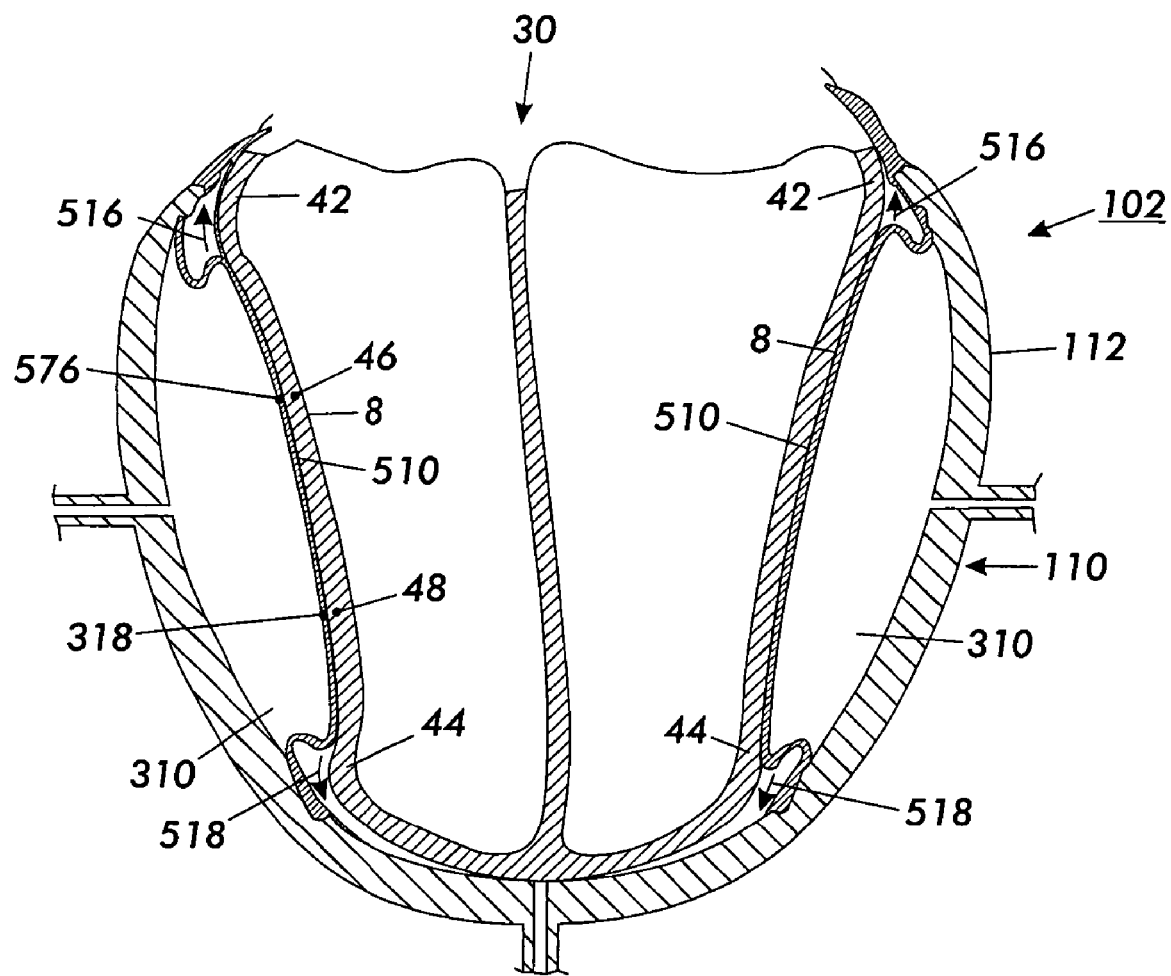
Figure 4C:
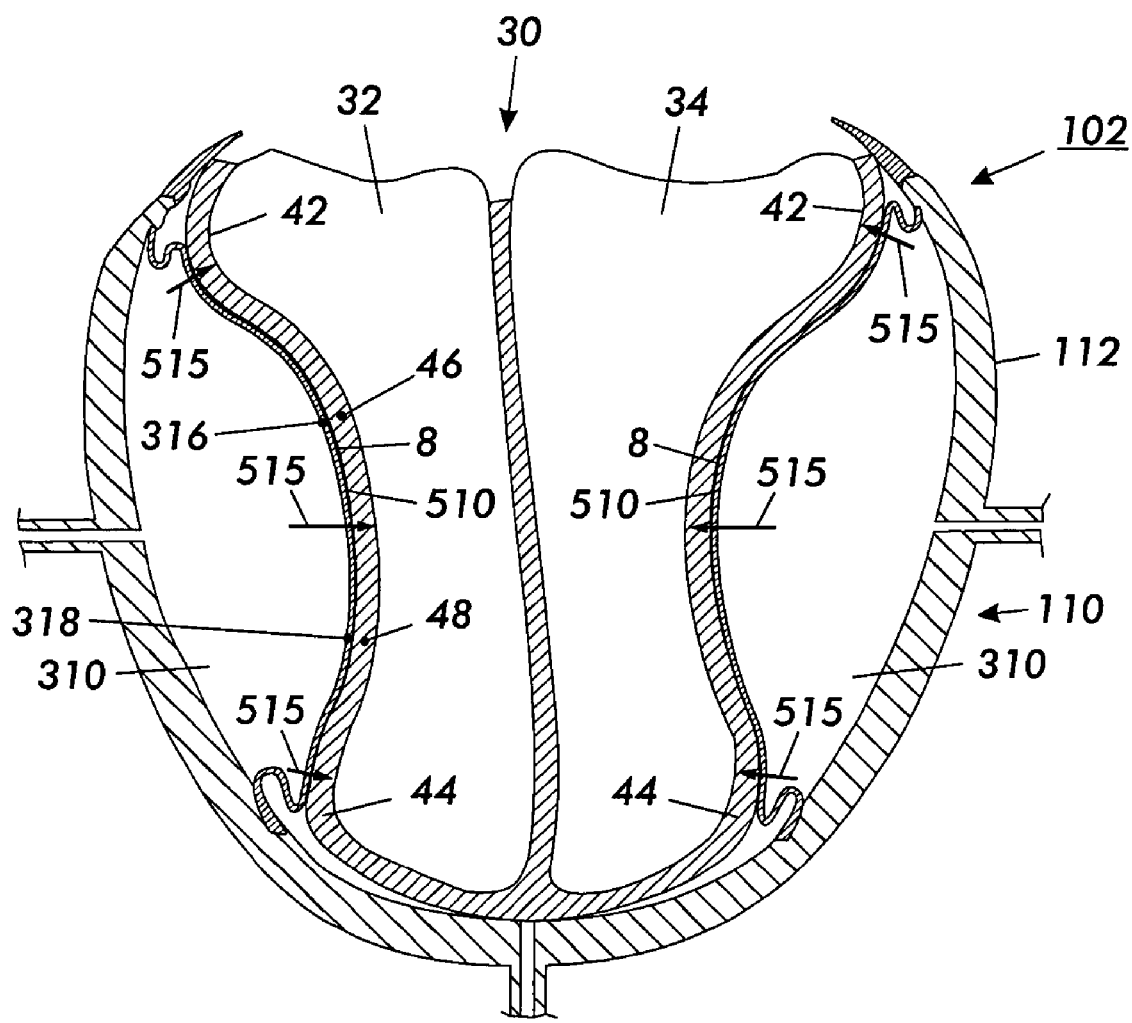

FIGS. 4A, 4B and 4C are cross-sectional schematic views depicting the action of the liner of the DMVA Cup of the present invention upon the wall of the heart. FIG. 4A depicts the diastole state of the device and the heart, FIG. 4B depicts the device assisting the systolic action of the heart at an intermediate stage of systolic action, and FIG. 4C depicts the completion of systolic action of the device and the heart. For the sake of simplicity of illustration, the heart 30 of FIGS. 4A-4C is shown with substantially thinner ventricle and septum walls than would typically be present in a DMVA assisted heart. Accordingly, there is no intent to limit the use of the DMVA device to a heart of such proportions.

Referring to FIG. 4A, DMVA device 100 comprises a cup-shaped shell 110 having a rigid or semi-rigid wall 112, and a liner 510 joined at upper region 512 and lower region 514 to shell wall 112. Liner 510 joined to shell wall 112 thus forms a cavity 310 (or potential space) therebetween, into which a fluid is intermittently delivered and withdrawn. Such intermittent delivery and withdrawal of fluid to/from cavity 310 effects the cycling of the DMVA device and the heart back and forth between the diastolic and systolic states.

In the preferred embodiment, liner 510 is provided with an upper rolling diaphragm section 520 and a lower rolling diaphragm section 570, the effect of which is to apply uniform pressure (positive or negative) to the surface of the heart that substantially eliminates stresses in cardiac tissue that otherwise result from the action of prior art devices previously described. In operation, liner 510 is completely unloaded and the action of the working fluid on the heart is purely hydrostatic and normal to the wall 40 thereof. In other words, this embodiment of the present invention prevents the formation of substantial forces within the heart muscle by applying forces to the heart that are perpendicular to and uniform over the surface of the heart. This embodiment also ensures that the magnitude of the difference between adjacent forces is very small, as the fluid pressure within cavity 310 is isotropic. The use of such rolling diaphragm, as well as preferred liner materials to be subsequently described in this specification, eliminate the formation of shear forces within the heart muscle which leads to bruising damage to the heart tissue which in turn leads to muscle fatigue and potential failure of the heart. Thus the DMVA apparatus of the present invention is atraumatic, i.e. the apparatus does not inflict any injury upon the heart.

Rolling diaphragm sections 520 and 570 at the top and bottom of liner 510 are intended to reduce shear stresses in cardiac tissue that otherwise would result from the action of the DMVA Cup 100. Regardless of how elastic the material chosen for the liner 510 is there will be some stress induced in cardiac tissue if the prior art liner configuration is used. As described previously, this is because there will be some central axis where there is no vertical motion (slip) or shear stress relative to the adjacent heart wall, but above and below this axis the liner will expand during systole and contract during diastole while the heart wall will not change in exactly the same manner. Thus, the only way known to the applicants to reduce this lateral shear stress is to create a situation where the liner is completely unloaded and the force of the working fluid on the heart is purely hydrostatic, or normal to the surface. This is a critical capability of one DMVA device of the present invention.

The rolling diaphragm geometry follows the approach used in traditional rolling diaphragm pumps and fluid-to-fluid isolators. The design also greatly reduces stress concentrations at the extreme upper and lower points where the liner 510 attaches to shell 110, thus increasing the reliability of liner 110, further enabling the use of materials that may previously not have been considered because of their susceptibility to fatigue failure in a prior art liner configuration.

Referring again to FIG. 4A, the rolling diaphragm liner 510 comprised of upper rolling diaphragm section 520 and lower rolling diaphragm section 570 also eliminates the single flexure regions of the diaphragms used in earlier Cup designs. As was previously described and shown in FIGS. 3A and 3B, such regions 12 and 14 of prior art device 2 where elastic liner 10 is joined to wall 4, are subjected to intermittent high bending and shear stresses as a result of the repeating transitions between systolic and diastolic action of such device 2.

In one embodiment, rolling diaphragm liner is directly bonded to DMVA Cup shell wall 112 at upper section 520 and lower section 570 thereof. FIG. 16B depicts one embodiment of such a bond between liner 540 and Cup shell wall 112 at lower joint region 514 therebetween. Details of this structure are provided subsequently in this specification, also in conjunction with FIG. 16A. Referring again to FIG. 4A, it will be apparent that a similar structure can be provided for upper joint region 512 as is described subsequently in this specification and shown in detail in FIG. 16B.

As a result of such liner structures for upper joint region 512 and lower joint region 514, the maximum deflection of rolling diaphragm liner 510 at the upper joint region 512 and lower joint region 514 is reduced. Stated another way, the bending of the diaphragm at joint regions 512 and 514 is distributed over a larger length of the rolling diaphragm liner 510. The effect of this design is to reduce the bending strain at any one point in the diaphragm 510 as it is actuated. Reducing the bending strain substantially increases the life of diaphragm 510 and therefore significantly improves its reliability.

Referring to FIG. 4B, it can be seen that the displacement of the liner 510 by the filling of cavity 310 with fluid effects the systolic action of the heart without inducing substantial stresses in the ventricular wall 40 thereof. At the interstice 8 of liner 510 and ventricle wall 40, point 316 in liner 510 and point 46 in ventricle wall 40 have remained substantially contiguous with each other, and point 318 in liner 310 and point 48 in ventricle wall 40 have remained substantially contiguous with each other. In addition it can be seen that the radius of curvature in upper region 42 and lower region 44 of ventricle wall 40 is substantially greater than such radius of curvature resulting from the use of the prior art device as depicted in FIG. 3B. Thus the bending stresses produced in regions 42 and 44 of ventricular wall 40 are substantially less as a result of the use of rolling diaphragm liner 510 of the present invention. It can be further seen that diaphragm liner 510 is engaged with ventricle wall 40 in a progressing rolling action as indicated by upper arrows 516 and lower arrows 518.

FIG. 4C is a cross-sectional view depicting the DMVA apparatus assisting a heart, at the completion of systolic action of the device and the heart. Referring to FIG. 4C, the displacement of liner 510 of apparatus 102 is at its maximum value, having squeezed ventricular walls 8 to an optimal conformational change wherein heart 30 has an approximately "hour-glass" or "apple-core" shape, with a minimum diameter, (i.e. the "cardiac core diameter") at the plane defined by opposing arrows 515. At the completion of systole, apparatus 100 has caused, or assisted in the displacement of, a cardiac ejection fraction of approximately 0.55 from left ventricle 32 and right ventricle 34.

Even at the maximum displacement of liner 510, it can be seen that at the interstice 8 of liner 510 and ventricle wall 40, point 316 in liner 510 and point 46 in ventricle wall 40 have remained substantially contiguous with each other, and point 318 in liner 310 and point 48 in ventricle wall 40 have remained substantially contiguous with each other; and that the radius of curvature in upper region 42 and lower region 44 of ventricle wall 40 is substantially greater than such radius of curvature resulting from the use of the prior art device as depicted in FIG. 3B. Thus the bending stresses produced in regions 42 and 44 of ventricular wall 40 are maintained at a low value.

Referring again to FIGS. 4B and 4C, it can also be seen that liner 501 has rolled progressively as indicated by arrows 516 and 518, to a maximum extent along upper ventricle regions 42 and lower ventricle regions 44 shown in FIG. 4C. The force applied by liner 510 upon ventricle walls 40 at all points along interstice 8, resulting from the isotropy of the fluid pressure within cavity 310, is substantially perpendicular to ventricle walls 40, as indicated by arrows 515. Thus the presence of any shear force in the ventricle walls 40 is minimized.

In the preferred embodiment of apparatus 102, liner 510 is deployed against ventricle walls 40 by a progressive rolling action as indicated by arrows 516 and 518. In contrast, prior art DMVA devices deploy the liner against the ventricle walls exclusively by an elastic and non-isotropic stretching of such liner, resulting in shear forces and/or abrasive slippage of such liner along the ventricle walls, as previously described. Thus the rolling diaphragm liner 501 of one embodiment of apparatus 102 has significant advantages over prior art DMVA devices.

Referring again to FIG. 4A, DMVA apparatus 102 is provided with a first DMVA drive fluid port 324 and a second DMVA drive fluid port 326. In one embodiment, the portion of cavity 310 that is in communication with drive fluid port 324 is made separate from the portion of cavity 310 that is in communication with drive fluid port 326. In addition, each of ports 324 and 326 are provided with separate DMVA fluid supply/withdrawal means. In this manner, the fluid cavity in communication with drive fluid port 324 can be filled and emptied independently of the fluid cavity in communication with drive fluid port 326, so that right ventricle 32 (see FIG. 2A) can be actuated independently of left ventricle 34 (see FIG. 2A).

Figure 5A:
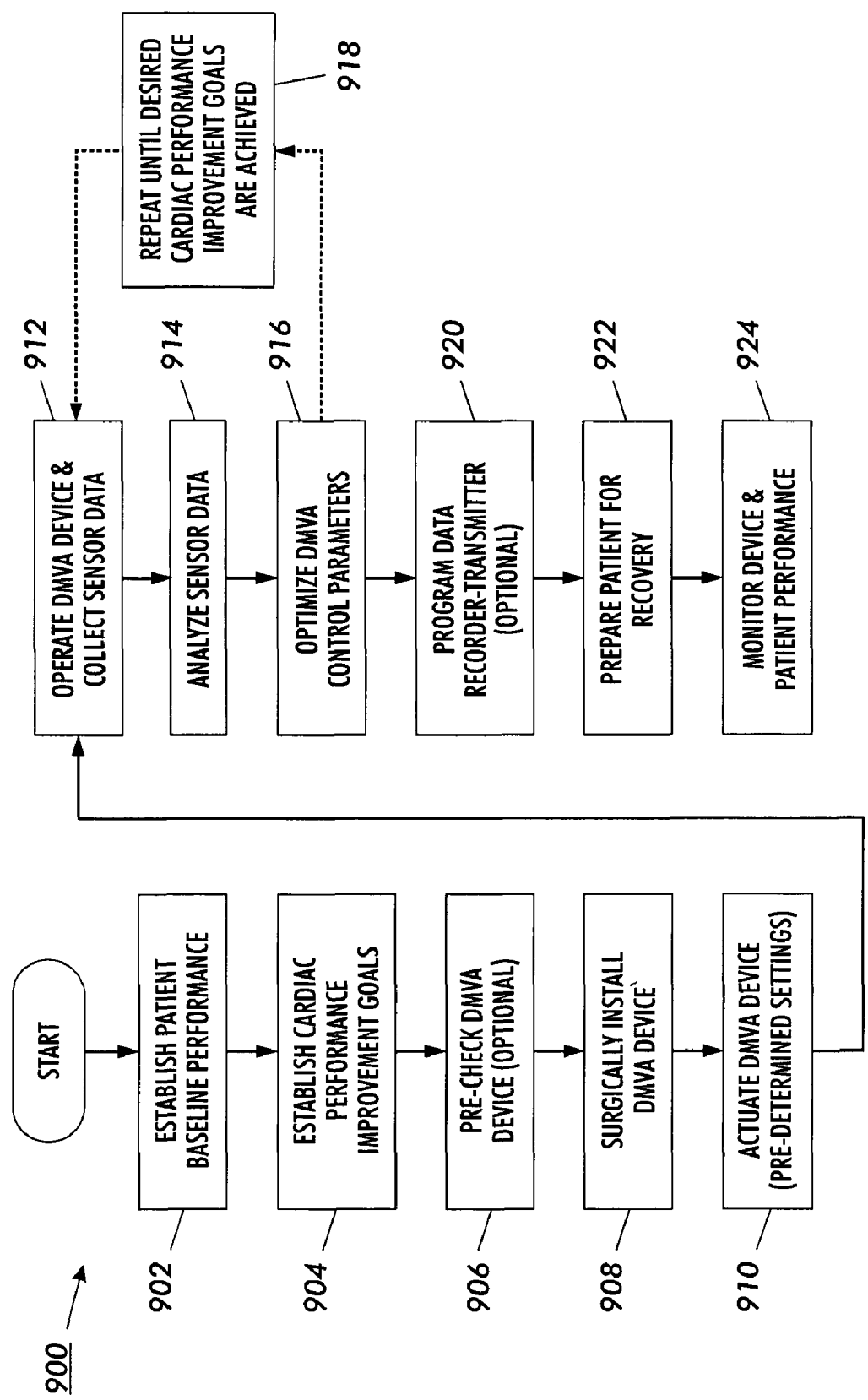
FIG. 5A is a flow chart of a general method for using sensor data to guide DMVA installation and assess cardiac performance under the influence of DMVA.

A more detailed description of Invention Aspect 1, which is a method for using sensor data in conjunction with cardiac assist devices, is now presented. FIG. 5A is a flow chart depicting such a method for using sensor data to guide DMVA installation and to assess cardiac performance under the influence of DMVA. Referring to FIG. 5A, method 900 includes the following steps 902-924, which are offered here as illustrative and not limiting:

In step 902, the patient's pre-DMVA cardiovascular state of health is established, which provides a baseline from which to assess improvement in patient health as a result of DMVA. Subsequently, in step 904 required performance improvement objectives are established. In step 904, the patient's existing pre-DMVA cardiovascular state of health is compared to normal cardiac performance for the patient's population group and clinical condition. The difference between the patient's baseline performance and normal population group and clinical condition is used to help establish DMVA performance improvement objectives.

Step 906 is an optional pre-check of the DMVA device to verify critical aspects of performance. In step 908, the DMVA device is surgically installed in the patient. The DMVA device is subsequently actuated using predetermined settings in step 910, based upon data from steps 902 and 904.

In step 912, the DMVA device is operated, and sensor data is collected to verify such factors as follows: proper positioning of the DMVA device on the heart; proper sealing of the DMVA device against the heart; the absence of excessive fluid between the heart and the inner wall of the DMVA device, and that the DMVA control parameters are achieving the desired systolic and diastolic action. Sensors and data acquisition means for performing such data collection are described later in this specification.

In step 914, acquired data on the performance of the DMVA Cup device, and on the condition of the patient are analyzed by computer/process controller means. Included in step 914 is the integration of other cardiovascular data (e.g. blood pressure), other cardiovascular devices (e.g. pacemakers, balloon pump, etc.) and/or the effects of initiation of other features incorporated into the Cup such as e.g., pacing electrodes.

Initial DMVA control parameters, such as the volume and timing of fluid delivery to the DMVA Cup, may not achieve optimum hemodynamic performance. Thus in step 916, the DMVA control parameters are adjusted to achieve desired hemodynamic performance (e.g., achievement and verification of balanced RV and LV outputs, optimization of such outputs to ensure adequate overall cardiac output, and optimization to avoid cardiac injury, thereby ensuring atraumatic operation of the DMVA apparatus). Such adjustment may be an iterative process as indicated by step 918, wherein steps 912, 914, and 916 are repeated. In such an iteration, additional sensor data is collected (a second step 912) and analyzed (a second step 914) after the initial adjustment of DMVA control parameters to determine if additional adjustment (a second step 916) is required. This sub-process (step 918) is repeated until desired hemodynamic performance is achieved.

In one embodiment of method 900 of FIG. 5A, wherein a data recording and transmitting system is utilized, the physician activates such unit in step 920, including setting acceptable levels of hemodynamic performance and programming these limits into the data recorder-transmitter. The data recorder/transmitter can then be remotely interrogated by the physician to evaluate hemodynamic performance. Alternately, the data recorder-transmitter can automatically report to the physician unacceptable trends or levels of hemodynamic performance, which could necessitate medical attention or changes in patient behavior.

With the DMVA device properly installed in the patient, and operating at an optimal steady-state condition, all surgical procedures are completed and the patient is placed into recovery in step 922. The condition of the patient and the performance of the DMVA device is then monitored as an ongoing process, with further intervention or adjustment of DMVA parameters made as required in step 924. Specific methods and apparatus to monitor the cardiac performance and overall condition of the patient are well known and are described elsewhere in this specification.

Figure 5B:
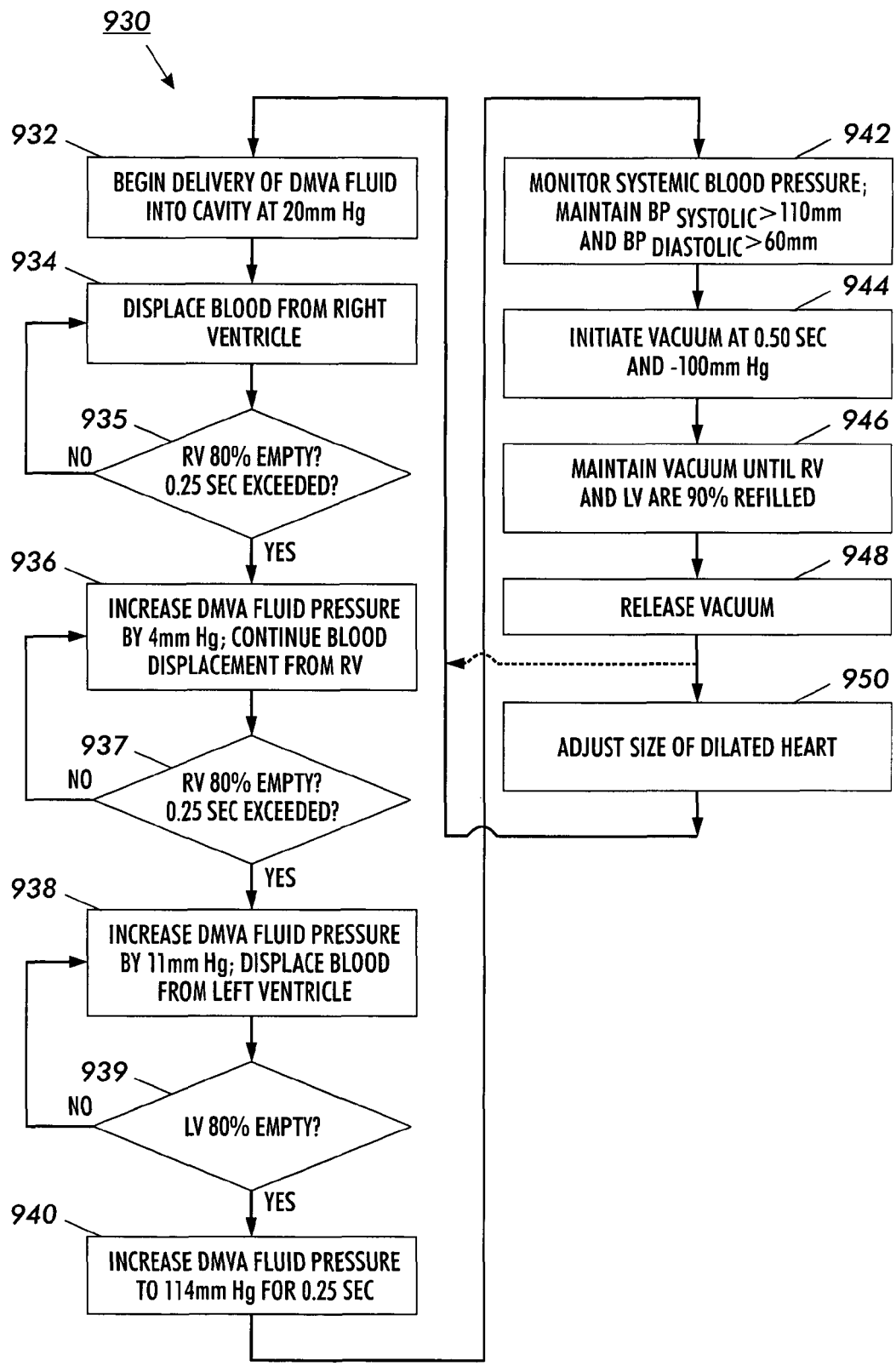
FIG. 5B is a flow chart of a more specific algorithm for automatically adjusting the function of an embodiment of the DMVA Cup.

More detailed descriptions of Invention Aspect 4, which is directed to methods and algorithms for specific feedback control of the DMVA Cup are now presented, with reference in particular to FIGS. 5B.

FIG. 5B is a flow chart of one specific algorithm for automatically adjusting the function of an embodiment of the DMVA Cup. It is to be understood that this algorithm is one example of many that are possible, which may be defined and selected according to the particular patient and cardiac disorder for which DMVA assistance is indicated. For a better understanding of the following description of algorithm 930 of FIG. 5B, reference may also be had to FIGS. 1M, and 2A-2I, which were previously described in this specification. It is to be understood that pressures provide in millimeters of mercury (Hg) are gage pressures, with 0 mm Hg being ambient atmospheric pressure.

Referring to FIG. 5B and FIG. 2C, method or algorithm 930 begins at the initiation of systole with step 932, wherein delivery of drive fluid into cavity 119 of DMVA device 100 begins, at a delivery pressure of 20 mm Hg. In step 934, blood is displaced from right ventricle 34. Blood volume and/or flow sensors, and imaging and/or other cardiac state sensors described elsewhere in this specification provide data to the DMVA controller, enabling check 935. If the RV is less than 80% empty at 0.25 sec, the DMVA drive fluid pressure is increased in step 936. The check is repeated in step 937, and the DMVA drive fluid pressure is again increased in step 938. Blood displacement from the left ventricle begins, and the heart transitions through the state shown in FIG. 2D. A check 939 is made of the volume of the left ventricle, and when the left ventricle is 80% empty, the DMVA drive fluid pressure is increased to 114 mm in step 940. Blood pressure is monitored and maintained to the completion of systole in step 942 as shown in FIG. 2I.

Diastole is then initiated in step 944 by applying vacuum to the DMVA drive fluid at a low level (e.g. −100 mm Hg) for 0.5 seconds. Such vacuum is maintained until data input to the DMVA controller indicates that the RV and LV are 90% refilled. The vacuum is then released in step 948. In an optional step 950, the vacuum is sustained for a brief additional period in order to adjust the size of the dilated heart to a slightly larger state.

A more detailed description of Invention Aspect 5, which is directed to Specific sensor types and sensor locations is now presented with reference to FIGS. 6A-13.

Figure 6A:
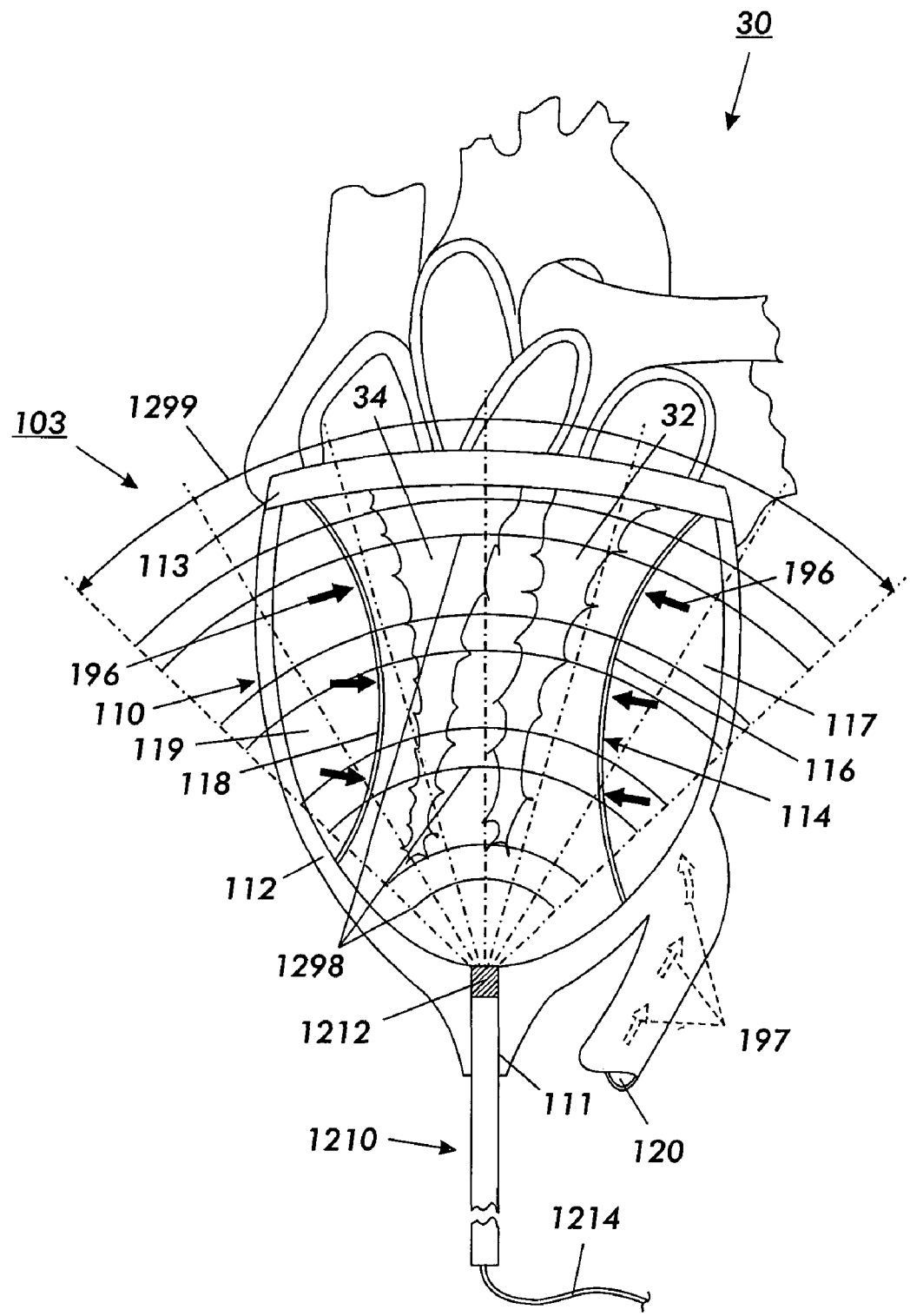
FIGS. 6A, 6B, and 6C are schematic representations of a sensor installed in a DMVA Cup engaged in systolic actuation.
Figure 6B:
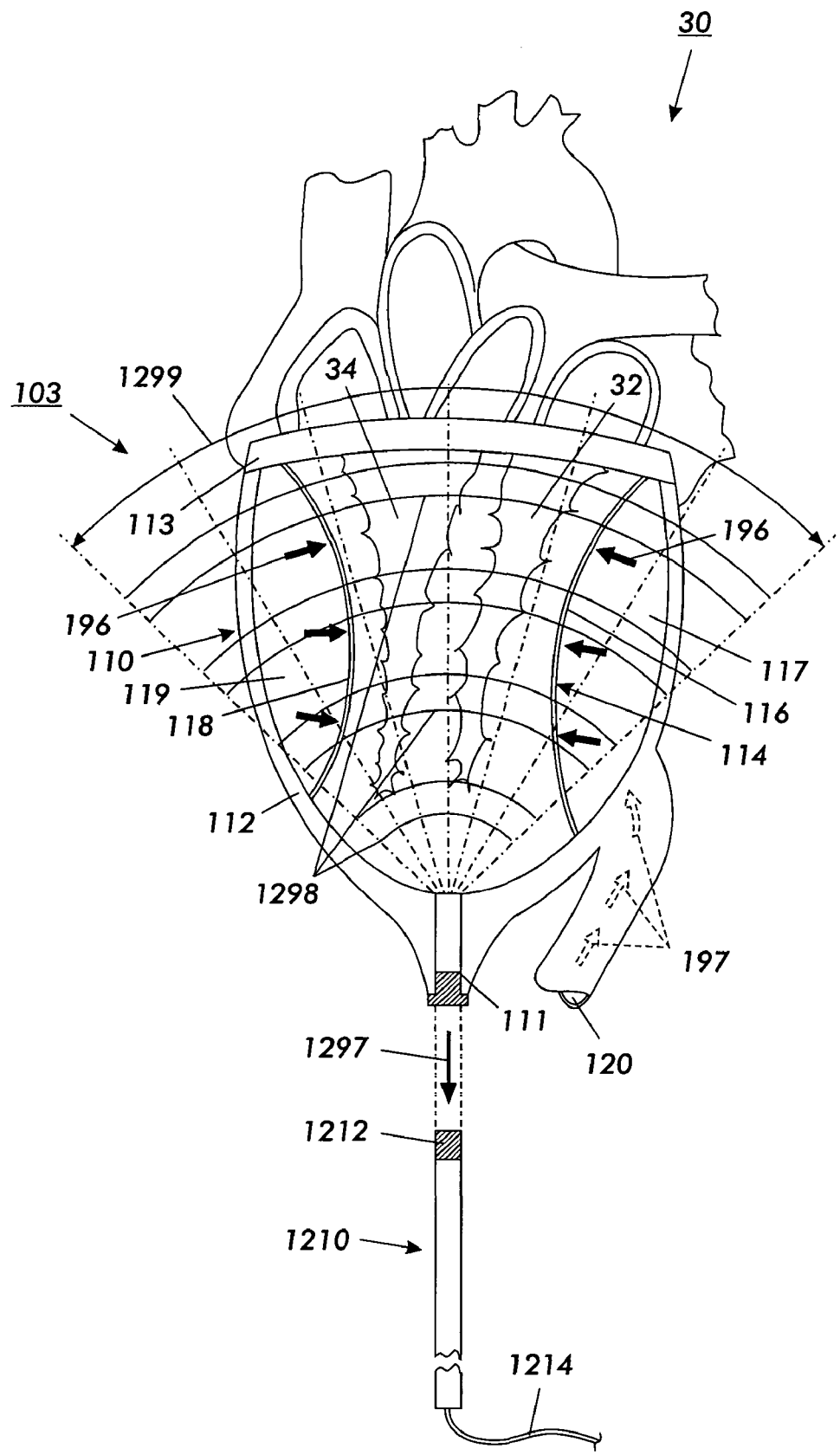
Figure 6C:
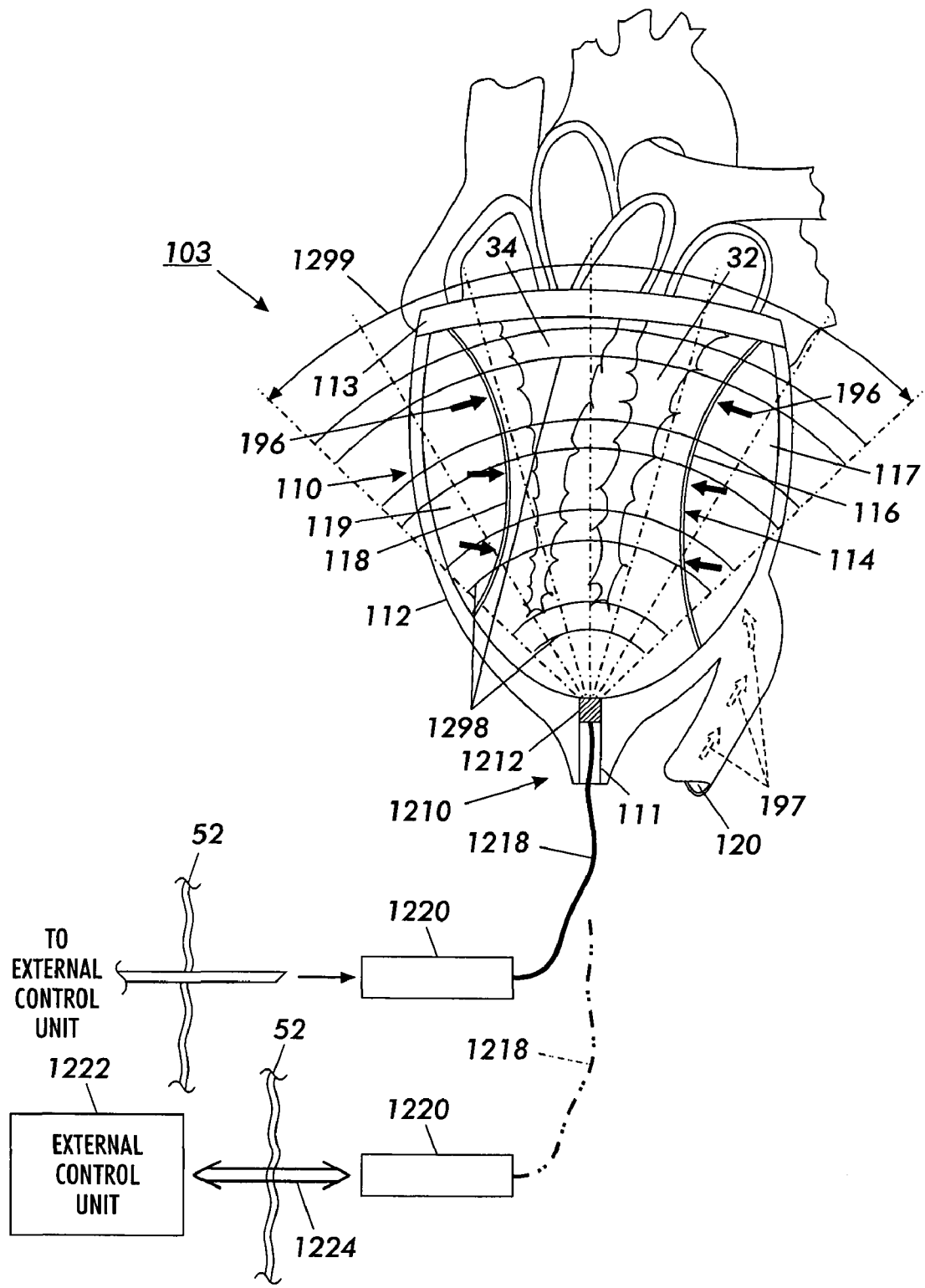
Figure 7:
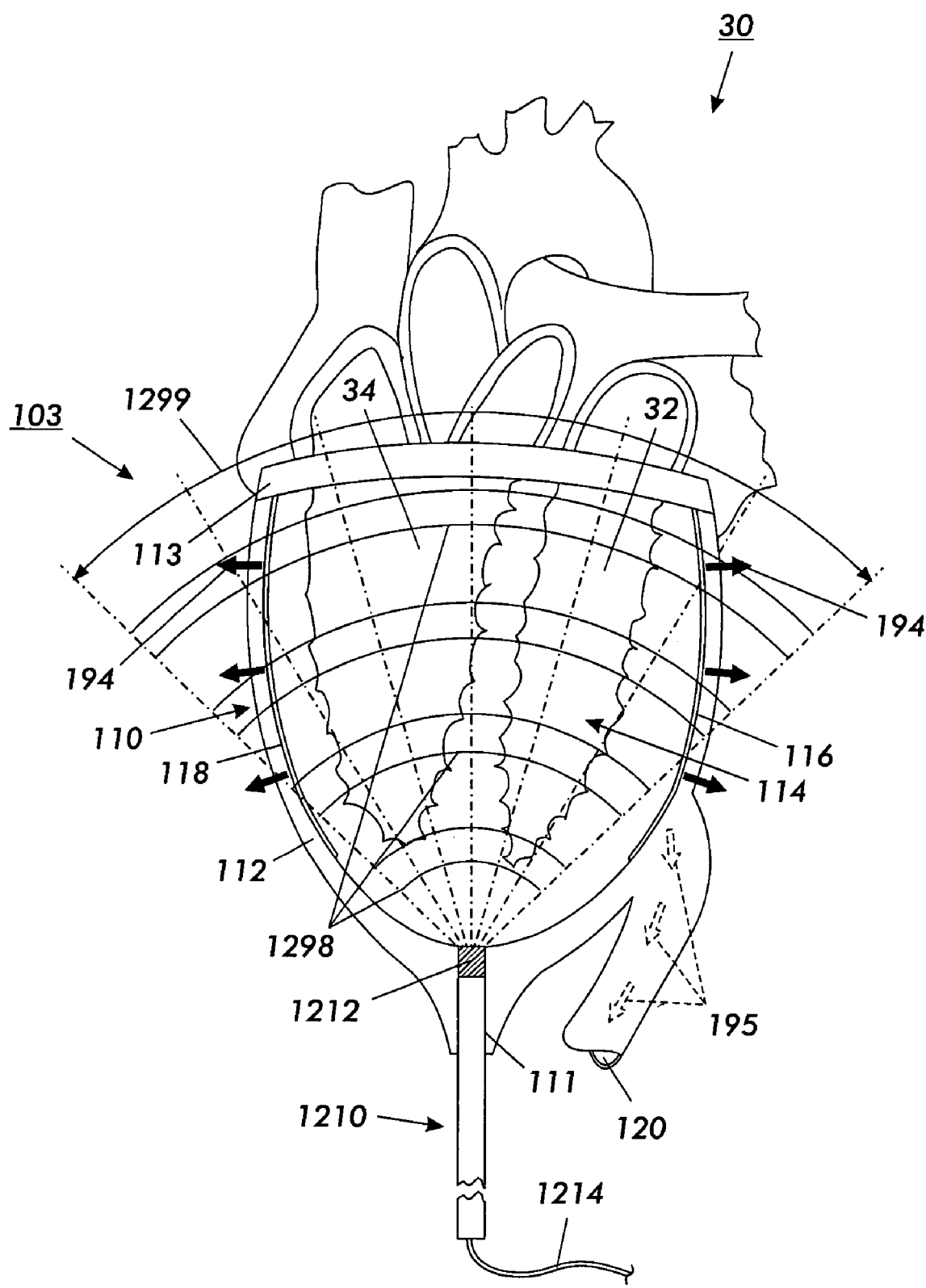
FIG. 7 is a schematic representation of a sensor installed in a DMVA Cup engaged in diastolic actuation.

FIGS. 6A, 6B, and 6C are schematic representations of a sensor installed in a DMVA Cup during systolic actuation, and FIG. 7 is a schematic representation of a sensor installed in a DMVA Cup during diastolic actuation. FIG. 6A is a preferred embodiment of the present invention, wherein sensor 1210 comprises an ultrasound probe(s) integrated directly and permanently into DMVA Cup 103. In this embodiment, sensor 1210 collects the types of data previously described in "Invention Aspect 2" during and following installation of the DMVA Cup 103. Other aspects of DMVA Cup 103 of FIG. 6A are similar to other DMVA Cups described in this specification, and include shell 110; vacuum duct 111; liner 114 comprising left portion 116 and right portion 118; liner inflation/deflation duct 120; working fluid as indicated by phantom arrows 197 shown flowing into the space between shell 110 and liner 114, thereby inflating liner 114 and compressing heart 30; and seal 113. In FIG. 6A, left ventricle 32 and right ventricle 34 of heart 30 are shown in systolic actuation, as indicated by bold arrows 196.

In the DMVA Cup 103 of FIG. 6A, sensor 1210 is disposed within vacuum duct 111, with it being understood that sufficient clearance is provided between sensor 1210 and the wall of vacuum duct 111 to enable vacuum to be applied within Cup shell 110, thereby seating and retaining heart 30 therein. In other embodiments, DMVA Cup 103 is provided with separate attachment ports for sensor 1210 and for vacuum application. Sensor 1210 further comprises cable 1214, which is used to link sensor transducer/receiver tip 1212 with externally located receiver and/or control unit (not shown).

In operation, sensor 1210 provides an approximately conical field of view 1299 of heart 30, resulting from the propagation of ultrasound as indicated by arcs 1298, and the reflection of such ultrasound back to tip 1212 by the objects within shell 112. Such reflected ultrasound is used by data acquisition and analysis means to provide images of the DMVA Cup shell 110, cavities 117 and 119, liner 114, and right and left ventricles 34 and 32 of heart 30. In particular, ultrasonic probe 1210 enables the capturing, observation, and measurement of changes in LV and RV geometry, LV and RV volume, relative RV/septal and LV/septal interactions, cup-epicardial interactions, and localized blood flow velocities in the ventricles, atria, and aorta, and evaluations of these variables to achieve optimal DMVA drive settings under a variety of physiologic conditions.

Reference may be had to the volume, pressure, and flow relationships of FIGS. 1A-1M; and to the illustrations of proper DMVA assistance provided in FIGS. 2A-2O; and to the illustrations of improper DMVA assistance of FIGS. 2P-2U. Sensor 1210 of DMVA apparatus 103 of FIGS. 6A-7 provides the capability of observation, measurement, and acquisition of such data for the DMVA apparatus and for the heart assisted therein, over the range of circumstances depicted in FIGS. 1A-2U. The DMVA apparatus is further provided with control capabilities to use such information to optimize the assistance to the heart, as will be described subsequently in this specification.

FIG. 7 is similar to FIG. 6A except that DMVA Cup 103 and heart 30 are shown in diastolic actuation. Working fluid is shown flowing completely out of the cavities 117 and 119 between shell 110 and liner 114 as indicated by arrows 195 and 194, thereby deflating liner 114, and expanding heart 30, enabling left ventricle 32 and right ventricle 34 to fill with blood.

In yet another embodiment of the present invention depicted in FIG. 6B, sensor 1210 is an ultrasound probe integrated directly and temporarily into the Cup to collect the same data as described for FIG. 6A, but further enabling the sensor 1210 to be removed following verification of proper Cup installation and initial operation as indicated by arrow 1297. Referring to FIG. 6B, plug 1216 or other suitable sealing means, including self-sealing means such as one-way valves, etc. is deployed from tip 1212 of sensor 1210, and used to prevent fluids from passing into shell 110 after sensor 1210 is removed.

In yet another embodiment of the present invention depicted in FIG. 6C, sensor tip 1212 of sensor 1210 is permanently installed within shell 112 of DMVA Cup 103, and an electrical interface 1220 is connected to sensor 1210 by cable 1218. Electrical interface 1220 is then connected to external instrumentation sensor control unit 1222 either percutaneously through skin 52 such as with a puncture, or transcutaneously through skin 52 such as via telemetry pulses 1224.

Figure 10A:
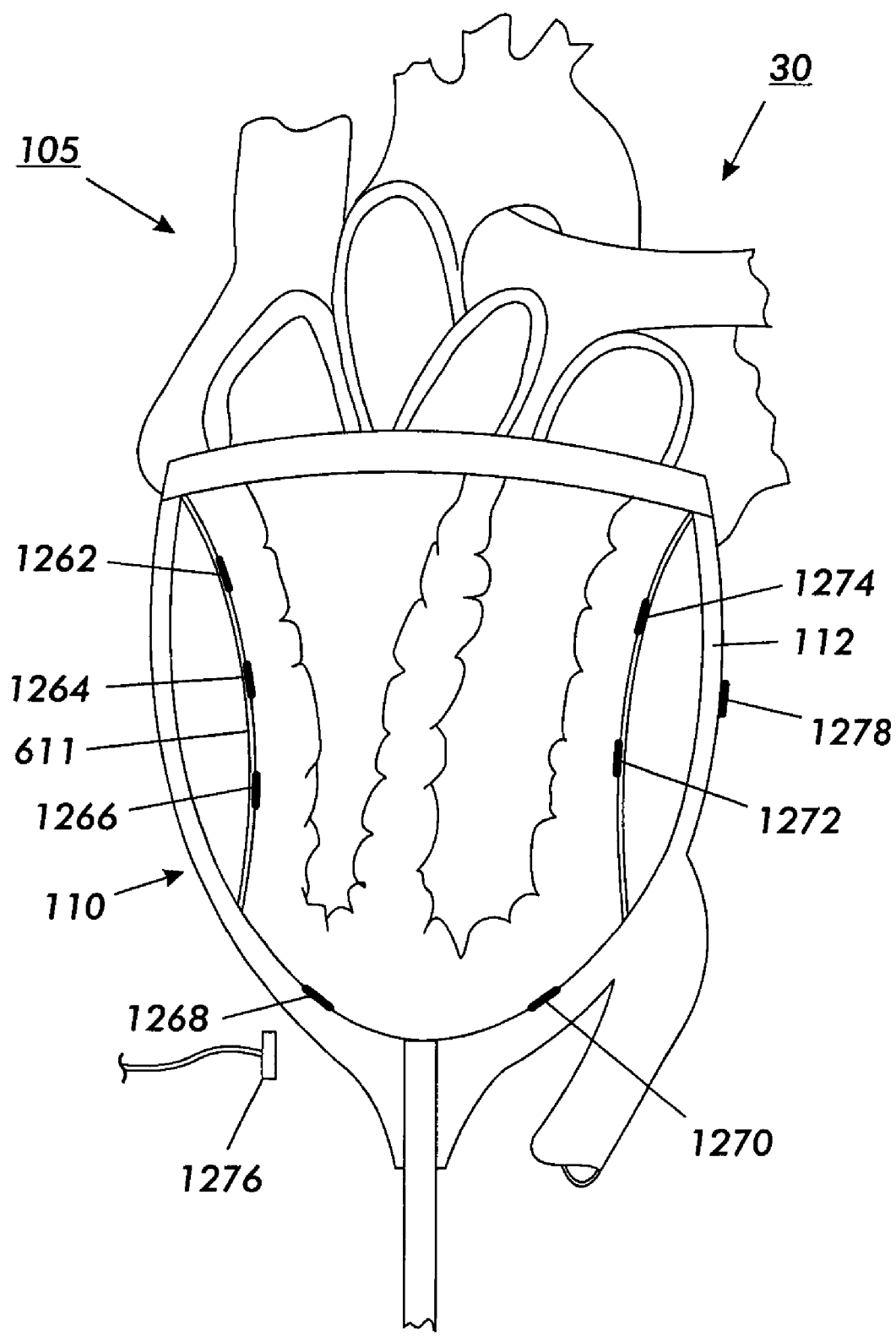
FIG. 10A is a schematic representation of electrophysiological sensors and/or electrodes integrated into a DMVA device, shown during systolic compression of a heart.

In a yet further embodiment of the present invention, the ultrasound image is not provided by a single sensor such as sensor 1210, but is provided by one or more pairs of individual piezoelectric crystals that are placed on either side of the heart, and utilize time-of-flight measurements and simple linear echo measurements to detect the position of tissue/fluid interfaces relative to themselves. Referring to FIG. 10A, any of the sensor elements 1262, 1264, 1266, 1272, and 1274 shown on the liner, or any of the sensor elements 1268, 1270, and 1278, shown on the shell, may be such piezoelectric crystals. These crystals may be used as individual pairs, or in such two-dimensional or three-dimensional combinations to provide the desired information relating to shape and movement of myocardial wall tissue and/or blood.

In yet another embodiment of the present invention (not shown) an external ultrasound probe is used as above.

Referring again to FIGS. 6A and 7, in yet another embodiment of the present invention, sensor 1210 is a magnetic resonance imaging (MRI) coil integrated directly and permanently into the Cup shell 110. These embodiments enable the sensor to collect the types of data outlined above in "Invention Aspect #2" during and following installation of the Cup on the heart 30 of the patient. In various embodiments, MRI coil 1210 can be a receive only coil, a transmit only coil, or a transmit and receive coil.

Referring again to FIG. 6B, in yet another embodiment of the present invention, sensor 1210 is a MRI coil integrated directly and temporarily into the Cup to collect the same data as described for FIG. 6A, but further enabling the coil to be removed following verification of proper Cup installation and initial operation as indicated by arrow 1297. Referring to FIG. 6B, plug 1216 or other suitable sealing means, including self-sealing means such as one-way valves, etc. is deployed from tip 1212 of sensor 1210, and used to prevent fluids from passing into shell 110 after coil 1210 is removed.

Referring again to FIG. 6C, in yet another embodiment of the present invention, MRI coil 1210 is permanently installed within shell 112 of DMVA Cup 103 and an electrical interface 1220 is connected to sensor 1210 by cable 1218. Electrical interface 1220 is then connected to external instrumentation sensor control unit 1222 either percutaneously through skin 52 such as with a puncture, or transcutaneously through skin 52 such as via telemetry pulses 1224.

In yet another embodiment of the present invention (not shown) an external MRI coil is used as in the foregoing description.

Figure 8:
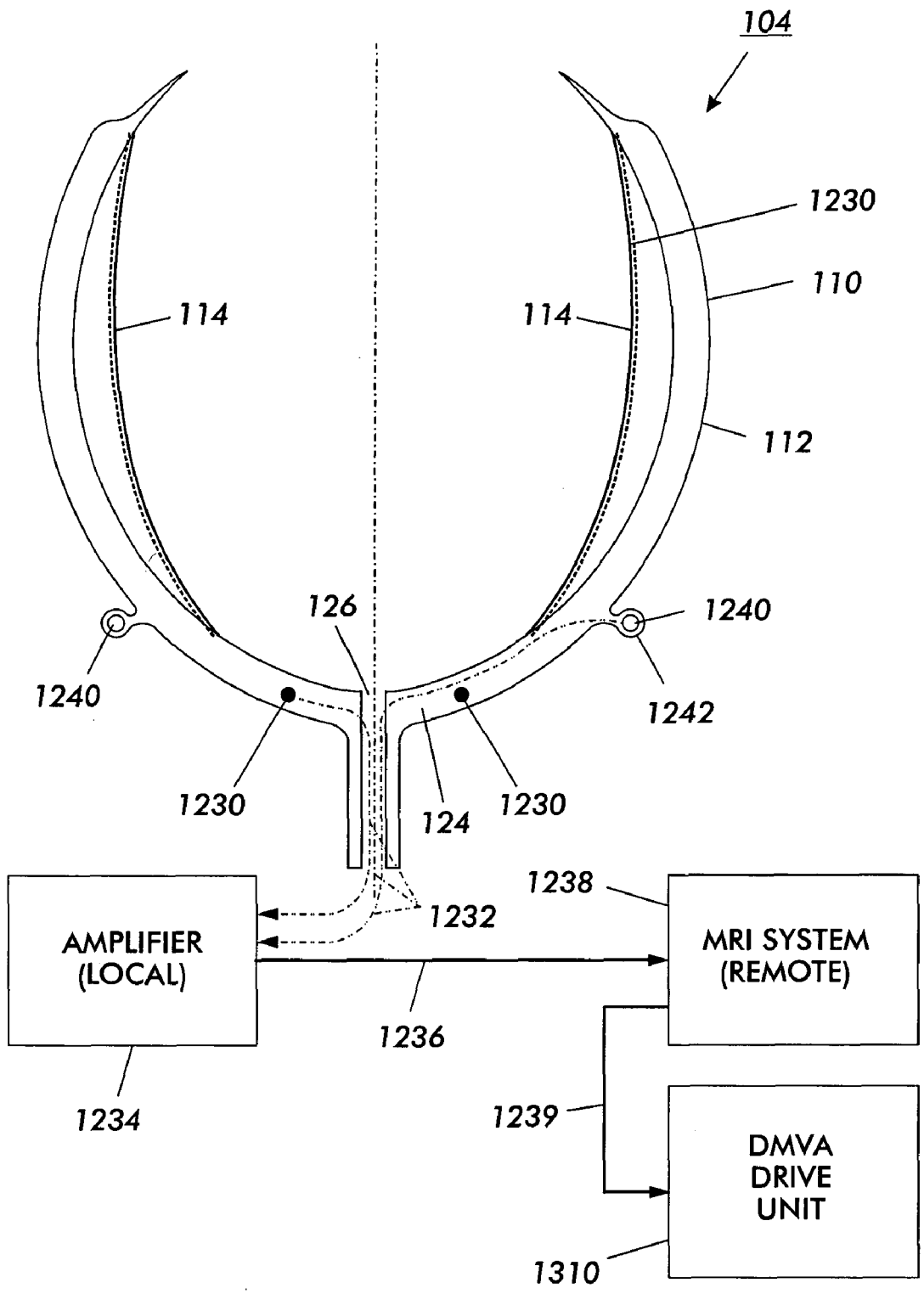
FIG. 8 is a schematic representation of a DMVA Cup with an MRI coil embedded therein.

FIG. 8 is a schematic representation of another embodiment of a DMVA Cup with an MRI coil embedded therein. Referring to FIG. 8, MRI coil 1230 or MRI coil 1240 can alternately be integrated into wall 112 of the Cup 104. This embodiment is particularly advantageous as the coil 1230/1240 completely encompasses the heart (not shown) enabling the entire heart and DMVA Cup interior to be imaged with a coil that is very close to the heart. Since the quality of the MR image increases with decreasing distance between the receive coil and the tissues to be imaged, this design enables very high quality images of the heart to be obtained due to the maximum signal produced in the coil. This maximum signal also enables scan times to be reduced without compromising image quality, which is very important when imaging the moving heart.

The quality of MR images is also dependent upon the strength of the static field used by the MRI system. Higher field strength systems (e.g. 3.0 or 4.5 Tesla field strength) provide greater image quality than lower field strength systems (e.g. 0.5 or 1.5 Tesla field strength). However, the maximum signal provided by the MRI coil of the present invention enables images to be obtained in lower strength with image quality equivalent to the quality of image obtained in higher strength systems. This is particularly important since lower strength "open MR" systems enable the physician to interact with patient during MRI, and these systems would be one type of MRI system used to help guide the installation and assessment of the DMVA Cup. The signal from embedded coil 1230/1240 can be obtained through a connection such the type illustrated in FIG. 6C, or through the use of external receive coils which monitor the currents induced in embedded MRI coil 1230/1240. The latter approach offers the advantage of being able to image the performance of the DMVA Cup and the heart in an MRI unit without the need to physically access and connect to the implanted DMVA Cup. The ability to image the DMVA Cup and heart using MRI is particularly important, since MRI is increasingly becoming a preferred imaging modality for a variety of reasons. MRI provides superb soft tissue contrast, and functional analysis capabilities. MRI requires no ionizing radiation or toxic contrast agents and is not obstructed by the presence of bone. MRI is capable of providing multi-plane images without repositioning the patient. The practice of MRI-guided surgery is becoming more common, indicating that DMVA Cup installation and assessment under MRI guidance is feasible.

Referring again to FIG. 8, DMVA Cup 104 having an integrated MRI coil comprises a typical shell 110 and liner 114. A ring-shaped MRI receiver coil 1230 is shown embedded in the lower portion 124 of the wall 112 of shell 110 in a region that is relatively mechanically stable during systolic and diastolic motion of the DMVA. Alternatively, MRI receiver coil 1240 is shown to be larger than coil 1230 and at a greater distance from the apex 126 of cup 104. The larger diameter of alternative coil 1240 permits improved resolution of the MRI image. Coil 1240 is surrounded by support ring 1242 that is molded as an extension of the shell 110 and that provides positioning of coil 1240 while at the same time isolates coil 1240 from the flexure of shell 110 that occurs during systolic and diastolic motion of the DMVA Cup 104. The choice of the diameter and location of the receiver coil (shown herein by two diameters and locations depicted by 1230 and 1240) is made to optimize the depth of field and resolution required by the MRI system, and may vary depending upon the type of MRI analysis being done and the power of the system (e.g. 0.2 Tesla, 1.5 Tesla, or 3.0 Tesla).

Referring again to FIG. 8, receiver coil 1230 or alternative receiver coil 1240 is connected by wires 1232 to an amplifier 1234 that is positioned close to the receiver coil 1230/1240 and amplifies the MRI signal received by coil 1230 or 1240. The amplifier 1234 is in turn connected by wires 1236 to an external MRI system 1238 that provides all of the signal conditioning and data representation that will be used by the medical team to assess the performance of the heart and performance of the DMVA system. Optionally, the MRI system 1238 may be connected directly to the DMVA drive unit 1310 via connection means 1239 (such as e.g. a cable, or telemetry) in a manner that permits the drive unit 1310 to actively interpret information coming from MRI system 1238 and use it to modify its operational parameters in controlling the systolic and diastolic motion of DMVA Cup 104.

Figure 9A:
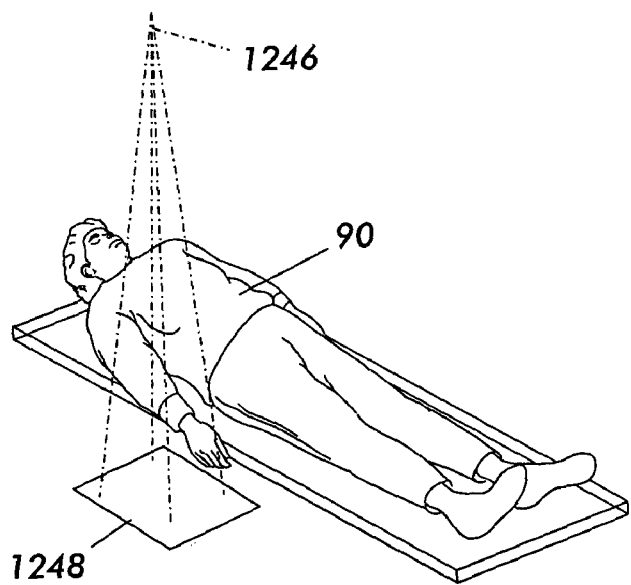
FIGS. 9A and 9B are schematic representations of an external X-ray imaging procedure used to collect data on a patient and data on a DMVA Cup fitted therein.
Figure 9B:
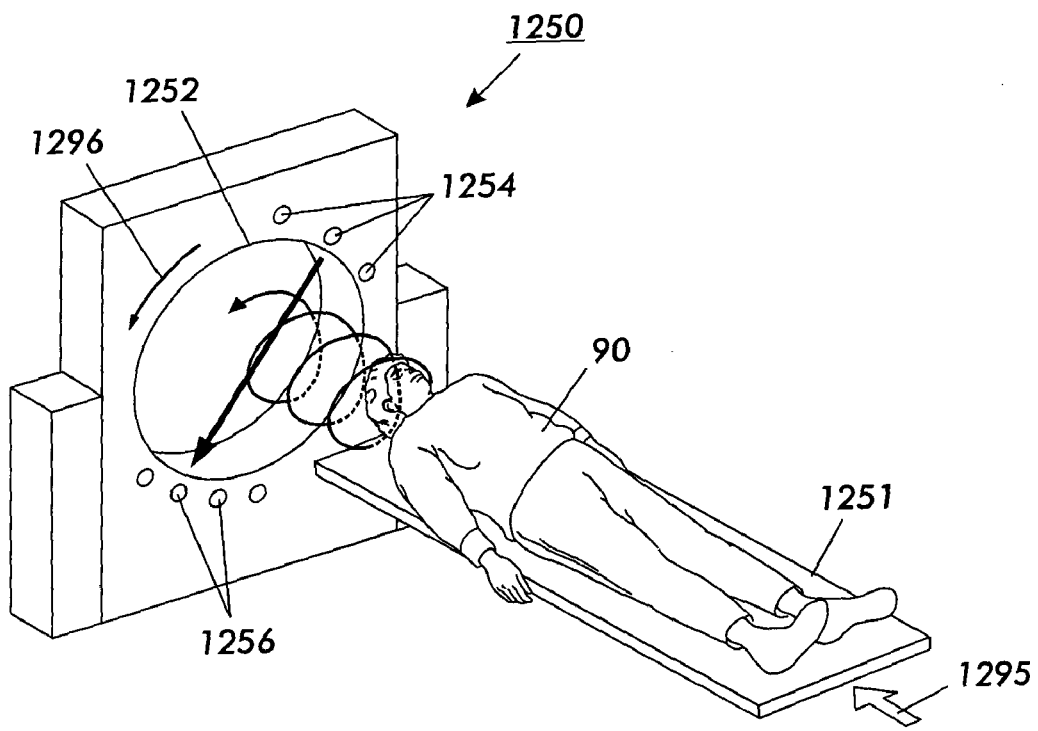

In yet another embodiment of the present invention, an external X-ray imaging procedure, such as Conventional X-radiography or Computed Tomography, is used to collect the following types of data during and following installation of the Cup: anatomical data, such as motion of the heart wall, fit of the Cup to the heart; hemodynamic data, such as blood flow rate, and/or blood pressure; and functional data, such as cardiac ejection fraction. FIG. 9A and FIG. 9B are schematic representations of one embodiment of such an external X-ray imaging procedure used to collect data on a patient and data on a DMVA Cup fitted therein. Referring to FIG. 9A, there is depicted a standard radiography or x-ray method and apparatus that is used to image a part of the body, in this case the heart. Typically, for use with soft tissues such as the heart, or fluids such as the blood, a contrast agent that preferentially absorbs x-rays is used to accentuate the features under study. In FIG. 9A, patient 90 is supported in a stationary position, between x-ray source 1246 and an imaging plane 1248. The image at plane 1248 may be acquired by a traditional photographic process providing a single image, or may be acquired by use of a fluoroscopic screen, providing an image that changes with movement of the feature being imaged.

FIG. 9B depicts a technique referred to as computed tomography (CT) and often referred to as a "CAT Scan". In this technique, patient 90 is supported on a movable structure 1251 and passes through a circular opening 1252 in the scanning system. Multiple pairs of x-ray sources 1254 and x-ray detectors 1256 are connected in a circular ring that spins around the subject with its rotation shown by arrow 1296. Support structure 1251 moves slowly through circular opening 1252 with motion shown by arrow 1295. The resulting information gathered by multiple detectors 1256 is analyzed by a computer algorithm, and creates a three-dimensional (3-D) image of the feature being imaged. While this 3-D image has substantially greater information content than a simple planar x-ray, it should be noted that the time to create a single 3-D image will be at least on the order of a minute.

FIG. 10A is a schematic representation of electrophysiological sensors and/or electrodes integrated into a DMVA device, shown during systolic compression of a heart. Referring to FIG. 10A, electrical sensors 1262, 1264, 1266, 1272, and 1274 are placed on or within liner 611 of Cup 105 to measure the electrophysiological signals produced by the heart 30. Sensor 1276 is placed on or within the external surfaces of Cup 105, or elsewhere on or within the body, to provide a ground plane or reference electrical measurement for sensors 1262-1274, which are in contact with the heart 30. Alternately, sensors 1262-1274 may be placed on or within the shell wall 112 of Cup 105, as indicated by sensors 1268, 1270, and 1278. In a preferred embodiment of the present invention, electro-physiological signals are measured by sensors 1262-1274 and are delivered to the DMVA device control unit (not shown), which in turn directs the inflation and/or deflation of Cup liners 611 in a pre-determined synchronization with the normal heart rhythm.

In an embodiment where the DMVA control unit device is positioned outside the body, electro-physiological signals are delivered to the DMVA control device either percutaneously through the skin such as with a puncture, or transcutaneously through the skin such as via telemetry pulses.

In an embodiment where the DMVA control unit device is positioned inside the body, electro-physiological signals are delivered to the DMVA control device through electrical conductors (not shown), optical wave guides (not shown), such as fiber optic cables (not shown), or via telemetry pulses.

In yet another embodiment of the present invention, electrical sensors 1262-1274 can be cardiac pacing electrodes, electrical sensors, or both, placed on or within the liner 611 of Cup 105, or on or within shell wall 112 of Cup 105, for patients who require active management of their cardiac disrhythmia. Electrodes and/or sensors 1262-1274 can be used without limitation in the following ways:

1. Electrodes 1262-1274 may be connected to an implanted or external cardiac pacemaker (not shown) for determining when a pacing pulse is required, and for delivering this pulse(s) to the heart.
2. Electrodes 1262-1274 may be connected to the DMVA Control Unit to enable the Control Unit to operate the DMVA device in desired synchrony or asynchrony with the pacing pulses.

In yet another embodiment of the present invention, electrical sensors can be cardioversion-defibrillation electrodes, electrical sensors, or both, placed on or within the Cup liner or Cup wall, for patients at risk of fibrillation or unnatural heart rhythm. These electrodes can be used without limitation in the following ways:

1. Electrodes 1262-1274 may be connected to an implanted cardioverter-defibrillator (ICD) for determining when a cardioversion-defibrillation (CD) pulse is required, such as the timing of cardioversion with compression (the synchronization of the delivered energy with the appropriate timing of systolic compression and degree of systolic compression), and for delivering this pulse.
2. Electrodes 1262-1274 may be connected to the DMVA Control Unit to enable the Control Unit to operate the DMVA device in desired synchrony or asynchrony with the delivered CD pulses.

In yet another embodiment of the present invention, a pacemaker (not shown) and/or cardioverter-defibrillator (not shown) are integrated directly into the DMVA control device.

Figure 10B:
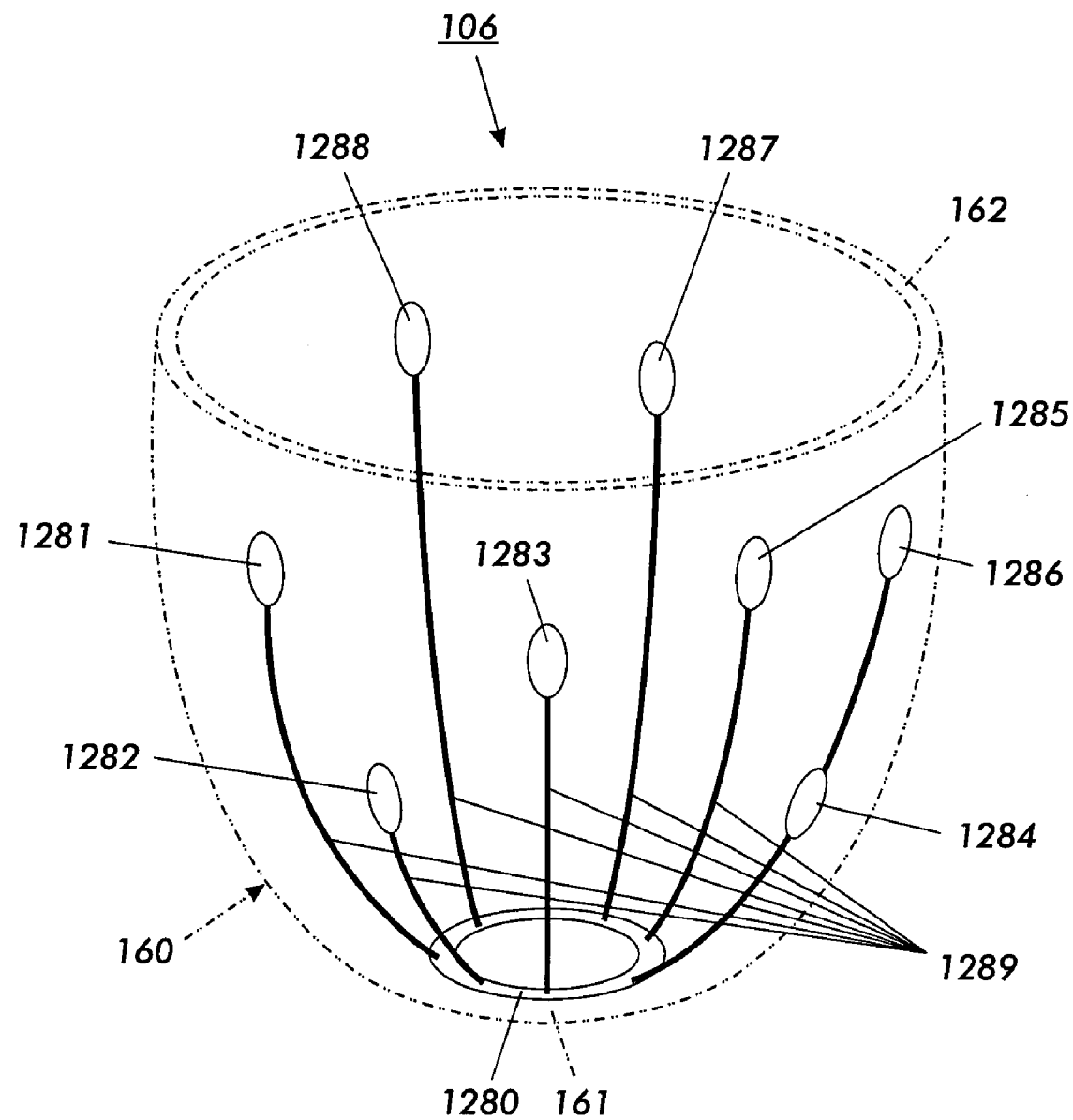
FIG. 10B is a schematic representation of the electrophysiological sensors and the liner of the DMVA device of FIG. 10A.

FIG. 10B is a schematic representation of the electrophysiological sensors and the liner of the DMVA device of FIG. 10A. Referring to FIG. 10B, DMVA Cup 106 comprises an outer shell 160, with electrophysiological sensors or electrodes 1281-1287 embedded within shell wall 162, or disposed on the inner surface thereof. Electrodes 1281-1287 may be used to excite cardiac tissue with an electrical pulse similar to a pacing pulse, a cardioversion pulse sequence, or a defibrillating pulse sequence. Electrodes 1281-1287 may also be used individually or in combination to sense cardiac electrical activity. The placement of such multiple electrodes around the heart permits 3D analysis of cardiac electrical activity. Any application of electrical stimulation may be done in a manner that has a net-zero DC current, in order to eliminate electrolytic tissue damage. This feature of the present invention is important to ensure the proper timing of compression with the stimulus for contraction to ensure that DMVA Cup does the work of pumping blood.

Additionally, the array of electrodes 1281-1287 can be used to apply complex cyclic three-dimensional electrical stimulation in a phased manner to heart tissues. Such stimulation can be used to optimize synchronization of the natural rhythm of the heart with the DMVA device, or to stimulate the heart slightly out of phase with the DMVA device in the use of a training algorithm to be described subsequently.

In one embodiment electrodes 1281-1288 disposed on the inner surface of the Cup shell wall 112 are small 'dots'. In another embodiment, electrodes 1281-1288 are larger 'patches'. In yet another embodiment, electrodes 1281-1288 are formed from a network of filaments, or a combination of dots, patches, and/or filaments. Referring again to FIG. 10B, in one embodiment, electrodes 1281-1288 are joined by conductors 1289 to a common electrical source such as e.g. conductive ring 1280. In another embodiment (not shown), electrodes 1281-1288 are in electrical communication external to the Cup and/or patient by individual wires or conductors. In such an embodiment, the DMVA Cup is capable of functioning as an endocardial pacemaker.

Electrodes 1281-1288, or electrodes in other configurations as previously described are applied to the liner via adhesive, mechanical attachment, or by being co-molded on the internal surface of the liner. Electrode material may be a biocompatible metal such as titanium or gold, or it may be a conductive polymer such as polypyrrole, or a carbon-doped or metal-doped non-conductive polymer, or a conductive paste containing a fine metal powder or other conductor. In one embodiment, electrodes 1281-1288, and/or conductors 1289, and/or ring 1280 are applied to the inner surface of Cup shell wall 162 by use of a direct circuit writing method and apparatus, such as a MicroPen applicator manufactured by OhmCraft Incorporated of Honeoye Falls, N.Y. Such an applicator is disclosed in U.S. Pat. No. 4,485,387 of Drumheller, the disclosure of which is incorporated herein by reference. The use of this applicator to write circuits and other electrical structures is described in e.g. U.S. Pat. No. 5,861,558 of Buhl et al, "Strain Gauge and Method of Manufacture", the disclosure of which is incorporated herein by reference. In a further embodiment, a protective overcoating is applied to such electrodes, conductors, and ring, or to the entire inner surface of Cup shell 160.

In another embodiment electrodes 1281-1288, and/or conductors 1289, and/or ring 1280 are manufactured as an integral part of the Cup wall 162, and are electrically conductive through the entire thickness of the Cup wall material. Electrodes 1281-1288 may take the form of 'dots', 'patches', filaments, or a combination thereof.

In a further embodiment, Cup shell wall 162 is sufficiently porous and/or thin such that electrical conduction will occur through an otherwise non-conductive shell wall material.

Depending upon the configuration of electrodes 1281-1288, the material, placement, and the method of manufacture, electrical conductors/leads 1289 may be on the inner or outer surface of the shell wall 162, or may be embedded therein. Leads 1289 may be made of electrically conductive wire, or of an electrically conductive native polymer or a non-conductive native polymer that is doped with carbon, metal, or other electrically conductive additive, or a conductive paste containing a fine metal powder or other conductor, as previously described. Leads 1289 may connect one or more electrodes individually or in combination. Leads may be further coated or treated or shielded in order to prevent leakage of electrical current and to minimize EMI interference with sensor signals. Such coatings and treatments are described e.g., in U.S. patent application Ser. Nos. 10/384,288, and 10/369,429, the disclosures of which are incorporated herein by reference.

In general; leads 1289 are collected in a region of the Cup shell 160 that minimizes flexure of such leads 1289 and any adverse effect on the liner or on the heart. In the preferred embodiment, leads 1289 are collected near the apex 161 of the Cup. A connector (not shown) may be used to provide ease of Cup installation, but in one embodiment there is no connector per se, in order to eliminate risk of circuit degradation or unintended cross-talk between electrodes.

In another embodiment (not shown), operational data on the patient and on the performance of the DMVA device is provided by externally positioned electrophysiological sensors/electrodes. These sensors/electrodes can include without limitation skin mounted EKG sensors and pacing electrodes, skin mounted cardioversion defibriallation (CD) sensors and electrodes, or temporary pacing and CD leads such as percutaneously installed or transesophageally delivered sensors and electrodes. These sensors and electrodes can be used without limitation in the following ways:

1. Sensors and electrodes may be connected to an externally positioned cardioverters-defibrillator for determining when a CD pulse is required, and for delivering this pulse.
2. Sensors and electrodes may be connected to the DMVA Control Unit to enable the Control Unit to operate the DMVA device in desired synchrony or asynchrony with the delivered pacing and/or CD pulses.

Other arrangements of such electrodes will be apparent to those skilled in the art. Such arrangements may include those performed in standard practice of electrocadiography, which is described in Bronzino, J. D., *The Biomedical Engineering Handbook*, Second Edition, Volume I, CRC Press, 2000, pp. 3-14 and 418-458; and in *Essential Cardiology*, Clive Rosendorf M. D., ed., W. B. Saunders Co., 2001, pp. 23-699.

The purpose of any DMVA device is to maintain cardiac output. This output may be characterized by stroke volume (the volume of blood expelled from the heart during each systolic interval) and pressure at which this volume is delivered from the heart. In yet another embodiment of the present invention, working fluid pressure and/or flow rate sensors are integrated into the Cup and/or Cup drive assembly to collect data that can be used to control the inflation/deflation of Cup liner, which in turn enables control of stroke volume and blood pressure.

Figure 11:
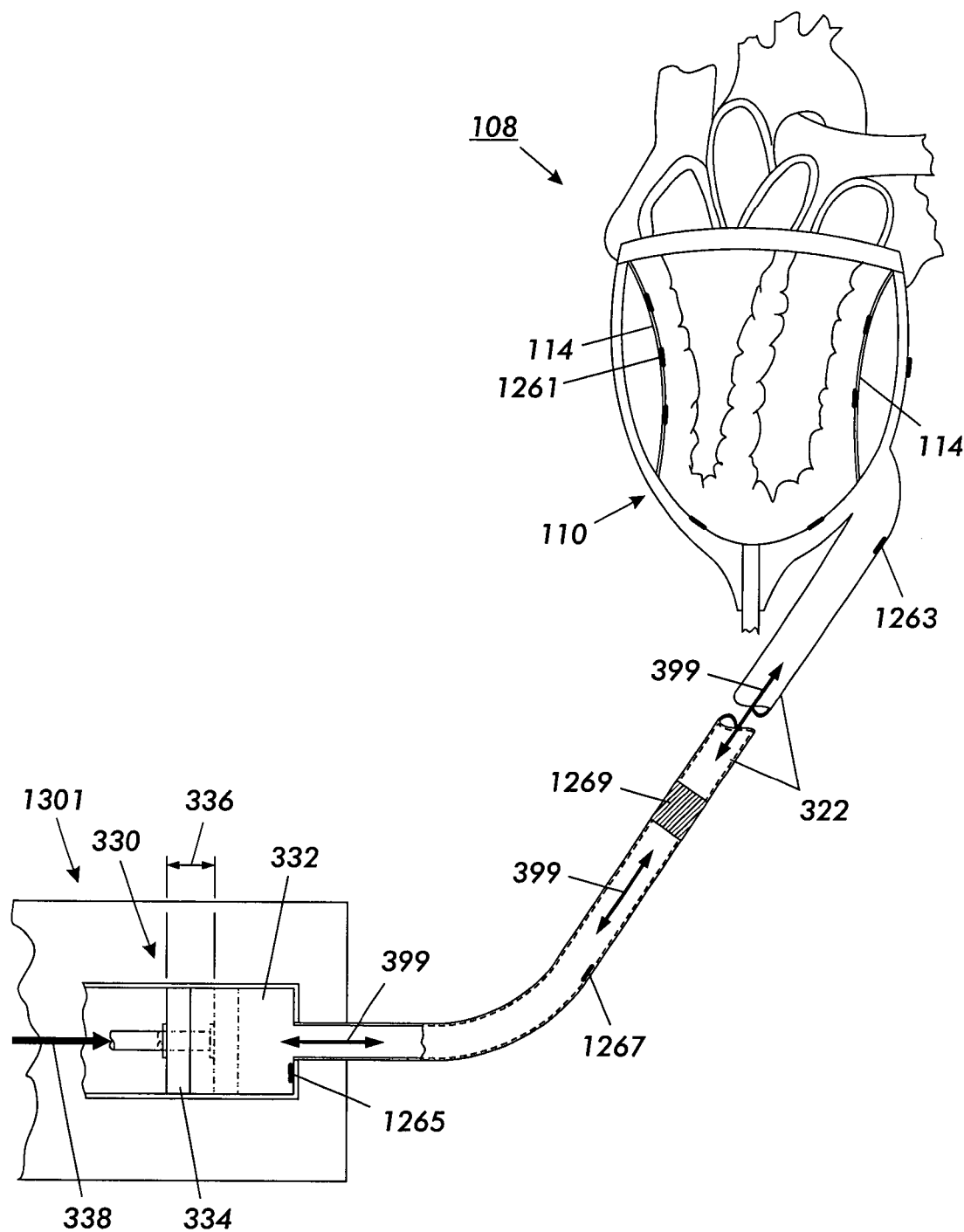
FIG. 11 is a schematic representation of working fluid pressure and/or flow rate sensors integrated into the Cup and Drive Assembly.

FIG. 11 is a schematic representation of working fluid pressure and/or flow rate sensors integrated into the Cup and the drive assembly thereof. Referring to FIG. 11 DMVA Cup 108 comprises fluid pressure sensors 1261, 1263, 1265, and 1267, which are placed between the Cup shell 110 and liner 114 (pressure sensor 1261), and/or within the liner inflation/deflation duct 322 (pressure sensors 1263 and 1267), and/or within the pump assembly 330 (pressure sensor 1265) used to pump DMVA working fluid indicated by arrows 399 from within DMVA device control unit 1301. By measuring the pressure of DMVA working fluid over time it is possible to infer the volume of working fluid delivered to Cup 108.

Alternately, the volume of working fluid delivered to Cup 108 can be measured directly by placing a flow rate sensor(s) 1269 within liner inflation/deflation duct 322 to measure the rate of flow of working fluid into or out of Cup 108 as indicated by arrows 399. Alternately, the flow of working fluid into Cup 108 can be determined by calculating the volumetric displacement of pump 330. In one embodiment wherein pump assembly 330 of DMVA device 108 comprises a piston pump, such volumetric displacement is determined by multiplying the cross-sectional area of the bore 332 of pump cylinder 332 or of pump piston 334 by pump stroke 336 due to piston driver 338. It is to be understood that similar means can be used to determine volumetric displacement of other types of fluid pumping devices.

Sensor output from sensors 1261, 1263, 1265, and 1267, and/or other sensors described previously or subsequently in this specification, is delivered to the DMVA device control unit 1301, which in turn directs the inflation and deflation of the Cup liner 114 as required to provide the desired amount of cardiac output. In one embodiment, ultrasound sensors as described previously and shown in FIGS. 6A-7 are used to monitor the LV/RV interactions, geometric and volumetric changes throughout systolic and diastolic compression, heart function, blood flow within the cardiac chambers, flow velocities and derived pressures across all four of the heart's native valves. Information will be used to optimize DMVA action on the heart, dictate weaning protocols and algorithms, etc. In another embodiment, fluid flow rate sensors monitor the inflation and deflation volume of the liner(s), which correspond respectively to the systolic output from and diastolic input to the heart. By controlling the total volume of fluid pumped into and out of the liner(s), the DMVA is able to precisely control stroke volume.

In other embodiments, blood pressure is controlled in a number of ways, including the use of Cup working fluid flow rate sensors. The vascular structure of the body has a variable resistance to blood flow as the body opens and closes resistance vessels depending upon a variety of internal and external factors. Typically, resistance does not change much in a minute. However, a sudden change such as e.g. a precipitous decrease in ambient temperature will produce a very rapid change in resistance, due to such factors as the diameter, length, and geometry of arteries, veins, etc. which restrict the flow of blood. Therefore increasing or decreasing the rate of Cup liner inflation against this hemodynamic resistance will either increase or decrease systolic blood pressure, respectively. Likewise, increasing or decreasing the rate of Cup liner deflation against this hemodynamic resistance will either increase or decrease diastolic blood pressure, respectively. Since the rate of flow of working fluid into the Cup liner directly controls liner inflation and deflation, measurement and control of Cup working fluid flow rate sensors can also be used to control blood pressure. In yet another preferred embodiment, the Cup working fluid consists essentially of an electro-rheological fluid (e.g. isotonic saline) that provides a unique and easily detectable flow rate signature.

In another embodiment, blood pressure is controlled by use of Cup working fluid pressure sensors. Since Cup liner inflation or deflation is dependent upon the pressure at which the working fluid is delivered to or removed from the liners, it is possible to use measurement and control of DMVA working fluid pressure to control blood pressure. Specifically, the higher or lower Cup liner inflation or deflation pressures can be used to control systolic or diastolic blood pressure, respectively.

Figure 12:
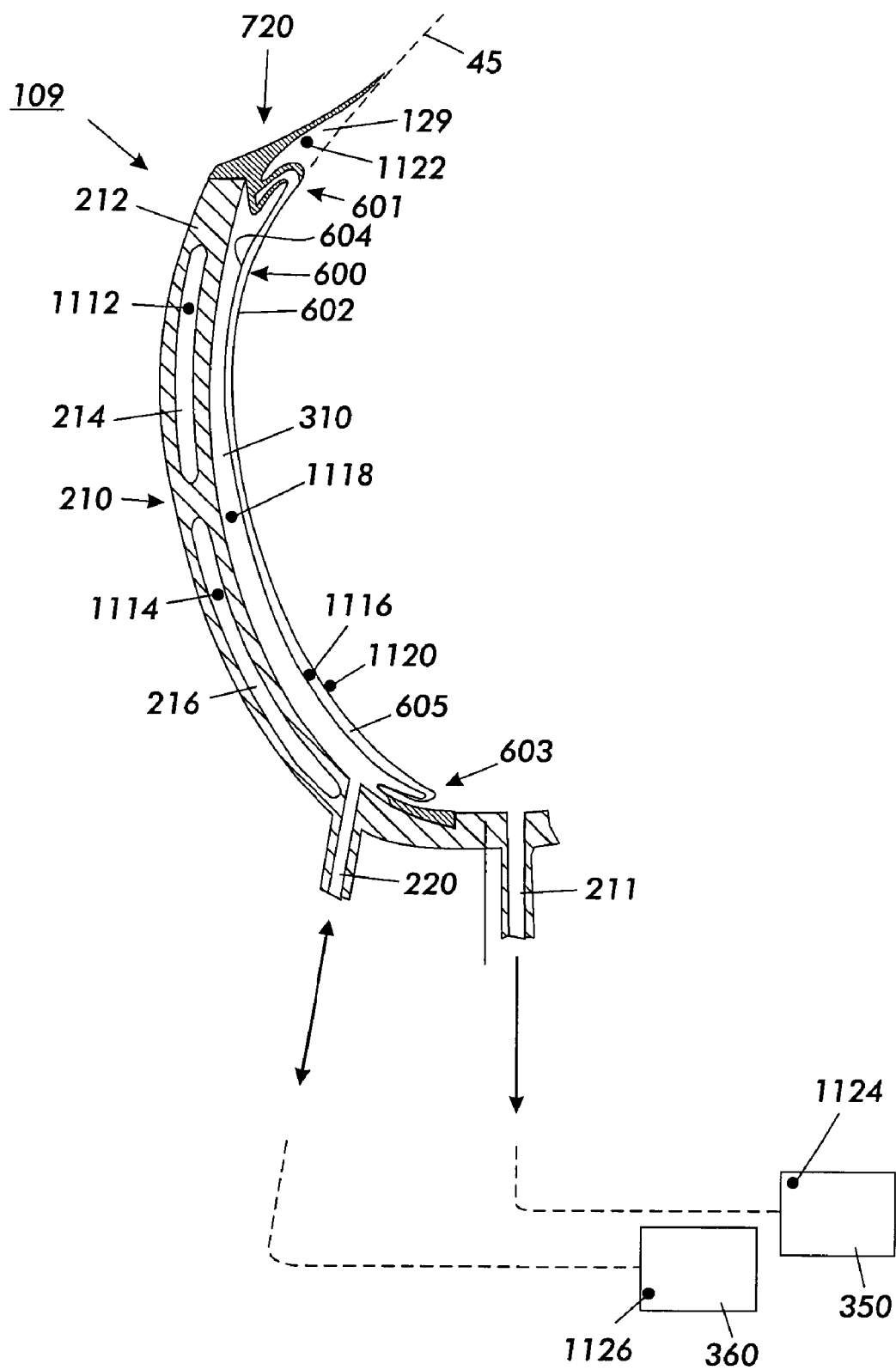
FIG. 12 is a schematic representation of an alternate embodiment of working fluid pressure sensors integrated into the Cup and Drive Assembly.

FIG. 12 is a schematic representation of an alternate embodiment of working fluid pressure sensors integrated into the Cup and Drive Assembly. Referring to FIG. 12, in one preferred embodiment, DMVA Cup comprises shell 210, liner 600, and seal 720. Shell 210 is provided with a wall 212 comprising multiple chambers 214 and 216. In other embodiments (not shown), shell wall 212 comprises three or more chambers. Such chambers 214 and 216 may be used to monitor pressure or flexure, or to apply pressure or other forms of modulation of wall properties to wall 212, or a combination thereof.

In the embodiment depicted in FIG. 12, the presumed use of the chambers is for pressurization and pressure measurements. A first pressure sensor 1112 is disposed in chamber 214, and a second pressure sensor 1114 is disposed in chamber 216. In other embodiments (not shown), there may be as many as 8 or 16 of these sensor positions depending on the approach taken to modulate the behavior of the Shell and on the number of discrete chambers that exist.

Referring again to FIG. 12, in the preferred embodiment depicted therein, liner 600 comprises an inner liner membrane 602 and an outer liner membrane 604, which are bonded to each other at upper liner region 601 and lower liner region 603. Upper and lower liner regions 601 and 603 may be rolling diaphragm structures described previously in this specification. Liner 600 is further provided with a pressure sensor 1116 disposed within the interstitial space 605 between inner liner membrane 602 and outer liner membrane 604 to monitor the pressure therebetween. Interstitial space 605 may contain a gas or more preferably, an incompressible fluid, thereby resulting in a fluid pressure therein during operation of the DMVA Cup. This pressure may be compared to other local pressures within the DMVA Cup to determine critical operating conditions such as e.g., whether there may be a leak in one or both of liner membranes 602 and 604. Sensor 1116 may also be used to monitor the pressure of a therapeutic agent that may be applied through a permeable embodiment of inner liner membrane 602.

In one such embodiment (not shown) a circumferential cavity connects an external source of pressurized therapeutic agent with a highly permeable center layer of the liner. In another embodiment, the size, shape, and surface energy of the cavity wall are designed to permit passive capillary movement of therapeutic agent from an external source to a highly permeable center layer of the liner. In a third embodiment, the same approach is taken, but with an active valve between the external source and the cavity, in order to control flow of therapeutic agent. In a fourth embodiment the size, shape, and surface energy of the cavity wall are designed to permit passive capillary movement of therapeutic agent from an external source to the highly permeable center layer of the liner, but the relative surface energy of the wall surface is controllable by external means in order to modulate flow of therapeutic agent.

In the embodiment depicted in FIG. 12, it will also be apparent that liner membrane 602 and liner membrane 604 may be provided as two separated functioning liners, so that they function as redundant liners. In the event that one liner were to fail in operation of the DMVA apparatus, the other liner would continue to function. This capability is considered to be an important safety and reliability feature of the present invention.

In the embodiment depicted in FIG. 12, DMVA Cup 109 may be further provided with several additional pressure sensors disposed within Cup shell 210. Sensor 1118 is disposed in cavity 310, in order to measure the working pressure of the DMVA drive fluid contained therein during systolic and diastolic actuation by the DMVA Cup. Sensor 1120 is disposed on the surface of inner liner 602 or in proximity thereto in order to measure the pressure between inner liner 602 and the wall of the heart (not shown). Sensor 1122 is disposed within a cavity 129 formed between seal 720 and heart surface 45, in order to measure pressure in proximity to seal 720, thereby enabling measurement of the effectiveness of seal 720.

In the embodiment depicted in FIG. 12, DMVA Cup 109 may be further provided with several additional pressure sensors disposed within the vacuum system 350 and/or fluid drive system 360. Sensor 1124 is disposed within vacuum system 350, or alternatively within vacuum duct 220, or both, in order to measure the vacuum applied to the. Cup shell.

Sensor 1126 is disposed within DMVA fluid drive system 360, or alternatively within drive fluid supply duct 211, or both, in order to measure the pressure and vacuum applied to the liner 600 during systolic and diastolic actuation, respectively. In the instance where sensors are provided in both locations, additional parameters such as frictional line losses, cardiac performance conditions, the phase of systolic/diastolic cycle, and/or system malfunction may be measured and/or detected.

In one embodiment the Cup controller receives pressure data from sensors 1112-1126 depicted in FIG. 12. The control algorithm monitors absolute pressure levels and pressure ratios against a table of acceptable values. In another embodiment the Controller inputs the above pressure data to a Cup performance-monitoring algorithm to monitor appropriate Cup performance. In yet another embodiment the Controller inputs the above pressure data to the Cup control algorithm, which monitors Cup performance, and when one or more performance parameters approaches or exceeds a limit, the algorithm applies compensation to the drive system, or to other output devices such as e.g., cardiac electrodes, to correct the fault. For example, if sensor 1122 indicates a minor loss of integrity of seal 720, the applied negative pressure from vacuum system 350 may be increased, and/or measures may be taken (see e.g., FIGS. 19A-19C) to increase the force of the seal against the heart wall.

Figure 13:
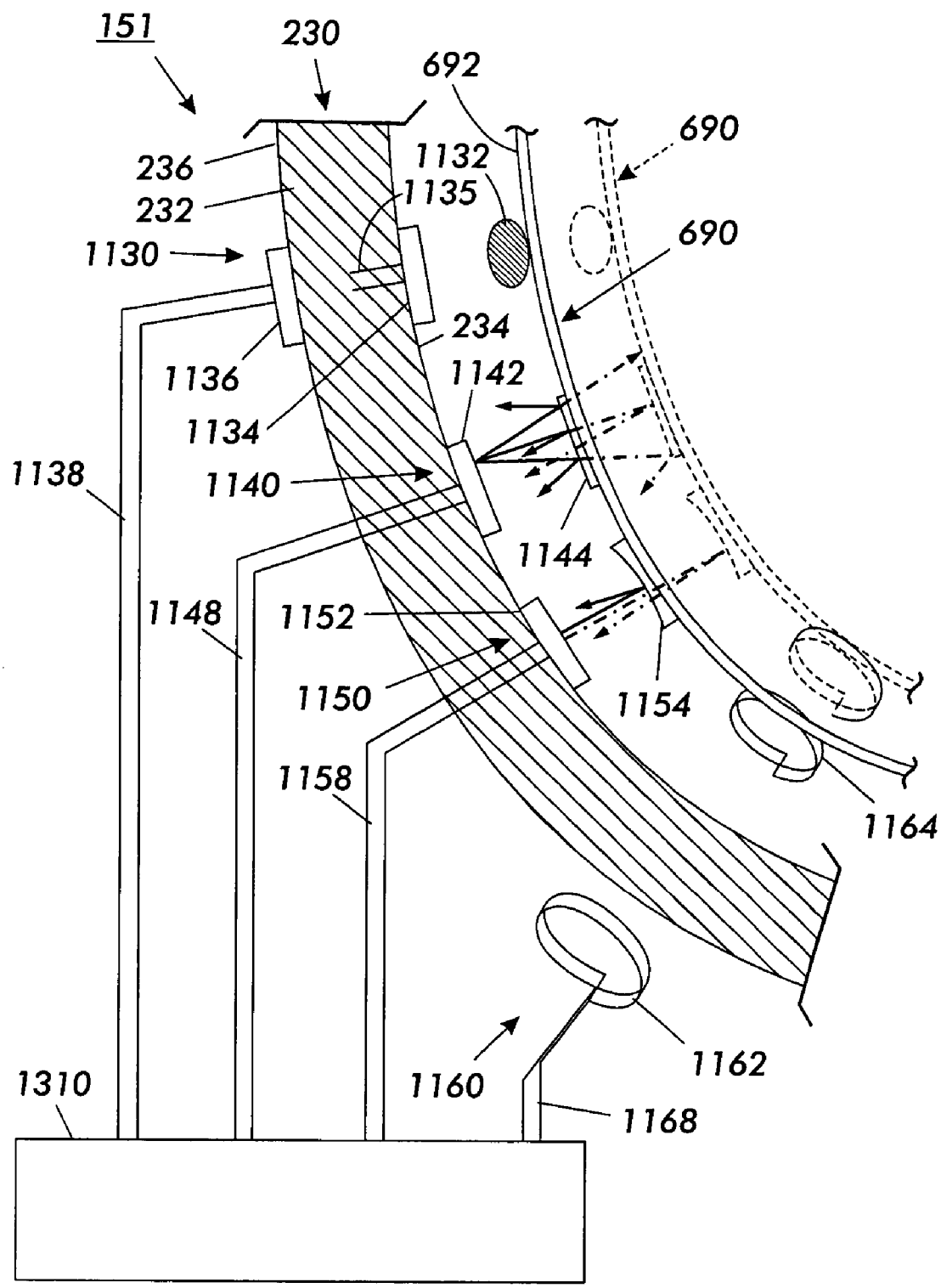
FIG. 13 is a schematic representation of several embodiments of position sensing means for detection of the position of the liner of the DMVA apparatus during operation.

FIG. 13 is a schematic representation of several embodiments of position sensing means for detection of the position of the liner of the DMVA apparatus during operation. Referring to FIG. 13, DMVA Cup 151 comprises shell 230, liner 690, and controller 1310. Liner 690 is depicted in two positions: in dotted line in a more inward position, e.g. at the end of systole or beginning of diastole; and in solid line in a more outward position, e.g. at the end of diastole or beginning of systole. Controller 1310 provides power for sensor operation, signal conditioning for sensor signals, and may provide analog-to-digital (A/D) conversion and/or software analysis. The logical outputs of sensors (to be described) are used to monitor Cup performance, monitor for Cup failures, and/or adapt Cup operation to other parameters, using sensor data as part of the algorithm input.

In the embodiment depicted in FIG. 13, DMVA Cup 151 is provided with several position detecting sensor means disposed within Cup shell 230. Sensor 1130 is a Hall Effect sensor comprising a small magnetic slug 1132 disposed on the outer surface 692 of liner 690, and a magnetic proximity pickup 1134 disposed on the inner surface 234 of shell 230, and further comprising a feedthrough conductor 235 passing through shell wall 232. In an alternate embodiment, magnetic proximity pickup 1136 is disposed on the outer surface 236 of shell 230, or embedded therein. Sensor 1130 detects the relative position of liner 690 with respect to shell 230 via the well known Hall Effect principle, and provides a signal correlating with such position to controller 1310 via wires 1138.

In another embodiment depicted in FIG. 13, DMVA Cup 151 is provided with an optical reflective sensor 1140 comprising a light source and photodetector 1142, and a reflective surface 1144 joined to the outer surface 692 of liner 690. In this embodiment, the sensor 1140 is of the type that transmits a diverging bundle of light from source 1142, and receives and detects this light after it reflects off surface 1144. It can be seen from FIG. 13 that as the distance between the source/detector 1142 and the reflective surface 1144 increases (e.g. movement from 690 in solid line to 690 in dotted line), the diverging bundle of light will expand accordingly. Thus if the light receptor area of the detector 1142 is fixed, the amount of light will vary approximately as the inverse square of the distance, and the distance from shell wall 232 to liner 690 can be inferred. Sensor 1140 is connected to controller 1310 by cable 1148. In one embodiment, cable 1148 comprises optical fiber. In another embodiment, cable 1148 comprises electrical wires.

In another embodiment depicted in FIG. 13, DMVA Cup 151 is provided with an optical transmission sensor 1150 comprising a light source and photodetector 1152, and a reflective surface 1154 joined to the outer surface 692 of liner 690. In this embodiment the sensor 1150 is of the type that transmits light in a relatively collimated bundle, so that inverse-square losses are minimal. In this embodiment, the DMVA working drive fluid is an optical element in the light path and has an optical density chosen to match the working characteristics of the transmission sensor 1150. The drive fluid may contain a dissolved dye that attenuates light at some wavelength of interest, i.e. that is detectable by detector 1152. As path length increases, sensor output decreases and thus the distance from shell wall 232 to liner 690 can be inferred. Sensor 1150 is connected to controller 1310 by cable 1158. In one embodiment, cable 1158 comprises optical fiber. In another embodiment, cable 1158 comprises electrical wires.

In another embodiment depicted in FIG. 13, DMVA Cup 151 is provided with an inductive coil sensor 1160 comprising an active inductive coil 1162 disposed near the surface 236 of shell wall 232 or embedded therein, and a passive inductive coil 1164 joined to the outer surface 692 of liner 690. In this embodiment active inductive coil 1162 cooperates across space with passive inductive coil 1164 in a manner that results in a change in the effective LRC circuit (within controller 1310 and connected to sensor 1160 by wires 1168), as the distance between active coil 1162 and passive coil 1164 changes.

In yet another embodiment of the present invention (not shown), blood pressure and/or blood flow rate sensors located in the patient's circulatory system are used to provide data to the DMVA control system, or the physician, for use in controlling and operating the DMVA Cup. Such sensors may include, but are not necessarily limited to a catheter (such as a Swan-Ganz catheter) located in the patient's right atrium, right ventricle, or pulmonary artery. Alternatively, sensors can also be located within the descending aorta (measuring the pressure and/or flow rate of blood delivered from the left ventricle), or the right atrium or superior vena cava (measuring the pressure and/or flow rate of blood delivered to the right ventricle). Sensor measurements are fed back to the DMVA control unit, which in turn regulates Cup liner inflation and deflation to maintain desired blood pressure and flow rate, as previously described.

It is to be understood that additional sensors could be installed in the Cup assembly, or elsewhere within the body, and connected to the control unit. These sensors would include without limitation sensors for measuring tissue oxygenation (i.e. detection of ischemic tissues—particularly tissues undergoing silent ischemia), blood oxygenation, tissue temperature, or other physiological parameters. Additional physiological data obtained by conventional measurement means that could be used to control Cup operation include without limitation respiratory rate and body physical motion.

Figure 14:
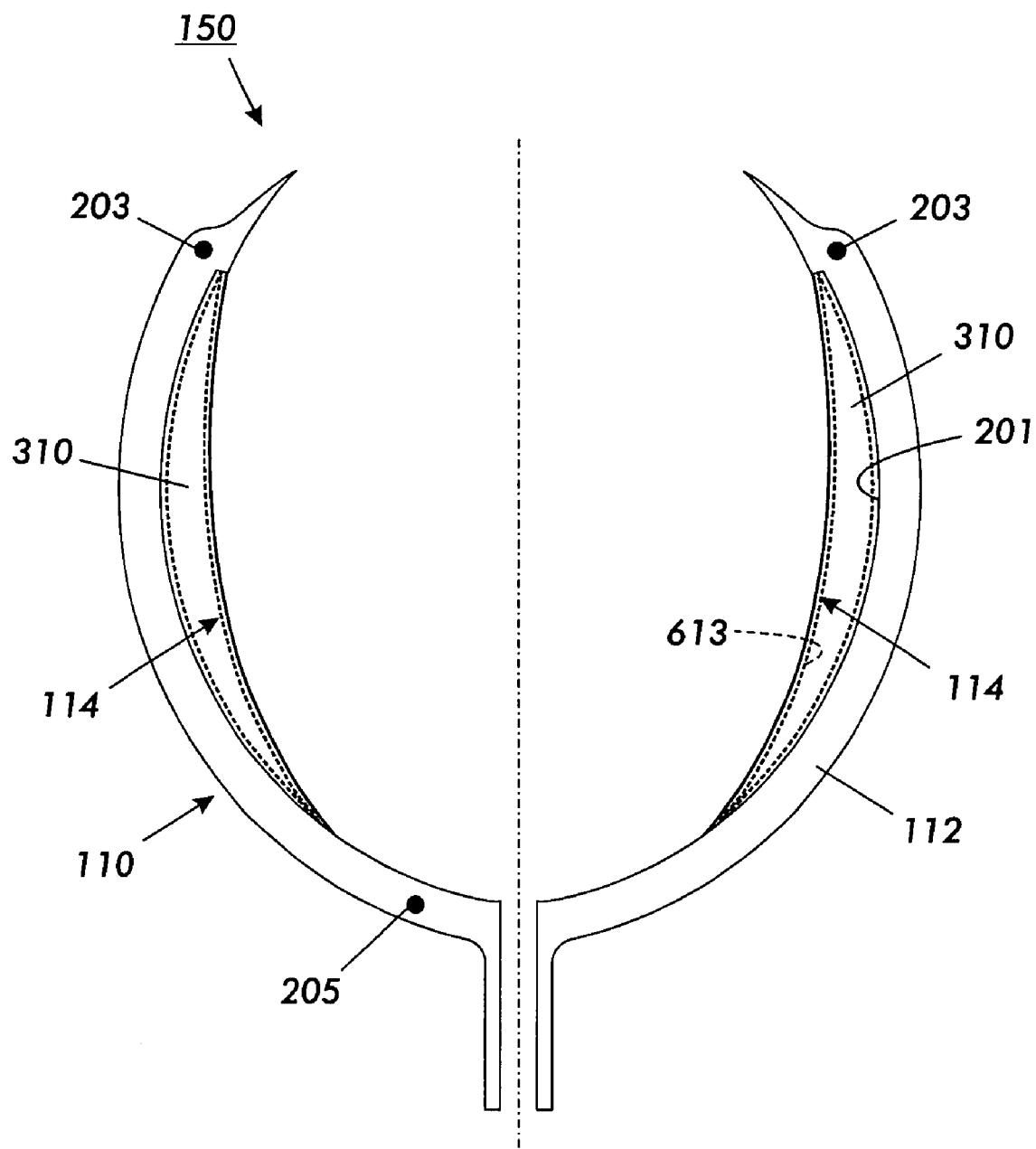
FIG. 14 is a schematic representation of a DMVA Cup with imaging contrast agents applied to critical Cup components.

A more detailed description of Invention Aspect 6, which is directed to imaging contrast agents incorporated into critical components of the Cup to enhance the images obtained thereof is now presented with reference in particular to FIG. 14. In yet another embodiment of the present invention, ultrasonic contrast agents are utilized without limitation according to the following descriptions.

In one embodiment, ultrasonic contrast agents are added to the surface of or imbibed into the liner of the Cup, making the thin liner much easier to visualize under ultrasonic imaging. Enhancing the liner image is critical to assess fit of the liner to the heart. One example of a suitable ultrasonic contrast agent is to ultrasound is ECHO-COAT® ultrasound echogenic coating from STS Biopolymers of Rochester N.Y. The thin, polymeric nature and very high ultrasonic contrast of this material lends itself well to the polymeric nature of the Cup and Cup liner. It is to be understood that any other component of the DMVA device could also be treated with ultrasonic contrast agent to enhance its image profile.

In another embodiment, ultrasonic contrast agents are incorporated into the working fluids used to inflate and deflate the Cup liners, to help visualize liner inflation and deflation performance. In yet another embodiment, ultrasonic contrast agents can also be incorporated into the blood flowing into and around the heart.

In similar embodiments of this particular invention (not shown), MRI contrast agents are utilized without limitation according to the following descriptions.

In one embodiment, MRI contrast agents are added to the surface of or imbibed into the liner of the Cup, making the thin liner much easier to visualize under magnetic resonance imaging. Enhancing the liner image is critical to assess proper fit of the liner to the heart. One example of a suitable MRI contrast agent is gadolinium. The thin and very high MR contrast of this material, and its ability to be easily attached to or imbibed into the polymeric Cup and Cup liner make this material a desirable choice. It is to be understood that any other component of the DMVA device could also be treated with MRI contrast agent to enhance its image profile.

In another embodiment, MRI contrast agents can be incorporated into the working fluids used to inflate and deflate the Cup liners, to help visualize liner inflation and deflation performance. In yet another embodiment, MRI contrast agents can also be incorporated into the blood flowing into and around the heart.

One example of an MRI contrast agent includes nano-particulate particles, including nano-magnetic particles. Nano-magnetic particles can be applied as thin-films (typically on the order of one micron in thickness) to objects to make them more visible under MRI. These particles act by temporarily storing MRI RF energy and re-radiating this energy away once the RF field is turned off, similarly to the way that the hydrogen nuclei (i.e. protons) in tissues behave. However, the nano-magnetic coatings have a relaxation time (similar to the spin-lattice relaxation time of a proton), i.e. the time it takes for the nano-magnetic particles to release the energy obtained from the RF pulse back to their surroundings in order to return to their equilibrium state, that is different from that of body tissues, thereby enabling the nano-magnetic coating to be visualized under MRI. Such a coating can be applied on or within the surfaces of the DMVA device, such as the surface or interior of the liners, to enable these components or features to be visualized under MRI. Such nano-magnetic coatings and materials are described e.g., in U.S. patent application Ser. Nos. 10/384,288, and 10/369,429, the disclosures of which are incorporated herein by reference.

In a similar embodiment of this particular invention (not shown), radiopaque (i.e. X-ray) contrast agents are utilized without limitation according to the following descriptions.

In one embodiment, radiopaque contrast agents are added to the surface of or imbibed into the liner of the Cup, making the thin liner much easier to visualize under ultrasonic imaging. Enhancing the liner image is critical to assess proper fit of the liner to the heart. One example of a suitable radiopaque contrast agent is Omnipaque™, a non-ionic aqueous solution of iohexol, N,N'-Bis(2,3-dihydroxypropyl)-5-[N-(2,3-dihydroxypropyl)-acetamido]-2,4,6-triiodo-isophthalamide made by the Amersham Health Corporation of Princeton, N.J. The very high X-ray contrast of this material, and its ability to be easily attached to or imbibed into the polymeric Cup and Cup liner make this material a desirable choice. It is to be understood that any other component of the DMVA device could also be treated with a radiopaque contrast agent to enhance its image profile.

In another embodiment, radiopaque contrast agents can be incorporated into the working fluids used to inflate and deflate the Cup liners, to help visualize liner inflation and deflation performance. In yet another embodiment, radiopaque contrast agents can also be incorporated into the blood flowing into and around the heart.

FIG. 14 is a schematic representation of Cup with imaging contrast agents applied to critical Cup components where contrast agents may be used to help define points or surfaces that are important in monitoring the function of the DMVA. Such contrast agents may be specific to x-ray (e.g. iodine compounds), to MRI (e.g. gadolinium compounds), to ultrasound (e.g. ECHO-COAT® ultrasound echogenic coating) or any other contrast agent that is suited to improve the resolution of an imaging modality used to determine the performance of the DMVA system by monitoring the shape of the cup and/or the shape of the myocardial surface.

Referring to FIG. 14, DMVA Cup 150 comprises shell 110 and liner 114 that define a lumen or cavity 310 that surrounds the lower half of the heart (not shown). Upon sequential application of positive and negative hydrostatic pressure to lumen 310, systolic and diastolic performance of the heart (respectively) are enhanced.

A contrast agent such as described above is applied to the inner surface 201 of the shell 110 in order to enhance imaging of the shell wall. A contrast agent is also applied to the outer surface 613 of liner 114 in order to enhance imaging thereof. Alternatively, the latter contrast agent may be applied to the inner surface of liner 114, but the use of the outer surface 613 may be preferred in order to avoid potential biocompatibility issues. Imaging of liner surface 613 provides measurements of the shape of the exterior of the heart itself. By monitoring this shape over time, the performance of the heart under DMVA assist may be analyzed. In a similar manner, imaging of both the liner surface 613 and the shell surface 201 provides measurements of the volume contained in lumen 310; this may also be monitored in order to analyze the performance of the heart under DMVA assist.

Most imaging techniques benefit from the use of reference points, comprising the same image enhancing materials as described above, that are used to offset drift in the imaging system electronics, or shifts in alignment of the object being imaged that would otherwise degrade the accuracy of measurement by the imaging technique. In the embodiment shown, multiple reference points 203 are shown in one possible position at the upper periphery of the cup shell 110. Alternatively, or additionally, one or more reference points 205 near the apex of the cup shell 110 may be employed to provide further information for purposes of referencing the imaging system during use. These reference points 203 and 205 may be in other locations, and may be extended as linear or surface elements in order to optimize the referencing process for a specific imaging method.

A more detailed description of embodiments of the present invention pertaining to Invention Aspect 3 (DMVA feedback control parameters), Invention Aspect 4 (DMVA feedback control methods and algorithms), Invention Aspect 9 (Sensor data recording and analysis capabilities), and Invention Aspect 10 (Specific device performance measures appropriate for sensing) is now presented with reference to FIGS. 6A-15, 26 and 27.

Figure 15:
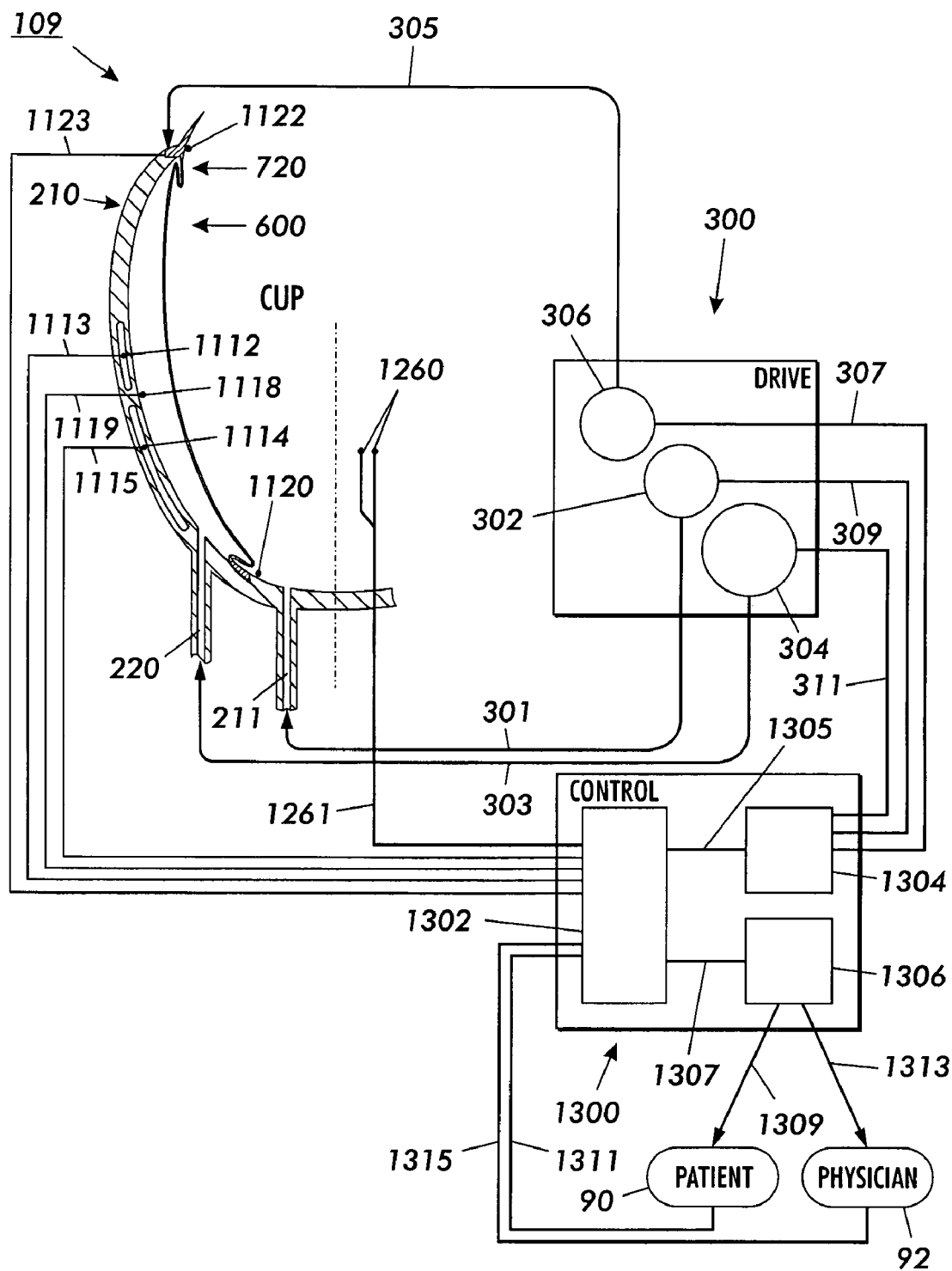
FIG. 15 is a schematic diagram of an overall control system with performance feedback, for operation and control of the DMVA apparatus.

FIG. 15 is a schematic diagram of an overall control system with performance feedback, for operation and control of the DMVA apparatus. Referring to FIG. 15, DMVA Cup 109 of FIG. 12 is connected to a fluid drive system 300 and a control system 1300. It is to be understood that many other embodiments of DMVA Cups as described in this specification may be substituted for DMVA Cup 109. DMVA Cup 109 comprises shell 210, liner 600, seal 720, and a plurality of sensors connected to control system 1300 by connection lines. It is to be understood that as used herein, lines are meant to be connection means used to place sensors in communication with control system 1330, and may comprise any of the following: tubing, sleeving, insulation, conducting wires, wires shielded by sleeves or coatings, optical fibers, telemetrically transmitted radio frequency or other electromagnetic or sonic signals, and combinations thereof.

DMVA Cup 109 further comprises seal sensor 1122 connected via line 1123; upper cavity pressure sensor 1112 connected via line 1113; lower cavity pressure sensor 1114 connected via line 1115; drive fluid lumen/cavity pressure sensor 1118 connected via line 1119; and internal pressure sensor 1120 connected via a line (not shown). Vacuum port 211 of DMVA Cup 109 is connected to drive system vacuum pump 302 by line 301. Fluid drive port 220 of DMVA Cup 109 is connected to drive system DMVA fluid drive pump 304 by line 303. In an embodiment wherein seal 720 is an active seal, as in active seal 820 of FIG. 19A or active seal 770 of FIG. 20, seal 720 is connected to drive system seal actuator 306 by line 305.

In a further embodiment, DMVA Cup 109 further comprises cardiac sensor 1260 connected to control system 1300 via line 1261, which may be any of a variety of electrical, optical, chemical, or other sensors that directly measure some parameter associated with cardiac performance and/or cardiac tissue status. In addition to sensors traditionally used for these purposes, this embodiment provides for measurement of blood components such as CRP(C-Reactive Protein, an indicator of tissue damage due to trauma or overwork) or Lactate (an indicator of muscle fatigue), or other markers that can be used to determine the level of stress in cardiac tissue, the degree of healing of damaged cardiac tissue, the degree of regeneration of cardiac tissue, or a combination of these. Cardiac sensor 1260 may also be used to measure the presence or concentration of a therapeutic agent. Cardiac sensor 1260 is connected to control system 1300 via line 1261.

In the preferred embodiment, control system 1300 comprises numerous subsystems and subcomponents, including microcontroller 1302 connected to programmable logic controller 1304 via interconnect line 1305, and connected to external transceiver 1306 via interconnect line 1307. Control system 1300 is in communication with patient 90 via transceived signal 1309 (such as e.g. a patient alert signal) and via line 1311. Control system 1300 is in communication with physician 92 via transceived signal 1313 (such as e.g. a physician alert signal) and via line 1315. Drive fluid pump 304 is in communication with controller 1300 via line 311. Vacuum pump 302 is in communication with controller 1300 via line 309. Seal actuator 306 is in communication with controller 1300 via line 307.

In a further embodiment, vacuum port 211, DMVA drive fluid port 220, and various sensor lines 305, 1113, 1115, 1119, and 1123 are integrated into a single multi-conduit, multi-wire connecting cable preferably entering the Cup shell 220 near the apex 161 (see FIG. 10B) of the Cup. Internal individual passageways are provided in the Cup shell wall for distribution of the various sensor wires and fluid passageways.

In yet a further embodiment, the line or lines connected to the DMVA cup are provided with a coating of an anti-infection agent and/or an anti-inflammatory agent. Descriptions of suitable agents may be found at e.g., "Preventing Complications of Intravenous Catheterization" New England Journal of Medicine, Mar. 20, 2003, 1123. In addition, at http://link-.springer-ny.com/link/service/journals/00284/bibs/ 33n1p1.html, there is described a hydrogel/silver coating that reduces adherence of *E-coli* (hydrogel effect) and reduces growth (silver); at http://www.infectioncontroltoday.com/articles/291 feat3.html there is described several antimicrobial surface treatments such as chlorhexidine-silver sulfadiazine, minocycline, and rifampin, as well as silver compounds (chloride or oxide). Those skilled in the art will be aware of a variety of such anti-infection and anti-inflammatory agents, each having specific beneficial properties, and each that may be used individually or in combination.

Figure 26:
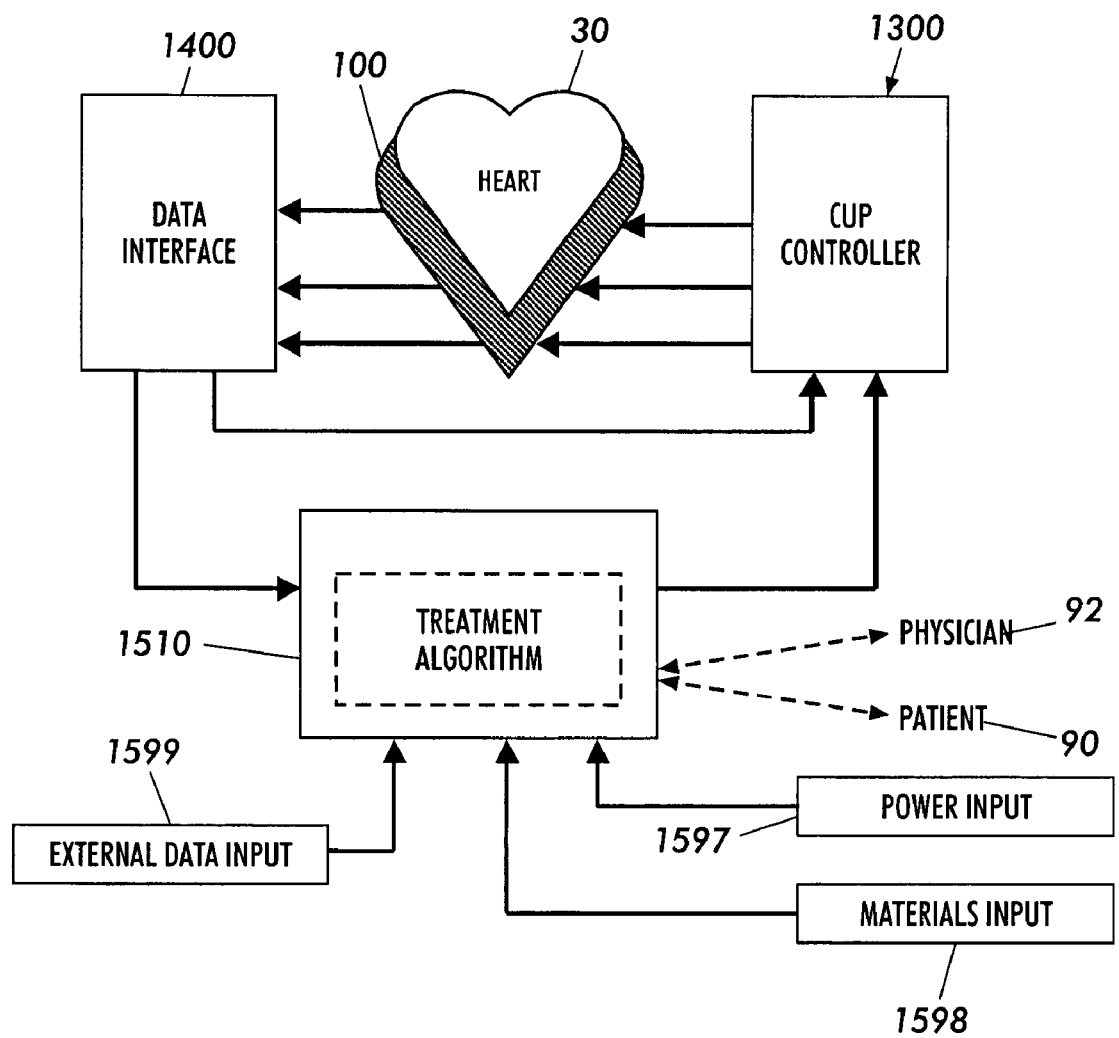
FIG. 26 is a schematic diagram of an overall control system with performance feedback, for operation and control of the DMVA apparatus.
Figure 27:
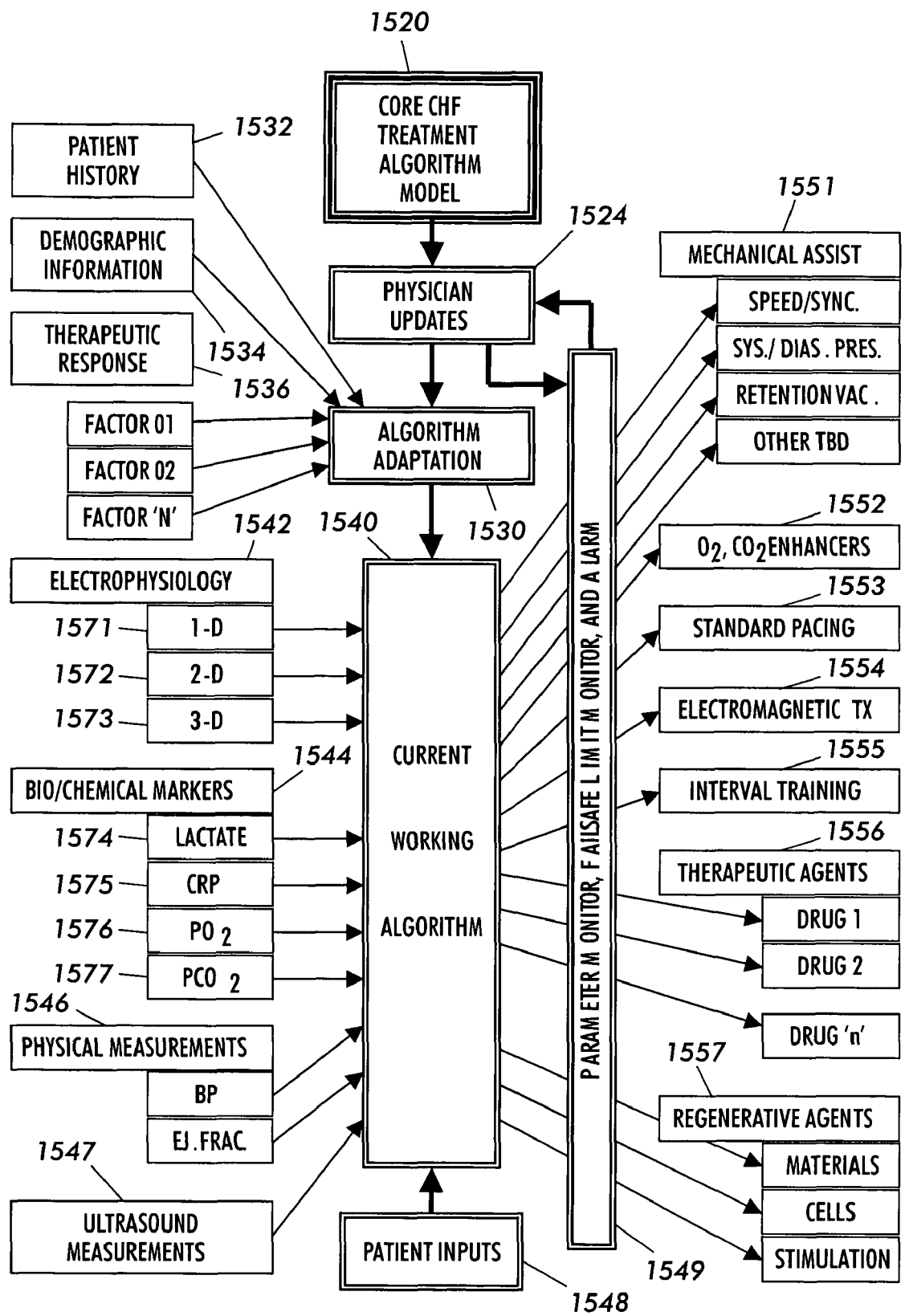
FIG. 27 is a schematic diagram of a DMVA control system, including the relationships between algorithms, input data, and output data for operation and control of a DMVA apparatus in the practice or cardiac regeneration.

With such a comprehensive fluid drive system 300 and control system 1300 interfaced with DMVA Cup 109, it will be apparent that a wide range of data acquisition, and Cup control and operating algorithms are possible. Further embodiments of the DMVA Cup of the present invention are directed to advanced control and use of such Cup device in cardiac regeneration. FIG. 26 is a schematic diagram of an overall control system with performance feedback, for operation and control of the DMVA apparatus; and FIG. 27 is a schematic diagram of a DMVA control system, including the relationships between algorithms, input data, and output data for operation and control of a DMVA apparatus in the practice or cardiac regeneration. Referring to FIG. 26, Cup controller 1300 operates DMVA Cup 100. There is further provided a data interface 1400 to which sensor data from DMVA Cup 100 is provided, and from which signal conditioned and/or analyzed data is provided as input to a treatment algorithm 1510. Such algorithm may be formulated by a human (e.g. patient 90 or physician 92) based upon intuition, experience, and physical sensation, as well as data from data interface 1400; or such algorithm may be formulated by a computer within Cup controller 1300, or other artificial intelligence device. In either instance, algorithm 1510 may be provided with additional input from external data input source 1599, materials input source 1598, and/or power input source 1597.

Algorithm 1510, in combination with various embodiments of the DMVA Cup described in this specification, may be designed to provide the heart with and/or assist the heart in biochemical regeneration, and/or cardiac training, and/or therapeutic recovery, as will be presently described and shown in FIG. 27.

The accepted practice of treating congestive heart failure (CHF) and other degenerative cardiac diseases has in the past been to attempt to slow the progress of disease (e.g. drug therapies and multi-chamber heart pacing), to compensate for the disease (e.g. restricted life style, oxygen support, mechanical ventricular assist devices), or in some cases to replace the diseased heart. The inability of the heart to recover from its diseased state, and the resulting inevitability of physical decline, morbidity, and death, have for some time been reluctantly accepted by the medical community, and society at large.

Recent parallel advances in cardiac medicine and in regenerative medicine have led some researchers to speculate as to whether some of the effects of CHF might be even more effectively delayed or compensated by use of regenerative medical treatment on the heart itself. However, the working premise of the instant invention goes well beyond the improved outcomes that are predicted based on results from prior art approaches. It is proposed that the entire course of CHF may in many cases be made totally reversible, and that an individual treated under the process of this invention may recover completely from CHF.

The aspects of this approach include the following:

An improved device and method for mechanical ventricular assist that is used to support life functions, and to permit the heart to operate in a low-stress environment.

A comprehensive historical information set relating to the individual, and to large populations of individuals with similar circumstance.

An exhaustive set of electronic, physical, and bio/chemical sensor measurements.

An array of treatment options, including physical, electromagnetic, chemical, and regenerative cellular techniques.

A treatment algorithm that draws all of the above aspects together in a control system that is knowledge-based and adaptive.

First Order Algorithm Elements

For the purpose of this disclosure, a first-order control algorithm element is defined as one that uses a single input to modify a single output, based on a predetermined mathematical relationship. For a system having 'n' inputs that are one-for-one related to outputs, the control algorithm is simple, having (n) elements that may be updated on a sequential or parallel basis. For a system comprising 'n' inputs and 'm' outputs, and where there is no one-for-one relationship, the maximum set of elements will be (m)×(n). While in theory these elements could be updated on a sequential or parallel basis, it becomes obvious that for any other than an extremely simple and linear system, the order and frequency of update will have a significant impact on the response of the system. The variability coming from this approach, especially if used to control a biological process, will result in an indeterminate result.

Second Order Algorithm Elements

For the purpose of this disclosure, a second-order control algorithm element is defined as one that uses multiple inputs to modify a single output, based on a predetermined relationship. In the case of 'n' inputs and 'm' outputs, each of the control elements will be far more complex, but there will be only (m) elements and the algorithm will be far more robust, especially if used to control a biological process.

Algorithm Updating and Adaptation Process

The biological process that the algorithm of this invention is intended to control is not the human heart, per se. The biological process this algorithm is intended to control is the healing of the heart, and the recovery from a degenerative cardiac disease such as congestive failure.

Thus, the cardiac regenerative algorithm or 'treatment algorithm' will not be one that is based on a premise of norms, stability, and control limits. Rather, the treatment algorithm of this invention will be based on a premise of gradual migration of a large set of parameters from a state of disease to a state of health. Each of these states, 'disease' and 'health', have a number of parameters each of which may vary over a range of values over time. In addition, the pathway from disease to health will vary from individual to individual. Thus for the purpose of creating an algorithm to guide the system in a manner that effectively moves this individual's heart from a diseased state to a healthy state, a fixed set of control equations will not suffice. What is required is an adaptive algorithm that continually updates itself, having 'knowledge' of a variety of pathways from disease to health that results from 1) generalized demographic information, used in combination with 2) detailed historical information on the individual, and 3) frequent pathway analysis and correction.

Algorithm Failsafes

Given the adaptive nature of the treatment algorithm, there is an increased possibility of 'traps' along the particular pathway that is being followed. The term 'trap' refers to a local optimum that precludes movement of the algorithm to the global optimum solution for the individual. In some cases a pathway trap may stall the process of healing, and in others it may have even more serious negative consequences. Thus the treatment algorithm also has failsafe measures built into it that monitor its progress and if a trapping situation is sensed, corrective actions and/or alarms can be activated.

Core Treatment Algorithm Model

Referring to FIG. 27, the core treatment algorithm model 1520 is essentially an adaptive, knowledge-based, software control algorithm, set at its initialization point and intended for use across the entire range of working scenarios. By analogy it is "right out of the box—batteries not installed" and must be set up by the attending physician for use with the specific individual.

The core treatment algorithm model 1520 may be updated from time to time, at a number of levels. However, the updating of the core model should not be confused with the behavior of a working algorithm 1540 that is constantly modifying its set points based on a variety of inputs. The working algorithm 1540 is intended to adapt to changes in patient state, to take advantage of information relating to a large population of patients in order to predict some aspects of patient response to therapy, to accept changes in control parameters from the attending physician, and to monitor its own performance.

However, all of these aspects of the working algorithm 1540 are based on protocols in the core algorithm model that are fixed. These core algorithm protocols may only be changed upon a version update that is beyond access to the patient or the physician.

Physician Inputs and Outputs 1524 are provided for use in the working algorithm. Inputs are provided such that the attending physician will be presented with an interactive software program that does the following:

- Prompts the physician with input questions
- Guarantees a comprehensive set of data on the specific patient.
- Challenges the physician in cases where data elements may be in conflict.
- Crosschecks inputs against patient record databases as a second failsafe.
- May suggest multiple treatment pathways based on access to a broader knowledge-based cardiac treatment database.

Outputs are provided such that feedback to the physician will be timed to match level of urgency:

- Regular status updates on patient condition and response to the chosen treatment.
- Advance warning if any patient condition parameter is approaching a control limit.
- Immediate warning via telemetry if any control limit is exceeded.

Algorithm Adaptation

The working algorithm 1540 is intended to adapt based on the following sets of conditions and inputs for algorithm adaptation 1530:

Initialization:
Initial choices for treatment and for alarm limits made by the attending physician.
Patient history 1532 for the individual.
Demographic information 1534 across a large population of similar patients.
Long-term:
Response to therapy 1536.
Update to core treatment model (only upon version change and with physician involvement).

The algorithm adaptation process 1530 has the following characteristics:

- It is a fixed routine that is part of the core model, so its behavior may only be changed by a version change to the core model.
- It accepts inputs listed above and modifies the working algorithm 1540 accordingly.

Working Algorithm

The working algorithm 1540 uses real-time inputs to control real-time operation of the therapeutic device. Inputs include:

Electrophysiological measurements 1542.
Bio/chemical measurements 1544.
Physical measurements 1546.
Imaging measurements 1547.
Patient inputs 1548.
Failsafe limit alarm 1549.

The working algorithm controls the following aspects of therapeutic device function:

Mechanical assist 1551, via the Heart Cup 100 (see FIG. 26).
Use of artificial blood components 1552 that act to enhance the effectiveness of oxygen and carbon dioxide exchange well beyond that of natural blood.
Standard electrical cardiac pacing 1553, with single- or multiple-chamber leads.
Advanced electromagnetic therapy 1554.
Interval training 1555, used to periodically stress the heart as in athletic conditioning.
Bio/chemical therapeutic agents 1556 applied topically via the Heart Cup, or into the bloodstream.
Regenerative medical agents 1557, including tissue scaffold materials, biochemical materials, stem cell and/or other cellular components, and electrical stimulation of tissue regeneration.

The working algorithm 1540 is fixed in its behavior over short periods between updates from the algorithm adaptation process 1530. However, the working algorithm 1540 is a complex, second-order control system that not only uses in the inputs listed above, but also analyzes the relationships between those inputs and is able to react in a non-linear fashion.

Patient Inputs & Outputs 1548

The patient will be provided with an input/output device that permits entry of information that may improve the effectiveness of the treatment. Examples of inputs include the following:

Information relating to planned physical activity or rest—this may be used to influence the scheduling of training-related portions of the treatment algorithm.
Information related to timing and content of meals—metabolic information may be useful in predicting cardiac response, and in some cases the drugs used by the treatment algorithm may be contraindicated in combination with some foods.

The I/O device permits communication output to the patient. Examples of outputs include the following:

The same information being sent to the physician.
Confirmation of, or challenge to, information input by the individual.
Suggested actions that extend the effectiveness of the treatment algorithm, relating to physical activity, rest, or other factors.

Parameter Monitor, Failsafe Limit Monitor, and Alarm 1549

This ("Failsafe") subroutine acts as a secondary safety feature, providing redundant measures to ensure the safety of the patient. It is not a redundant controller and does not affect the operation of the primary working algorithm. Rather, it has a baseline set of parameter limits, and parameter-to-parameter limits that can be modified by the physician at the outset. During initialization of the system, the failsafe algorithm 1549 (as modified by the physician) is compared against the working algorithm 1540 (as modified by the physician, and by input of patient history and demographic information) to determine if there are operational inconsistencies. Once the overall system is initialized and started, the failsafe algorithm 1549 monitors the control outputs of the working algorithm 1540 on a real-time basis and reacts to both limits that are exceeded, and trends in performance that are approaching limits in a manner that is inconsistent with nominal operation. It then provides an appropriate warning or alarm output to the physician and/or patient, as appropriate.

External Data

Individual Patient History 1532: Patient history input 1532 is a set of numerical values that describe or quantify a variety of prior aspects of the individual patient preceding the implementation of the DMVA apparatus, the specific cardiac disease being treated, and other health-related factors that may be important to proper operation of the working algorithm

1540, and especially as the interval training 1555 aspects are utilized. Typical elements in patient history include the following: history of cardiac disease conditions such as pulmonary hypertension, systemic hypertension, dilated cardiomyopathy, congestive heart failure, and myocardial infarction; hereditary factors; smoking or substance abuse; and history of other large organ diseases.

Demographic Information 1534: Any individual patient, healthy or unhealthy, provides opportunity for retrospective analysis of their responses to disease and to treatment (physical, bio/chemical, electromechanical, etc.). But the individual patient history provides only the opportunity for retrospective analysis, and no opportunity for predictive analysis. A database of demographic information, i.e. predictive numerical parameters, provides the opportunity for prediction of the individual patient's response to the above stimuli by comparison to others with similar conditions and an analysis of the outcomes from specific pathways chosen in treatment. The kinds of demographic information useful to the working algorithm include information such as age, race/ethnicity, and gender.

Therapeutic Response 1536: Input parameters shown in FIG. 27 by indicia 1542, 1544, 1546, and 1547 are measurements made by individual sensors or groups of sensors, indicating the value of a specific parameter in real time. These parameters are used by the working algorithm 1540 in its real time control of system function. In aggregate, they may be analyzed along with other inputs, such as physician observations and patient observations, to create a set of factors that correlate to the general state of health of the patient, of the cardiovascular system, and individual subcomponents of the heart such as regions of tissue that may have been damaged during a myocardial infarction, or a particular part of the circulatory system of the heart itself.

The therapeutic response factors 1536 are used as inputs to the algorithm adaptation process 1530 as a means of indicating the recent and longer-term effectiveness of the working algorithm 1540 (as currently configured) to stabilize, heal, and/or regenerate the heart. Use of these therapeutic response factors along with patient history and demographic information, are analyzed by the algorithm adaptation process 1530 to either continue or modify the current working algorithm 1540.

The therapeutic response function 1536 may also periodically provide status and trend data to the physician and/or the patient, as appropriate.

Internal Data

Electrophysiology input 1542 includes one-dimensional data 1571, two-dimensional-dimensional data 1572, and three-dimensional data 1573. One-dimensional data 1571 entails typical electrophysiological signals such as are used in controlling pacemakers and cardio-defibrillators. These are typically point measurements made by sensors that contact cardiac tissue at specific parts. With regard to two-dimensional data 1572, the electrophysiology of heart function is not a set of distinct traditional nerve pathways connecting a set of points in the heart tissue. Rather, it involves a wave front that propagates through the tissue in a very complex way. By making electrophysiological measurements at multiple distributed surface sites (and conversely providing the opportunity for pacing the heart at these multiple sites), more information may be collected regarding the state of tissue at specific locations within the heart. This information may be key to application of regenerative therapies and specifically to the use of "training" regimens. See, for example, U.S. Pat. No. 5,674,259, "Multifocal leadless apical cardiac pacemaker," the disclosure of which is incorporated herein by reference. With regard to three-dimensional data, reference may be had to, "When Time Breaks Down—The Three-Dimensional Dynamics of Electrochemical Waves and Cardiac Arrhythmias", Arthur T. Winfree, Princeton University Press, ISBN 0-691-02402-2, the disclosure of which is incorporated herein by reference.

Bio/Chemical Markers 1544

Lactate 1574: Lactate is well known as a marker for muscle fatigue. It may be measured directly via a chemical analysis of blood. It may also be measured by spectroscopic means. If the latter approach is taken it may also be measured directly in cardiac tissue thus providing a feedback mechanism for the degree of stress involved in a cardiac muscle training regimen.

C-Reactive Protein 1575: CRP is produced in the liver in response to inflammation and/or tissue damage. The biochemical pathway resulting in an increase in CRP concentration appears to be somewhat complex. Thus it is unlikely to find a precursor molecule at the heart that would be an early indicator of cardiac tissue damage due to excess physical exertion, or some other form of impending damage to the heart.

$PO_2$ 1576: Concentration of oxygen and carbon dioxide in arteries, capillaries, and veins supporting cardiac tissue may be an important indication of tissue health, and the ability of the heart to do effective pumping work.

$PCO_2$ 1577: See above for $PO_2$.

As stated previously, the present invention avoids the production of stress forces within the heart muscle by applying forces to the heart that are perpendicular to the surface of the heart, while also ensuring that the magnitude of the difference between adjacent forces is very small. In other words, the application of the force to the heart is substantially uniform, taken over a distance scale that is relevant to the imposition of significant (i.e. traumatic) shear stress on the heart muscle. In particular, the applied force is uniform circumferentially, i.e. around the heart, such that the heart is compressed to form a core shape with a substantially circular cardiac core diameter as previously described. Each of these features eliminates the formation of shear forces within the heart muscle, which leads to bruising damage to the heart tissue which leads to muscle fatigue and potentially failure of the heart. The DMVA device of the present invention is thus atraumatic with respect to the heart.

Specific features of the present invention which provide these capabilities include the following:

A. Near-isotropic Liner Material

Liner materials that are near-isotropic will expand uniformly from internal pressure or vacuum applied by the internal working fluid. This uniform expansion or contraction prevents "less stiff" portions of the liner from "ballooning" into the heart tissue and creating higher forces on the heart tissue, relative to "more stiff" adjacent portions of the liner, which would cause shear stresses throughout the heart wall and bruising of heart tissue, which would ultimately lead to damage to the heart tissue. Over time, this damage could lead to total failure of the heart.

In addition, some materials either stiffen after being flexed or stretched ("strain hardening"), or weaken after flex or stretch (strain softening). In metals, this results from changes in grain structure, and in elastomers, it results from changes in polymer chain bonds. Optimal materials for the DMVA Cup liner and shell are "strain neutral", and maintain original properties after repeated cyclic loadings. The near-isotropic and strain neutral liner avoids this problem by enabling all areas of the liner to expand at the same rate and preventing areas of the liner from "ballooning" into the myocardium and creating shear stresses within the heart tissue. Furthermore, isotropic materials allow the heart to be actuated (compressed and dilated) in a manner dictated by the tissue characteristics, and pressure points are minimized as the material does not fold or bend in a non-uniform fashion. In one embodiment, a suitable near-isotropic and strain neutral elastic material is a heat curable liquid silicone rubber sold, by the NuSil Technology Company, of Carpenteria, Calif.

B. Fatigue-resistant liner material

Fatigue of the liner material would create a "weak spot" such as described above, and result in shear within the heart tissue. Liner materials that are fatigue-resistant ensure that the liner will avoid "weak spots" and prevent a difference in forces from being applied to the heart tissue and the shear stresses that such differences create.

C. Dynamic Cup Shell Structure and Material.

The compliant nature of the preferred Cup shell of the present invention results in the constantly adaptation of the shape thereof in response both to the actuating forces applied to the heart and changes in the heart's size and/or shape. This characteristic contributes to decreased ventricular trauma, ease of application as the housing can be deformed to fit through small incisions, and important dynamic conformational changes that constantly respond to the heart's changing shape.

The housing (shell) of the device is constructed of a flexible material that has appropriate compliance and elastic properties that allow it to absorb the systolic and diastolic actuating forces in a manner that somewhat buffers the effect of the liner on the heart. The unique qualities of this housing lessen the risk for inadvertent excessive forces to be applied to the heart at any time of the cycle. The shell conforms to the dynamic changes in the right and left ventricles throughout compression and relaxation cycles as well as overall, ongoing changes related to variances in heart size over time which occur as a consequence of continued mechanical actuation and related "remodeling" effects on the heart.

In one embodiment, the Cup shell consists essentially of the aforementioned liquid silicone rubber polymer having a wall thickness of between about 2 millimeters and about 8 millimeters. It is preferable to form the Cup shell with walls as thin as possible while retaining the desired dynamic capabilities.

D. Liner Design Improvements:

In another embodiment, the requirement for an isotropic or near-isotropic material is greatly reduced or eliminated by the provision of a liner that applies a uniform force to the heart without undergoing elastic deformation one such a liner is a rolling diaphragm liner that is deployed against ventricle walls of the heart by a progressive rolling action, as described previously in this specification and shown in FIGS. 4A-4C.

2. Absence of Surface Abrasion

The Cup liner described above creates a near-zero shear stress or minimum-slip condition at liner-myocardium interface, similar to the "rolling interface" that exists between mechanical gears. This no-slip condition minimizes or eliminates abrasion of the heart tissue, which over time can result in serious damage to the heart tissue.

Figure 16A:
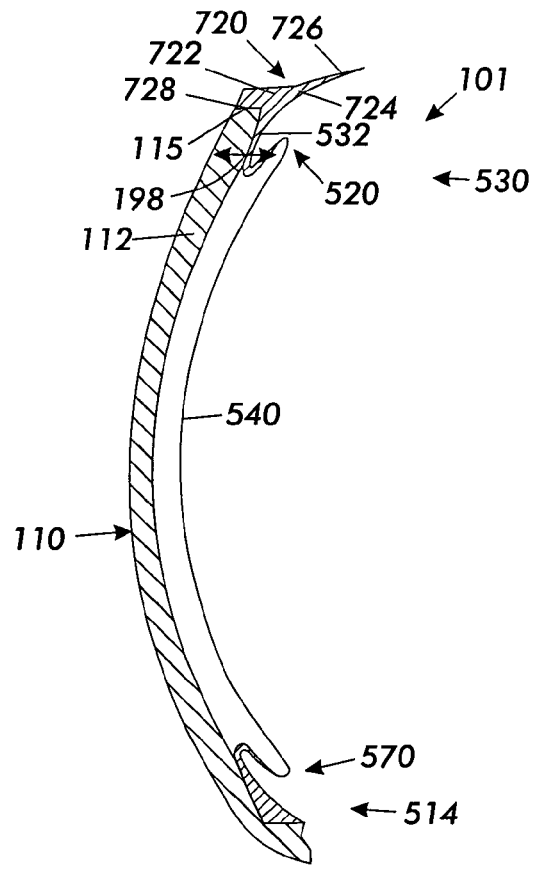
FIG. 16A is a schematic representation of a further embodiment of the DMVA apparatus of the present invention, comprising an integrated seal and liner with a rolling diaphragm.
Figure 16B:
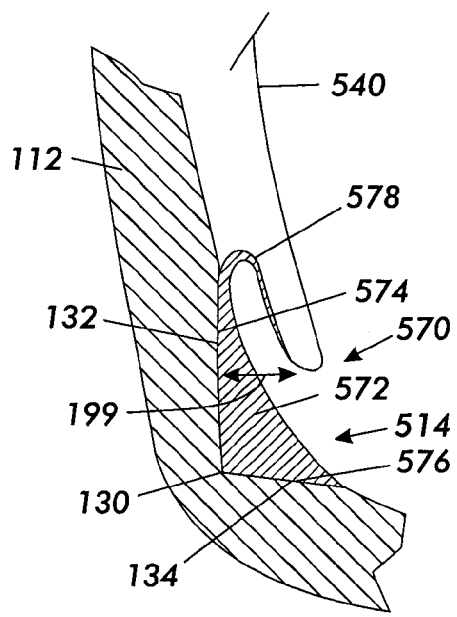
FIG. 16B is a detailed view of one embodiment of a bond between a rolling diaphragm and a cup shell of the DMVA apparatus of FIG. 16A.

FIG. 16A is a schematic representation of a further embodiment of the DMVA apparatus of the present invention, comprising an integrated seal and liner with a rolling diaphragm. This embodiment demonstrates the concept of making the shell and the liner as separate, precisely molded components, and bonding them together in a secondary process using fixtures to locate and clamp them. Referring to FIG. 16A, DMVA apparatus 101 comprises shell 110, depicted therein as a simple thick-walled cup-shaped structure. For sake of simplicity of illustration, no attempt is made to show ports or other features in shell 110. In other embodiments, shell 110 may have variable thickness and/or variable material in both vertical and circumferential sectors in order to provide desired mechanical properties. In a further embodiment, shell 110 comprises a core of non-biocompatible material with an outer layer of biocompatible material.

Referring again to FIG. 16A, DMVA apparatus 101 further comprises integral liner and seal assembly 530 joined to Cup shell 110. Integral liner and seal assembly 530 is formed of a unitary piece, preferably by a molding process, such as e.g., by an injection molding or compression molding technique, or by pre-molding the seal and bond area features thereof via injection molding, then placing such piece in an insert mold such that the thin liner sections may be molded and bonded thereto simultaneously.

Assembly 530 comprises seal 720, upper rolling diaphragm section 520, liner membrane 540, and lower rolling diaphragm section 570. In the preferred embodiment, seal 720 is formed with a structure similar to seal 730 of FIG. 18A, which is described subsequently in this specification. Seal 720 preferably comprises base 722, tapered section 724, tip 726, and surface 728, which is formed to mate with corresponding upper edge 115 of Cup shell 110. Surface 728 of assembly 530 is joined to Cup shell 110 by suitable means such as e.g., adhesive, as described subsequently in this specification for the joining of lower joint region of liner 510 to Cup shell 110 and shown in FIG. 19B. In the preferred embodiment, surface 728 of assembly 530 is joined to upper edge 115 of Cup shell 110, while transition section 532 of assembly 530 is not joined to shell 110. Thus in a manner similar to that described subsequently and shown in FIG. 16B, assembly 530 is free to flex at transition section 532 as indicated by bi-directional arrow 198, thereby distributing bending stress over transition section 532. It is noted that FIG. 19A depicts an alternate embodiment comprising a transition section 533 for distributing stress in assembly 530 according to the same general principles.

In one embodiment, rolling diaphragm liner is directly bonded to DMVA Cup shell wall 112 at upper section 520 and lower section 570 thereof. FIG. 16B depicts one embodiment of such a bond between liner 510 and Cup shell wall 112 at lower joint region 514 therebetween. Referring to FIG. 16B, shell wall 112 is provided with a groove 130 having surfaces 132 and 134 in shell wall 112, formed preferably during the shell manufacturing process such as e.g., molding, or less preferably, by a secondary operation such as e.g., milling or etching. Lower rolling diaphragm section 570 of liner 510 is provided with a rim 572 having surfaces 574 and 576, which are formed to mate with corresponding surfaces 132 and 134 of groove 130 of Cup shell wall 112. In one embodiment (not shown), during the manufacturing process, an adhesive is dispensed such that a thin film of adhesive is formed in the interstice between rim 572 and groove 130, thereby bonding lower joint region 514 of liner 510 to Cup shell wall 112.

In the preferred embodiment, surfaces 576 and 134 are bonded, while surfaces 574 and 132 are not bonded. With such a structure, rim 572 of lower rolling diaphragm section 570 is free to flex as indicated by arrow 199 when liner membrane 540 is displaced outwardly and inwardly, thereby widely distributing stress within lower rolling diaphragm section 570, such that fatigue of the material thereof is greatly diminished. Thus the safety, reliability and longevity of the DMVA device 101 are significantly enhanced.

It is known that sudden changes in cross-section of components that undergo repetitive bending result in stress-concentrations that reduce fatigue life of such components. A number of approaches are traditionally taken to effect stress relief, but one of the simplest is a gradual change in section. Thus it can be seen that there is a continuous, gradual thinning of the liner material in the progression from the rim 572, from surface 576 upwardly to the portion thereof bounded by surface 574, an on through transition section 578 to liner membrane 540 in order to achieve such a reduction in stress concentration.

Other means of bonding liner 510 to shell wall 112 will be suitable and will be apparent to those skilled in the art, with the exact choice of means depending upon the particular material selections for Cup shell 110 and liner 510. One example of a material suited for both shell 110 and liner 510 is MED4850 Liquid Silicone Rubber. One example of an adhesive well suited for bonding elements consisting essentially of this material is MED1-4213. Both of these materials are products of the NuSil Technology Company of Carpenteria, Calif.

Figure 17A:
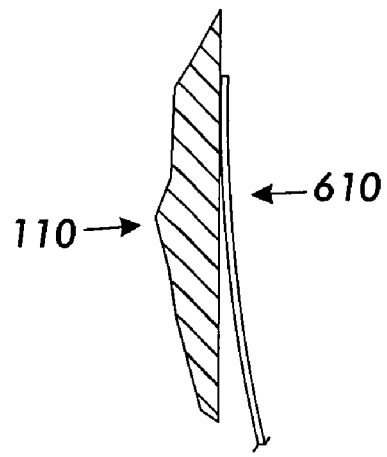
FIG. 17A-17H are detailed views of alternate embodiments of flat and rolling diaphragm liners of the DMVA apparatus, particularly showing the bonds between such flat and rolling diaphragm liners and the cup shell.
Figure 17B:
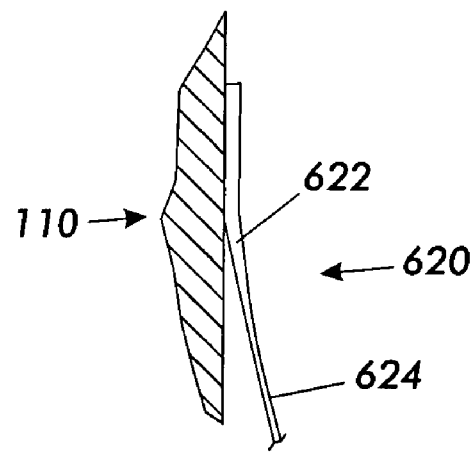
Figure 17C:
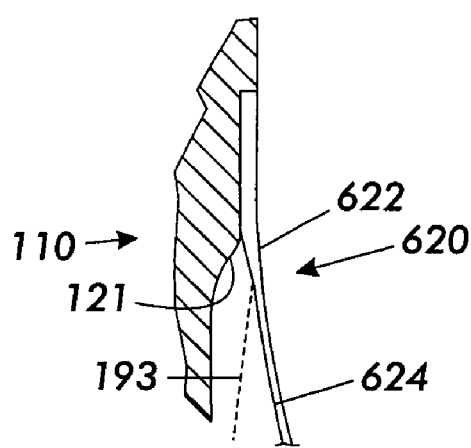

FIG. 17D-17H are detailed views of alternate embodiments of rolling diaphragm liners of the DMVA apparatus, particularly showing the bonds between such rolling diaphragm liners and the cup shell. FIGS. 17A, 17B, and 17C depict liner attachments having simple designs that will result in shear stress in the surface tissue of the heart, and are thus less preferred. However, such designs demonstrate one aspect that should be considered, i.e. a gradual shape transition from liner 610 or 620, (which moves during systole and diastole) and shell 110 (which moves far less). Thus, sharp edges and shape transitions in the liner that act as stress concentrators are to be avoided. In the embodiments of FIGS. 17B and 17C, liner 620 comprises a tapered unbonded transition section 622, which reduces in thickness to a thin section forming liner membrane 624. The DMVA device of FIG. 17C is further provided with a shell 110 having a recess 121, so that during diastolic actuation, liner 620 can flex beyond a 180 degree angle as indicated by dotted line 193. Liner 620 may even be displaced such that unbonded transition section 622 is contiguous with recess 121 of shell 110 at the completion of diastole.

Figure 17D:
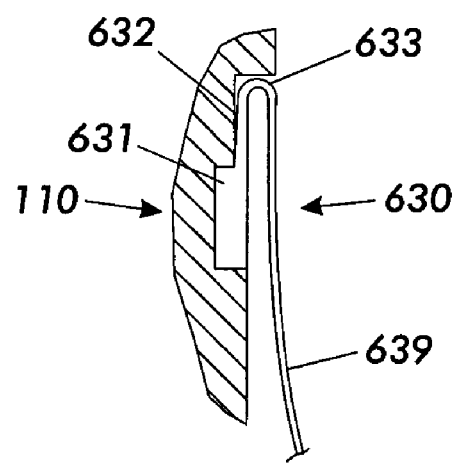

FIG. 17D depicts an embodiment of a rolling diaphragm 630 comprising bonded rim 631, unbonded tapered transition section 632, rolling bend 633, and liner membrane section 639. In this embodiment, single bend 633 is used to minimize the motion of the heart wall (not shown) relative to liner 630; however, this design will still result in relatively high bending stress in the material of liner 630 at bend 633.

Figure 17E:
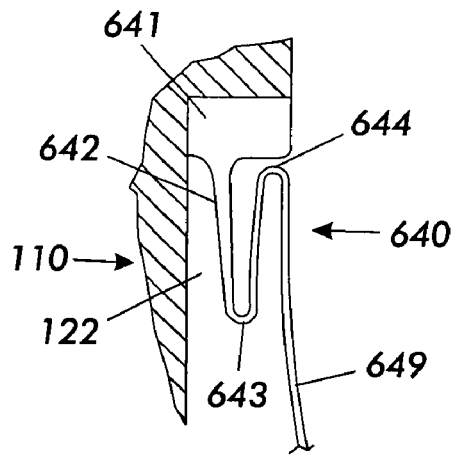

FIG. 17E depicts another embodiment of a rolling diaphragm provided with two folds or bends. Referring to FIG. 17E, rolling diaphragm 640 comprises bonded rim 641, unbonded tapered transition section 642, first rolling bend 643, second rolling bend 644, and liner membrane section 649. The presence of two bends 643 and 644, along with a larger recess 122 in shell 110, further reduces tissue shear stress and liner material fatigue.

Figure 17F:
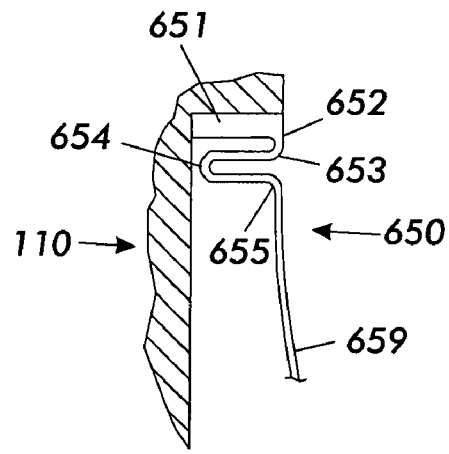
Figure 17G:
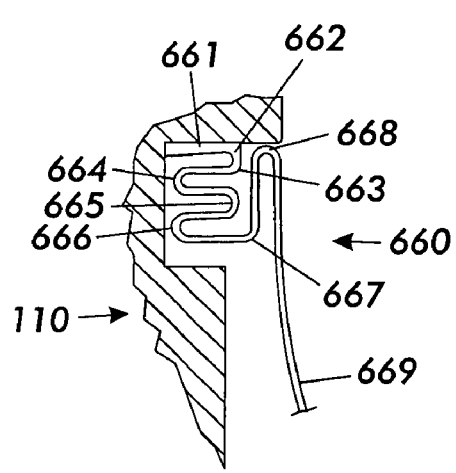

FIG. 17F depicts another embodiment of a rolling diaphragm provided with three bends. Referring to FIG. 17F, rolling diaphragm 650 comprises bonded rim 651, short tapered transition section 652, first elbow bend 653, first U bend 654, second elbow bend 655, and liner membrane section 659. FIG. 17G depicts yet another embodiment of a rolling diaphragm provided with a plurality of stress-relieving bends. Referring to FIG. 17G, rolling diaphragm 660 comprises bonded rim 661, short tapered transition section 662, first elbow bend 663, first U bend 664, second U bend 665, third U bend 666, second elbow bend 667, fourth U bend 668, and liner membrane section 669. The presence of multiple bends in these embodiments further reduces tissue shear stress and liner material fatigue.

Figure 17H:
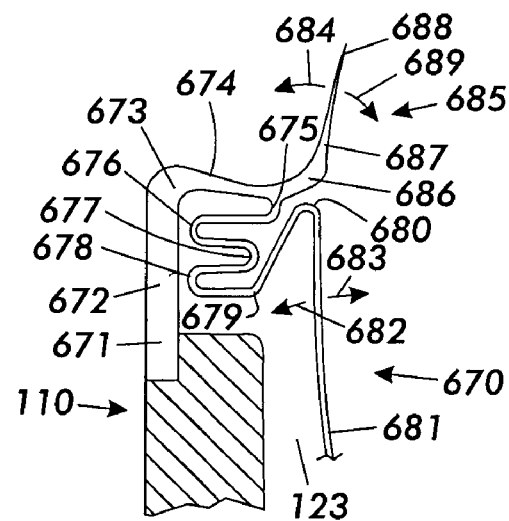

FIG. 17H depicts yet another embodiment of a rolling diaphragm provided with a plurality of stress-relieving bends and with an active seal, rather than a passive "self-bailer" or "check valve" seal. Referring to FIG. 17H, rolling diaphragm 670 comprises bonded rim 671, riser section 672, riser bend 673, tapered transition section 674, first elbow bend 675, first U bend 676, second U bend 677, third U bend 678, second elbow bend 679, fourth U bend 680, and liner membrane section 681. The presence of multiple bends in these embodiments further reduces tissue shear stress and liner material fatigue. Rolling diaphragm 670 further comprises seal 685 comprised of base 686, tapered section 687, and tip 688.

Arrows 682, 683, 689, and 684 indicate the linkage between motion of liner membrane 681 and seal 685 during systole and diastole that results from pressurization of the cavity 123 between shell 110 and liner 670 with DMVA drive fluid. During systole, liner membrane moves as indicated by arrow 683, and seal 685 moves as indicated by arrow 684; such that during systole, seal 685 is relatively looser on the heart (not shown). During diastole, liner membrane 681 moves as indicated by arrow 682, and seal 685 moves as indicated by arrow 689; such that during diastole, seal 685 is relatively tighter on the heart. Thus the "self-bailing" efficiency of active seal 685 is improved. This effect results directly from the shapes, dimensions and materials chosen for liner/seal 670. It will be apparent to those skilled in the art that there are many variants of liner seal 670 with regard to material thicknesses and bend configurations comprising at least one bend that will achieve the same result, i.e. the linkage between motion of liner membrane 681 and seal 685 as indicated by arrows 682, 683, 689, and 684, an that such variants are to be considered within the scope of the present invention.

Figure 18A:
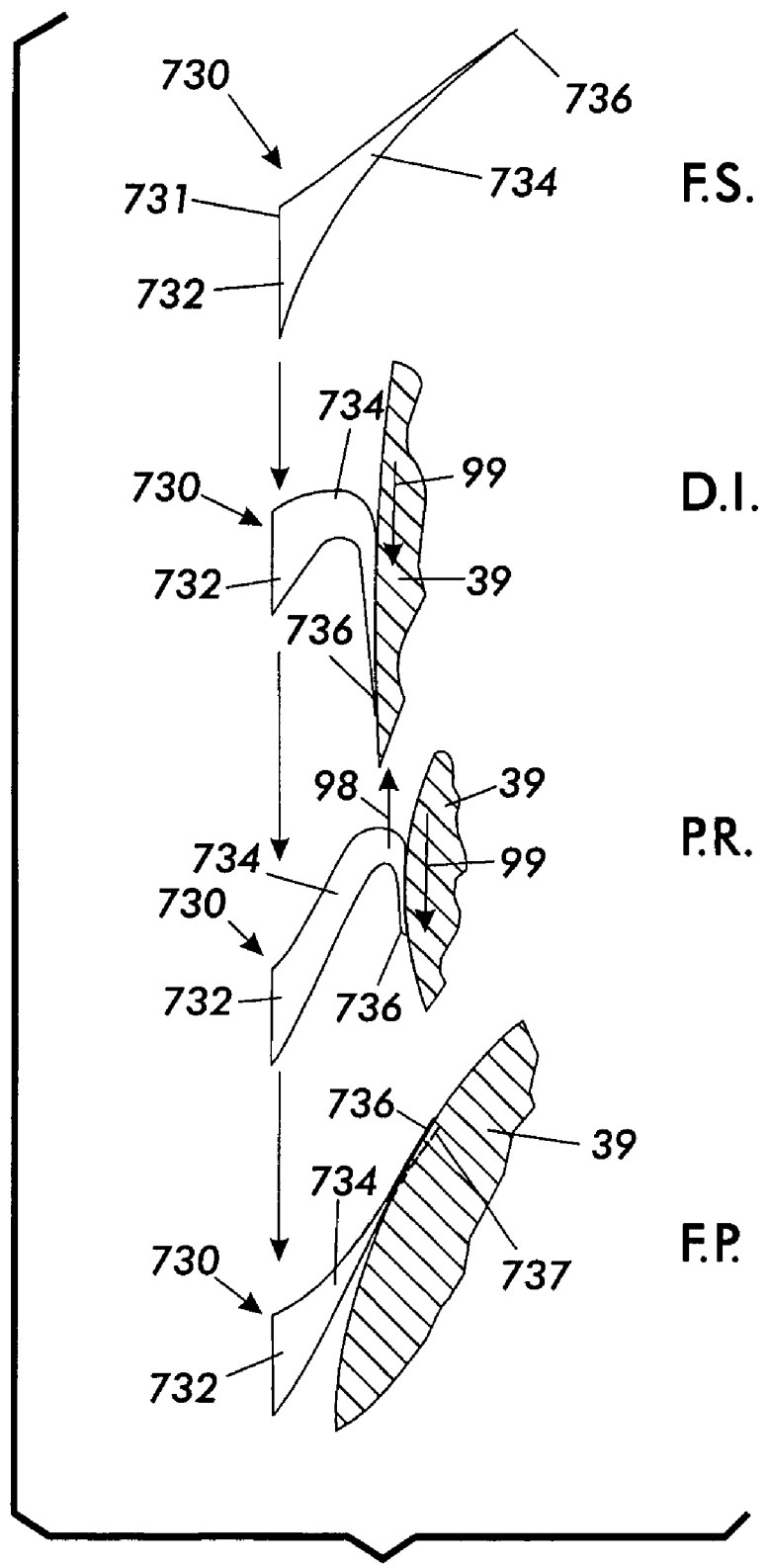
FIG. 18A-18C are detailed views of alternate embodiments of several DMVA cup seals, in which the free shape, initial installed shape, partially recovered shape, and final position are shown.
Figure 18B:
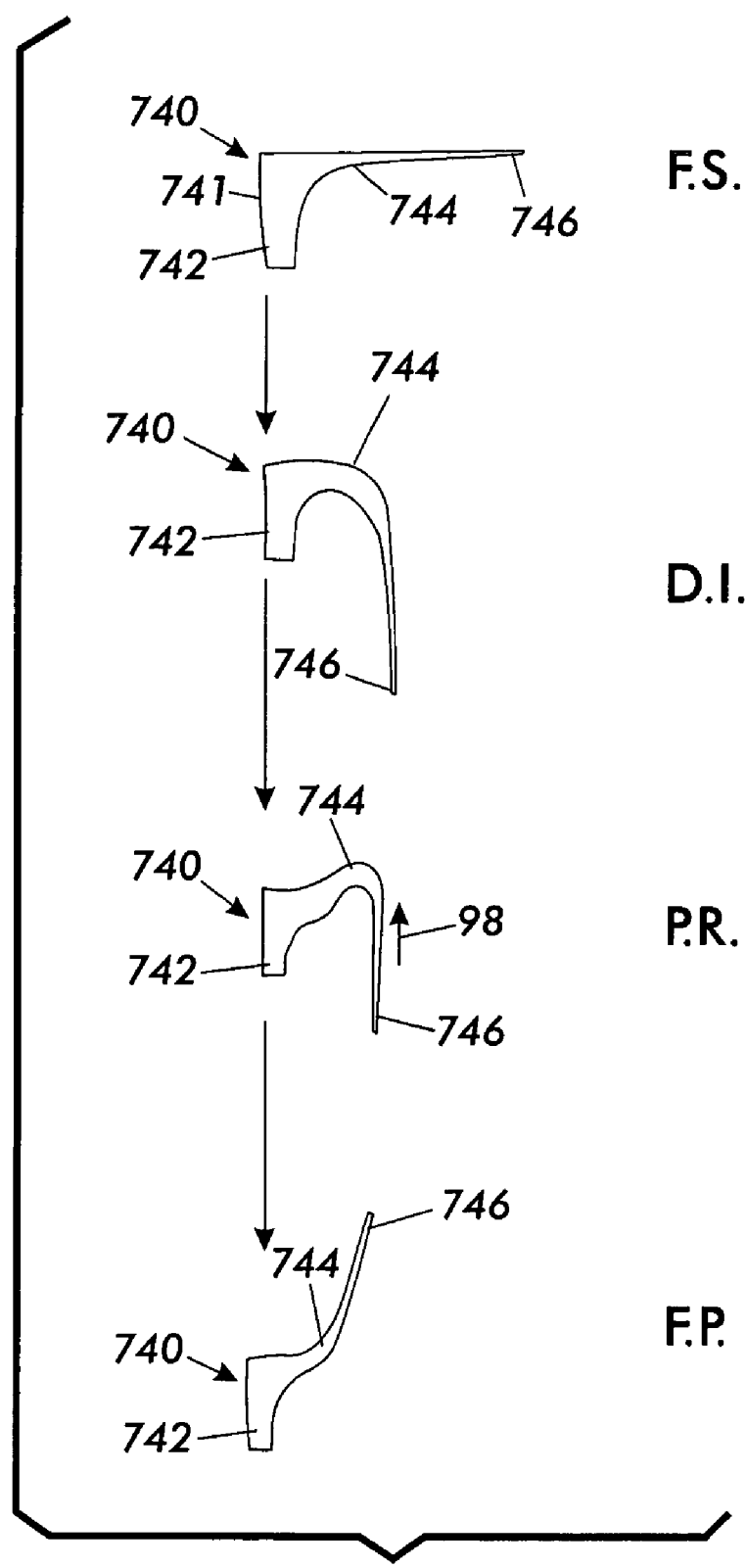
Figure 18C:
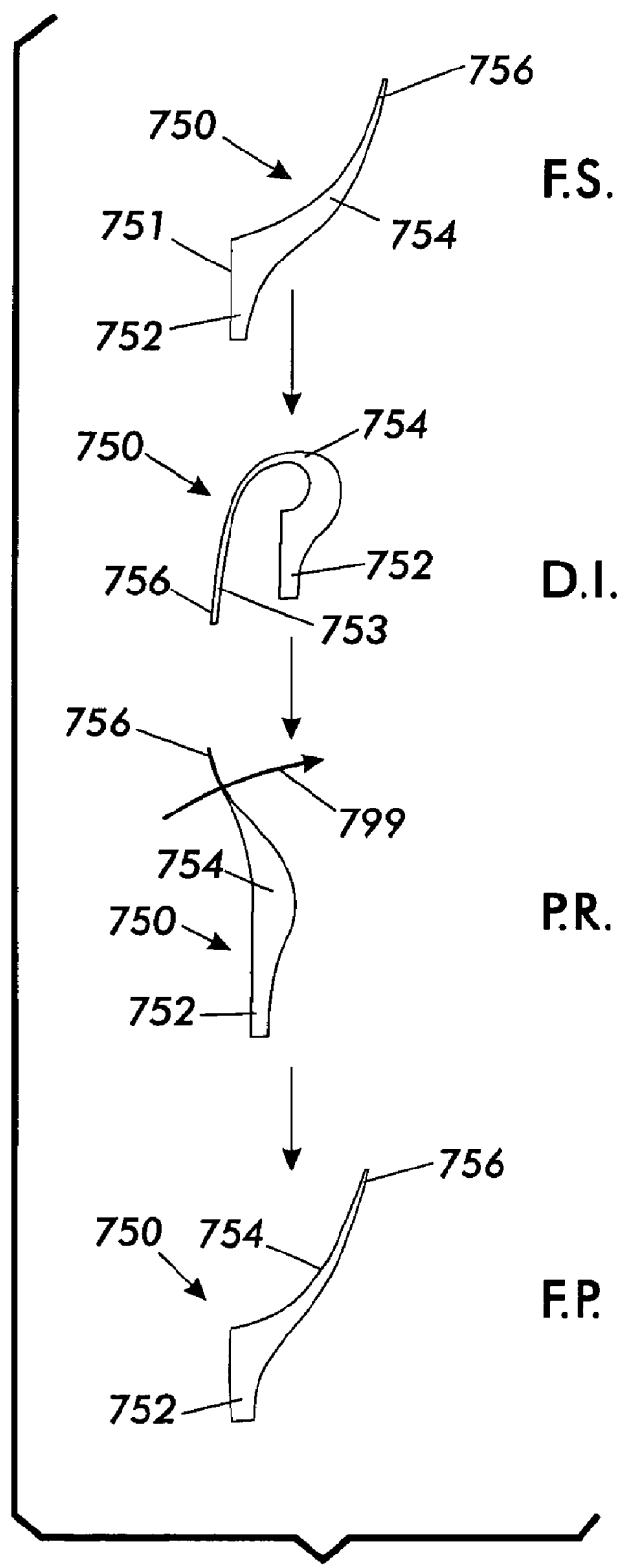
Figure 19A:
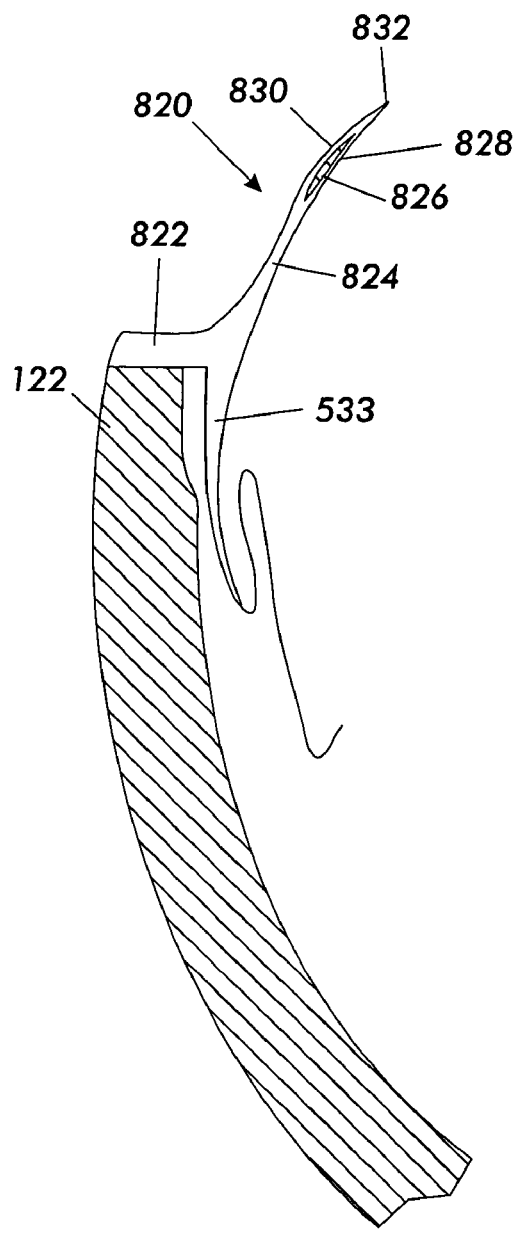
FIG. 19A is a cross-sectional view of an active seal by which the DMVA apparatus more firmly engages the heart.

FIG. 18A-18C are detailed views of alternate embodiments of several DMVA cup seals, in which the free shape, initial installed shape, partially recovered shape, and final position are shown. Referring to FIG. 18A, obtuse seal 730 comprises structural base 732, which is joined to shell 112 of DMVA Cup 100 (see e.g., FIG. 4A). Obtuse seal 730 further comprises a tapered midsection 734, which tapers to an apex or tip 736. Tip 736 of seal 730 is tapered to a very thin section terminating at a distinct edge, thus conforming to the details of heart surface effectively. In a further embodiment, the overall shape of the seal annulus is not perfectly circular, but instead seal 730 is molded or formed to adapt to the non-circular shape of the heart at this vertical position near the atrio-ventricular groove of the heart.

Referring again in particular to the upper portion of FIG. 18A, labeled F.S., seal 730 is depicted in the free state (F.S.). When seal 730 is in the free state, tapered midsection 734 and apex 736 are generally disposed at an obtuse angle with respect to surface 731 of structural base 732. Seal 730 is shown as inwardly-facing, in order to maximize the "self-bailing" properties associated with diastolic and systolic movement of the Cup and the Heart. By self bailing, it is meant that the action of seal 730 against the heart surface is intended to act like a check valve, encouraging any trapped fluid to be easily pushed out during systole, and discouraging any external fluid from entering during diastole. The seal-to-heart interface is maintained partly by shape and elastic forces, and partly by hydrostatic pressure on the outer surface of seal 730. In a further embodiment (not shown), seal 730 further comprises an internal core section having different material and physical properties than the outer surface, and may or may not be biocompatible.

When the DMVA Cup is to be installed upon a heart, the Cup is slipped over the heart, such that heart tissue 39 is placed in sliding contact with seal 730. During installation (D.I.), seal 730 bends at midsection 734, and apex 736 is displaced downwardly by the downward sliding action of heart tissue 39 indicated by arrow 99, as indicated in the second part of the sequence labeled D.I.

As the heart is slipped into the DMVA Cup, and the portion of maximum girth of the heart passes seal 730, seal 730 begins to recoil in the tapered midsection 734, thereby drawing apex 736 upwardly as indicated by arrow 98. The third graphic of FIG. 18A, labeled P.R., shows such a partial recovery of seal 730. When the heart is fully seated and retained in the DMVA Cup, and the recoiling action of seal 730 is complete, seal 730 is in final position (F.P.), as shown in the final graphic of FIG. 18A. The recoil of seal 730 may occur spontaneously during installation; or it may occur by some manual manipulation thereof; or it may occur after several cardiac cycles that "work" the heart in the Cup, thereby facilitating the flexure and recoiling of seal 730.

Seal 730 is configured such that apex 736 is in tension against heart tissue 39. In addition to such tension, the pressure differential that is present between the outside and inside of the Cup wall during diastole further enhances engagement and sealing contact between heart tissue 39 and seal 730. As a result of such tension and engagement, after seal 730 has been thus engaged with the heart for a period of time, tissue ingrowth occurs, such that apex 736 becomes embedded in heart tissue 39, as indicated by apex 737 shown in phantom in FIG. 18A.

Seal 730 is preferably formed of a deformable elastic polymer. In one embodiment, seal 730 is made of a silicone polymer known commercially as Silastic, or Liquid Silicone Rubber. One example of a material suited for seal 730 is MED4850 Liquid Silicone Rubber. One example of an adhesive well suited for bonding elements consisting essentially of this material is MED1-4213. Both of these materials are products of the NuSil Technology Company, of Carpenteria, Calif.

In a further embodiment, seal 730 is provided with a coating of a biocompatible thin film to facilitate such ingrowth and adhesion of tissue.

FIG. 18B is a cross sectional view of a perpendicular seal, the geometry of which is similar to the prior art design of Anstadt. Referring to FIG. 18B, perpendicular seal 740 comprises surface 741, and structural base 742, which is joined to shell 112 of DMVA Cup 100 (see e.g., FIG. 4A). Perpendicular seal 740 further comprises a tapered midsection 744, which tapers to an apex or tip 746. Referring in particular to the upper portion of FIG. 18B, labeled F.S., seal 740 is depicted in the free state (F.S.). When seal 740 is in the free state, tapered midsection 744 and apex 746 are generally disposed perpendicular to surface 741 of structural base 742. In the remaining views of seal 740 of FIG. 18B, there are depicted in descending sequence views of seal 740 during installation (D.I.), partially recovered (P.R.), and in final position (F.P.). The manner in which the DMVA Cup comprising seal 740 is fitted to a heart is as described previously and shown in FIG. 18A.

Seal 740 is a less-preferred design, compared to seal 730 of FIG. 18A. Seal 740 provides substantially the same wiping action and spring-back during installation as described for seal 730, but seal 740 is more dependent upon elastic force than upon hydrostatic loading during diastole in order to maintain a good seal to the heart, as compared with seal 730. Seal 740 is more likely to trap minor amounts of fluid within the DMVA Cup, thus being less effective as a 'self-bailer'. This condition may require that an active vacuum pump be used to maintain negative pressure within the Cup during diastole, for a DMVA Cup comprising seal 740. FIG. 18C is a cross sectional view of a seal that is 'self-bailing' during operation, and that is actively retained during installation to keep it out of contact with the heart wall, thus minimizing possible tissue damage thereto. Referring to FIG. 18C, self-bailing seal 750 comprises surface 751, and structural base 752, which is joined to shell 110 of DMVA Cup 100 (see e.g., FIG. 4A). Self-bailing seal 750 further comprises a tapered midsection 754, which tapers to an apex or tip 756. Referring in particular to the upper portion of FIG. 18C, labeled F.S., seal 750 is depicted in the free state (F.S.). In the next view down in FIG. 18C, seal 750 is depicted during installation (D.I.). It can be seen that seal 750 is bent outwardly and downwardly approximately 180 degrees along tapered section 754, such that during installation of the DMVA Cup on the heart, seal 750 does not contact the heart, thereby eliminating the risk of any damage to heart tissue by seal 750.

In the next view down in FIG. 18C, seal 750 is depicted in a state of partial recovery (P.R.). It can be seen that the apex 756 of seal 750 has been released, and that apex 756 of seal 750 is snapping upwardly and inwardly as indicated by arrow 799, to engage with heart tissue 39 (see FIG. 18A). Subsequently, seal 750 achieves final position (F.P.) against the heart tissue 39 as shown in FIG. 18A.

In one embodiment (not shown), seal 750 is provided with water soluble adhesive applied to surface 753, which temporarily bonds surface 753 to the outer surface of shell 110 of the DMVA Cup 100 (see e.g., FIG. 4A). Apex 756 is retained during installation, and upon exposure to bodily fluid, such adhesive dissolves, thereby releasing apex 756 as shown in the P.R and F.P states in FIG. 18C. In another embodiment (not shown), seal 750 is provided with an active physical feature such as a tear-away strip to release apex 756.

Figure 20:
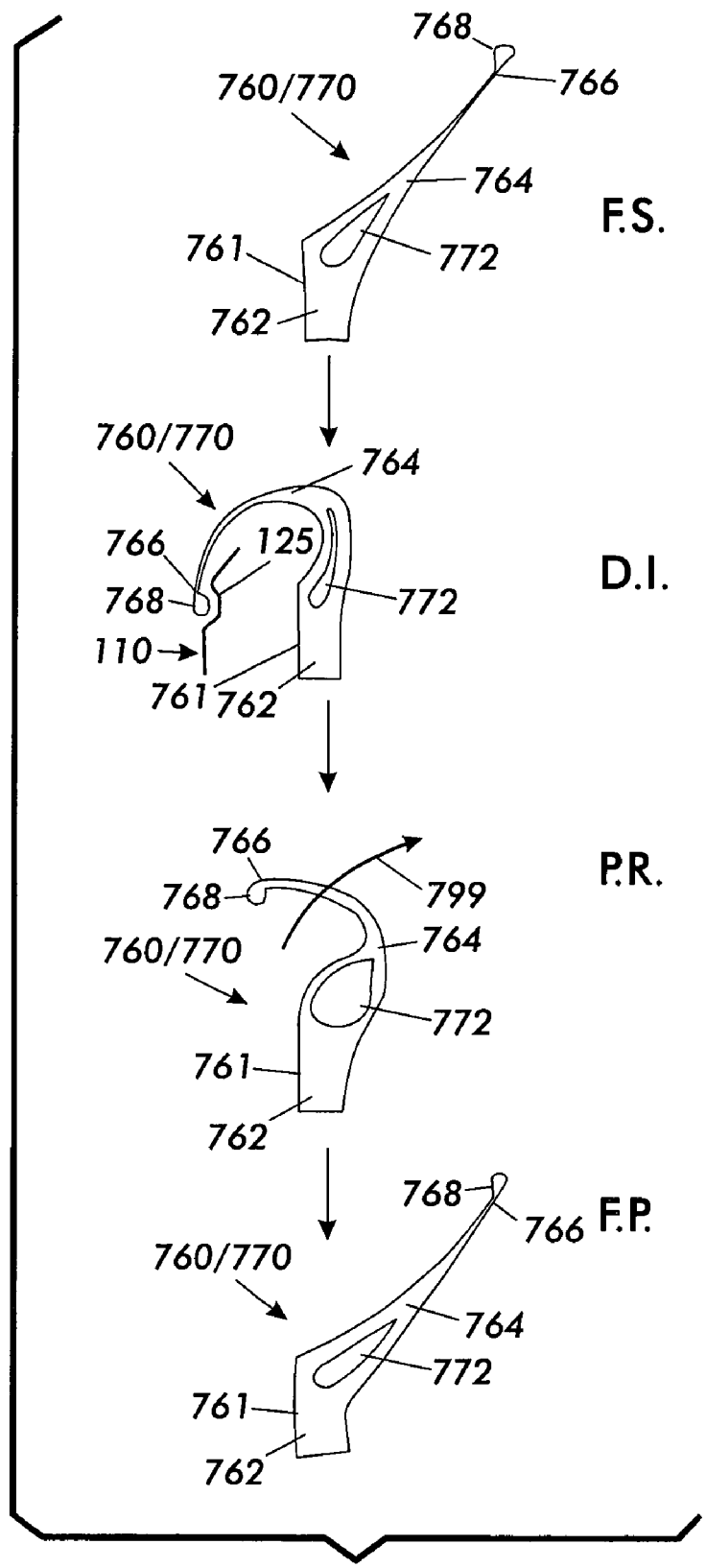
FIG. 20 is a cross-sectional view of an active seal similar to the seal of FIG. 19A-19C, further comprising an active release mechanism that is activated when the DMVA apparatus is installed on the heart.

In yet another embodiment depicted in FIG. 20, the seal is provided with a passive physical feature such as a ring at the apex of the seal that is disposed in a corresponding groove in wall 112 of Cup shell 110. Referring to FIG. 20, passive release seal 760 seal comprises structural base 762, which is joined to shell 112 of DMVA Cup 100 (see e.g., FIG. 4A). Passive release seal 760 further comprises a tapered midsection 764, which tapers to an apex or tip 766, to which is joined an elastic ring 768. During installation (graphic D.I of FIG. 20), ring 768 is disposed in a corresponding groove 125 that is formed in Cup shell wall 116, so that seal 760 does not contact the heart, thereby eliminating the risk of any damage to heart tissue by seal 760. After the heart is fully seated in the DMVA cup, ring 768 is rolled or stretched out of groove 125, so that apex 766 of seal 760 snaps upwardly and inwardly during recovery (P.R.) as indicated by arrow 799, to engage with heart tissue 39 (see FIG. 18A). Subsequently, seal 760 achieves final position (F.P.) against the heart tissue 39 as shown in FIG. 18A. In one embodiment, in order to reduce the effect of a relatively large cross-section at apex 766 of seal 760, and the resulting inelasticity of seal 760, ring 768 may be segmented (not shown). The retention properties of ring 768 will remain, and seal 760 will be far more elastic.

FIG. 20 further depicts an embodiment of an active seal similar to the seal of FIG. 18C, further comprising an active release mechanism, which is used to temporarily restrain the seal during Cup installation and which is activated when the DMVA apparatus is installed on the heart. Referring to FIG. 20, active release seal 770 further comprises cavity or annulus 772. During installation (see the graphic of FIG. 20 labeled D.I.), air within annulus 772 is displaced, or actively evacuated, out of a port (not shown) provided in annulus 772. After the heart is fully seated in the DMVA cup, annulus 772 is inflated with positive pressure such that ring 768 is displaced out of groove 125. Apex 766 of seal 760 snaps upwardly and inwardly during recovery (P.R.) as indicated by arrow 799, to engage with heart tissue 39 (see FIG. 18A). Subsequently, seal 770 achieves final position (F.P.) against the heart tissue 39 as shown in FIG. 18A.

In a further embodiment, annulus 772 is filled with a fluid containing a therapeutic drug or other therapeutic agent, and the material of seal 770 is permeable to such drug or agent, or provided with microscopic pores for the passage of the drug therethrough, so that the drug may be delivered directly to the heart. Such therapeutic agents include but are not limited to anti-inflammatory agents, gene therapy agents, gene transfer agents, stem cells, chemo-attractants, cell regeneration agents, ventricular remodeling agents, anti-infection agents, tumor suppressants, tissue and/or cell engineering agents, imaging contrast agents, tissue staining agents, nutrients, and mixtures thereof.

Figure 19B:
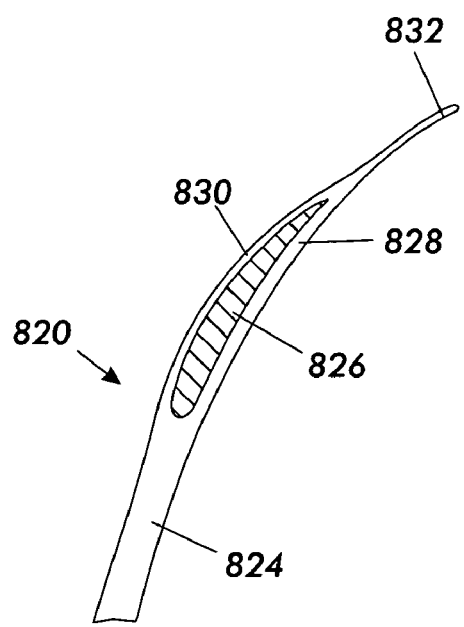
FIGS. 19B and 19C are detailed cross-sectional views of the active seal of FIG. 19A, shown in the passive and active states, respectively.
Figure 19C:
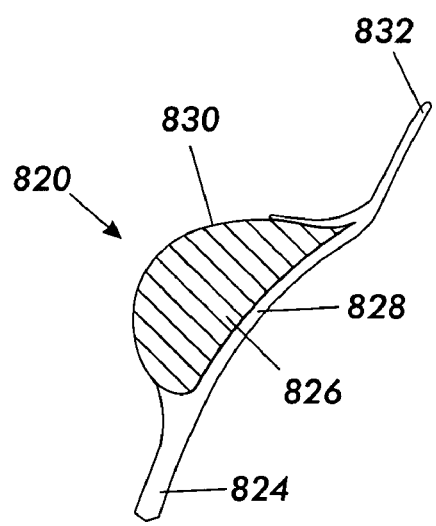

FIG. 19A is a cross-sectional view of an active seal by which the DMVA apparatus more firmly engages the heart, and FIGS. 19B and 19C are detailed cross-sectional views of the active seal of F*igure* 19A, shown in the passive and active states, respectively. Referring to FIG. 19A, active seal 820 comprises structural base 822, tapered neck 824, cavity 826 disposed between inner wall 828 and outer wall 830, and tip 832. Referring to FIGS. 19B and 19C, it can be seen that cavity 836 may be pressurized through a port into such cavity that is connected to a fluid pressure source.

With proper choice of the shape of active seal 820 with respect to the heart to which the DMVA Cup is fitted, to the shape and size of cavity 826, and to the relative thickness and elastic moduli of inner wall 828 and outer wall 830 of cavity 826, pressurization of cavity 826 may be used to force seal 820 inwardly against the heart wall (not shown). In one embodiment, this pressurization is timed to coincide with action of the Cup so that seal 820 is relatively relaxed during systole and relatively tight during diastole.

Figure 21A:
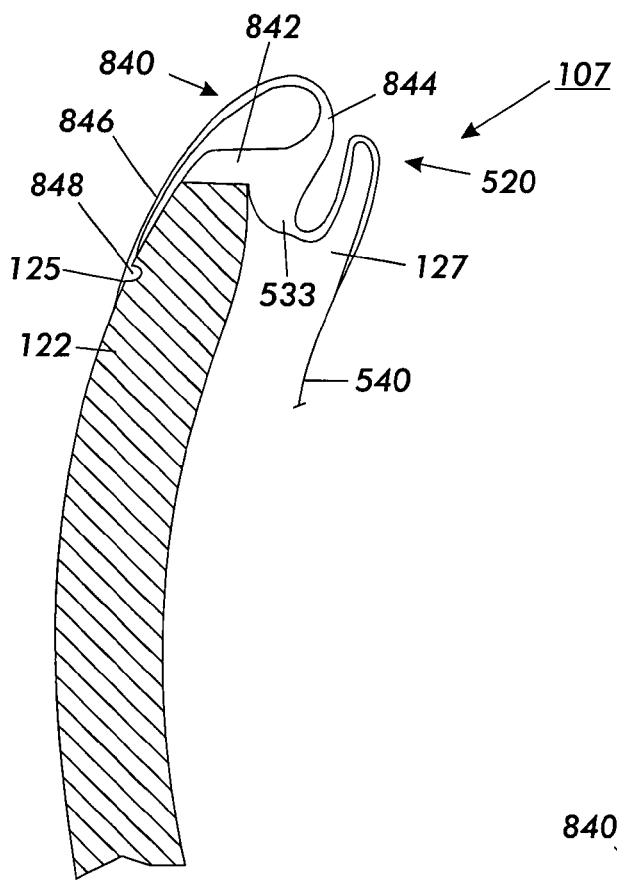
FIG. 21A is a cross-sectional view of a passive seal comprising a release mechanism that is deployed when the DMVA apparatus is installed on the heart, shown prior to engagement and sealing thereto.
Figure 21B:
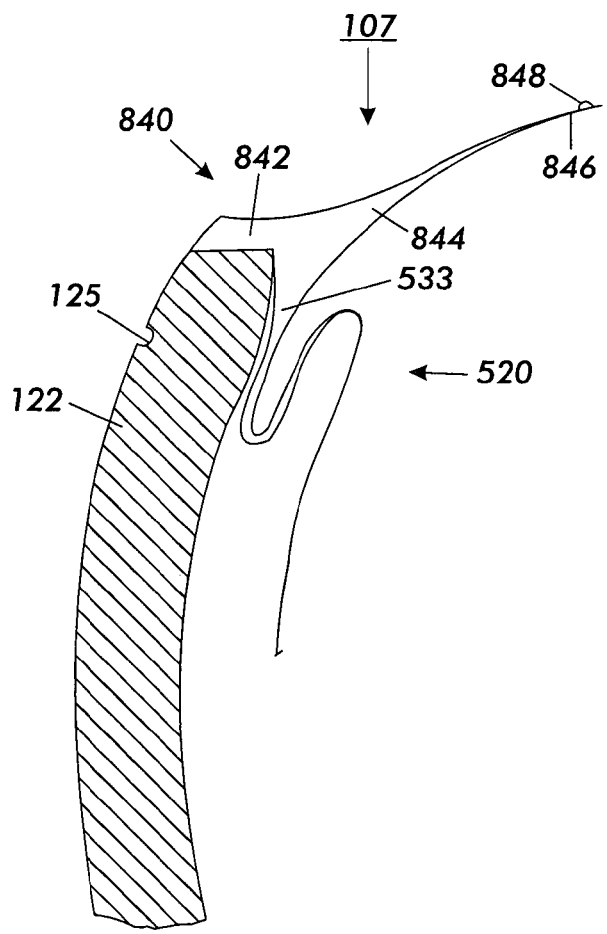
FIG. 21B is a cross-sectional view of the passive seal of FIG. 21A, shown in the free and the engaged/sealed state.

FIG. 21A is a cross-sectional view of a passive seal comprising a release mechanism that is deployed when the DMVA apparatus is installed on the heart, shown prior to engagement and sealing thereto; and FIG. 21B is a cross-sectional view of the passive seal of FIG. 21A, shown in the free and the engaged/sealed state. Referring to FIGS. 21A and 21B, passive seal 840 comprises structural base 842, tapered neck 844, and ring 848 bonded, formed, or otherwise disposed proximate to tip 846. In the embodiment of the DMVA Cup 107 depicted in FIGS. 21A and 21B, passive seal 840 is integrated with liner 510, in a manner similar to that of integrated liner and seal assembly 530 shown in FIG. 16A and previously described in this specification. Passive seal 840 is also similar to passive seal 660 of FIG. 20, previously described in this specification.

Referring again to FIG. 21A, during installation, ring 848 is engaged with and retained within retention groove 125 during the entire installation procedure. Upon the first systolic action of the Cup 107, the working drive fluid expands the space 127 between the shell 112 and liner membrane 540, stretching upper rolling diaphragm section 520 and causing the ring 848 to be released from the retention groove 125. This action causes seal 840 to move from the configuration shown in FIG. 21A to the working position shown in FIG. 21B.

Figure 22A:
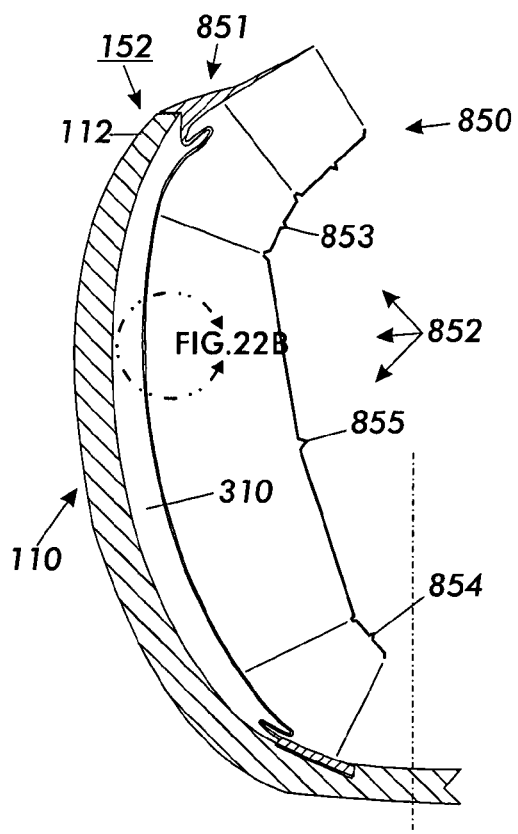
FIG. 22A is a cross-sectional view of one embodiment of a liner and seal of the DMVA apparatus, comprising locally specialized materials and/or surface textures.
Figure 22B:
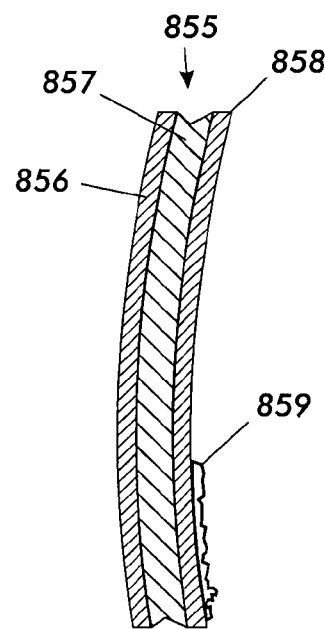
FIG. 22B is a detailed cross-sectional view of one liner of the DMVA apparatus of FIG. 22A.

FIG. 22A is a cross-sectional view of one embodiment of a liner and seal of the DMVA apparatus, comprising locally specialized materials and/or textures; and FIG. 22B is a detailed cross-sectional view of one liner of the DMVA apparatus of FIG. 22A.

Referring to FIGS. 22A and 22B, DMVA Cup 152 comprises shell 110, and integral liner and seal assembly 850 comprised of seal 851 and liner 852. Alternatively, the liner and seal may be configured as depicted in various other Figures shown and described herein.

In various embodiments, liner 852 is further specialized, in terms of material, surface texture, surface lubricity, elasticity and fatigue resistance, and either inducement or inhibition of tissue in-growth. These forms of specialization may be localized in specific areas of the liner. In one embodiment, upper liner region 853 and lower liner region 854 are shaped to optimize fatigue resistance and to minimize local and general shear stress in the heart, both at the heart wall surface and within the cardiac muscle, as described previously in this specification. Since the design of a rolling diaphragm will likely result in some rubbing contact between layers of the same material, the core material—or a coating applied thereto—is chosen to optimize the wear characteristics thereof. Thus, for example, a coating of a fluoropolymer such as polytetrafluoroethylene may be applied to regions 853 and 854. Liner membrane 855 is the region of liner 852 that is in constant physical contact with the heart. Depending upon whether the specific Cup 850 is indicated for acute or chronic use, the liner membrane 855 may be provided with a particular surface texture, topically applied materials, or imbibed materials, to either enhance or inhibit tissue in-growth into the surface thereof. In one embodiment depicted in FIG. 22B, liner membrane 855 is provided as a multilayer structure, comprising an inner layer 856, at least one center layer 857, and an inner layer 858, wherein such topically applied materials or imbibed or diffused or impregnated materials are provided within one or more of such layers to benefit the heart. Such beneficial materials may include, but are not limited to anti-inflammatory agents, gene therapy agents, gene transfer agents, stem cells, chemo-attractants, cell regeneration agents, ventricular remodeling agents, anti-infection agents, tumor suppressants, tissue and/or cell engineering agents, imaging contrast agents, tissue staining agents, nutrients, and mixtures thereof. In a further embodiment, a surface texture 859 is provided on the outer surface of inner layer 858 to enhance tissue in-growth into the surface thereof. Such a surface texture may be created by the primary manufacturing process (e.g. injection molding), by a secondary mechanical process (e.g. abrasion, scoring, extrusion, or calendaring), by a chemical process (e.g. etching or solvent softening), by plasma treatment, by a direct writing device, or by a combination of these and other processes.

Referring again to FIG. 22A, seal 851 may or may not be designed to encourage tissue in-growth thereto, depending upon the expected term of use of the Cup in a specific patient and for a specific disease state. Factors that affect tissue in-growth are texture, topical compounds (applied at time of installation), and imbibed compounds (gradually eluted to work over time). The seal section 851 of assembly 850 also is provided with specific mechanical and surface characteristics to optimize its sealing and 'self-bailing' performance.

Referring yet again to FIG. 22B it may be seen that if outer liner layer 856 is impermeable, if center liner layer 857 is highly porous, and if inner liner layer 858 is porous, but substantially less porous that center liner layer 857, the construction of the overall liner 855 is such that fluid may be ported into it at a convenient location, and that liquid will be uniformly applied to any material that is adjacent to the inner surface of the liner. Thus the liner may be used to actively apply topical therapeutic compounds under processor control. One or more topical compounds including but not limited to anti-inflammatory agents, gene therapy agents, gene transfer agents, stem cells, chemo-attractants, cell regeneration agents, ventricular remodeling agents, anti-infection agents, tumor suppressants, tissue and/or cell engineering agents, imaging contrast agents, tissue staining agents, nutrients, and mixtures thereof may be applied by this method, either separately or in sequence. The control of delivery of these materials may be coordinated with other forms of cardiac therapy.

FIG. 23A is a cross-sectional view of another embodiment of the DMVA apparatus, further comprising means for disengagement of the seal thereof that is attached to the heart; and FIGS. 23B and 23C are detailed cross-sectional views of embodiments of detachable seals of the DMVA apparatus of FIG. 23A. Referring to FIG. 23A, DMVA Cup 153 comprises shell 240, integral liner and seal assembly 850 comprised of seal 860 and liner 852. Alternatively, the liner and seal may be configured as depicted in various other Figures shown and described herein.

DMVA Cup shell 240 comprises a cup-shaped wall 242, drive fluid port 220 in communication with cavity 310, and vacuum port 211. Drive fluid port 220 connects the cavity 310 between shell 240 and liner 852 with a local or remote fluid drive subsystem 360 that pumps drive fluid to act on the heart (not shown) through liner membrane 855. Drive fluid port 220 also provides access for internal pressure measurements. Port 220 may be a simple tube accessing the lumen in one place, or alternately may have a network of small channels that provides uniform flow to all areas of the cavity 310. Cross-section and internal shape changes may be optimized to minimize friction losses in order to maximize Cup energy efficiency.

Vacuum port 211 connects the internal cavity 128 of the Cup shell 240 to a local or remote vacuum subsystem 350 that may be used to generate negative differential pressure ("vacuum") between the interior 128 and exterior of the Cup 153 in order to retain the Cup 153 on the heart (not shown). Some Cup and seal designs may not require vacuum at all. Other Cup and seal designs used for acute applications may use a vacuum pump as part of vacuum system 360. In one embodiment, the pump is a bi-directional pump 352, the pumping action of which can be alternated between pressure and vacuum, so that the Cup 153 can be easily removed from the patient. Pump 352 is connected to DMVA drive unit or controller 1310 (see FIG. 13) via wires 354.

Yet other Cup and seal designs may require vacuum during and shortly following installation, but make use of tissue in-growth for long-term retention. In this last case vacuum port 211 may be disconnected from its vacuum source at a time when retentive vacuum is no longer needed to secure the Cup 153 on the heart. In some circumstances, where applied vacuum is not used for either installation or retention, where tissue in-growth either does not occur or can be countered for reasons of Cup removal, and where the innate negative pressure created by the 'self-bailing' nature of the Cup seal 860 makes Cup removal difficult or impossible, a valve 356 connected to controller 1310 by wiring 358 provides for active venting of vacuum from the Cup interior at the time of Cup removal.

In another embodiment, vacuum system 350 comprises vacuum pump 360 connected to vacuum port 211 of Cup shell 240 through valve 362. Valve 362 is preferably a three way valve, with a first position closing off flow into/out of vacuum port 211, a second position allowing flow from vacuum port 211 to pump 360, and a third position venting port 211 to the external atmosphere. Pump 360 is connected to DMVA drive unit or controller 1310 via wires 364, and valve 362 is connected to DMVA drive unit or controller 1310 via wires 366.

In a further embodiment, means are provided in the DMVA apparatus for enhanced aspiration of fluid from any volumes formed between the heart and the liner or between the heart and the interior surface of the Cup shell wall. Referring to FIG. 2L, it can be seen that when cavitation occurs, and there is a volume 51 and/or 53 of fluid between the heart 30 and the Cup liner 116/118, such fluid must be forced out past seal 113, or alternatively, aspirated by vacuum out of vacuum port 111. There is, however, a possibility that the apex 38 of the heart 30 will occlude port 111 when subjected to a strong vacuum, and prevent the flow of fluid from volume 51 and/or 53 out of port 111.

In such a circumstance, one means of enhancing aspiration of such fluid out of volumes 51 and/or 53 is to provide drainage grooves 142 on the interior wall of the Cup shell 110 near vacuum port 111. Such grooves are preferably disposed radially from port 111, with the number of aspiration grooves preferably being between four and twelve. In a further embodiment, a grating or screen is provided or formed integrally in shell 110 at the entry of port 111 to prevent the apex of the heart from being sucked into port 111 and deformed. Such a similar use of drainage grooves and a grating in a batch fluid delivery device is described at column 7 lines 46-61 of U.S. Pat. No. 5,205,722, the disclosure of which is incorporated herein by reference. In yet a further embodiment, a plurality of raised ribs are provided disposed radially outwardly from vacuum port 111 on the inner surface of Cup shell 110, which prevent the occlusion of port 111 by apex 38 of heart 30, thereby achieving substantially the same result as the grooves 142 of FIG. 2L.

In a further embodiment (not shown), aspiration ports are provided within the Cup shell wall, preferably disposed either in proximity to port 111, and/or in proximity to seal 113. Such ports are connected within cup shell 110 either to vacuum port 111, or to another vacuum port (not shown) provided for aspiration. In another embodiment, such aspiration ports are provided in a seal comprising a cavity, such as seal 820 of FIG. 19A, or seal 770 of FIG. 20. Such aspiration ports are disposed between the cavity and the inner surface of the tapered midsection of such seal that is in contact with the heart. In a further embodiment, aspiration grooves may be provided on such inner surface of such seal, as described previously. In yet a further embodiment, the inner surface of the liner of the DMVA device that is in contact with the heart is provided with a texture that facilitates aspiration, such as grooves, ribs, or other texture that provides fluid passageways during such contact.

FIGS. 23B and 23C are detailed cross-sectional views of embodiments of detachable seals of the DMVA apparatus of FIG. 23A. Referring to FIG. 23B, in one embodiment, seal 860 comprises a tear away feature 861, enabling the surgeon to easily separate the distal portion of the seal comprised of taper 862 and tip 863 from the base 864 of seal 860, thereby facilitating Cup removal. Tear away feature may be a notch, a cord, or a wire, or another linear feature that tears the seal 860 sufficiently to permit removal of the Cup 153.

Referring to FIG. 23C, in another embodiment, seal 860 comprises a separation section 865, separable by a feature 866 in seal 860 that permits non-mechanical action to separate the tip of the Seal from the body of the Cup. Examples of feature 866 include a section that is electrically conductive and melts sufficiently to separate, or a small channel that provides access to a biocompatible fluid that causes an adhesive material to part the Seal from the body of the Cup.

Referring to FIG. 23A, in another embodiment, feature 861 of FIG. 23B and/or feature 866 of FIG. 23C are provided at upper liner region 853 and lower liner region 854 of liner 850 of DMVA Cup 153, thereby rendering liner 850 of DMVA Cup detachable at such time when Cup 153 is removed from the patient. In such a situation, liner 580 is preferably made of a biocompatible material or provided with a surface coating thereof that promotes ingrowth and permanent attachment to the surface of the heart (not shown). Liner 850 is further provided with properties and/or materials that can continue to provide benefit to the heart, including but not limited to providing beneficial mechanical properties such as limiting end-diastolic volumes (i.e. a "girdle effect"); and/or continued delivery of pharmacologic therapies to the myocardium such as drugs gene therapies, and the like.

Figure 24:
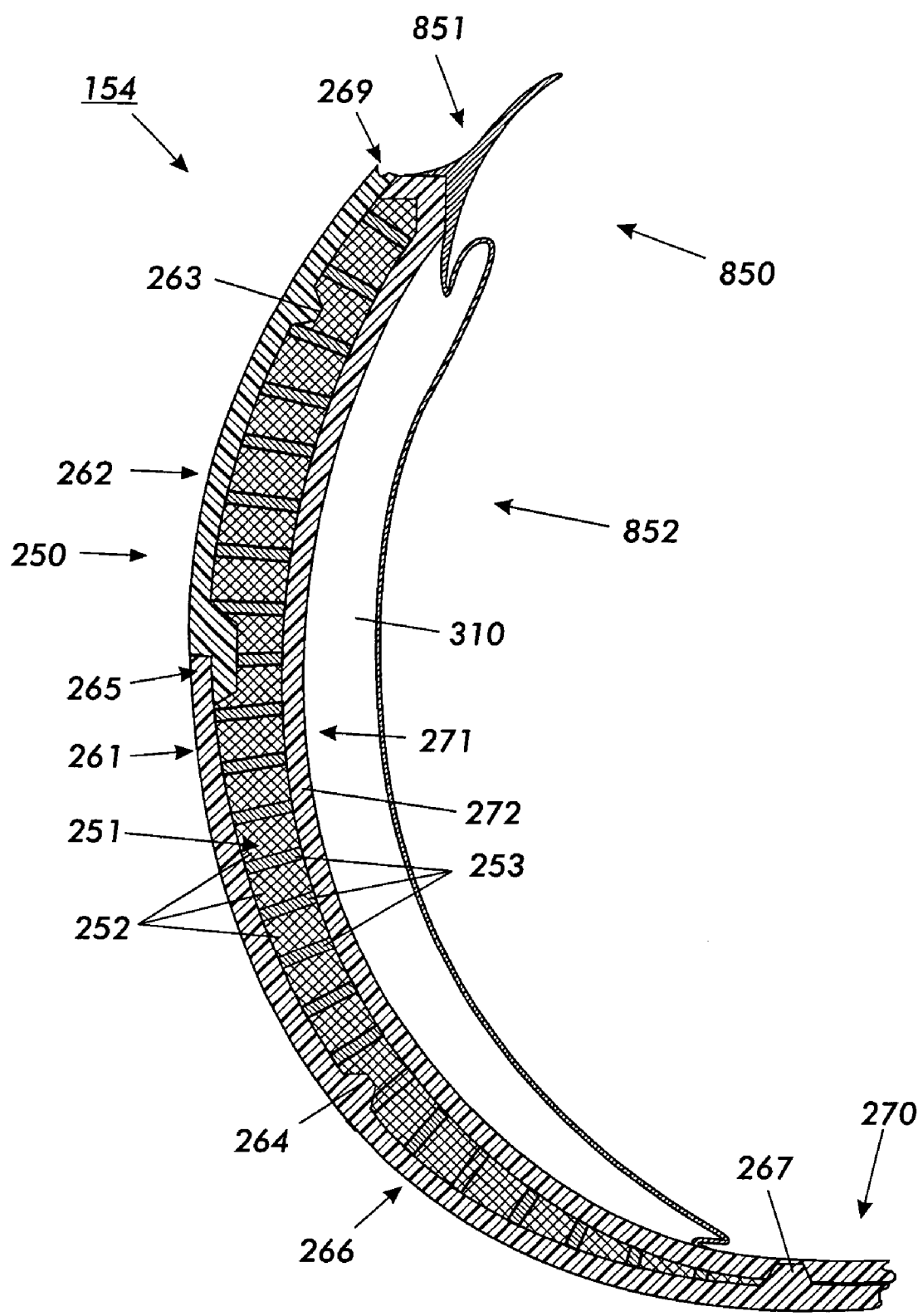
FIG. 24 is a cross-sectional side view of one embodiment of a DMVA cup formed with a hollow wall structure comprised of alternating structural ribs and cavities disposed in horizontal planes.

FIG. 24 is a cross-sectional side view of one embodiment of a DMVA cup formed with a hollow wall structure comprised of alternating structural ribs and cavities disposed in horizontal planes. Prior art devices similar to the DMVA Cup of the present invention typically comprise an outer shell that is either rigid or highly flexible. There are advantages to having a Cup shell that may be more easily compressed during installation, that may have a level of rigidity that can be adjusted on a one-time basis or on an on-going basis, or that has specialized rebound characteristics during systolic and diastolic action, thus enhancing the performance of the Cup and the heart itself.

Referring to FIG. 24, DMVA Cup 154 is provided with a hollow wall assembly approach to designing and manufacturing the Cup shell 250 having the above advantages and also permitting individual shell 250 assembly components to have relatively thin wall sections, thus optimizing the uniformity of injection molding techniques and reducing cycle time of injection molding manufacturing processes for shell 250. By using finite element modeling (FEM) techniques, shell 250 can be designed such that the shell assembly and the overall Cup 154 have virtually any combination of strength and flexibility that is desired, and such that the flexibility of shell 250 is 'tuned' to specific needs in specific areas. Stress and fatigue behavior can also be predicted.

Referring again to FIG. 24, DMVA Cup 154 comprises shell assembly 250, and integrated liner and seal assembly 850 comprised of seal 851 and liner 852. Shell assembly 250 comprises an inner shell 251, a shell outer wall 261, and a shell inner wall 271. Inner shell preferably comprises a series of hollow cavities 252 interspersed with a series of latitudinal ribs or fins 253 joining shell inner wall 271 to shell outer wall 261. Such ribs provide beam strength in the assembled shell 250, and also provide multiple individual chambers that may or may not be filled or pressurized, and that have external edges that are bonded to shell outer wall 261 and shell inner wall 271. Provision is made for uniform wall thickness so that an injection molding process can be very precise and repeatable; and provision is also made for location features and bonding features that facilitate assembly, both of which are described presently. In addition, the hollow shell construction permits the Cup 154 to be compressed to a greater extent during installation, thus minimizing surgical trauma.

Referring again to FIG. 24, shell outer wall 261 comprises an upper section 262, and a lower section 266. Upper section 262 generally has a thin ring shape, designed to have reasonable mold release characteristics and to have a geometry that makes final assembly and bonding relatively simple. Lower section 266 generally has a hemispherical shape, also designed to have reasonable mold release characteristics and to have a geometry that makes final assembly and bonding relatively simple. Shell inner wall 271 is preferably provided with a thickness of between about 0.060 inch thick and 0.150 inch thick at the largest diameter 272 thereof, with the same shape and surface characteristics as those for a solid-wall shell described previously. The shape of the inner shell 271 is provided to also have reasonable mold release characteristics (assuming an elastic material) and to have a geometry that makes final assembly and bonding relatively simple.

Upper section 262 of shell outer wall 261 is joined to lower section 266 of outer shell wall 261 at bond area 265. Inner shell wall 271 is joined to outer shell wall 261 at upper bond area 269, at lower bond area 270, and at the contact surfaces between ribs 253 and inner shell wall 271 and outer shell wall 261. Several alignment features 263, 264, and 267 are provided on inner shell wall 271 and outer shell wall 261 to facilitate alignment thereof prior to and during bonding therebetween.

Figure 25A:
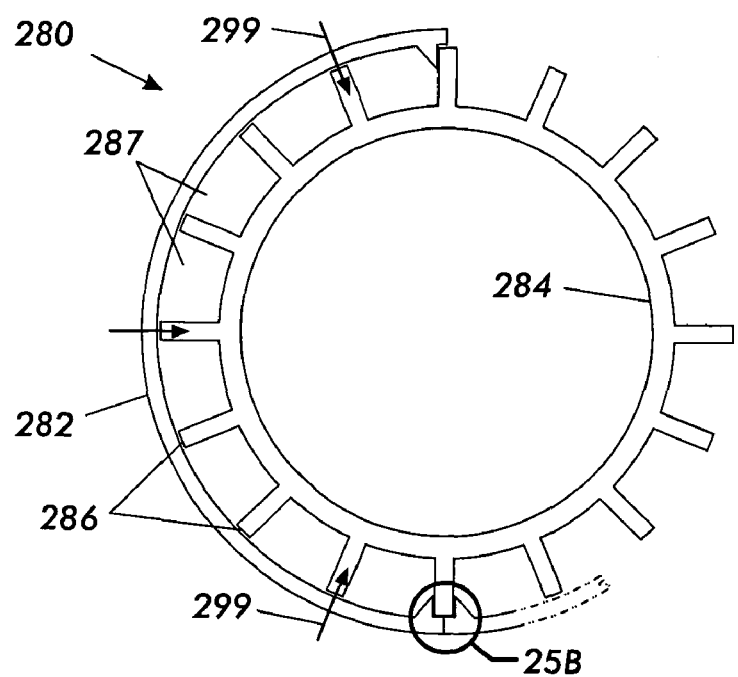
FIG. 25A is a cross-sectional top view of another embodiment of a DMVA apparatus formed with a hollow wall structure comprised of alternating structural ribs and cavities disposed in longitudinal planes.
Figure 25B:
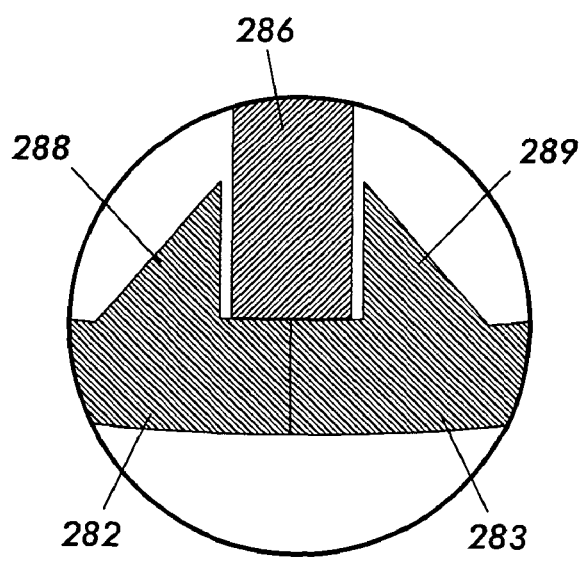
FIG. 25B is a detailed cross-sectional top view of a structural joint between a rib and an outer shell of the DMVA apparatus of FIG. 25A.

FIG. 25A is a cross-sectional top view of another embodiment of a DMVA apparatus formed with a hollow wall structure comprised of alternating structural ribs and cavities disposed in longitudinal planes; and FIG. 25B is a detailed cross-sectional top view of a structural joint between a rib and an outer shell of the DMVA apparatus of FIG. 25A. Referring to FIG. 25A, shell 280 comprises a first outer wall segment 282 forming approximately a first half of the outer wall of shell 280, and a second outer wall segment (not shown) forming the corresponding second half of the outer wall of shell 280. Shell 280 further comprises an inner shell wall 284, and a series of longitudinal ribs 286 interspersed with a series of cavities 287. Longitudinal ribs 286 are joined to the inner surface of outer wall segment 282, and to the inner surface of the corresponding outer wall segment half not shown, and to the outer surface of inner shell wall 284, in a manner similar to that described previously and shown in FIG. 24. Although in FIG. 25A outer wall segment 282 is shown separated from ribs 286, in use, outer wall segment 282 is joined to ribs 286 as indicated by arrows 299. It is to be noted that in this embodiment, the outer wall segments 282 and the corresponding one not shown are parted in the vertical plane rather than the horizontal plane (as in shell 250 of FIG. 24). This design provides two identical components rather than an upper and lower component that are different, thereby reducing manufacturing costs.

Shell 280 is preferably provided with attachment features to ensure a strong bond between the subcomponents thereof. Referring to FIG. 25B, outer wall segments 282 and 283 are provided with joining gussets 288 and 289, respectively, within which is nested and joined rib 286. Such a construction ensures a strong bond between outer wall segments 282 and 283, rib 286, and inner shell wall 284.

Figure 28:
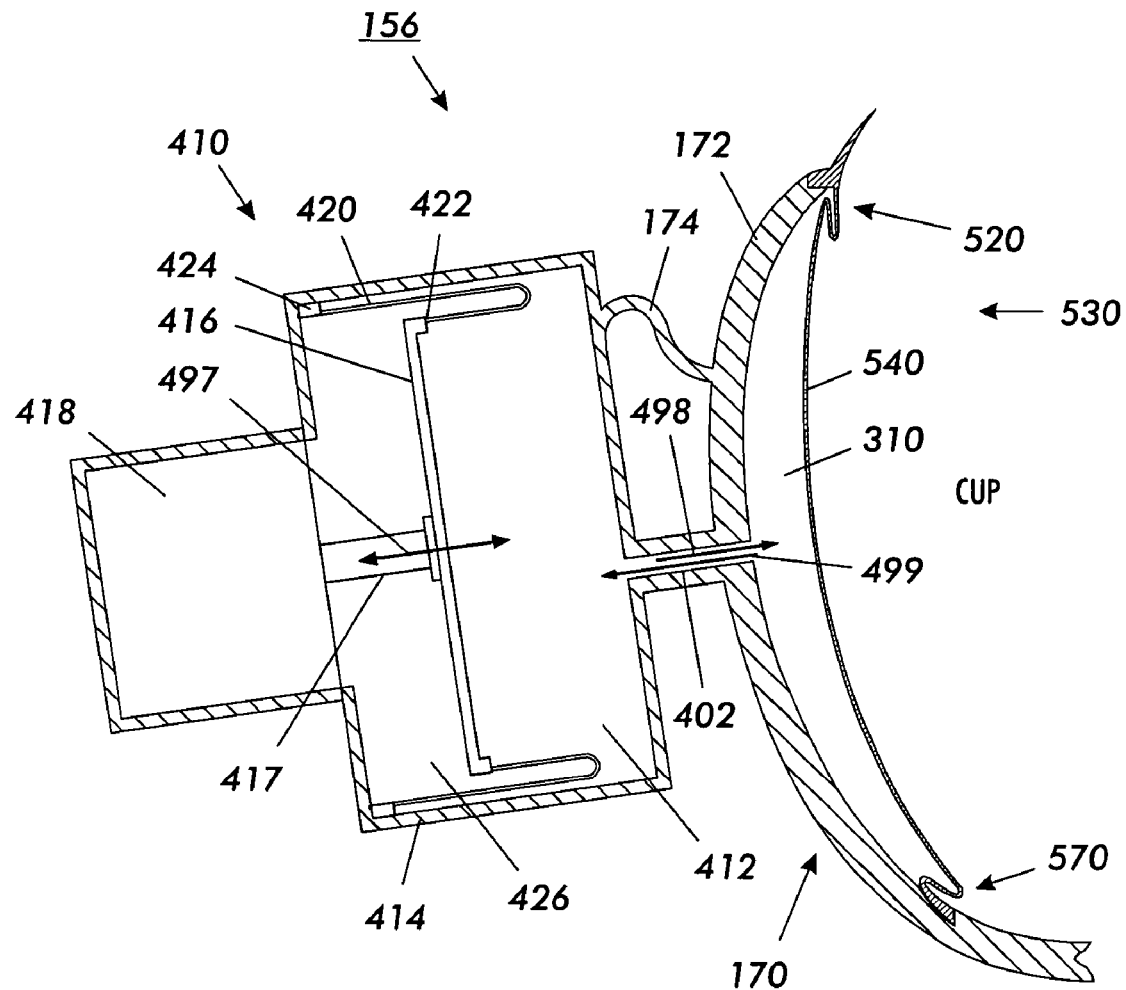
FIG. 28 is a cross-sectional view of another embodiment of a DMVA apparatus, further comprising an implantable reciprocating pump used to drive systolic and diastolic actuation of the DMVA Cup and heart therein.

FIG. 28 is a cross-sectional view of another embodiment of a DMVA apparatus, further comprising an implantable pump used to drive systolic and diastolic actuation of the DMVA Cup and heart therein. Referring to FIG. 28, DMVA apparatus 156 comprises Cup shell 170 to which is joined liner 530 and seal 720. Apparatus 156 further comprises pump assembly 410 joined to Cup shell 170 by conduit 402. Pump assembly 410 delivers DMVA drive fluid to and from cavity 310 of DMVA apparatus 156 through hollow conduit 402, thereby displacing liner membrane 540 and performing systolic and diastolic actuation of the heart (not shown) as described previously.

Pump assembly 410 may be any suitable pumping mechanism, which is designed to alternatingly deliver a fluid outwardly through conduit 402 as indicated by arrow 498, and withdraw a fluid inwardly through conduit 402 as indicated by arrow 499. In one embodiment, the DMVA drive fluid delivered and withdrawn into cavity 310 of DMVA apparatus 156 is a compressible fluid, i.e. a gas such as e.g., air. In another embodiment, the DMVA drive fluid is an incompressible liquid.

In the preferred embodiment, pump assembly 410 comprises a reciprocating pump, such as a piston pump comprising a reciprocating piston, or a diaphragm pump comprising a reciprocating diaphragm. Such a reciprocating pump is preferable, because such a pump inherently comprises a fluid reservoir 412 contained within a housing 414, and a reciprocating element 416 driven by reciprocating drive means 418, as indicated by bi-directional arrow 497. Such a reciprocating pump assembly does not require a separate fluid reservoir and valving means to switch the direction of fluid flow, and can thus be made as a very compact assembly.

In the preferred embodiment, reciprocating drive means 418 comprises a linear actuator that is capable of providing bi-directional linear motion. Such a linear actuator may be any of a variety of linear actuator devices, including but not limited to a standard alternating current or direct current continuous or stepper type electric motor engaged with the following: a ball-screw or other rotational-to-linear mechanism, a rack and pinion, a cam linkage, a four bar or other linkage, a crankshaft, or a hydraulic or pneumatic power source. Alternatively, such linear actuator may comprise an electrical solenoid; an inchworm drive using piezoelectric, electrostrictive, or other short-range linear power source; an electrostrictive or electroactive polymer artificial muscle (EPAM) such as e.g., a silicone EPAM or a polyurethane EPAM; or a skeletal muscle affixed to reciprocating element 416, sustained by an artificial capillary bed, and driven by an electrical stimulus. For a detailed description of EPAMs, reference may be had to SPIE Proceedings Volume 3669, *Smart Structures and Materials* 1999: *Electroactive Polymer Actuators and Devices*, and in particular, paper 3669-01, *Electroactive polymer actuators and devices* by S. G. Wax et al, the disclosure of which is incorporated herein by reference. Actuator shaft 417 connects any of these actuator devices to reciprocating element 416.

Alternatively, reciprocating drive means 418 may comprise a camshaft engaged directly with reciprocating element 416, as described in U.S. Pat. No. 5,368,451 of Hammond, the disclosure of which is incorporated herein by reference. Such camshaft driven reciprocating means may further include means to vary the timing and duration of the reciprocation thereof, as is practiced in providing variable reciprocation of objects such as e.g., automotive engine valves. Such variable timing enables the programming and control of a wide range of systolic and diastolic actuation conditions as described previously in this specification. In yet another embodiment, reciprocating drive means 418 may be hydraulic and may comprise a closed loop reciprocating fluid system as described in U.S. Pat. No. 5,205,722 of Hammond, the disclosure of which is incorporated herein by reference. Such a reciprocating fluid system may be coupled to reciprocating element 416, or it may be coupled directly to conduit 402, thereby directly reciprocating liner 530 in systolic and diastolic actuation.

Referring again to FIG. 28, and in the preferred embodiment depicted therein, pump assembly 410 comprises a reciprocating pump comprised of a diaphragm 420 joined at an inner perimeter 422 thereof to a cylindrical plate reciprocating element 416, and at an outer perimeter 424 thereof to housing 414. In one embodiment, diaphragm 420 is an elastic diaphragm. In the preferred embodiment depicted in FIG. 28, diaphragm 420 is a rolling diaphragm, operating in a manner similar to, and with the same advantages of the rolling diaphragm Cup liners described previously in this specification. Such a rolling diaphragm is also preferred, as it eliminates the need for seals that may wear or leak over time. Reciprocating element 416 serves to provide a rigid attachment for interior perimeter 422 of rolling diaphragm 420, and an attachment point for the actuator shaft 417. It will be apparent that other embodiments may use variations on diaphragm designs, bellows pump designs, or piston/seal pump designs in order to move the DMVA drive fluid.

Referring again to FIG. 28, and in the preferred embodiment depicted therein, rolling diaphragm 420 comprises a cylindrical flexible polymer membrane that provides a moving seal between DMVA drive fluid in cavity 412 and a secondary fluid contained in cavity 426. The material and thickness of diaphragm 420 are chosen to be compatible with both fluids, and to have excellent fatigue resistance over the expected working life of the DMVA apparatus 156. In a further embodiment (not shown), diaphragm 420 is joined to reciprocating plate 416 and to housing 414 with annular shaped attachments, which minimize bending fatigue.

In the preferred embodiment, the secondary fluid contained in cavity 426 is preferably a gas, either at a neutral pressure, or at negative pressure with respect to the implant environment. As reciprocating plate 416 displaces the DMVA drive fluid in cavity 412, thereby displacing liner membrane 540, the secondary fluid in cavity 426 will undergo expansion. This will require increased force on actuator shaft 417 during systole, but will also provide useful force during diastole to pull DMVA drive fluid back through conduit 402, thus pulling the liner 540 and expanding the heart (not shown). In this embodiment the use of positive or negative pressure in the secondary fluid in cavity 426 is somewhat immaterial, since the compressible nature of the gas will not affect the energy efficiency of the cyclic process. However, in order to keep physical forces and resulting wear to a minimum, the pressure is best selected to be about neutral (physiologic pressure) at the center of the stroke of the actuator shaft 417. In another less preferred embodiment not shown, cavity 426 containing the secondary fluid may be 'vented' to the interior of the body of the patient, but contained within an expandable envelope, fluid bag, or other sealed collection means.

Referring again to FIG. 28, in one embodiment of DMVA assembly 156, Cup shell 170 and pump housing 414 are molded as a compact unitary part, joined by a short length of conduit 402, and preferably further reinforced by attachment web 174, or other suitable reinforcement means. Attachment web 174 thus provides a semi-rigid attachment between the pump housing 414 and the Cup shell 170, permitting reliable physical connection and compliance therebetween, as is necessary in an implanted device of this size. Such a compact assembly enables the implantability of the entire DMVA apparatus 156 solely within the thoracic region of the body.

In another embodiment (not shown), DMVA apparatus comprises a longer flexible conduit 402, thus providing greater separation of pump assembly 410 from Cup shell 170, so that pump assembly 410 may be implanted at a more distal location within the body. In either instance, DMVA apparatus 156 is provide as an assembly that is entirely implantable within the body. In another embodiment, conduit 402 is provided with a biocidal anti-infection and/or anti-inflammatory coating as described previously in this specification.

In a further embodiment (not shown), pump assembly 410 of DMVA apparatus 156 is provided with means to heat or cool the DMVA drive fluid contained within cavity 412. Such means provides the DMVA apparatus with the capability of using chilled DMVA drive fluid to cool the heart and the blood pumped therefrom, and hence to also cool the brain and other organs during resuscitation efforts. Such cooling is a well-established method to significantly extend the period that the brain can withstand anoxia, and is thus uniquely suited to the use of the DMVA apparatus and method of resuscitation. Accordingly, such a capability may greatly enhance the clinical effectiveness in acute resuscitations using the DMVA apparatus of the present invention.

It will be apparent that pump housing 414 provides structural support for elements contained therein, such as piston/reciprocating element 416, diaphragm 420, seals not shown, motor and/or linear actuator or other reciprocating means 418, and any sensors (not shown). In addition, pump housing 414 must be secured to Cup shell wall 172 in a manner that guarantees reliable operation under physiologic conditions and under physical exercise, and obviously must be biocompatible. The diameter of pump housing 414 and the linear travel of reciprocating element 416 are selected to provide sufficient volume so as to displace a large heart in a normal manner. In the preferred embodiment, the typical displacement volume of pump assembly 410, defined approximately by the cross sectional area of reciprocating element 416 times the stroke length of reciprocating element 416, will be on the order of 150 to 250 cubic centimeters.

Figure 29:
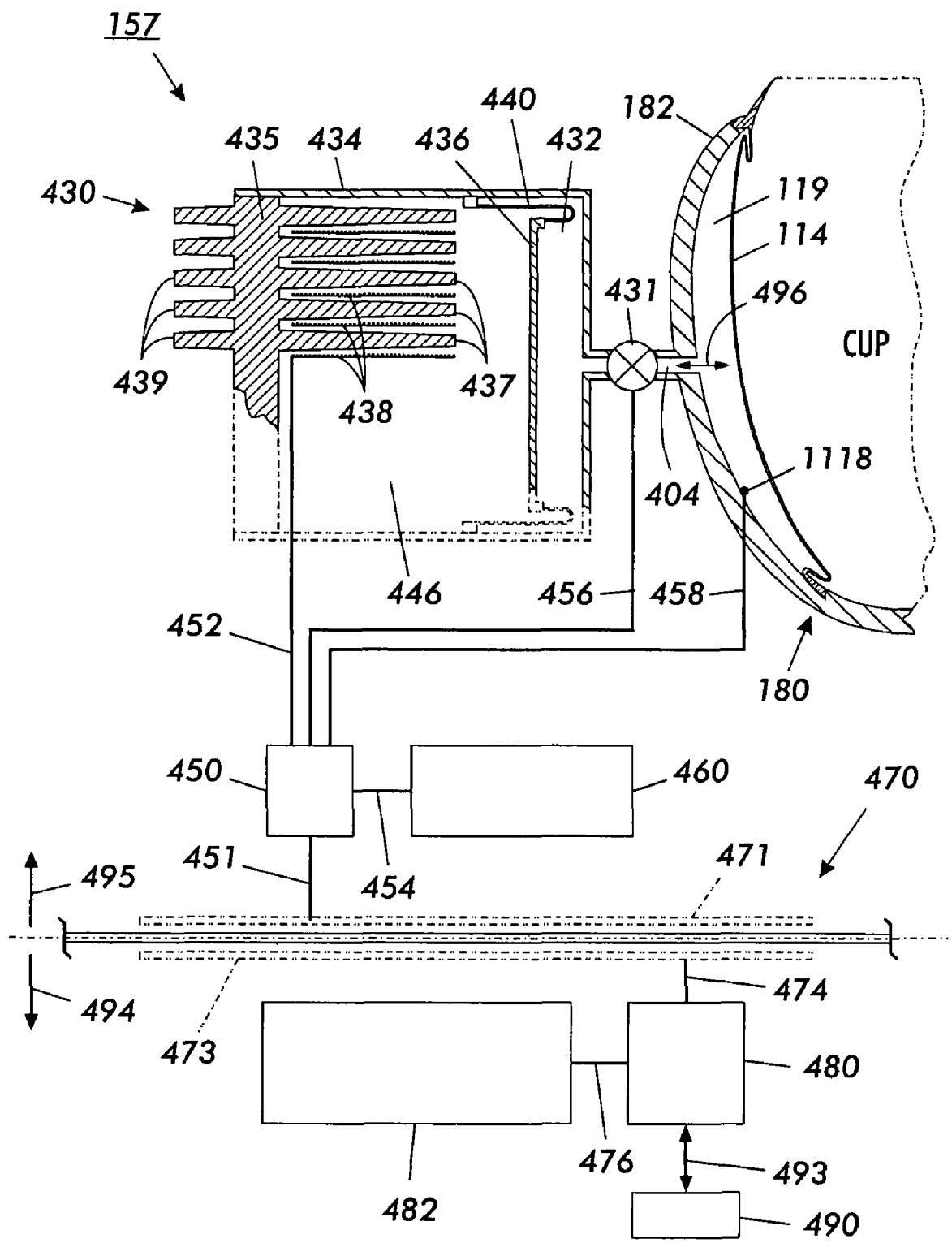
FIG. 29 is a cross-sectional view of another embodiment of a DMVA apparatus, further comprising an implantable phase change pump used to drive systolic and diastolic actuation of the DMVA Cup and heart therein.

FIG. 29 is a cross-sectional view of another embodiment of a DMVA apparatus, further comprising an implantable phase change pump used to drive systolic and diastolic actuation of the DMVA Cup and heart therein. Referring to FIG. 29, DMVA apparatus 157 comprises Cup shell 180 to which is joined liner 114 and a seal (not shown), as described previously in this specification. Apparatus 157 further comprises pump assembly 430 joined to Cup shell 180 by conduit 404. Pump assembly 430 delivers DMVA drive fluid to and from cavity 119 of DMVA apparatus 157 through hollow conduit 404, thereby displacing liner 114 and performing systolic and diastolic actuation of the heart (not shown) as described previously.

In the embodiment depicted in FIG. 29, pump assembly 430 is a phase change or flash pump, which is designed to alternatingly deliver a fluid outwardly and inwardly through conduit 404 as indicated by bi-directional arrow 496. The term "flash" refers to the rapid "flashing" or "flash evaporation" of a liquid phase into a vapor phase. In the preferred embodiment, pump assembly 430 comprises a housing 434 containing a reservoir 432 and a reciprocating element 436. Housing 434 and reciprocating element 436 are preferably cylindrical, with rolling diaphragm 440 being joined to reciprocating element 436 and housing 434, as described previously for pump assembly 410 of FIG. 28.

Referring again to FIG. 29, housing 434 of pump assembly 430 further comprises a heat sink 435 having a plurality of internal fins 437 and a plurality of external fins 439. Heat sink 435 is either integrally formed as part of housing 434, or contained therein. Housing 434 further contains an array of resistive filaments 438 consisting essentially of fine wire or another suitable material that increases in temperature when conducting electrical current. Resistive filaments 438 are preferably interspersed with internal fins 437 as shown in FIG. 29. Resistive filaments 438 are connected to implanted controller 450 by control line 452. Implanted battery 460 provides electrical power to controller 450 via line 454.

Pump assembly 430 further comprises a valve 431 disposed in conduit 404 between pump housing 434 and Cup shell 180, and connected to controller 450 via line 456. DMVA apparatus further comprises a pressure sensor 1118 disposed in cavity 119, and connected to controller 450 via line 458.

Implanted battery 460 is preferably a rechargeable battery, and is provided with recharging means 470. In one embodiment, recharging means 470 comprises an internal inductive coil 471 connected directly to implanted battery 460, or connected through controller 450 via line 451 as indicated in FIG. 29. As also indicated in FIG. 29, inductive coil 471 is preferably implanted subcutaneously within the patient, with arrow 495 indicating the space within the body cavity of the patient, and arrow 494 indicating the space external to the patient. Recharging means 470 further comprises external inductive coil 473 connected to external controller 480 via line 474. External battery or battery pack 482 is connected to external coil 473 through controller 480 via line 476. In a further embodiment, external controller 480 is in communication with remote transceiver 490, as indicated by bi-directional arrow 493. Remote transceiver 490 comprises a modem connection or other suitable means that enables controller 480 to communicate bidirectionally with a physician or others.

In operation, pump assembly 430 operates on the principle of fluid phase change from liquid to gas, and from gas to liquid. A flash pump fluid having a low boiling point and high vapor pressure is contained in cavity 446, and is alternatingly boiled and condensed. Boiling of fluid in cavity 446 produces an expanding pressurized vapor that flows through conduit 404 and displaces liner 114 in systolic actuation; condensation of fluid in cavity 446 results in the withdrawal of vapor from conduit 404 and the retraction of liner 114 in diastolic actuation, with the effects of boiling and condensation being indicated by bidirectional arrow 496. Valve 431 is controlled by controller 450 to adjust the volume and flow rate of the vapor as it flows between pump cavity 432 and Cup cavity 119.

The pump fluid in cavity 446 is chosen to have a boiling point (or flash point) slightly above physiologic temperature. One fluid that has appropriate thermodynamic properties is ethyl bromide ($C_2H_5Br$), with a boiling point at 1 atm of 38.4 degrees Centigrade (° C.), and having a vapor pressure of 2 atm at 60.2° C. Since the positive pressure needed in order to displace the DMVA drive fluid to provide systolic blood pressure is on the order of 0.17 atm (~125 mm Hg), a temperature rise of 3.7° C. above its 38.4° C. boiling point will be sufficient to drive liner 114 in systolic actuation.

To perform the boiling portion of the cycle (systolic actuation), electrical current is supplied from controller 450 to resistive filaments 438, thereby rapidly heating such filaments, preferably to a temperature of about 39° C. Pump fluid immediately surrounding filaments 438 instantaneously flashes to vapor at a pressure sufficient to displace liner 114 in systolic actuation. The condensation portion of the cycle (diastolic actuation) is performed subsequently, when electrical current through filaments 438 is ceased. Fins 437 and 439 rapidly conduct heat from the liquid and vapor within cavity 446, resulting in rapid withdrawal and condensation of the vapor within cavity 119, such that diastolic actuation is achieved. By proper selection of size and spacing of both fins 437 and 439, and filaments 438, this thermodynamic cycle can be made to occur extremely quickly, and can be controlled by valve 431 or by modulating electrical current input to the filaments 438, or a combination of both.

Properties, requirements, materials, and/or characteristics of various components of pump assembly 430 will now be described.

Referring again to FIG. 29, fins 437 and 439 are preferably metal fins, consisting essentially of a material (e.g. aluminum or copper) that has very high thermal conductivity and relatively high heat capacity. Fins 437 are spaced apart so as to provide very rapid cooling of the pump fluid, but far enough apart so the cooling effect thereof does not prevent the flashover of the pump fluid into gas upon heating by the filaments 438. Because fins 439 are exposed to the internal body cavity of the patient, such fins 439 must be biocompatible or be coated with a biocompatible film. In one embodiment, pump housing 434 may comprise part or all of the external heat sink 435, depending upon the efficiency of the thermal circuit and on the overall cooling demands of the pump assembly 430. It should also be understood that exposure to a temperature of 39 degrees Centigrade does not pose a risk to tissues. In a heat sink design of even modest energy efficiency, such tissues in contact with pump assembly 430 are exposed to a temperature only slightly higher than 37 degrees Centigrade during pump operation.

In the preferred embodiment, filaments 438 are preferably formed of fine wire or other resistive material. Such material is chosen to have a negative thermal coefficient of electrical resistivity, thus permitting uniform heating of the entire filament length, irrespective of minor fluctuations in cross-section that would otherwise result in non-uniform heating along the length thereof.

Some liquid-vapor flashing fluid materials with appropriate thermodynamic properties (e.g. ethyl bromide) are not biocompatible and may also permeate materials such as silastic and other flexible polymers. Accordingly, a barrier to such material coming in contact with the liner and shell of the DMVA Cup is provided by reciprocating element 436 disposed between the pump fluid cavity 446 and DMVA drive fluid reservoir 432. It will be apparent that reciprocating element must be made of a material that is impermeable and insoluble to the pump fluid and the DMVA drive fluid. In circumstances where the liquid-vapor flashing fluid material is biocompatible and does not permeate Cup materials, the flash pump may be used to directly reciprocate the liner 114 of the apparatus 157.

Conduit 404 between the cup shell 170 and the pump assembly 430 may be either short (as shown) or longer, depending upon the preferred placement of pump assembly 430. It will be apparent that the cup shell 180 must surround the subject heart, but a location chosen for the pump assembly 430 will be based on a comfortable body cavity that has heat-sink properties, on proximity to the cup shell 180 (to minimize friction losses in conduit 404) and on proximity to battery 460, recharging means 470, and controller 450. In general, pump assembly 430 is designed to be comfortably implanted and to be biocompatible. The overall size for a pump assembly 430 that delivers a DMVA drive fluid volume of 250 cubic centimeters is preferably on the order of 600 to 800 cubic centimeters.

Another factor to be considered is the amount of thermal energy that is dissipated into the patient having an implanted flash pump 430. Simply put, any device that provides energy to physically pump the heart via a heart cup or other related assist device will, in addition to the physical pumping of blood, dissipate mechanical and/or electrical energy that is used in the operation thereof. The end result is a modest amount of thermal energy or heat that must be dissipated by the body. While use of the physical phenomenon of liquid flashing into gas gives the impression of substantial heating, such is not the case, as condensation of the vapor in the diastolic portion of the cycle occurs at near-physiologic temperature. Accordingly, a flash pump may be designed to have the same or better energy efficiency as a mechanical pump, thus requiring the same amount of body heat dissipation, or less.

In operation, small rechargeable battery 460 is used to continue operation of DMVA Cup 157 during periods when the primary external battery pack 482 is being replaced, or when emergency backup power is required due to malfunction. In one embodiment, DMVA apparatus comprises two redundant batteries 482 for increased reliability. External battery pack 482 is preferably a rechargeable lithium battery pack, which typically has up to 80% capacity after 500 charge/discharge cycle. Such a battery pack 482 weighing approximately 5 lb has the capacity to store sufficient energy for operation of DMVA apparatus 157 over a full day. Battery pack 482 may be conveniently recharged during sleep cycle or at other times.

In operation, implanted inductive charging coil 471 is used to power DMVA apparatus 157 and to keep implanted battery 460 charged. Implanted inductive charging coil 471 is preferably placed subcutaneously, with such coil 471 inductively coupled to external coil 473. Coils 473 and 471 must transfer approximately 10-25 watts of electrical power, depending upon overall system efficiency and upon the degree of patient dependence on DMVA apparatus 157.

In operation, implanted controller 450 performs multiple control functions as follows: overall power management for the implanted part of the system, particularly pump assembly 430; real time control of the operation DMVA Cup 157, based on programming and on sensor data; and control of DMVA fluid pressure delivered to cavity 310 during each systolic/diastolic cycle. External controller 480 performs multiple control functions as follows: overall power management for the DMVA system 157; output control data, other information, and alarms to remote transceiver 490; and control of the recharging process for primary battery pack 482.

It will be apparent that the entire power supply and control system of DMVA apparatus 157 can be used in a like manner to power and control the DMVA apparatus 156 of FIG. 28. It will be further apparent that other power sources would be suitable to power DMVA apparatus 156 of FIGS. 28 and 157 of FIG. 29, including but not limited to a kinetic power source, a piezoelectric power source, an electrostrictive power source, a thermal power source, and the like.

It is, therefore, apparent that there has been provided, in accordance with the present invention, a method and apparatus for Direct Mechanical Ventricular Assist (DMVA). While this invention has been described in conjunction with preferred embodiments thereof, it is evident that many alternatives, modifications, and variations will be apparent to those skilled in the art. Accordingly, it is intended to embrace all such alternatives, modifications and variations that fall within the spirit and broad scope of the appended claims.

We claim:

1. A method of treating a patient requiring heart function assistance or therapy comprising:
   1) connecting the patient to a cardiac assist device, said device comprising:
      a) a cup configured to encompass, and to seal and conform to said heart from atrio-ventricular groove to apex throughout systolic and diastolic actuation by imposing negative pressure between said cup and said heart, said cup having a compliant exterior wall attached to a compliant interior liner forming a continuous annular cavity between said wall and said liner, wherein the liner comprises a tapered unbonded transition section reducing in thickness to a thin section forming the liner adjacent a liner portion attached to the wall;
      b) a drive system in closed fluid communication with said cavity to effect displacement of said cavity;
      c) a sensor measuring at least one parameter; and
      d) a control system in communication with said drive system and with said sensor;

2) collecting data from said sensor and importing said data into said control system;
3) using an algorithm to formulate a command instruction from said control system in response to said data; and
4) exporting said command instruction from said controller to said drive system to effect displacement of said annular cavity and wherein said displacement actively supports systolic and diastolic actuation of the heart.

2. The method of claim 1, wherein data imported into the control system corresponds to the fluid pressure within said annular cavity.

3. The method of claim 1, wherein said command instruction maintains constant cardiac performance.

4. The method of claim 1, wherein said sensor detects one or more of: device operational data; anatomical data; hemodynamic data; electrophysiological data; biochemical/biological data; acoustical data; tissue characteristic data; temperature data; optical data; and/or device mechanical data.

5. The method of claim 4, further comprising one or more sensors remote to said cup.

6. The method of claim 5, wherein one or more sensors is an electrophysiological sensor positioned externally on said patient.

7. The method of claim 1, wherein said sensor is used to guide installation of the device and/or to assess cardiac performance under the influence of the device.

8. The method of claim 1, wherein said sensor collects data relating to liner conformation to, and contact with, an exterior surface of the heart corresponding to the right and/or left ventricles throughout systolic and diastolic actuation.

9. The method of claim 1, wherein said sensor collects data relating to fit of the cup on the heart.

10. The method of claim 1, wherein the compliant exterior wall and compliant interior liner are the same material.

11. The method of claim 10, wherein the wall and liner material is a strain neutral material that retains isotropic or near-isotropic properties after repeated cyclic loadings.

12. The method of claim 10, wherein the wall and liner material is a heat curable liquid silicone rubber.

13. The method of claim 10, wherein the compliant exterior wall has a wall thickness between about 2 millimeters and about 8 millimeters.

14. The method of claim 10, wherein the liner is a rolling diaphragm liner.

15. The method of claim 14, wherein the exterior wall and interior liner are joined through an integral liner and seal assembly.

16. The method of claim 15, wherein the seal of the integral liner and seal assembly is the same material as wall and liner.

17. The method of claim 1, wherein the liner portion attached to the wall is configured to mate with a recess in said wall.

18. The method of claim 1, wherein said at least one parameter is input by said patient.

19. The method of claim 1, wherein said at least one parameter is a therapeutic response factor.

20. The method of claim 1, wherein said at least one parameter is an electrophysiological parameter.

21. The method of claim 1, wherein said at least one parameter is a three-dimensional data array of electrophysiological parameters.

22. The method of claim 1, wherein said at least one parameter is a biochemical marker.

23. The method of claim 22, wherein said biochemical marker is selected from the group consisting of lactate, C-reactive protein, oxygen, and carbon dioxide.

24. The method of claim 1, wherein said at least one parameter is blood pressure.

25. The method of claim 1, wherein said at least one parameter is blood flow velocity.

26. The method of claim 1, wherein said at least one parameter is cardiac ejection fraction.

27. The method of claim 1, wherein said at least one parameter is inferred from ultrasonic image data.

28. The method of claim 27, wherein said at least one parameter inferred from ultrasonic image data is right ventricle volume.

29. The method of claim 27, wherein said at least one parameter inferred from ultrasonic image data is left ventricle volume.

30. The method of claim 1, wherein said at least one parameter is inferred from magnetic resonance image data.

31. The method of claim 30, wherein said at least one parameter inferred from magnetic resonance image data is right ventricle volume.

32. The method of claim 30, wherein said at least one parameter inferred from magnetic resonance image data is left ventricle volume.

33. The method of claim 1, wherein said at least one parameter is a numerical values that quantifies a prior aspect of said patient.

34. The method of claim 1, wherein said at least one parameter is predictive parameter of said patient.

35. The method of claim 1, wherein said command instruction instructs said cardiac assist device to provide training to said heart.

36. The method of claim 1, wherein said command instruction instructs said cardiac assist device to assist in regeneration of said heart.

37. The method of claim 1, wherein said command instruction instructs delivery of a first therapeutic agent.

38. The method of claim 37, wherein said first therapeutic agent is selected from the group consisting of anti-inflammatory agents, gene therapy agents, gene transfer agents, stem cells, chemo-attractants, cell regeneration agents, ventricular remodeling agents, anti-infection agents, tumor suppressants, tissue and/or cell engineering agents, imaging contrast agents, tissue staining agents, nutrients, and mixtures thereof.

39. The method of claim 1, wherein said command instruction instructs delivery of a first regenerative agent.

40. The method of claim 39, wherein the first regenerative agent is selected from the group consisting of tissue scaffold materials, biochemical materials, stem cells, and electrical stimulation.

41. A method of treating a patient requiring heart function assistance or therapy comprising:
1) connecting the patient to a cardiac assist device, said device comprising:
a) a cup having a compliant exterior wall joined to a compliant interior rolling diaphragm liner continuously along two circumferential lines forming a continuous annular cavity said wall and said liner, wherein the liner comprises a tapered unbonded transition section reducing in thickness to a thin section, said cup configured to encompass, and to seal and conform to said heart from apex to atrio-ventricular groove throughout systolic and diastolic actuation by imposing negative pressure between said cup and said heart; and
b) a drive system in closed fluid communication with said cavity to effect displacement of said cavity;
c) a sensor; and d) a control system in communication with said drive system and with said sensor;

2) collecting from said sensor and importing said data into said control system;

3) using an algorithm to formulate a command instruction from said control system in response to said data; and 4) exporting said command instruction from said controller to said drive system to effect displacement of said annular cavity, and wherein said displacement actively supports systolic and diastolic actuation of the heart.

42. The method of claim 41, wherein data imported into the control system corresponds to fluid pressure within said annular cavity.

43. The method of claim 41, wherein said command instruction maintains constant pump function of said heart.

44. The method of claim 41, wherein said sensor detects one or more of: device operational data; anatomical data; hemodynamic data; electrophysiological data; biochemical/biological data; acoustical data; tissue characteristic data; temperature data; optical data; and/or device mechanical data.

45. The method of claim 41, further comprising one or more sensors remote to said cup.

46. The method of claim 45, wherein one or more sensors is an electrophysiological sensor positioned externally on said patient.

47. The method of claim 41, wherein said sensor collects data relating to fit of the cup on the heart.

48. The method of claim 41, wherein said sensor collects data relating to liner conformation and contact with the heart surface throughout systolic and diastolic actuation.

49. The method of claim 41, wherein said sensor collects data relating to pump function of the heart under the influence of the device.

50. The method of claim 41, wherein the exterior wall and interior rolling diaphragm liner are joined through an integral liner and seal assembly.

51. The method of claim 41, wherein the seal is the same material as wall and liner.

52. The method of claim 41, wherein the liner portion attached to the exterior wall is configured to fit in a recess within said wall.

* * * * *